United States Patent
Altman et al.

(10) Patent No.: US 9,216,173 B2
(45) Date of Patent: *Dec. 22, 2015

(54) 2-PYRIDYL CARBOXAMIDE-CONTAINING SPLEEN TYROSINE KINASE (SYK) INHIBITORS

(71) Applicants: Michael D. Altman, Needham, MA (US); Corey E. Bienstock, Natick, MA (US); John W. Butcher, Berlin, MA (US); Kaleen Konrad Childers, Newton, MA (US); Maria Emilia Di Francesco, Houston, TX (US); Anthony Donofrio, Cambridge, MA (US); John Michael Ellis, Needham, MA (US); Christian Fischer, Natick, MA (US); Andrew M. Haidle, Cambridge, MA (US); James P. Jewell, Somerville, MA (US); Sandra Lee Knowles, Princeton, NJ (US); Alan B. Northrup, Reading, MA (US); Ryan D. Otte, Natick, MA (US); Scott L. Peterson, Salem, MA (US); Graham Frank Smith, Sudbury, MA (US)

(72) Inventors: Michael D. Altman, Needham, MA (US); Corey E. Bienstock, Natick, MA (US); John W. Butcher, Berlin, MA (US); Kaleen Konrad Childers, Newton, MA (US); Maria Emilia Di Francesco, Houston, TX (US); Anthony Donofrio, Cambridge, MA (US); John Michael Ellis, Needham, MA (US); Christian Fischer, Natick, MA (US); Andrew M. Haidle, Cambridge, MA (US); James P. Jewell, Somerville, MA (US); Sandra Lee Knowles, Princeton, NJ (US); Alan B. Northrup, Reading, MA (US); Ryan D. Otte, Natick, MA (US); Scott L. Peterson, Salem, MA (US); Graham Frank Smith, Sudbury, MA (US)

(73) Assignee: Merck Sharp & Dohme Corp., Rahway, NJ (US)

(*) Notice: Subject to any disclaimer, the term of this patent is extended or adjusted under 35 U.S.C. 154(b) by 0 days.

This patent is subject to a terminal disclaimer.

(21) Appl. No.: 14/349,551

(22) PCT Filed: Oct. 1, 2012

(86) PCT No.: PCT/US2012/058219
§ 371 (c)(1),
(2) Date: Apr. 3, 2014

(87) PCT Pub. No.: WO2013/052394
PCT Pub. Date: Apr. 11, 2013

(65) Prior Publication Data
US 2014/0243336 A1     Aug. 28, 2014

Related U.S. Application Data

(60) Provisional application No. 61/543,539, filed on Oct. 5, 2011.

(51) Int. Cl.
*C07D 213/73* (2006.01)
*A61K 31/4439* (2006.01)
(Continued)

(52) U.S. Cl.
CPC ........... *A61K 31/4439* (2013.01); *A61K 31/444* (2013.01); *A61K 31/496* (2013.01); *A61K 31/506* (2013.01); *A61K 31/5025* (2013.01); *A61K 31/519* (2013.01); *A61K 31/5377* (2013.01); *C07D 213/81* (2013.01); *C07D 401/12* (2013.01); *C07D 401/14* (2013.01); *C07D 405/14* (2013.01); *C07D 409/14* (2013.01); *C07D 413/14* (2013.01); *C07D 417/14* (2013.01); *C07D 487/04* (2013.01); *C07D 495/04* (2013.01)

(58) Field of Classification Search
CPC .................................................. C07D 213/73
USPC .................................. 546/264; 514/332, 335
See application file for complete search history.

(56) References Cited

U.S. PATENT DOCUMENTS

| | | |
|---|---|---|
| 5,710,129 A | 1/1998 | Lynch et al. |
| 6,248,790 B1 | 6/2001 | Uckun et al. |

(Continued)

FOREIGN PATENT DOCUMENTS

| | | |
|---|---|---|
| EP | 1392684 B1 | 9/2006 |
| JP | 2004203748 A | 12/2002 |

(Continued)

OTHER PUBLICATIONS

Notice of Allowance, U.S. Appl. No. 14/349,558, mailed Nov. 18, 2014.

(Continued)

*Primary Examiner* — Patricia L Morris
(74) *Attorney, Agent, or Firm* — Eric A. Meade; Catherine D. Fitch

(57) ABSTRACT

The invention provides certain 2-pyridyl carboxamide-containing compounds of the Formula (I) or pharmaceutically acceptable salts thereof, wherein A and B are as defined herein. The invention also provides pharmaceutical compositions comprising such compounds, and methods of using the compounds for treating diseases or conditions mediated by Spleen Tyrosine Kinase (Syk) kinase.

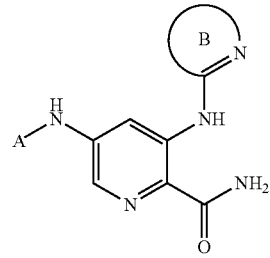

(I)

16 Claims, No Drawings

(51) Int. Cl.

| | | |
|---|---|---|
| *C07D 401/14* | (2006.01) | |
| *C07D 405/14* | (2006.01) | |
| *C07D 413/14* | (2006.01) | |
| *C07D 213/81* | (2006.01) | |
| *C07D 401/12* | (2006.01) | |
| *C07D 409/14* | (2006.01) | |
| *C07D 417/14* | (2006.01) | |
| *C07D 487/04* | (2006.01) | |
| *C07D 495/04* | (2006.01) | |
| *A61K 31/444* | (2006.01) | |
| *A61K 31/496* | (2006.01) | |
| *A61K 31/5025* | (2006.01) | |
| *A61K 31/506* | (2006.01) | |
| *A61K 31/519* | (2006.01) | |
| *A61K 31/5377* | (2006.01) | |

(56) References Cited

U.S. PATENT DOCUMENTS

| | | | |
|---|---|---|---|
| 6,432,963 | B1 | 8/2002 | Hisamichi et al. |
| 6,589,950 | B1 | 7/2003 | Collingwood et al. |
| 6,770,643 | B2 | 8/2004 | Cox et al. |
| 6,797,706 | B1 | 9/2004 | Hisamichi et al. |
| 6,897,207 | B2 | 5/2005 | Cox et al. |
| 6,897,208 | B2 | 5/2005 | Edwards et al. |
| 6,911,443 | B2 | 6/2005 | Yura et al. |
| 7,060,827 | B2 | 6/2006 | Singh et al. |
| 7,122,542 | B2 | 10/2006 | Singh et al. |
| 7,227,020 | B2 | 6/2007 | Cox et al. |
| 7,259,154 | B2 | 8/2007 | Cox et al. |
| 7,259,161 | B2 | 8/2007 | Bethiel et al. |
| 7,276,502 | B2 | 10/2007 | Brenchley et al. |
| 7,915,287 | B2 | 3/2011 | Bellon et al. |
| 8,987,456 | B2 * | 3/2015 | Altman et al. ............ 546/159 |
| 2004/0029902 | A1 | 2/2004 | Singh et al. |
| 2004/0054179 | A1 | 3/2004 | Yura et al. |
| 2006/0135543 | A1 | 6/2006 | Singh et al. |
| 2006/0178407 | A1 | 8/2006 | Argade et al. |
| 2006/0205731 | A1 | 9/2006 | Kodama et al. |
| 2006/0211657 | A1 | 9/2006 | Singh et al. |
| 2006/0234483 | A1 | 10/2006 | Araki et al. |
| 2006/0247262 | A1 | 11/2006 | Baenteli et al. |
| 2007/0004626 | A1 | 1/2007 | Masuda et al. |
| 2007/0129362 | A1 | 6/2007 | Bhamidipati et al. |
| 2007/0197782 | A1 | 8/2007 | Clough et al. |
| 2010/0197652 | A1 | 8/2010 | Bergman et al. |
| 2010/0267709 | A1 | 10/2010 | Young et al. |
| 2014/0243337 | A1 | 8/2014 | Altman et al. |
| 2014/0303206 | A1 | 10/2014 | Altman et al. |

FOREIGN PATENT DOCUMENTS

| | | | |
|---|---|---|---|
| WO | WO02096905 | A1 | 12/2002 |
| WO | WO03057659 | A1 | 7/2003 |
| WO | WO03078404 | A1 | 9/2003 |
| WO | WO2004080463 | A1 | 9/2004 |
| WO | WO2004087698 | A2 | 10/2004 |
| WO | WO2004087699 | A2 | 10/2004 |
| WO | WO2005013996 | A2 | 2/2005 |
| WO | WO2005026158 | A1 | 3/2005 |
| WO | WO2005028475 | A2 | 3/2005 |
| WO | WO2005033103 | A2 | 4/2005 |
| WO | WO2005056547 | A2 | 6/2005 |
| WO | WO2006004865 | A1 | 1/2006 |
| WO | WO2006028833 | A1 | 3/2006 |
| WO | WO2006050480 | A2 | 5/2006 |
| WO | WO2006068770 | A1 | 6/2006 |
| WO | WO2006078846 | A1 | 7/2006 |
| WO | WO2006093247 | A1 | 9/2006 |
| WO | WO2006129100 | A1 | 12/2006 |
| WO | WO2006133426 | A2 | 12/2006 |
| WO | WO2006135915 | A2 | 12/2006 |
| WO | WO2007009681 | A1 | 1/2007 |
| WO | WO2007009773 | A1 | 1/2007 |
| WO | WO2007028445 | A1 | 3/2007 |
| WO | WO2007042298 | A1 | 4/2007 |
| WO | WO2007042299 | A1 | 4/2007 |
| WO | WO2007070872 | A1 | 6/2007 |
| WO | WO2007085540 | A1 | 8/2007 |
| WO | WO2007107469 | A2 | 9/2007 |
| WO | WO2007120980 | A2 | 10/2007 |
| WO | WO2009031011 | A2 | 3/2009 |
| WO | WO2009084695 | A1 | 7/2009 |
| WO | WO2009097287 | A1 | 8/2009 |
| WO | WO2009102468 | A2 | 8/2009 |
| WO | WO2009131687 | A2 | 10/2009 |
| WO | WO2009136995 | A2 | 11/2009 |
| WO | WO2009145856 | A1 | 12/2009 |
| WO | WO2010027500 | A1 | 3/2010 |
| WO | WO2010068257 | A1 | 6/2010 |
| WO | WO2010068258 | A1 | 6/2010 |
| WO | WO2010129802 | A1 | 11/2010 |

OTHER PUBLICATIONS

Notice of Allowance, U.S. Appl. No. 14/349,563, mailed Nov. 17, 2014.

International Search Report & Written Opinion of PCT/US2012/058219, mailed Nov. 30, 2012.

* cited by examiner

2-PYRIDYL CARBOXAMIDE-CONTAINING SPLEEN TYROSINE KINASE (SYK) INHIBITORS

CROSS REFERENCE TO RELATED APPLICATIONS

This application is a U.S. National Phase application under 35 U.S.C. §371 of PCT Application No. PCT/US2012/058219, filed Oct. 1, 2012, which claims priority under 35 U.S.C. §119(e) from U.S. Provisional Application No. 61/543,539, filed Oct. 5, 2011.

FIELD OF THE INVENTION

The present invention relates to certain 2-pyridyl carboxamide-containing compounds of the Formula (I) (also referred to herein as the "compounds of the Formula (I)" or "compounds of Formula (I)") which are inhibitors of Spleen Tyrosine Kinase (Syk) kinase activity. The present invention also provides compositions comprising such compounds, and methods of using such compounds for treating conditions or disorders associated with inappropriate Syk activity, in particular in the treatment and prevention of disease states mediated by Syk. Such disease states may include inflammatory, allergic and autoimmune diseases, for example, asthma, chronic obstructive pulmonary disease (COPD), adult respiratory distress syndrome (ARDS), ulcerative colitis, Crohns disease, bronchitis, dermatitis, allergic rhinitis, psoriasis, scleroderma, urticaria, rheumatoid arthritis, idiopathic thrombocytopenic purpura (ITP), multiple sclerosis, cancer, HIV and lupus.

BACKGROUND OF THE INVENTION

Spleen Tyrosine Kinase (Syk) is a protein tyrosine kinase which has been described as a key mediator of immunoreceptor signalling in a host of inflammatory cells including mast cells, B-cells, macrophages and neutrophils. These immunoreceptors, including Fc receptors and the B-cell receptor, are important for both allergic diseases and antibody-mediated autoimmune diseases and thus pharmacologically interfering with Syk could conceivably treat these disorders.

Allergic rhinitis and asthma are diseases associated with hypersensitivity reactions and inflammatory events involving a multitude of cell types including mast cells, eosinophils, T cells and dendritic cells. Following exposure to allergen, high affinity immunoglobulin receptors for IgE and IgG become cross-linked and activate downstream processes in mast cells and other cell types leading to the release of pro-inflammatory mediators and airway spasmogens. In the mast cell, for example, IgE receptor cross-linking by allergen leads to release of mediators including histamine from pre-formed granules, as well as the synthesis and release of newly synthesized lipid mediators including prostaglandins and leukotrienes.

Syk kinase is a non-receptor linked tyrosine kinase which is important in transducing the downstream cellular signals associated with cross-linking $Fc_{epsilon}RI$ and or $Fc_{epsilon}RI$ receptors, and is positioned early in the signalling cascade. In mast cells, for example, the early sequence of $Fc_{epsilon}RI$ signalling following allergen cross-linking of receptor-IgE complexes involves first Lyn (a Src family tyrosine kinase) and then Syk. Inhibitors of Syk activity would therefore be expected to inhibit all downstream signalling cascades thereby alleviating the immediate allergic response and adverse events initiated by the release of pro-inflammatory mediators and spasmogens (Wong et al. 2004, *Expert Opin. Investig. Drugs* (2004) 13 (7) 743-762).

Recently, it has been shown that the Syk kinase inhibitor R112 (Rigel), dosed intranasally in a phase I/II study for the treatment of allergic rhinitis, gave a statistically significant decrease in $PGD_2$, a key immune mediator that is highly correlated with improvements in allergic rhinorrhea, as well as being safe across a range of indicators, thus providing the first evidence for the clinical safety and efficacy of a topical Syk kinase inhibitor. (Meltzer, Eli O.; Berkowitz, Robert B.; Grossbard, Elliott B. 2005, *Journal of Allergy and Clinical Immunology* 115(4): 791-796). In a more recent phase II clinical trial for allergic rhinitis (Clinical Trials.gov Identifier NCT0015089), R112 was shown as having a lack of efficacy versus placebo.

Rheumatoid Arthritis (RA) is an auto-immune disease affecting approximately 1% of the population. It is characterised by inflammation of articular joints leading to debilitating destruction of bone and cartilage. Recent clinical studies with Rituximab, which causes a reversible B cell depletion, (J. C. W. Edwards et al. 2004, *New Eng. J. Med.* 350: 2572-2581) have shown that targeting B cell function is an appropriate therapeutic strategy in auto-immune diseases such as RA. Clinical benefit correlates with a reduction in auto-reactive antibodies (or Rheumatoid Factor) and these studies suggest that B cell function and indeed auto-antibody production are central to the ongoing pathology in the disease.

Studies using cells from mice deficient in the Spleen Tyrosine Kinase (Syk) have demonstrated a non-redundant role of this kinase in B cell function. The deficiency in Syk is characterised by a block in B cell development (M. Turner et al. 1995 *Nature* 379: 298-302 and Cheng et al. 1995, *Nature* 378: 303-306). These studies, along with studies on mature B cells deficient in Syk (Kurasaki et al. 2000, *Immunol. Rev.* 176:19-29), demonstrate that Syk is required for the differentiation and activation of B cells. Hence, inhibition of Syk in RA patients is likely to block B cell function, and thereby reduce Rheumatoid Factor production. In addition to the role of Syk in B cell function, and of further relevance to the treatment of RA, is the requirement for Syk activity in Fc receptor (FcR) signalling. FcR activation by immune complexes in RA has been suggested to contribute to the release of multiple pro-inflammatory mediators.

SUMMARY OF THE INVENTION

The present invention provides novel compounds that are potent inhibitors of Syk as well as pharmaceutical compositions containing them. As Syk inhibitors compounds of Formula (I) are useful in the treatment and prevention of diseases and disorders mediated by the Syk protein; such diseases and disorders include, but are not limited to, rheumatoid arthritis, asthma, COPD, cancer and idiopathic thrombocytopenic purpura.

DETAILED DESCRIPTION OF THE INVENTION

Compounds of the Invention

The present invention provides compound of Formula (I) or pharmaceutically acceptable salts thereof, wherein A and B are as defined below. Described below are embodiments of the compound of Formula (I). The compound of Formula (IA) and (IB), as are described in detail below, are embodiments of the compound of Formula (I).

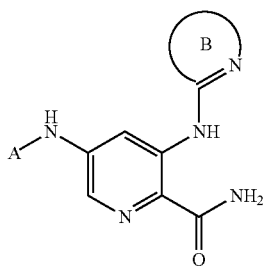

(I)

In embodiment no. 1 the present invention provides a compound of the Formula (I), or a pharmaceutically acceptable salt thereof, wherein:

B is a 5- to 10-membered, mono- or bicyclic heteroaryl optionally containing 1 to 3 heteroatoms in addition to the illustrated ring N atom, selected from the group consisting of N, O, and S;
  wherein B is unsubstituted or substituted by 1 to 3 $R^3$ moieties, wherein each $R^3$ moiety is independently selected from the group consisting of $C_1$-$C_3$ alkyl, $C_1$-$C_3$ alkoxy, $C_1$-$C_3$ fluoroalkyl, $C_1$-$C_3$ hydroxyalkyl, halo, hydroxy, amino, ($C_1$-$C_3$ alkyl)amino, di($C_1$-$C_3$ alkyl)amino, —N(H)SO$_2$—($C_1$-$C_3$ alkyl), —CO$_2$H, —C(O)NH$_2$, —C(O)N(H)($C_1$-$C_3$ alkyl), —C(O)N(H)($C_1$-$C_3$ alkyl)$_2$, —CH$_2$O—($C_1$-$C_4$ alkylene)-OH, and E;

E is
  (a) -$E^1$,
  (b) —CH$_2$-$E^1$ or
  (c) O—CH$_2$-$E^1$;
  wherein $E^1$ is:
    (i) a 5- to 10-membered heteroaryl containing 1 to 3 heteroatoms selected from the group consisting of N, O, and S;
    (ii) a 5- to 6-membered heterocyclyl containing 1 to 2 heteroatoms selected from the group consisting of N, O, and S;
    (iii) phenyl; or
    (iv) $C_3$-$C_6$ cycloalkyl;
  wherein $E^1$ is unsubstituted or substituted by 1 to 2 moieties independently selected from the group consisting of $C_1$-$C_3$ alkyl, $C_1$-$C_3$ alkoxy, halo, hydroxy, nitro, carboxy, $C_1$-$C_3$ hydroxyalkyl, —O—($C_1$-$C_3$ fluoroalkyl), —C(H)(OH)—($C_1$-$C_3$ fluoroalkyl), —N(CH$_3$)SO$_2$—($C_1$-$C_3$ alkyl), ($C_1$-$C_3$ alkyl)piperazinyl, and $R^{E1}$;
    wherein $R^{E1}$ is
    (a) (CH$_2$)$_x$—$R^{E1a}$, wherein x is 1, 2, or 3; or
    (b) $R^{E1a}$;
    wherein $R^{E1a}$ is
      (i) phenyl;
      (ii) a 5- to 6-membered heteroaryl containing 1 to 3 heteroatoms selected from the group consisting of N and O; or
      (iii) a 5- to 6-membered heterocyclyl containing 1 to 3 heteroatoms selected from the group consisting of N and O;
      wherein $R^{E1a}$ is unsubstituted or substituted by 1 to 2 moieties independently selected from the group consisting of $C_1$-$C_3$ alkyl, $C_1$-$C_3$ alkoxy and halo;

A is selected from the group consisting of
  (a)

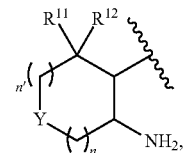

wherein
  Y is CH$_2$—, S(O)$_2$—, or —O—;
  $R^{11}$ and $R^{12}$ are independently H or F; and
  n is 1 or 2;
  n' is 0 or 1; or
  (b)

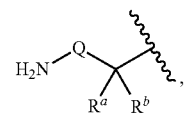

wherein
  $R^a$ and $R^b$ are independently H, $C_1$-$C_6$ alkyl, or phenyl;
    or $R^a$ and $R^b$ together with the carbon atom to which they are attached form —C(O)—;
  Q is

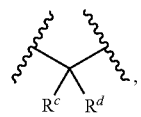

C(O)—, or CH$_2$CH$_2$—;
  wherein $R^c$ is H, $C_1$-$C_6$ alkyl, $C_1$-$C_3$ fluoroalkyl, $C_3$-$C_6$ cycloalkyl, (CH$_2$)$_t$OR$^{13}$, —C(O)NH$_2$, —C(O)N(H)($C_1$-$C_3$ alkyl), —C(O)N($C_1$-$C_3$ alkyl)$_2$, (CH$_2$)$_r$S(O)$R^{14}$, —(CH$_2$)$_r$-phenyl, or (CH$_2$)$_r$N(H)C(O)—($C_1$-$C_3$ alkyl);
  $R^{13}$ is H or $C_1$-$C_3$ alkyl; and
  $R^{14}$ is $C_1$-$C_3$ alkyl;
  r is 1 or 2;
  t is 0, 1, or 2;
  $R^d$ is H or $C_1$-$C_6$ alkyl; or
  $R^c$ and $R^d$ together with the carbon atom to which they are attached form a group of the formula
  (i)

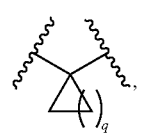

wherein q is 1, 2, 3, or 4; or (ii)

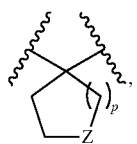

wherein
Z is O or —S(O)$_2$—; and
p is 1 or 2;

(c)

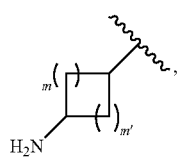

wherein m is 1 or 2 and m' is 0 or 1;

(d)

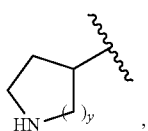

wherein y is 1 or 2;
(e) H;
(f) —C(O)N(H)—(C$_1$-C$_3$ alkyl); and
(g) —S(O)$_2$CH$_2$CH$_2$NH$_2$.

In embodiment no. 2, B is selected from the group consisting of:

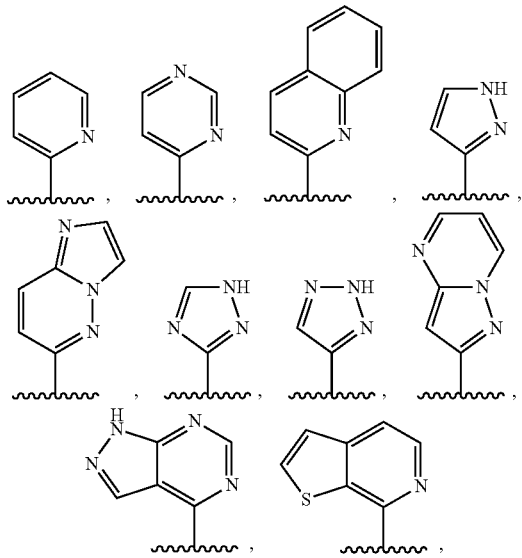

-continued

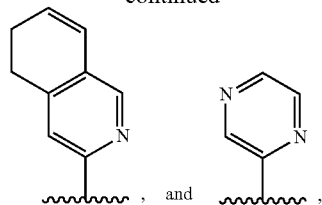

, and , wherein said B is unsubstituted or substituted by 1 to 2 R$^3$ moieties; and the remaining variables are as described in embodiment no. 1.

In embodiment no. 3, B is substituted by no more than two R$^3$ moieties, and no more than 1 of said R$^3$ moieties is E, and the remaining variables are as described in any one of embodiments no. 1 or 2.

In embodiment no. 4, B is substituted no more than two R$^3$ moieties, and one of said R$^3$ moieties is E, and the remaining variables are as described in any one of embodiments no. 1 or 2.

In embodiment no 5, A is

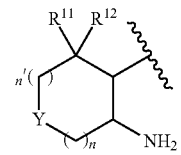

Y is CH$_2$—, S(O)$_2$—, or —O—;
R$^{11}$ and R$^{12}$ are independently H or F; and
n is 1 or 2;
n' is 0 or 1;
and the remaining variables are as described in any one of embodiment nos. 1-4.

In embodiment no. 6, A is selected from the group consisting of:

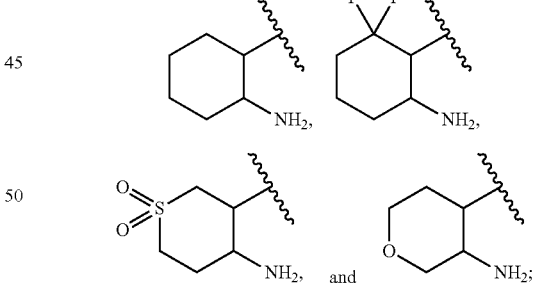

and the remaining variables are as described in any one of embodiment nos. 1-4.

In embodiment no. 7, A is selected from the group consisting of:

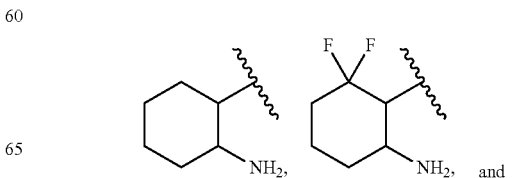

-continued

[structure: thiane-1,1-dioxide with NH2 substituent]

and the remaining variables are as described in any one of embodiment nos. 1-4.

In embodiment no. 8, A is

[structure: H2N–Q–C(R^a)(R^b)–]

wherein $R^a$ and $R^b$ are independently H, $C_1$-$C_6$ alkyl, or phenyl;
or $R^a$ and $R^b$ together with the carbon atom to which they are attached form —C(O)—;
Q is

[structure: –C(R^c)(R^d)–]

C(O)—, or CH$_2$CH$_2$—;
wherein $R^c$ is H, $C_1$-$C_6$ alkyl, $C_1$-$C_3$ fluoroalkyl, $C_3$-$C_6$ cycloalkyl, $(CH_2)_rOR^{13}$, —C(O)NH$_2$, —C(O)N(H)($C_1$-$C_3$ alkyl), —C(O)N($C_1$-$C_3$ alkyl)$_2$, $(CH_2)_rS(O)_tR^{14}$, —$(CH_2)_r$-phenyl, or $(CH_2)_rN(H)C(O)$—($C_1$-$C_3$ alkyl);
$R^{13}$ is H or $C_1$-$C_3$ alkyl; and
$R^{14}$ is $C_1$-$C_3$ alkyl;
r is 1 or 2;
t is 0, 1, or 2;
$R^d$ is H or $C_1$-$C_6$ alkyl; or
$R^c$ and $R^d$ together with the carbon atom to which they are attached form a group of the formula
(i)

[structure: cyclopropyl-type ring with (CH2)q]

wherein q is 1, 2, 3, or 4; or
(ii)

[structure: spirocyclic ring with Z and (CH2)p]

wherein
Z is O or —S(O)$_2$—;
p is 1 or 2; and
the remaining variables are as described in any one of embodiment nos. 1-4.

In embodiment no. 9, $R^a$ and $R^b$ are independently H or $C_1$-$C_4$ alkyl;
Q is C(O)— or

[structure: –C(R^c)(H)–]

$R^c$ is H, $C_1$-$C_4$ alkyl, cyclopropyl, $CH_2OR^{13}$, or $CH_2SR^{14}$;
$R^{13}$ is H or $C_1$-$C_3$ alkyl; and
$R^{14}$ is $C_1$-$C_3$ alkyl;
and the remaining variables are as described in any one of embodiment nos. 1-4.

In embodiment no. 10, the compound of the Formula (I) has the Formula (IA)

(IA)

[structure: pyridine core with R^3a, R^3b, R^3c substituents, NH linkages to A and to aminopyridine carboxamide]

wherein
$R^{3a}$ is halo, $C_1$-$C_3$ alkyl, $C_3$-$C_6$ cycloalkyl, $C_1$-$C_3$ fluoroalkyl, or a mono or bicyclic 5- to 9-membered heteroaryl containing 1 to 3 heteroatoms selected from the group consisting of N and S;
wherein said heteroaryl of $R^{3a}$ is unsubstituted or substituted by 1 to 2 moieties selected from the group consisting of $C_1$-$C_3$ alkyl and $C_1$-$C_3$ hydroxyalkyl;
$R^{3b}$ is H, $C_1$-$C_3$ alkyl, $C_1$-$C_3$ alkoxy, halo, $C_3$-$C_6$ cycloalkyl, $C_1$-$C_3$ fluoroalkyl, or a mono or bicyclic 5- to 9-membered heteroaryl containing 1 to 3 heteroatoms selected from the group consisting of N and S;
wherein said heteroaryl of $R^{3b}$ is unsubstituted or substituted by 1 to 2 moieties selected from the group consisting of $C_1$-$C_3$ alkyl;
$R^{3c}$ is H, $C_1$-$C_3$ alkyl, $C_1$-$C_3$ alkoxy, halo, $C_3$-$C_6$ cycloalkyl, $C_1$-$C_3$ fluoroalkyl, or a 5-membered heteroaryl containing 1 to 3 N atoms;
wherein said heteroaryl of $R^{3c}$ is unsubstituted or substituted by 1 to 2 moieties selected from the group consisting of $C_1$-$C_3$ alkyl;
A is selected from the group consisting of
(a)

[structure: cyclohexyl-type ring with R^11, R^12, Y, NH2 and (CH2)n, (CH2)n']

wherein
Y is CH$_2$—, S(O)$_2$—, or —O—;
$R^{11}$ and $R^{12}$ are independently H or F; and
n is 1 or 2;
n' is 0 or 1; or (b)

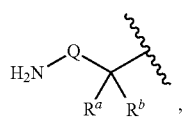

wherein
$R^a$ and $R^b$ are independently H or $C_1$-$C_4$ alkyl; and
Q is C(O)— or

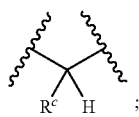

$R^c$ is H, $C_1$-$C_3$ alkyl, cyclopropyl, $CH_2OR^{13}$, or $CH_2SR^{14}$;
$R^{13}$ is H or $C_1$-$C_3$ alkyl; and
$R^{14}$ is $C_1$-$C_3$ alkyl.

In embodiment no. 11, no more than one of $R^{3a}$, $R^{3b}$, and $R^{3c}$ is heteroaryl or $C_3$-$C_6$ cycloalkyl; and the remaining variables are as described in embodiment no. 10.

In embodiment no. 12, $R^{3a}$ and $R^{3c}$ are both methyl, and $R^{3b}$ is H; and the remaining variables are as described in embodiment no. 10.

In embodiment no. 13, A is selected from the group consisting of:

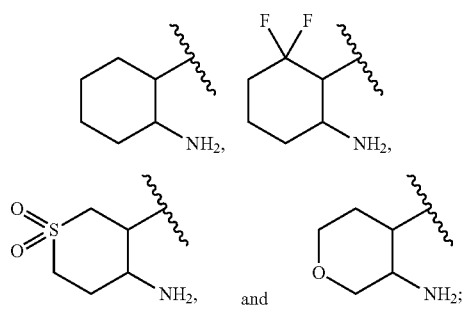

and the remaining variables are as described in any one of embodiments nos. 10-12.

In embodiment no. 14, A is

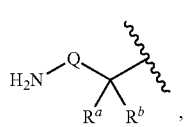

wherein
$R^a$ and $R^b$ are independently H or $C_1$-$C_4$ alkyl; and
Q is C(O)— or

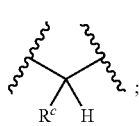

$R^c$ is H, $C_1$-$C_3$ alkyl, cyclopropyl, $CH_2OR^{13}$, or $CH_2SR^{14}$;
$R^{13}$ is H or $C_1$-$C_3$ alkyl; and
$R^{14}$ is $C_1$-$C_3$ alkyl;
and the remaining variables are as described in any one of embodiment nos. 10-12.

In embodiment no. 15, A is as described in embodiment no. 14, wherein $R^a$ and $R^b$ are both H;
Q is

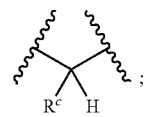

$R^c$ is H, $CH_2OR^{13}$, and $R^{13}$ is $C_1$-$C_3$ alkyl;
and the remaining variables are as described in embodiment no. 14.

In embodiment no. 16, the compound of the Formula (I) has the Formula (IB)

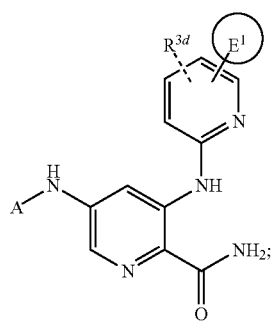

wherein
$E^1$ is
(i) a 5- to 9-membered heteroaryl containing one N atom and 1 to 2 additional heteroatoms heteroatoms selected from the group consisting of N and S; and
(ii) cyclopropyl;
wherein $E^1$ is unsubstituted or substituted by 1 moiety selected from the group consisting of $C_1$-$C_3$ alkyl and $C_1$-$C_3$ hydroxyalkyl;
$R^{3d}$ is present or absent, and if present, is selected from the group consisting of $C_1$-$C_3$ alkyl;
A is selected from the group consisting of
(a)

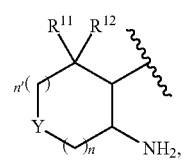

wherein
Y is —$CH_2$—, —$S(O)_2$—, or —O—;
$R^{11}$ and $R^{12}$ are independently H or F; and
n is 1 or 2;
n' is 0 or 1; or (b)

[structure: H₂N-Q-C(Rᵃ)(Rᵇ)-], wherein
$R^a$ and $R^b$ are independently H or $C_1$-$C_4$ alkyl; and
Q is —C(O)— or

[structure: -C(Rᶜ)(H)-];

$R^c$ is H, $C_1$-$C_3$ alkyl, cyclopropyl, —CH$_2$OR$^{13}$, or —CH$_2$SR$^{14}$;
$R^{13}$ is H or $C_1$-$C_3$ alkyl; and
$R^{14}$ is $C_1$-$C_3$ alkyl.

In embodiment no. 17, $E^1$ is selected from the group consisting of

[structures: pyridin-2-yl, pyrazol-4-yl (N-NH), pyrazol-3-yl (NH-N), thiazol-5-yl, triazolyl, tetrahydroindolizinyl, dihydropyrrolizinyl, triazol-1-yl, imidazol-4-yl]

, and wherein $E^1$ is unsubstituted or substituted by 1 moiety selected from the group consisting of $C_1$-$C_3$ alkyl and $C_1$-$C_3$ hydroxyalkyl; and the remaining variables are as described in embodiment no. 16.

In embodiment no. 18, $E^1$ is unsubstituted cyclopropyl, and the remaining variables as described in embodiment no. 16.

In embodiment no. 19, A is selected from the group consisting of:

[structures: 2-aminocyclohexyl, 2-amino-1,1-difluorocyclohexyl, 1,1-dioxothian-3-yl-amine, tetrahydropyran-3-yl-amine]

, and and the remaining variables are as described in any one of embodiments nos. 16-18.

In embodiment no. 20, A is

[structure: H₂N-Q-C(Rᵃ)(Rᵇ)-], wherein
$R^a$ and $R^b$ are independently H or $C_1$-$C_4$ alkyl; and
Q is C(O)— or

[structure: -C(Rᶜ)(H)-];

$R^c$ is H, $C_1$-$C_3$ alkyl, cyclopropyl, CH$_2$OR$^{13}$, or CH$_2$SR$^{14}$,
$R^{13}$ is H or $C_1$-$C_3$ alkyl; and
$R^{14}$ is $C_1$-$C_3$ alkyl;

and the remaining variables are as described in any one of embodiment nos. 16-18.

In embodiment no. 21, A is as described in embodiment no. 20, wherein $R^a$ and $R^b$ are both H;
Q is

[structure: -C(Rᶜ)(H)-];

$R^c$ is H, CH$_2$OR$^{13}$, and $R^{13}$ is $C_1$-$C_3$ alkyl;
and the remaining variables are as described in embodiment no. 20.

Representative compounds of the present invention are as follows, as well as pharmaceutically acceptable salts thereof:

rel-5-{[(1R,2S)-2-aminocyclohexyl]amino}-3-[(5,6-dimethylpyridin-2-yl)amino]pyridine-2-carboxamide;
rel-5-{[(1R,2S)-2-aminocyclohexyl]amino}-3-{[6-methyl-5-(1-methyl-1H-pyrazol-4-yl)pyridin-2-yl]amino}pyridine-2-carboxamide;
rel-5-{[(1R,2S)-2-aminocyclohexyl]amino}-3-[(6-methylpyridin-2-yl)amino]pyridine-2-carboxamide;
rel-5-{[(1R,2S)-2-aminocyclohexyl]amino}-3-[(6-cyclopropylpyridin-2-yl)amino]pyridine-2-carboxamide;
rel-5-{[(1R,2S)-2-aminocyclohexyl]amino}-3-{[6-(1-methylethyl)pyridin-2-yl]amino}pyridine-2-carboxamide;
rel-5-{[(1R,2S)-2-aminocyclohexyl]amino}-3-[(4-chloro-6-methylpyridin-2-yl)amino]pyridine-2-carboxamide;
rel-5-{[(1R,2S)-2-aminocyclohexyl]amino}-3-[(6-chloro-4-methylpyridin-2-yl)amino]pyridine-2-carboxamide;
rel-5-{[(1R,2S)-2-aminocyclohexyl]amino}-3-(2,2'-bipyridin-6-ylamino)pyridine-2-carboxamide;
5-[(2-aminoethyl)amino]-3-{[6-(2H-1,2,3-triazol-2-yl)pyridin-2-yl]amino}pyridine-2-carboxamide;
rel-5-{[(1R,2S)-2-aminocyclohexyl]amino}-3-{[6-methyl-5-(2H-1,2,3-triazol-2-yl)pyridin-2-yl]amino}pyridine-2-carboxamide;
rel-5-{[(1R,2S)-2-aminocyclohexyl]amino}-3-[(4,6-dimethylpyridin-2-yl)amino]pyridine-2-carboxamide;
5-{[2-aminopropyl]amino}-3-[(4,6-dimethylpyridin-2-yl)amino]pyridine-2-carboxamide;

rel-5-{[(3S,4S)-4-amino-1,1-dioxidotetrahydro-2H-thiopyran-3-yl]amino}-3-[(4,6-dimethylpyridin-2-yl)amino]pyridine-2-carboxamide;

rel-5-{[(1R,2S)-2-aminocyclohexyl]amino}-3-[(4,6-dichloropyridin-2-yl)amino]pyridine-2-carboxamide;

rel-5-{[(1R,2S)-2-aminocyclohexyl]amino}-3-[(6-ethylpyridin-2-yl)amino]pyridine-2-carboxamide;

rel-5-{[(1R,2S)-2-aminocyclohexyl]amino}-3-{[6-(2H-1,2,3-triazol-2-yl)pyridin-2-yl]amino}pyridine-2-carboxamide;

rel-5-{[(1R,2S)-2-aminocyclohexyl]amino}-3-{[4-methyl-6-(2H-1,2,3-triazol-2-yl)pyridin-2-yl]amino}pyridine-2-carboxamide;

rel-5-{[(1S,6S)-6-amino-2,2-difluorocyclohexyl]amino}-3-{[6-(2H-1,2,3-triazol-2-yl)pyridin-2-yl]amino}pyridine-2-carboxamide;

5-{[2-aminopropyl]amino}-3-{[6-(trifluoromethyl)pyridin-2-yl]amino}pyridine-2-carboxamide;

rel-5-{[(1S,6S)-6-amino-2,2-difluorocyclohexyl]amino}-3-{[6-(trifluoromethyl)pyridin-2-yl]amino}pyridine-2-carboxamide;

rel-5-{[(1R,2S)-2-aminocyclohexyl]amino}-3-{[4-methyl-6-(1-methyl-1H-pyrazol-4-yl)pyridin-2-yl]amino}pyridine-2-carboxamide;

rel-5-{[(1R,2S)-2-aminocyclohexyl]amino}-3-[(5-methoxy-6-methylpyridin-2-yl)amino]pyridine-2-carboxamide;

rel-5-{[(1R,2S)-2-aminocyclohexyl]amino}-3-{[4-methyl-6-(1-methyl-1H-pyrazol-5-yl)pyridin-2-yl]amino}pyridine-2-carboxamide;

rel-5-{[(1R,2S)-2-aminocyclohexyl]amino}-3-{[4-methyl-6-(4,5,6,7-tetrahydropyrazolo[1,5-a]pyridin-3-yl)pyridin-2-yl]amino}pyridine-2-carboxamide;

rel-5-{[(1R,2S)-2-aminocyclohexyl]amino}-3-({6-[2-(1-hydroxy-1-methylethyl)-1,3-thiazol-5-yl]-4-methylpyridin-2-yl}amino)pyridine-2-carboxamide;

rel-5-{[(1R,2S)-2-aminocyclohexyl]amino}-3-{[6-(5,6-dihydro-4H-pyrrolo[1,2-b]pyrazol-3-yl)-4-methylpyridin-2-yl]amino}pyridine-2-carboxamide;

5-{[1-(aminomethyl)propyl]amino}-3-{[6-(2H-1,2,3-triazol-2-yl)pyridin-2-yl]amino}pyridine-2-carboxamide;

5-{[2-aminopropyl]amino}-3-[(6-ethylpyridin-2-yl)amino]pyridine-2-carboxamide;

rel-5-{[(1R,2S)-2-aminocyclohexyl]amino}-3-{[6-methyl-4-(1-methylethoxy)pyridin-2-yl]amino}pyridine-2-carboxamide;

rel-5-{[(1R,2S)-2-aminocyclohexyl]amino}-3-[(4-methoxy-6-methylpyridin-2-yl)amino]pyridine-2-carboxamide;

rel-5-{[(1R,2S)-2-aminocyclohexyl]amino}-3-{[6-methyl-5-(propan-2-yloxy)pyridin-2-yl]amino}pyridine-2-carboxamide;

rel-5-{[(1R,2S)-2-aminocyclohexyl]amino}-3-{[6-(trifluoromethyl)pyridin-2-yl]amino}pyridine-2-carboxamide;

5-{[2-amino-3-methoxypropyl]amino}-3-[(4,6-dimethylpyridin-2-yl)amino]pyridine-2-carboxamide;

5-[(2-amino-3-ethoxypropyl)amino]-3-[(4,6-dimethylpyridin-2-yl)-amino]pyridine-2-carboxamide;

5-{[2-amino-3-methoxypropyl]amino}-3-{[6-(trifluoromethyl)pyridin-2-yl]amino}pyridine-2-carboxamide;

rel-5-{[(1R,2S)-2-aminocyclohexyl]amino}-3-{[6-methyl-4-(1H-1,2,3-triazol-1-yl)pyridin-2-yl]amino}pyridine-2-carboxamide;

rel-5-{[(1R,2S)-2-aminocyclohexyl]amino}-3-[(6-fluoropyridin-2-yl)amino]pyridine-2-carboxamide;

rel-5-{[(1R,2S)-2-aminocyclohexyl]amino}-3-{[6-methyl-4-(2H-1,2,3-triazol-2-yl)pyridin-2-yl]amino}pyridine-2-carboxamide;

rel-5-{[(1R,2S)-2-aminocyclohexyl]amino}-3-[(6-methoxypyridin-2-yl)amino]pyridine-2-carboxamide;

N²-{6-carbamoyl-5-[(4,6-dimethylpyridin-2-yl)amino]pyridin-3-yl}-leucinamide;

5-{[2-aminopropyl]amino}-3-[(5-bromo-6-methylpyridin-2-yl)amino]pyridine-2-carboxamide;

5-{[2-amino-3-(methyl sulfanyl)propyl]amino}-3-[(4,6-dimethylpyridin-2-yl)amino]pyridine-2-carboxamide;

5-{[2-amino-3-methoxypropyl]amino}-3-{[6-(2H-1,2,3-triazol-2-yl)pyridin-2-yl]amino}pyridine-2-carboxamide;

5-{[1-(aminomethyl)propyl]amino}-3-[(6-ethylpyridin-2-yl)amino]pyridine-2-carboxamide;

5-{[2-aminopropyl]amino}-3-{[6-methyl-5-(1-methyl-1H-imidazol-4-yl)pyridin-2-yl]amino}pyridine-2-carboxamide;

rel-5-{[(1R,2S)-2-aminocyclohexyl]amino}-3-{[6-methyl-5-(1H-1,2,3-triazol-1-yl)pyridin-2-yl]amino}pyridine-2-carboxamide;

N²-{6-carbamoyl-5-[(4,6-dimethylpyridin-2-yl)amino]pyridin-3-yl}leucinamide;

5-{[2-amino-3-methoxypropyl]amino}-3-[(6-ethylpyridin-2-yl)amino]pyridine-2-carboxamide;

rel-5-{[(1R,2S)-2-aminocyclohexyl]amino}-3-[(5-fluoro-6-methylpyridin-2-yl)amino]pyridine-2-carboxamide;

rel-5-{[(1S,6S)-6-amino-2,2-difluorocyclohexyl]amino}-3-{(4,6-dimethylpyridin-2-yl)amino}pyridine-2-carboxamide;

rel-5-{[(3S,4S)-4-amino-1,1-dioxidotetrahydro-2H-thiopyran-3-yl]amino}-3-{[6-(2H-1,2,3-triazol-2-yl)pyridin-2-yl]amino}pyridine-2-carboxamide;

rel-5-{[(1S,6S)-6-amino-2,2-difluorocyclohexyl]amino}-3-[(6-ethylpyridin-2-yl)amino]pyridine-2-carboxamide;

5-[(2-amino-1-methylethyl)amino]-3-[(4,6-dimethylpyridin-2-yl)amino]pyridine-2-carboxamide;

5-[(2-amino-2-cyclopropylethyl)amino]-3-[(4,6-dimethylpyridin-2-yl)amino]pyridine-2-carboxamide;

5-[(2-aminoethyl)amino]-3-[(4,6-dimethylpyridin-2-yl)amino]pyridine-2-carboxamide;

N²-{6-carbamoyl-5-[(4,6-dimethylpyridin-2-yl)amino]pyridin-3-yl}-leucinamide;

rel-5-{[(1R,2S)-2-aminocyclohexyl]amino}-3-{[4-(1-hydroxy-1-methylethyl)-6-methylpyridin-2-yl]amino}pyridine-2-carboxamide;

5-[(2-amino-1,1-dimethylethyl)amino]-3-[(4,6-dimethylpyridin-2-yl)amino]pyridine-2-carboxamide;

5-[(1-carbamoyl-2-methylpropyl)amino]-3-[(4,6-dimethylpyridin-2-yl)amino]pyridine-2-carboxamide;

5-[(2-amino-1-methyl-2-oxoethyl)amino]-3-[(4,6-dimethylpyridin-2-yl)amino]pyridine-2-carboxamide;

5-[(2-aminoethyl)amino]-3-[(6-methylpyridin-2-yl)amino]pyridine-2-carboxamide;

5-{[2-amino-3-methoxypropyl]amino}-3-[(4,6-dimethylpyridin-2-yl)amino]pyridine-2-carboxamide;

5-[(2-amino-3,3-difluoropropyl)amino]-3-[(4,6-dimethylpyridin-2-yl)amino]pyridine-2-carboxamide;

5-[(2-amino-3-hydroxypropyl)amino]-3-[(4,6-dimethylpyridin-2-yl)amino]pyridine-2-carboxamide;

rel-5-{[(3R,4R)-3-aminotetrahydro-2H-pyran-4-yl]amino}-3-[(4,6-dimethylpyridin-2-yl)amino]pyridine-2-carboxamide;

rel-5-{[(3R,4R)-3-aminotetrahydro-2H-pyran-4-yl]amino}-3-[(4-methoxy-6-methylpyridin-2-yl)amino]pyridine-2-carboxamide; and rel-5-{[(3S,4S)-4-amino-1,1-dioxidotetrahydro-2H-thiopyran-3-yl]amino}-3-[(4-methoxy-6-methylpyridin-2-yl)amino]pyridine-2-carboxamide.

Further, representative compounds of the present invention are as follows, as well as pharmaceutically acceptable salts thereof:

5-{[(1R,2S)-2-aminocyclohexyl]amino}-3-[(5,6-dimethylpyridin-2-yl)amino]pyridine-2-carboxamide;
5-{[(1R,2S)-2-aminocyclohexyl]amino}-3-{[6-methyl-5-(1-methyl-1H-pyrazol-4-yl)pyridin-2-yl]amino}pyridine-2-carboxamide;
5-{[(1R,2S)-2-aminocyclohexyl]amino}-3-[(6-methylpyridin-2-yl)amino]pyridine-2-carboxamide;
5-{[(1R,2S)-2-aminocyclohexyl]amino}-3-[(6-cyclopropylpyridin-2-yl)amino]pyridine-2-carboxamide;
5-{[(1R,2S)-2-aminocyclohexyl]amino}-3-{[6-(1-methylethyl)pyridin-2-yl]amino}pyridine-2-carboxamide;
5-{[(1R,2S)-2-aminocyclohexyl]amino}-3-[(4-chloro-6-methylpyridin-2-yl)amino]pyridine-2-carboxamide;
5-{[(1R,2S)-2-aminocyclohexyl]amino}-3-[(6-chloro-4-methylpyridin-2-yl)amino]pyridine-2-carboxamide;
5-{[(1R,2S)-2-aminocyclohexyl]amino}-3-(2,2'-bipyridin-6-ylamino)pyridine-2-carboxamide;
5-[(2-aminoethyl)amino]-3-{[6-(2H-1,2,3-triazol-2-yl)pyridin-2-yl]amino}pyridine-2-carboxamide;
5-{[(1R,2S)-2-aminocyclohexyl]amino}-3-{[6-methyl-5-(2H-1,2,3-triazol-2-yl)pyridin-2-yl]amino}pyridine-2-carboxamide;
5-{[(1R,2S)-2-aminocyclohexyl]amino}-3-[(4,6-dimethylpyridin-2-yl)amino]pyridine-2-carboxamide;
5-{[(2S)-2-aminopropyl]amino}-3-[(4,6-dimethylpyridin-2-yl)amino]pyridine-2-carboxamide;
5-{[(3S,4S)-4-amino-1,1-dioxidotetrahydro-2H-thiopyran-3-yl]amino}-3-[(4,6-dimethylpyridin-2-yl)amino]pyridine-2-carboxamide;
5-{[(1R,2S)-2-aminocyclohexyl]amino}-3-[(4,6-dichloropyridin-2-yl)amino]pyridine-2-carboxamide;
5-{[(1R,2S)-2-aminocyclohexyl]amino}-3-[(6-ethylpyridin-2-yl)amino]pyridine-2-carboxamide;
5-{[(1R,2S)-2-aminocyclohexyl]amino}-3-{[6-(2H-1,2,3-triazol-2-yl)pyridin-2-yl]amino}pyridine-2-carboxamide;
5-{[(1R,2S)-2-aminocyclohexyl]amino}-3-{[4-methyl-6-(2H-1,2,3-triazol-2-yl)pyridin-2-yl]amino}pyridine-2-carboxamide;
5-{[(1S,6S)-6-amino-2,2-difluorocyclohexyl]amino}-3-{[6-(2H-1,2,3-triazol-2-yl)pyridin-2-yl]amino}pyridine-2-carboxamide;
5-{[(2S)-2-aminopropyl]amino}-3-{[6-(trifluoromethyl)pyridin-2-yl]amino}pyridine-2-carboxamide;
5-{[(1S,6S)-6-amino-2,2-difluorocyclohexyl]amino}-3-{[6-(trifluoromethyl)pyridin-2-yl]amino}pyridine-2-carboxamide;
5-{[(1R,2S)-2-aminocyclohexyl]amino}-3-{[4-methyl-6-(1-methyl-1H-pyrazol-4-yl)pyridin-2-yl]amino}pyridine-2-carboxamide;
5-{[(1R,2S)-2-aminocyclohexyl]amino}-3-[(5-methoxy-6-methylpyridin-2-yl)amino]pyridine-2-carboxamide;
5-{[(1R,2S)-2-aminocyclohexyl]amino}-3-{[4-methyl-6-(1-methyl-1H-pyrazol-5-yl)pyridin-2-yl]amino}pyridine-2-carboxamide;
5-{[(1R,2S)-2-aminocyclohexyl]amino}-3-{[4-methyl-6-(4,5,6,7-tetrahydropyrazolo[1,5-a]pyridin-3-yl)pyridin-2-yl]amino}pyridine-2-carboxamide;
5-{[(1R,2S)-2-aminocyclohexyl]amino}-3-({6-[2-(1-hydroxy-1-methyl ethyl)-1,3-thiazol-5-yl]-4-methylpyridin-2-yl}amino)pyridine-2-carboxamide;
5-[(1R,2S)-2-aminocyclohexyl]amino-3-{[6-(5,6-dihydro-4H-pyrrolo[1,2-b]pyrazol-3-yl)-4-methylpyridin-2-yl]amino}pyridine-2-carboxamide;
5-{[1-(aminomethyl)propyl]amino}-3-{[6-(2H-1,2,3-triazol-2-yl)pyridin-2-yl]amino}pyridine-2-carboxamide;
5-{[(2S)-2-aminopropyl]amino}-3-[(6-ethylpyridin-2-yl)amino]pyridine-2-carboxamide;
5-{[(1R,2S)-2-aminocyclohexyl]amino}-3-{[6-methyl-4-(1-methylethoxy)pyridin-2-yl]amino}pyridine-2-carboxamide;
5-{[(1R,2S)-2-aminocyclohexyl]amino}-3-[(4-methoxy-6-methylpyridin-2-yl)amino]pyridine-2-carboxamide;
5-{[(1R,2S)-2-aminocyclohexyl]amino}-3-{[6-methyl-5-(propan-2-yloxy)pyridin-2-yl]amino}pyridine-2-carboxamide;
5-{[(1R,2S)-2-aminocyclohexyl]amino}-3-{[6-(trifluoromethyl)pyridin-2-yl]amino}pyridine-2-carboxamide;
5-{[(2R)-2-amino-3-methoxypropyl]amino}-3-[(4,6-dimethylpyridin-2-yl)amino]pyridine-2-carboxamide;
5-[(2-amino-3-ethoxypropyl)amino]-3-[(4,6-dimethylpyridin-2-yl)-amino]pyridine-2-carboxamide;
5-{[(2R)-2-amino-3-methoxypropyl]amino}-3-{[6-(trifluoromethyl)pyridin-2-yl]amino}pyridine-2-carboxamide;
5-{[(1R,2S)-2-aminocyclohexyl]amino}-3-{[6-methyl-4-(1H-1,2,3-triazol-1-yl)pyridin-2-yl]amino}pyridine-2-carboxamide;
5-{[(1R,2S)-2-aminocyclohexyl]amino}-3-[(6-fluoropyridin-2-yl)amino]pyridine-2-carboxamide;
5-{[(1R,2S)-2-aminocyclohexyl]amino}-3-{[6-methyl-4-(2H-1,2,3-triazol-2-yl)pyridin-2-yl]amino}pyridine-2-carboxamide;
5-{[(1R,2S)-2-aminocyclohexyl]amino}-3-[(6-methoxypyridin-2-yl)amino]pyridine-2-carboxamide;
$N^2$-{6-carbamoyl-5-[(4,6-dimethylpyridin-2-yl)amino]pyridin-3-yl}-leucinamide;
5-{[(2S)-2-aminopropyl]amino}-3-[(5-bromo-6-methylpyridin-2-yl)amino]pyridine-2-carboxamide;
5-{[2-amino-3-(methylsulfanyl)propyl]amino}-3-[(4,6-dimethylpyridin-2-yl)amino]pyridine-2-carboxamide;
5-{[(2R)-2-amino-3-methoxypropyl]amino}-3-{[6-(2H-1,2,3-triazol-2-yl)pyridin-2-yl]amino}pyridine-2-carboxamide;
5-{[1-(aminomethyl)propyl]amino}-3-[(6-ethylpyridin-2-yl)amino]pyridine-2-carboxamide;
5-{[(2S)-2-aminopropyl]amino}-3-{[6-methyl-5-(1-methyl-1H-imidazol-4-yl)pyridin-2-yl]amino}pyridine-2-carboxamide;
5-{[(1R,2S)-2-aminocyclohexyl]amino}-3-{[6-methyl-5-(1H-1,2,3-triazol-1-yl)pyridin-2-yl]amino}pyridine-2-carboxamide;
$N^2$-{6-carbamoyl-5-[(4,6-dimethylpyridin-2-yl)amino]pyridin-3-yl}leucinamide;
5-{[(2R)-2-amino-3-methoxypropyl]amino}-3-[(6-ethylpyridin-2-yl)amino]pyridine-2-carboxamide;
5-{[(1R,2S)-2-aminocyclohexyl]amino}-3-[(5-fluoro-6-methylpyridin-2-yl)amino]pyridine-2-carboxamide;
5-{[(1S,6S)-6-amino-2,2-difluorocyclohexyl]amino}-3-[(4,6-dimethylpyridin-2-yl)amino]pyridine-2-carboxamide;
5-{[(3S,4S)-4-amino-1,1-dioxidotetrahydro-2H-thiopyran-3-yl]amino}-3-{[6-(2H-1,2,3-triazol-2-yl)pyridin-2-yl]amino}pyridine-2-carboxamide;
5-{[(3R,4R)-4-amino-1,1-dioxidotetrahydro-2H-thiopyran-3-yl]amino}-3-{[6-(2H-1,2,3-triazol-2-yl)pyridin-2-yl]amino}pyridine-2-carboxamide;
5-{[(1S,6S)-6-amino-2,2-difluorocyclohexyl]amino}-3-[(6-ethylpyridin-2-yl)amino]pyridine-2-carboxamide;
5-[(2-amino-1-methylethyl)amino]-3-[(4,6-dimethylpyridin-2-yl)amino]pyridine-2-carboxamide;
5-[(2-amino-2-cyclopropylethyl)amino]-3-[(4,6-dimethylpyridin-2-yl)amino]pyridine-2-carboxamide;

5-[(2-aminoethyl)amino]-3-[(4,6-dimethylpyridin-2-yl) amino]pyridine-2-carboxamide;
5-{[(1R,6R)-6-amino-2,2-difluorocyclohexyl]amino}-3-[(4, 6-dimethylpyridin-2-yl)amino]pyridine-2-carboxamide;
$N^2$-{6-carbamoyl-5-[(4,6-dimethylpyridin-2-yl)amino]pyridin-3-yl}-leucinamide;
5-{[(1R,2S)-2-aminocyclohexyl]amino}-3-{[4-(1-hydroxy-1-methylethyl)-6-methylpyridin-2-yl]amino}pyridine-2-carboxamide;
5-[(2-amino-1,1-dimethylethyl)amino]-3-[(4,6-dimethylpyridin-2-yl)amino]pyridine-2-carboxamide;
5-[(1-carbamoyl-2-methylpropyl)amino]-3-[(4,6-dimethylpyridin-2-yl)amino]pyridine-2-carboxamide;
5-[(2-amino-1-methyl-2-oxoethyl)amino]-3-[(4,6-dimethylpyridin-2-yl)amino]pyridine-2-carboxamide;
5-[(2-aminoethyl)amino]-3-[(6-methylpyridin-2-yl)amino]pyridine-2-carboxamide;
5-{[(2S)-2-amino-3-methoxypropyl]amino}-3-[(4,6-dimethylpyridin-2-yl)amino]pyridine-2-carboxamide;
5-{[(3R,4R)-4-amino-1,1-dioxidotetrahydro-2H-thiopyran-3-yl]amino}-3-[(4,6-dimethylpyridin-2-yl)amino]pyridine-2-carboxamide;
5-[(2-amino-3,3-difluoropropyl)amino]-3-[(4,6-dimethylpyridin-2-yl)amino]pyridine-2-carboxamide;
5-[(2-amino-3-hydroxypropyl)amino]-3-[(4,6-dimethylpyridin-2-yl)amino]pyridine-2-carboxamide;
5-{[(3R,4R)-3-aminotetrahydro-2H-pyran-4-yl]amino}-3-[(4,6-dimethylpyridin-2-yl)amino]pyridine-2-carboxamide;
5-{[(3R,4R)-3-aminotetrahydro-2H-pyran-4-yl]amino}-3-[(4-methoxy-6-methylpyridin-2-yl)amino]pyridine-2-carboxamide;
5-{[(3S,4S)-4-amino-1,1-dioxidotetrahydro-2H-thiopyran-3-yl]amino}-3-[(4-methoxy-6-methylpyridin-2-yl) amino]pyridine-2-carboxamide; and
5-{[(3R,4R)-4-amino-1,1-dioxidotetrahydro-2H-thiopyran-3-yl]amino}-3-[(4-methoxy-6-methylpyridin-2-yl) amino]pyridine-2-carboxamide.

The invention also provides a compound of Formula (I) or a pharmaceutically acceptable salt thereof in purified form.

Definitions

The terms used herein have their ordinary meaning and the meaning of such terms is independent at each occurrence thereof. That notwithstanding and except where stated otherwise, the following definitions apply throughout the specification and claims. Chemical names, common names, and chemical structures may be used interchangeably to describe the same structure. If a chemical compound is referred to using both a chemical structure and a chemical name, and an ambiguity exists between the structure and the name, the structure predominates. These definitions apply regardless of whether a term is used by itself or in combination with other terms, unless otherwise indicated. Hence, the definition of "alkyl" applies to "alkyl" as well as the "alkyl" portions of "hydroxyalkyl," "fluoroalkyl," "—O-alkyl," etc.

As used herein, and throughout this disclosure, the following terms, unless otherwise indicated, shall be understood to have the following meanings:

A "patient" is a human or non-human mammal. In one embodiment, a patient is a human. In another embodiment, a patient is a chimpanzee.

The term "therapeutically effective amount" as used herein, refers to an amount of the compound of Formula (I) and/or an additional therapeutic agent, or a composition thereof that is effective in producing the desired therapeutic, ameliorative, inhibitory or preventative effect when administered to a patient suffering from a disease or disorder mediated by Syk. In the combination therapies of the present invention, a therapeutically effective amount can refer to each individual agent or to the combination as a whole, wherein the amounts of all agents administered are together effective, but wherein the component agent of the combination may not be present individually in an effective amount.

The term "preventing," as used herein with respect to a disease or disorder mediated by Syk, refers to reducing the likelihood of the occurrence of the disease or condition.

The term "alkyl," as used herein, refers to an aliphatic hydrocarbon group having one of its hydrogen atoms replaced with a bond having the specified number of carbon atoms. In different embodiments, an alkyl group contains from 1 to 6 carbon atoms ($C_1$-$C_6$ alkyl) or from 1 to 3 carbon atoms ($C_1$-$C_3$ alkyl). Non-limiting examples of alkyl groups include methyl, ethyl, n-propyl, isopropyl, n-butyl, sec-butyl, isobutyl, tert-butyl, n-pentyl, neopentyl, isopentyl, n-hexyl, isohexyl and neohexyl. In one embodiment, an alkyl group is linear. In another embodiment, an alkyl group is branched.

The term "alkoxy" as used herein, refers to an —O-alkyl group, wherein an alkyl group is as defined above. Non-limiting examples of alkoxy groups include methoxy, ethoxy, n-propoxy, isopropoxy, n-butoxy and t-butoxy. An alkoxy group is bonded via its oxygen atom.

The term "aryl," as used herein, refers to an aromatic monocyclic or multicyclic ring system comprising from about 6 to about 14 carbon atoms. In one embodiment, an aryl group contains from about 6 to 10 carbon atoms ($C_6$-$C_{10}$ aryl). In another embodiment an aryl group is phenyl. Non-limiting examples of aryl groups include phenyl and naphthyl.

The term "cycloalkyl," as used herein, refers to a saturated ring containing the specified number of ring carbon atoms, and no heteroatom. In a like manner the term "$C_3$-$C_6$ cycloalkyl" refers to a saturated ring having from 3 to 6 ring carbon atoms. Non-limiting examples of monocyclic cycloalkyls include cyclopropyl, cyclobutyl, cyclopentyl, and cyclohexyl.

The term "halo," as used herein, means —F, —Cl, —Br or —I. In one embodiment, a halo group is —F or —Cl. In another embodiment, a halo group is —F.

The term "fluoroalkyl," as used herein, refers to an alkyl group as defined above, wherein one or more of the alkyl group's hydrogen atoms has been replaced with a fluorine atom. In one embodiment, a fluoroalkyl group has from 1 to 6 carbon atoms. In another embodiment, a fluoroalkyl group has from 1 to 3 carbon atoms. In another embodiment, a fluoroalkyl group is substituted with from 1 to 3 fluorine atoms. Non-limiting examples of fluoroalkyl groups include —$CH_2F$, —$CHF_2$, and —$CF_3$. The term "$C_1$-$C_3$ fluoroalkyl" refers to a fluoroalkyl group having from 1 to 3 carbon atoms.

The term "heteroaryl," as used herein, refers to an aromatic monocyclic or multicyclic ring system comprising about 5 to about 14 ring atoms, wherein from 1 to 3 of the ring atoms is independently N, O, or S and the remaining ring atoms are carbon atoms. In one embodiment, a heteroaryl group has 5 to 10 ring atoms. In another embodiment, a heteroaryl group is monocyclic ring system and has 5 or 6 ring atoms. In another embodiment, a heteroaryl group is a bicyclic ring system. A heteroaryl group is joined via a ring carbon atom. The term "heteroaryl" also includes a heteroaryl as defined above fused to a heterocyclyl as defined below. The term "heteroaryl" also encompasses a heteroaryl group, as defined above, which is fused to a benzene, a cyclohexadiene or a cyclohexene ring. Non-limiting examples of heteroaryls include pyridyl, pyrazinyl, furanyl, thienyl, pyrimidinyl, pyridone (including N-substituted pyridones), isoxazolyl, isothiazolyl, oxazolyl, oxadiazolyl, thiadiazolyl, pyrazolyl, furyl, pyrrolyl, triazolyl, 1,2,4-thiadiazolyl, pyrazinyl, pyridazinyl, indolyl, quinoxalinyl, phthalazinyl, oxindolyl, imidazo[1,2-a]pyridinyl, imidazo[2,1-b]thiazolyl, and the like. In one embodiment, a heteroaryl group is a 5-membered heteroaryl. In another embodiment, a heteroaryl group is a 6-membered heteroaryl.

The term "heterocyclyl," as used herein, refers to a non-aromatic saturated monocyclic or multicyclic ring system containing 3 to 11 ring atoms, wherein from 1 to 4 of the ring atoms are independently O, S, or N, and the remainder of the ring atoms are carbon atoms. A heterocyclyl group can be joined via a ring carbon or ring nitrogen atom. In one embodiment, a heterocyclyl group is monocyclic and has from 3 to 7 ring atoms. In another embodiment, a heterocyclyl group is monocyclic and has from about 4 to 7 ring atoms. In another embodiment, a heterocyclyl group is bicyclic and has from 7 to 11 ring atoms. In still another embodiment, a heterocyclyl group is monocyclic and has 5 or 6 ring atoms. In one embodiment, a heterocyclyl group is monocyclic. In another embodiment, a heterocyclyl group is bicyclic. The nitrogen or sulfur atom of the heterocyclyl can be optionally oxidized to the corresponding N-oxide, S-oxide or S,S-dioxide. Non-limiting examples of monocyclic heterocyclyl rings include oxetanyl, piperidyl, pyrrolidinyl, piperazinyl, morpholinyl, thiomorpholinyl, thiazolidinyl, 1,4-dioxanyl, tetrahydrofuranyl, tetrahydrothiophenyl, delta-lactam, delta-lactone, and the like.

In one embodiment, a heterocyclyl group is a 5- to 6-membered monocyclic heterocyclyl. In another embodiment, a heterocyclyl group is a 5-membered monocyclic heterocyclyl. In another embodiment, a heterocyclyl group is a 6-membered monocyclic heterocyclyl. The term "5- to 6-membered heterocyclyl" refers to a monocyclic heterocyclyl group having from 5 to 6 ring atoms.

The term "substituted" means that one or more hydrogens on the atoms of the designated are replaced with a selection from the indicated group, provided that the atoms' normal valencies under the existing circumstances are not exceeded, and that the substitution results in a stable compound. Combinations of substituents and/or variables are permissible only if such combinations result in stable compounds. By "stable compound" or "stable structure" is meant a compound that is sufficiently robust to survive isolation to a useful degree of purity from a reaction mixture, and formulation into an efficacious therapeutic agent.

When any substituent or variable occurs more than one time in any constituent or the compound of Formula (I), its definition on each occurrence is independent of its definition at every other occurrence, unless otherwise indicated.

The term "in purified form," as used herein, refers to the physical state of a compound after the compound is isolated from a synthetic process (e.g., from a reaction mixture), a natural source, or a combination thereof. The term "in purified form," also refers to the physical state of a compound after the compound is obtained from a purification process or processes described herein or well-known to the skilled artisan (e.g., chromatography, recrystallization and the like), in sufficient purity to be characterizable by standard analytical techniques described herein or well-known to the skilled artisan.

It should also be noted that any carbon as well as heteroatom with unsatisfied valences in the text, schemes, examples and tables herein is assumed to have the sufficient number of hydrogen atom(s) to satisfy the valences.

One or more compounds of the invention may exist in unsolvated as well as solvated forms with pharmaceutically acceptable solvents such as water, ethanol, and the like, and it is intended that the invention embrace both solvated and unsolvated forms. "Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is $H_2O$.

The compounds of Formula (I) may contain one or more stereogenic centers and can thus occur as racemates, racemic mixtures, single enantiomers, diastereomeric mixtures and individual diastereomers. Additional asymmetric centers may be present depending upon the nature of the various substituents on the molecule. Each such asymmetric center will independently produce two optical isomers and it is intended that all of the possible optical isomers and diastereomers in mixtures and as pure or partially purified compounds are included within the ambit of this invention. Any formulas, structures or names of compounds described in this specification that do not specify a particular stereochemistry are meant to encompass any and all existing isomers as described above and mixtures thereof in any proportion. When stereochemistry is specified, the invention is meant to encompass that particular isomer in pure form or as part of a mixture with other isomers in any proportion.

In addition, the prefix "rel", when used in naming a compound that contains two asymmetric carbon atoms, indicates that the relative stereochemistry between the two asymmetric carbon atoms is as described, but that the absolute stereochemistry is unknown. Thus, by way of example, a compound containing two contiguous asymmetric carbon atoms whose chemical name is preceded by the prefix "rel" and which also indicates a "3R,4S" configuration, means that the relationship between the two asymmetric carbon atoms could have the absolute configuration of "(3R,4S)" or the absolute configuration of 3S,4R.

Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Also, some of the compounds of Formula (I) may be atropisomers (e.g., substituted biaryls) and are considered as part of this invention. Enantiomers can also be separated by use of chiral HPLC column.

It is also possible that the compounds of Formula (I) may exist in different tautomeric forms, and all such forms are embraced within the scope of the invention.

All stereoisomers (for example, geometric isomers, optical isomers and the like) of the present compounds (including those of the salts and solvates of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention. Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the *IUPAC* 1974 Recommendations.

The compounds of Formula (I) can form salts which are also within the scope of this invention. Reference to a compound of Formula (I) herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of Formula (I) contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Such acidic and basic salts used within the scope of the invention are pharmaceutically acceptable (i.e., non-toxic, physiologically acceptable) salts. Salts of the compounds of Formula (I) may be formed, for example, by reacting a compound of Formula (I) with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates) and the like. Additionally, acids which are generally considered suitable for the formation of pharmaceutically useful salts from basic pharmaceutical compounds are discussed, for example, by P. Stahl et al, Camille G. (eds.) *Handbook of Pharmaceutical Salts. Properties, Selection and Use.* (2002) Zurich: Wiley-VCH; S. Berge et al, *Journal of Pharmaceutical Sciences* (1977) 66(1) 1-19; P. Gould, *International J. of Pharmaceutics* (1986) 33 201-217; Anderson et al, *The Practice of Medicinal Chemistry* (1996), Academic Press, New York; and in *The Orange Book* (Food & Drug Administration, Washington, D.C. on their website). These disclosures are incorporated herein by reference.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamines, t-butyl amines, and salts with amino acids such as arginine, lysine and the like. Basic nitrogen-containing groups may be quaternized with agents such as lower alkyl halides (e.g., methyl, ethyl, and butyl chlorides, bromides and iodides), dialkyl sulfates (e.g., dimethyl, diethyl, and dibutyl sulfates), long chain halides (e.g., decyl, lauryl, and stearyl chlorides, bromides and iodides), aralkyl halides (e.g., benzyl and phenethyl bromides), and others.

The present invention further includes the compounds of Formula (I) in all their isolated forms. For example, the above-identified compounds are intended to encompass all forms of the compounds such as, any solvates, hydrates, stereoisomers, and tautomers thereof.

As used herein, the term "composition" is intended to encompass a product comprising the specified ingredients in the specified amounts, as well as any product which results, directly or indirectly, from combination of the specified ingredients in the specified amounts.

In the compounds of generic Formula (I), the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of generic Formula (I). For example, different isotopic forms of hydrogen (H) include protium ($^1$H) and deuterium ($^2$H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within generic Formula (I) can be prepared without undue experimentation by conventional techniques well known to those skilled in the art or by processes analogous to those described in the Schemes and Examples herein using appropriate isotopically-enriched reagents and/or intermediates.

Uses of the Compounds

Compounds of Formula (I) or its pharmaceutically acceptable salts and pharmaceutical compositions containing such compounds can be used to treat or prevent a variety of conditions or diseases mediated by Spleen tyrosine kinase (Syk). Such conditions and diseases include, but are not limited to: (1) arthritis, including rheumatoid arthritis, juvenile arthritis, psoriatic arthritis and osteoarthritis; (2) asthma and other obstructive airways diseases, including chronic asthma, late asthma, airway hyper-responsiveness, bronchitis, bronchial asthma, allergic asthma, intrinsic asthma, extrinsic asthma, dust asthma, adult respiratory distress syndrome, recurrent airway obstruction, and chronic obstruction pulmonary disease including emphysema; (3) autoimmune diseases or disorders, including those designated as single organ or single cell-type autoimmune disorders, for example Hashimoto's thyroiditis, autoimmune hemolytic anemia, autoimmune atrophic gastritis of pernicious anemia, autoimmune encephalomyelitis, autoimmune orchitis, Goodpasture's disease, autoimmune thrombocytopenia including idiopathic thrombopenic purpura, sympathetic ophthalmia, myasthenia gravis, Graves' disease, primary biliary cirrhosis, chronic aggressive hepatitis, ulcerative colitis and membranous glomerulopathy, those designated as involving systemic autoimmune disorder, for example systemic lupus erythematosis, immune thrombocytopenic purpura, rheumatoid arthritis, Sjogren's syndrome, Reiter's syndrome, polymyositis-dermatomyositis, systemic sclerosis, polyarteritis nodosa, multiple sclerosis and bullous pemphigoid, and additional autoimmune diseases, which can be B-cell (humoral) based or T-cell based, including Cogan's syndrome, ankylosing spondylitis, Wegener's granulomatosis, autoimmune alopecia, Type I or juvenile onset diabetes, and thyroiditis; (4) cancers or tumors, including alimentary/gastrointestinal tract cancer, colon cancer, liver cancer, skin cancer including mast cell tumor and squamous cell carcinoma, breast and mammary cancer, ovarian cancer, prostate cancer, lymphoma and leukemia (including but not limited to acute myelogenous leukemia, chronic myelogenous leukemia, mantle cell lymphoma, NHL B cell lymphomas (e.g., precursor B-ALL, marginal zone B cell lymphoma, chronic lymphocytic leukemia, diffuse large B cell lymphoma, Burkitt lymphoma, mediastinal large B-cell lymphoma), Hodgkin lymphoma, NK and T cell lymphomas; TEL-Syk and ITK-Syk fusion driven tumors) myelomas including multiple myeloma, myeloproliferative disorders kidney cancer, lung cancer, muscle cancer, bone cancer, bladder cancer, brain cancer, melanoma including oral and metastatic melanoma, Kaposi's sarcoma, proliferative diabetic retinopathy, and angiogenic-associated disorders including solid tumors, and pancreatic cancer; (5) diabetes, including Type I diabetes and complications from diabetes; (6) eye diseases, disorders or conditions including autoimmune diseases of the eye, keratoconjunctivitis, vernal conjunctivitis, uveitis including uveitis associated with Behcet's disease and lens-induced uveitis, keratitis, herpetic keratitis, conical keratitis, corneal epithelial dystrophy, keratoleukoma, ocular premphigus, Mooren's ulcer, scleritis, Grave's ophthalmopathy, Vogt-Koyanagi-Harada syndrome, keratoconjunctivitis sicca (dry eye), phlyctenule, iridocyclitis, sarcoidosis, endocrine ophthalmopathy, sympathetic ophthalmitis, allergic conjunctivitis, and ocular neovascularization; (7) intestinal inflammations, allergies or conditions including Crohn's disease and/or ulcerative colitis, inflammatory bowel disease, coeliac diseases, proctitis, eosinophilic gastroenteritis, and mastocytosis; (8) neurodegenerative diseases including motor neuron disease, Alzheimer's disease, Parkinson's disease, amyotrophic lateral sclerosis, Huntington's disease, cerebral ischemia, or neurodegenerative disease caused by traumatic injury, strike, glutamate neurotoxicity or hypoxia; ischemic/reperfusion injury in stroke, myocardial ischemica, renal ischemia, heart attacks, cardiac hypertrophy, atherosclerosis and arteriosclerosis, organ hypoxia; (9) platelet aggregation and diseases associated with or caused by platelet activation, such as arteriosclerosis, thrombosis, intimal hyperplasia and restenosis following vascular injury; (10) conditions associated with cardiovascular diseases, including restenosis, acute coronary syndrome, myocardial infarction, unstable angina, refractory angina, occlusive coronary thrombus occurring post-thrombolytic therapy or post-coronary angioplasty, a thrombotically mediated cerebrovascular syndrome, embolic stroke, thrombotic stroke, transient ischemic attacks, venous thrombosis, deep venous thrombosis, pulmonary embolus, coagulopathy, disseminated intravascular coagulation, thrombotic thrombocytopenic purpura, thromboangiitis obliterans, thrombotic disease associated with heparin-induced thrombocytopenia, thrombotic complications associated with extracorporeal circulation, thrombotic complications associated with instrumentation such as cardiac or other intravascular catheterization, intra-aortic balloon pump, coronary stent or cardiac valve, conditions requiring the fitting of prosthetic devices, and the like; (11) skin diseases, conditions or disorders including atopic dermatitis, eczema, psoriasis, scleroderma, pruritus and other pruritic conditions; (12) allergic reactions including anaphylaxis, allergic rhinitis, allergic dermatitis, allergic urticaria, angioedema, allergic asthma, or allergic reaction to insect bites, food, drugs, or pollen; (13) transplant rejection, including pancreas islet transplant rejection, bone marrow transplant rejection, graft-versus-host disease, organ and cell transplant rejection such as bone marrow, cartilage, cornea, heart, intervertebral disc, islet, kidney, limb, liver, lung, muscle, myoblast, nerve, pancreas, skin, small intestine, or trachea, and xeno transplantation; (14) low grade scarring including scleroderma, increased fibrosis, keloids, post-surgical scars, pulmonary fibrosis, vascular spasms, migraine, reperfusion injury, and post-myocardial infarction.

The invention thus provides compounds of Formula (I) and pharmaceutically acceptable salts thereof for use in therapy, and particularly in the treatment of diseases and conditions mediated by inappropriate Syk activity. The inappropriate Syk activity referred to herein is any Syk activity that deviates from the normal Syk activity expected in a particular patient. Inappropriate Syk activity may take the form of, for instance, an abnormal increase in activity, or an aberration in the timing and or control of Syk activity. Such inappropriate activity may result then, for example, from overexpression or mutation of the protein kinase leading to inappropriate or uncontrolled activation.

In a further embodiment, the present invention is directed to methods of regulating, modulating, or inhibiting Syk for the prevention and/or treatment of disorders related to unregulated Syk activity.

In a further embodiment, the present invention provides a method of treatment of a patient suffering from a disorder mediated by Syk activity, which comprises administering to said patient an effective amount of a compound of Formula (I) or a pharmaceutically acceptable salt, solvate, or a physiologically functional derivative thereof. In a further embodiment, the present invention provides for the use of a compound of Formula (I), or a pharmaceutically acceptable salt or solvate thereof, or a physiologically functional derivative thereof, in the preparation of a medicament for the treatment of a disorder mediated by Syk activity.

In a further embodiment said disorder is rheumatoid arthritis. In yet another embodiment, said disorder is cancer. In a further embodiment said disorder mediated by Syk activity is asthma. In a further embodiment said disorder is ocular conjunctivitis.

Yet another aspect of the present invention provides a method for treating diseases caused by or associated with Fc receptor signaling cascades, including FceRI and/or FcgRI-mediated degranulation as a therapeutic approach towards the treatment or prevention of diseases characterized by, caused by and/or associated with the release or synthesis of chemical mediators of such Fc receptor signaling cascades or degranulation. In addition, Syk is known to play a critical role in immunotyrosine-based activation motif (ITAM) signaling, B cell receptor signaling, T cell receptor signaling and is an essential component of integrin beta (1), beta (2), and beta (3) signaling in neutrophils. Thus, compounds of the present invention can be used to regulate Fc receptor, ITAM, B cell receptor and integrin signaling cascades, as well as the cellular responses elicited through these signaling cascades. Non-limiting examples of cellular responses that may be regulated or inhibited include respiratory burst, cellular adhesion, cellular degranulation, cell spreading, cell migration, phagocytosis, calcium ion flux, platelet aggregation and cell maturation.

Compositions and Administration

While it is possible that, for use in therapy, a compound of Formula (I), as well as pharmaceutically acceptable salts thereof, may be administered as the raw chemical, it is possible to present the active ingredient as a pharmaceutical composition. Accordingly, the invention further provides a pharmaceutical composition, which comprises a compound of Formula (I) and pharmaceutically acceptable salts thereof, and a pharmaceutically acceptable carrier. The compounds of the Formula (I) and pharmaceutically acceptable salts thereof, are as described above. The carriers must be acceptable in the sense of being compatible with the other ingredients of the formulation and not deleterious to the recipient thereof. In accordance with another aspect of the invention there is also provided a process for the preparation of a pharmaceutical composition including admixing a compound of the Formula (I), or a pharmaceutically acceptable salt thereof, with one or more pharmaceutically acceptable carriers.

Pharmaceutical compositions of the present invention may be presented in unit dose forms containing a predetermined amount of active ingredient per unit dose. Such a unit may contain, for example, 5 μg to 1 g, preferably 1 mg to 700 mg, more preferably 5 mg to 100 mg of a compound of the Formula (I), depending on the condition being treated, the route of administration and the age, weight and condition of the patient. Such unit doses may therefore be administered more than once a day. Preferred unit dosage compositions are those containing a daily dose or sub-dose (for administration more than once a day), as herein above recited, or an appropriate fraction thereof, of an active ingredient. Furthermore, such pharmaceutical compositions may be prepared by any of the methods well known in the pharmacy art.

Pharmaceutical compositions of the present invention may be adapted for administration by any appropriate route, for example by the oral (including buccal or sublingual), rectal, topical, inhaled, nasal, ocular, or parenteral (including intravenous and intramuscular) route. Such compositions may be prepared by any method known in the art of pharmacy, for example by bringing into association the active ingredient with the carrier(s) or excipient(s). Dosage forms include tablets, troches, dispersions, suspensions, solutions, capsules, creams, ointments, aerosols, and the like.

In a further embodiment, the present invention provides a pharmaceutical composition adapted for administration by the oral route, for treating, for example, rheumatoid arthritis.

In a further embodiment, the present invention provides a pharmaceutical composition adapted for administration by the nasal route, for treating, for example, allergic rhinitis.

In a further embodiment, the present invention provides a pharmaceutical composition adapted for administration by the inhaled route, for treating, for example, asthma, COPD or ARDS.

In a further embodiment, the present invention provides a pharmaceutical composition adapted for administration by the inhaled route, for treating, for example, asthma or COPD.

In a further embodiment, the present invention provides a pharmaceutical composition adapted for administration by the ocular route, for treating, diseases of the eye, for example, conjunctivitis.

In a further embodiment, the present invention provides a pharmaceutical composition adapted for administration by the parenteral (including intravenous) route, for treating, for example, cancer.

Pharmaceutical compositions of the present invention which are adapted for oral administration may be presented as discrete units such as capsules or tablets; powders or granules; solutions or suspensions in aqueous or non-aqueous liquids; edible foams or whips; or oil-in-water liquid emulsions or water-in-oil liquid emulsions.

For instance, for oral administration in the form of a tablet or capsule, the active drug component can be combined with an oral, non-toxic pharmaceutically acceptable inert carrier such as ethanol, glycerol, water and the like. Powders are prepared by comminuting the compound to a suitable fine size and mixing with a similarly comminuted pharmaceutical carrier such as an edible carbohydrate, as, for example, starch or mannitol. Flavoring, preservative, dispersing and coloring agent can also be present.

Capsules are made by preparing a powder mixture, as described above, and filling formed gelatin sheaths. Glidants and lubricants such as colloidal silica, talc, magnesium stearate, calcium stearate or solid polyethylene glycol can be added to the powder mixture before the filling operation. A disintegrating or solubilizing agent such as agar-agar, calcium carbonate or sodium carbonate can also be added to improve the availability of the medicament when the capsule is ingested.

Moreover, when desired or necessary, suitable binders, lubricants, disintegrating agents and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch, methyl cellulose, agar, bentonite, xanthan gum and the like. Tablets are formulated, for example, by preparing a powder mixture, granulating or slugging, adding a lubricant and disintegrant and pressing into tablets. A powder mixture is prepared by mixing the compound, suitably comminuted, with a diluent or base as described above, and optionally, with a binder such as carboxymethylcellulose, an aliginate, gelatin, or polyvinyl pyrrolidone, a solution retardant such as paraffin, a resorption accelerator such as a quaternary salt and/or an absorption agent such as bentonite, kaolin or dicalcium phosphate. The powder mixture can be granulated by wetting with a binder such as syrup, starch paste, acadia mucilage or solutions of cellulosic or polymeric materials and forcing through a screen. As an alternative to granulating, the powder mixture can be run through the tablet machine and the result is imperfectly formed slugs broken into granules. The granules can be lubricated to prevent sticking to the tablet forming dies by means of the addition of stearic acid, a stearate salt, talc or mineral oil. The lubricated mixture is then compressed into tablets. The compounds of the present invention can also be combined with a free flowing inert carrier and compressed into tablets directly without going through the granulating or slugging steps. A clear or opaque protective coating consisting of a sealing coat of shellac, a coating of sugar or polymeric material and a polish coating of wax can be provided. Dyestuffs can be added to these coatings to distinguish different unit dosages.

Oral fluids such as solution, syrups and elixirs can be prepared in dosage unit form so that a given quantity contains a predetermined amount of the compound. Syrups can be prepared by dissolving the compound in a suitably flavored aqueous solution, while elixirs are prepared through the use of a non-toxic alcoholic vehicle. Suspensions can be formulated by dispersing the compound in a non-toxic vehicle. Solubilizers and emulsifiers such as ethoxylated isostearyl alcohols and polyoxy ethylene sorbitol ethers, preservatives, flavor additive such as peppermint oil or natural sweeteners or saccharin or other artificial sweeteners, and the like can also be added.

Where appropriate, dosage unit compositions for oral administration can be microencapsulated. The formulation can also be prepared to prolong or sustain the release, for example, by coating or embedding particulate material in polymers, wax or the like.

The compounds of Formula (I) and pharmaceutically acceptable salts thereof can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

The compounds of Formula (I) and pharmaceutically acceptable salts thereof may also be delivered by the use of monoclonal antibodies as individual carriers to which the compound molecules are coupled. The compounds may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxide-polylysine substituted with palmitoyl residues. Furthermore, the compounds may be coupled to a class of biodegradable polymers useful in achieving controlled release of a drug, for example, polylactic acid, polyepsilon caprolactone, polyhydroxy butyric acid, polyorthoesters, polyacetals, polydihydropyrans, polycyanoacrylates and cross-linked or amphipathic block copolymers of hydrogels.

Dosage forms for inhaled administration may conveniently be formulated as aerosols or dry powders.

For compositions suitable and/or adapted for inhaled administration, it is preferred that the compound or salt of Formula (I) is in a particle-size-reduced form, and more preferably the size-reduced form is obtained or obtainable by micronisation. The preferable particle size of the size-reduced (e.g., micronised) compound or salt or solvate is defined by a D50 value of about 0.5 to about 10 microns (for example as measured using laser diffraction).

Aerosol formulations, e.g., for inhaled administration, can comprise a solution or fine suspension of the active substance in a pharmaceutically acceptable aqueous or non-aqueous solvent. Aerosol formulations can be presented in single or multidose quantities in sterile form in a sealed container, which can take the form of a cartridge or refill for use with an atomising device or inhaler. Alternatively the sealed container may be a unitary dispensing device such as a single dose nasal inhaler or an aerosol dispenser fitted with a metering valve (metered dose inhaler) which is intended for disposal once the contents of the container have been exhausted.

Where the dosage form comprises an aerosol dispenser, it preferably contains a suitable propellant under pressure such as compressed air, carbon dioxide or an organic propellant such as a hydrofluorocarbon (HFC). Suitable HFC propellants include 1,1,1,2,3,3,3-heptafluoropropane and 1,1,1,2-tetrafluoroethane. The aerosol dosage forms can also take the form of a pump-atomiser. The pressurised aerosol may contain a solution or a suspension of the active compound. This may require the incorporation of additional excipients e.g., co-solvents and/or surfactants to improve the dispersion characteristics and homogeneity of suspension formulations. Solution formulations may also require the addition of co-solvents such as ethanol. Other excipient modifiers may also be incorporated to improve, for example, the stability and/or taste and/or fine particle mass characteristics (amount and/or profile) of the formulation.

For pharmaceutical compositions suitable and/or adapted for inhaled administration, it is preferred that the pharmaceutical composition is a dry powder inhalable composition. Such a composition can comprise a powder base such as lactose, glucose, trehalose, mannitol or starch, the compound of Formula (I) or salt or solvate thereof (preferably in particle-size-reduced form, e.g., in micronised form), and optionally a performance modifier such as L-leucine or another amino acid, and/or metals salts of stearic acid such as magnesium or calcium stearate. Preferably, the dry powder inhalable composition comprises a dry powder blend of lactose and the compound of Formula (I) or salt thereof. The lactose is preferably lactose hydrate e.g., lactose monohydrate and/or is preferably inhalation-grade and/or fine-grade lactose. Preferably, the particle size of the lactose is defined by 90% or more (by weight or by volume) of the lactose particles being less than 1000 microns (micrometers) (e.g., 10-1000 microns e.g., 30-1000 microns) in diameter, and/or 50% or more of the lactose particles being less than 500 microns (e.g., 10-500 microns) in diameter. More preferably, the particle size of the lactose is defined by 90% or more of the lactose particles being less than 300 microns (e.g., 10-300 microns, e.g., 50-300 microns) in diameter, and/or 50% or more of the lactose particles being less than 100 microns in diameter. Optionally, the particle size of the lactose is defined by 90% or more of the lactose particles being less than 100-200 microns in diameter, and/or 50% or more of the lactose particles being less than 40-70 microns in diameter. It is preferable that about 3 to about 30% (e.g., about 10%) (by weight or by volume) of the particles are less than 50 microns or less than 20 microns in diameter. For example, without limitation, a suitable inhalation-grade lactose is E9334 lactose (10% fines) (Borculo Domo Ingredients, Hanzeplein 25, 8017 J D Zwolle, Netherlands).

Optionally, in particular for dry powder inhalable compositions, a pharmaceutical composition for inhaled administration can be incorporated into a plurality of sealed dose containers (e.g., containing the dry powder composition) mounted longitudinally in a strip or ribbon inside a suitable inhalation device. The container is rupturable or peel-openable on demand and the dose of e.g., the dry powder composition can be administered by inhalation via the device such as the DISKUS® device (GlaxoSmithKline). Other dry powder inhalers are well known to those of ordinary skill in the art, and many such devices are commercially available, with representative devices including Aerolizer® (Novartis), Airmax™ (IVAX), ClickHaler® (Innovata Biomed), Diskhaler® (GlaxoSmithKline), Accuhaler (GlaxoSmithKline), Easyhaler® (Orion Pharma), Eclipse™ (Aventis), FlowCaps® (Hovione), Handihaler® (Boehringer Ingelheim), Pulvinal® (Chiesi), Rotahaler® (GlaxoSmithKline), SkyeHaler™ or Certihaler™ (SkyePharma), Twisthaler (Merck), Turbuhaler® (AstraZeneca), Ultrahaler® (Aventis), and the like.

Dosage forms for ocular administration may be formulated as solutions or suspensions with excipients suitable for ophthalmic use.

Dosage forms for nasal administration may conveniently be formulated as aerosols, solutions, drops, gels or dry powders.

Pharmaceutical compositions adapted for administration by inhalation include fine particle dusts or mists, which may be generated by means of various types of metered, dose pressurised aerosols, nebulizers or insufflators.

For pharmaceutical compositions suitable and/or adapted for intranasal administration, the compound of Formula (I) or a pharmaceutically acceptable salt or solvate thereof may be formulated as a fluid formulation for delivery from a fluid dispenser. Such fluid dispensers may have, for example, a dispensing nozzle or dispensing orifice through which a metered dose of the fluid formulation is dispensed upon the application of a user-applied force to a pump mechanism of the fluid dispenser. Such fluid dispensers are generally provided with a reservoir of multiple metered doses of the fluid formulation, the doses being dispensable upon sequential pump actuations. The dispensing nozzle or orifice may be configured for insertion into the nostrils of the user for spray dispensing of the fluid formulation into the nasal cavity. A fluid dispenser of the aforementioned type is described and illustrated in WO-A-2005/044354, the entire content of which is hereby incorporated herein by reference. The dispenser has a housing which houses a fluid discharge device having a compression pump mounted on a container for containing a fluid formulation. The housing has at least one finger-operable side lever which is movable inwardly with respect to the housing to cam the container upwardly in the housing to cause the pump to compress and pump a metered dose of the formulation out of a pump stem through a nasal nozzle of the housing. A particularly preferred fluid dispenser is of the general type illustrated in FIGS. 30-40 of WO-A-2005/044354.

The following are examples of representative pharmaceutical dosage forms for the compounds of this invention:

| Injectable Suspension (I.M.) | mg/mL |
|---|---|
| Compound of Formula (I) | 10 |
| Methylcellulose | 5.0 |
| Tween 80 | 0.5 |
| Benzyl alcohol | 9.0 |
| Benzalkonium chloride | 1.0 |

Water for injection to a total volume of 1 mL

| Tablet | mg/tablet |
|---|---|
| Compound of Formula (I) | 25 |
| Microcrystalline Cellulose | 415 |
| Providone | 14.0 |
| Pregelatinized Starch | 43.5 |
| Magnesium Stearate | 2.5 |
| | 500 |

| Capsule | mg/capsule |
|---|---|
| Compound of Formula (I) | 25 |
| Lactose Powder | 573.5 |
| Magnesium Stearate | 1.5 |
| | 600 |

| Aerosol | Per canister |
|---|---|
| Compound of Formula (I) | 24 mg |
| Lecithin, NF Liquid Concentrate | 1.2 mg |
| Trichlorofluoromethane, NF | 4.025 gm |
| Dichlorodifluoromethane, NF | 12.15 gm |

It will be appreciated that when the compound of the present invention is administered in combination with other therapeutic agents normally administered by the inhaled, intravenous, oral or intranasal route, that the resultant pharmaceutical composition may be administered by the same routes.

It should be understood that in addition to the ingredients particularly mentioned above, the compositions may include other agents conventional in the art having regard to the type of formulation in question, for example those suitable for oral administration may include flavouring agents.

A therapeutically effective amount of a compound of the present invention will depend upon a number of factors including, for example, the age and weight of the animal, the precise condition requiring treatment and its severity, the nature of the formulation, and the route of administration, and will ultimately be at the discretion of the attendant physician or veterinarian. However, an effective amount of a compound of Formula (I) for the treatment of diseases or conditions associated with inappropriate Syk activity, will generally be in the range of 5 μg to 100 mg/kg body weight of recipient (patient) per day and more usually in the range of μg to 10 mg/kg body weight per day. This amount may be given in a single dose per day or more usually in a number (such as two, three, four, five or six) of sub-doses per day such that the total daily dose is the same. An effective amount of a salt or solvate, thereof, may be determined as a proportion of the effective amount of the compound of Formula (I) per se.

The compositions of the invention can further comprise one or more additional therapeutic agents, as discussed in further detail below. Accordingly, in one embodiment, the present invention provides compositions comprising: (i) a compound of Formula (I) or a pharmaceutically acceptable salt thereof; (ii) one or more additional therapeutic agents, that are not compounds of Formula (I); and (iii) a pharmaceutically acceptable carrier, wherein the amounts in the composition are together effective to treat one of the disease or conditions discussed above.

Combination Therapy

The compounds of Formula (I) or their pharmaceutically acceptable salts may be used in combination, either in a single formulation or co-administered as separate formulations with at least one additional therapeutic agent to treat or prevent the diseases and conditions described herein. These additional therapeutic agents include, but are not limited to: (1) a DP receptor antagonist, such as S-5751 and laropiprant; (2) a corticosteroid, such as triamcinolone acetonide, budesonide, beclomethasone, fluticasone and mometasone; (3) a β2-adrenergic agonist, such as salmeterol, formoterol, arformoterol, terbutaline, metaproterenol, albuterol and the like; (4) a leukotriene modifier, including a leukotriene receptor antagonist, such as montelukast, zafirlukast, pranlukast, or a lipooxygenase inhibitor including 5-lipooxygenase inhibitors and FLAP (5-lipooxygenase activating protein) inhibitors, such as zileuton; (5) an antihistamine such as bromopheniramine, chlorpheniramine, dexchlorpheniramine, triprolidine, clemastine, diphenhydramine, diphenylpyraline, tripelennamine, hydroxyzine, methdilazine, promethazine, trimeprazine, azatadine, cyproheptadine, antazoline, pheniramine pyrilamine, astemizole, terfenadine, loratadine, cetirizine, fexofenadine, descarboethoxyloratadine, and the like; (6) a decongestant, including phenylephrine, phenylpropanolamine, pseudophedrine, oxymetazoline, ephinephrine, naphazoline, xylometazoline, propylhexedrine, or levo-desoxyephedrine; (7) an antiitussive, including codeine, hydrocodone, caramiphen, carbetapentane, or dextramethorphan; (8) another prostaglandin ligand, including prostaglandin F agonist such as latanoprost; misoprostol, enprostil, rioprostil, ornoprostol or rosaprostol; (9) a diuretic; (10) non-steroidal antiinflammatory agents (NSAIDs), such as propionic acid derivatives (alminoprofen, benoxaprofen, bucloxic acid, carprofen, fenbufen, fenoprofen, fluprofen, flurbiprofen, ibuprofen, indoprofen, ketoprofen, miroprofen, naproxen, oxaprozin, pirprofen, pranoprofen, suprofen, tiaprofenic acid, and tioxaprofen), acetic acid derivatives (indomethacin, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin, and zomepirac), fenamic acid derivatives (flufenamic acid, meclofenamic acid, mefenamic acid, niflumic acid and tolfenamic acid), biphenylcarboxylic acid derivatives (diflunisal and flufenisal), oxicams (isoxicam, piroxicam, sudoxicam and tenoxican), salicylates (acetyl salicylic acid, sulfasalazine) and the pyrazolones (apazone, bezpiperylon, feprazone, mofebutazone, oxyphenbutazone, phenylbutazone); (11) cyclooxygenase-2 (COX-2) inhibitors, such as celecoxib and rofecoxib; (12) inhibitors of phosphodiesterase type IV (PDE-IV) e.g., Ariflo, roflumilast; (13) antagonists of the chemokine receptors, especially CCR-1, CCR-2, and CCR-3; (14) cholesterol lowering agents such as HMG-CoA reductase inhibitors (lovastatin, simvastatin and pravastatin, fluvastatin, atorvastatin, and other statins), sequestrants (cholestyramine and colestipol), nicotinic acid, fenofibric acid derivatives (gemfibrozil, clofibrat, fenofibrate and benzafibrate), and probucol; (15) anti-diabetic agents such as insulin, sulfonylureas, biguanides (metformin), α-glucosidase inhibitors (acarbose) and glitazones (troglitazone, pioglitazone, englitazone, rosiglitazone and the like); (16) preparations of interferon beta (interferon beta-1a, interferon beta-1b); (17) anticholinergic agents, such as muscarinic antagonists (ipratropium bromide and tiotropium bromide), as well as selective muscarinic M3 antagonists; (18) steroids such as beclomethasone, methylprednisolone, betamethasone, prednisone, dexamethasone, and hydrocortisone; (19) triptans commonly used for the treatment of migraine such as sumitriptan and rizatriptan; (20) alendronate and other treatments for osteoporosis; (21) other compounds such as 5-aminosalicylic acid and prodrugs thereof, antimetabolites such as azathioprine and 6-mercaptopurine, cytotoxic cancer chemotherapeutic agents, bradykinin (BK2) antagonists such as FK-3657, TP receptor antagonists such as seratrodast, neurokinin antagonists (NK1/NK2), VLA-4 antagonists, such as those described in U.S. Pat. No. 5,510,332, WO97/03094, WO97/02289, WO96/40781, WO96/22966, WO96/20216, WO96/01644, WO96/06108, WO95/15973 and WO96/31206. In addition, the invention encompasses a method of treating prostaglandin D2 mediated diseases comprising: administration to a patient in need of such treatment a nontoxic therapeutically effective amount of a compound of Formula (I), optionally co-administered with one or more of such ingredients as listed immediately above.

When administering a combination therapy to a patient in need of such administration, the therapeutic agents in the combination, or a pharmaceutical composition or compositions comprising the therapeutic agents, may be administered in any order such as, for example, sequentially, concurrently, together, simultaneously and the like.

In one embodiment, the compound of Formula (I) is administered during a time when the additional therapeutic agent(s) exert their prophylactic or therapeutic effect, or vice versa.

In another embodiment, the compound of Formula (I) and the additional therapeutic agent(s) are administered in doses commonly employed when such agents are used as monotherapy for treating the disorder.

In another embodiment, the compound of Formula (I) and the additional therapeutic agent(s) are administered in doses lower than the doses commonly employed when such agents are used as monotherapy for treating the disorder.

In one embodiment, the compound of Formula (I) and the additional therapeutic agent(s) are present in the same composition, which is suitable for oral administration.

The compound of Formula (I) and the additional therapeutic agent(s) can act additively or synergistically. A synergistic combination may allow the use of lower dosages of one or more agents and/or less frequent administration of one or more agents of a combination therapy. A lower dosage or less frequent administration of one or more agents may lower toxicity of the therapy without reducing the efficacy of the therapy.

The doses and dosage regimen of the additional therapeutic agent(s) used in the combination therapies of the present invention for the treatment or prevention of a disease or disorder can be determined by the attending clinician, taking into consideration the approved doses and dosage regimen in the package insert; the age, sex and general health of the patient; and the type and severity of the viral infection or related disease or disorder.

Another aspect of this invention is a kit comprising a therapeutically effective amount of the compound of Formula (I) or a pharmaceutically acceptable salt of said compound, optionally at least one additional therapeutic agent listed above and a pharmaceutically acceptable carrier, vehicle or diluent.

Methods of Preparing the Compounds of Formula (I)

The compounds of this invention may be made by a variety of methods, including standard chemistry. Any previously defined variable will continue to have the previously defined meaning unless otherwise indicated. Illustrative general synthetic methods are set out below and then specific compounds of the Formula (I) are prepared in the Examples.

Compounds of general Formula (I) may be prepared by methods known in the art of organic synthesis as set forth in part by the following synthesis schemes. In all of the schemes described below, it is well understood that protecting groups for sensitive or reactive groups are employed where necessary in accordance with general principles of chemistry. Protecting groups are manipulated according to standard methods of organic synthesis (T. W. Green and P. G. M. Wuts (1991) Protecting Groups in Organic Synthesis, John Wiley & Sons). These groups are removed at a convenient stage of the compound synthesis using methods that are readily apparent to those skilled in the art. The selection of protecting groups as well as the reaction conditions and order of reaction steps shall be consistent with the preparation of compounds of Formula (I). Those skilled in the art will recognize whether a stereocenter exists in compounds of Formula (I). Accordingly, the present invention includes all possible stereoisomers and includes not only mixtures of stereoisomers (such as racemic compounds) but the individual stereoisomers as well. When a compound is desired as a single enantiomer, it may be obtained by stereospecific synthesis or by resolution of the final product or any convenient intermediate. Resolution of the final product, an intermediate, or a starting material may be effected by any suitable method known in the art. See, for example, Stereochemistry of Organic Compounds by E. L. Eliel, S. H. Wilen, and L. N. Mander (Wiley-Interscience, 1994).

The following solvents, reagents, protecting groups, moieties, and other designations may be referred to by their abbreviations in parenthesis:

Me=methyl; Et=ethyl; Pr=propyl; iPr=isopropyl, Bu=butyl; t-Bu=tert-butyl; Ph=phenyl, and Ac=acetyl
μl=microliters
AcOH or HOAc=acetic acid
ACN=acetonitrile
Ad=adamantyl
aq=aqueous
Bn=benzyl
Boc or BOC=tert-butoxycarbonyl
Bz=benzoyl
Cbz=benzyloxycarbonyl
Dba=dibenzylideneacetone
DBU=1,8-Diaza-7-bicyclo[5.4.0]undecene
DCM=dichloromethane
DMAP=4-Dimethylaminopyridine
DIBAL=diisobutylaluminum hydride
DIEA or Htinig's Base=N,N-diisopropylethylamine
DMA=1,2-dimethylacetamide
DMF=dimethylformamide
DMSO=dimethyl sulfoxide
Dppf=1,1'-Bis(diphenylphosphino)ferrocene
DMT=Dimercaptotriazine
DTT=dithiothreitol
EDTA=ethylenediamine tetraacetic acid
ESI=Electrospray ionization EtOAc=ethyl acetate
g=grams
GST=glutathione S-transferase
h=hour
HMDS=1,1,1,3,3,3-hexamethyldisilazane
HATU=N,N,N,N'-tetramethyl-O-(7-azabenzotriazol-1-yl)uronium hexafluorophosphate
HPLC=high-performance liquid chromatography
HOBt=1-hydroxybenzotriazole
LDA=lithium diisopropylamide
LC=liquid chromatography
LCMS=liquid chromatography mass spectrometry
min=minute
mg=milligrams
mL=milliliters
mmol=millimoles
Me=methyl
MeOH=methanol
MS=mass spectrometry
NBS=N-bromosuccimide
NMP=N-methylpyrrolidone
NMR=nuclear magnetic resonance spectroscopy
rac=racemic mixture
RT or rt=room temperature (ambient, about 25° C.)
sat=saturated
SFC=supercritical fluid chromatography
TBSCl=t-butyldimethylsilyl chloride
TBS=t-butyldimethylsilyl
TEA=triethylamine ($Et_3N$)
TFA=trifluoroacetic acid
TFAA=trifluoroacetic anhydride
THF=tetrahydrofuran
TLC=thin layer chromatography
TMS=trimethylsilyl
Tris=tris(hydroxymethyl)aminomethane
Xantphos 4,5-Bis(diphenylphosphino)-9,9-dimethylxanthene General Methods Compounds of the Formula (I) can be prepared according to one of the synthetic schemes procedures set forth in Schemes 1-5 below, and/or by methods similar to those described in the Examples below.

SCHEME 1

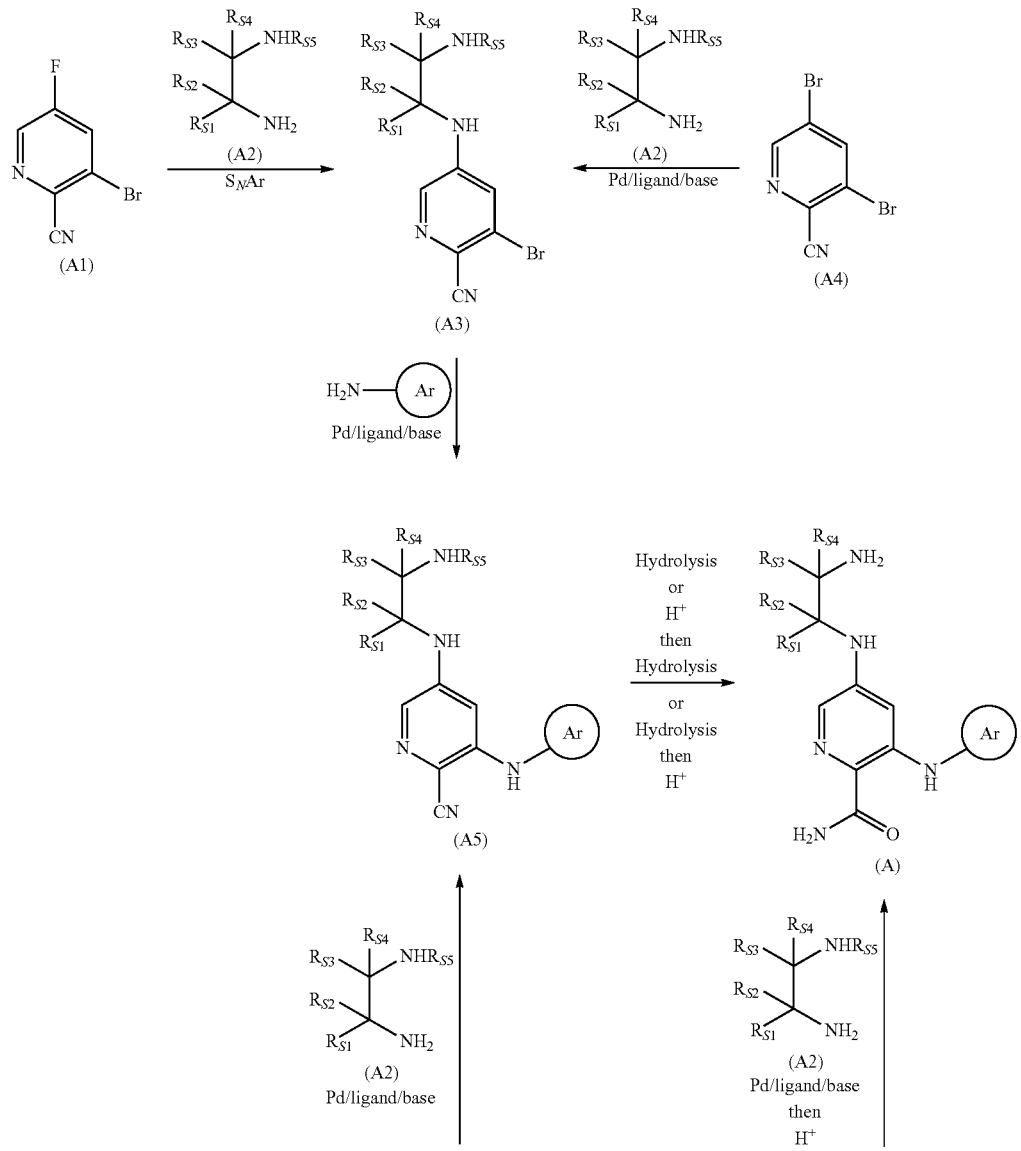

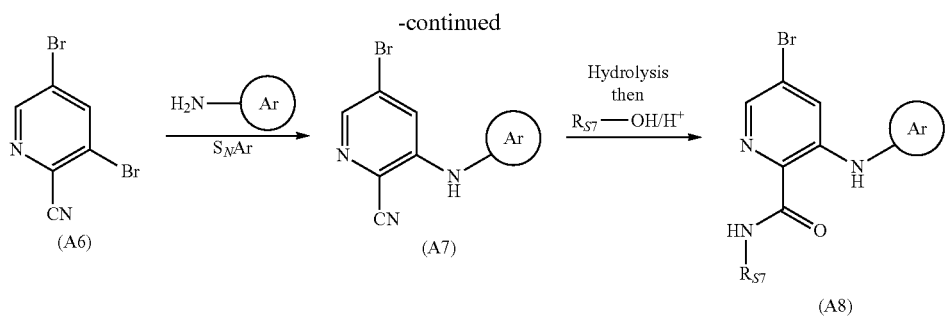

Compounds of structural subtype A (wherein $R_{S1}$-$R_{S4}$ are various substituents on the ethylenediamine moiety and Ar are various heteroaryl moieties) are prepared from substituted pyridine-2-carbonitriles (A5) (wherein $R_{S5}$ is an alkylamino protecting group) by one of the following methods: a) hydrolysis of the nitrile, or b) acidic deprotection of the alkylamino protecting group followed by hydrolysis of the nitrile, or c) hydrolysis of the nitrile followed by acidic deprotection of the alkylamino protecting group. The substituted pyridine-2-carbonitriles (A5) are prepared by the palladium-mediated coupling of an arylamine with substituted 3-bromopyridine-2-carbonitriles (A3), which in turn are prepared by either the reaction of 3-bromo-5-fluoropyridine-2-carbonitrile (A1) with substituted diamines (A2) via an $S_NAr$ reaction or, alternatively, from the reaction of 3,5-dibromopyridine-2-carbonitrile (A4) with substituted diamines (A2) via a palladium mediated coupling. The substituted pyridine-2-carbonitriles (A5) are also prepared by the palladium-mediated coupling of substituted diamines (A2) with substituted 5-bromopyridine-2-carbonitriles (A7), which are prepared from the reaction of 5-bromo-3-fluoropyridine-2-carbonitrile (A6) with arylamines via $S_NAr$ conditions. Compounds of structural subtype A also are obtained by the palladium-mediated coupling of substituted diamines (A2) with protected carboxamides (A8) followed by acidic deprotection. The protected carboxamides (A8) (wherein $R_{S7}$ is a carboxamido protecting group) are prepared by the hydrolysis of the carbonitriles (A7) followed by acid catalyzed reaction with the desired alcohol.

SCHEME 2

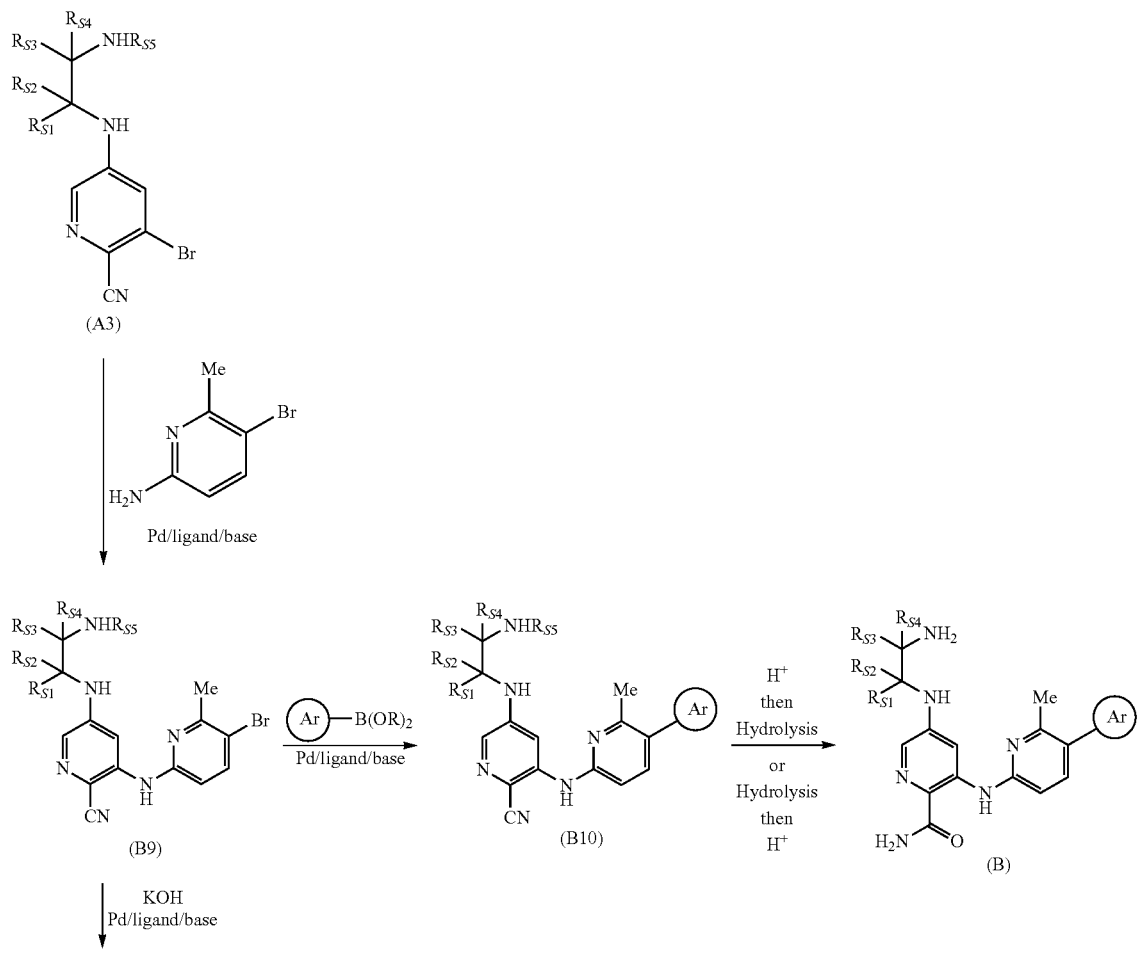

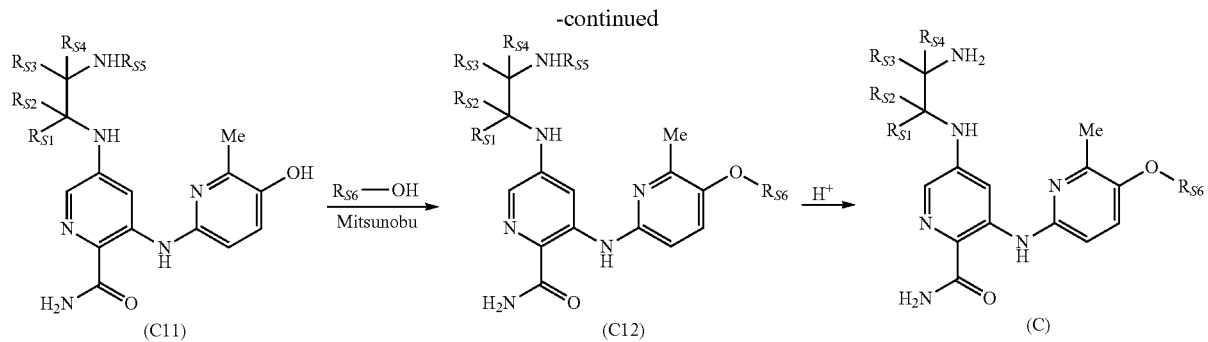

A shown in Scheme 2, compounds of structural subtype (B) are prepared from substituted pyridine-2-carbonitriles (B10) by either (a) acidic deprotection of the alkylamino protecting group followed by hydrolysis of the nitrile, or (b) hydrolysis of the nitrile followed by acidic deprotection of the alkylamino protecting group. Substituted pyridine-2-carbonitriles (B10) are prepared by the palladium-mediated reaction of aryl boronic acids with the 5-bromopyridine precursors (B9), which, in turn, are formed by the reaction of substituted 3-bromopyridine-2-carbonitriles (A3) with 5-bromo-6-methylpyridin-2-amine under palladium-mediated conditions. Compounds of structural subtype (C) are formed from the acidic deprotection of substituted pyridine-2-carboxamides (C12) (wherein $R_{S6}$ is an alkyl group). The substituted pyridine-2-carboxamides (C12) are prepared from the reaction of the phenols (C11) with various alcohols under Mitsunobu conditions. The phenols (C11) are formed from the reaction of the 5-bromopyridine precursors (B9) with a hydroxide source via palladium-mediated conditions.

SCHEME 3

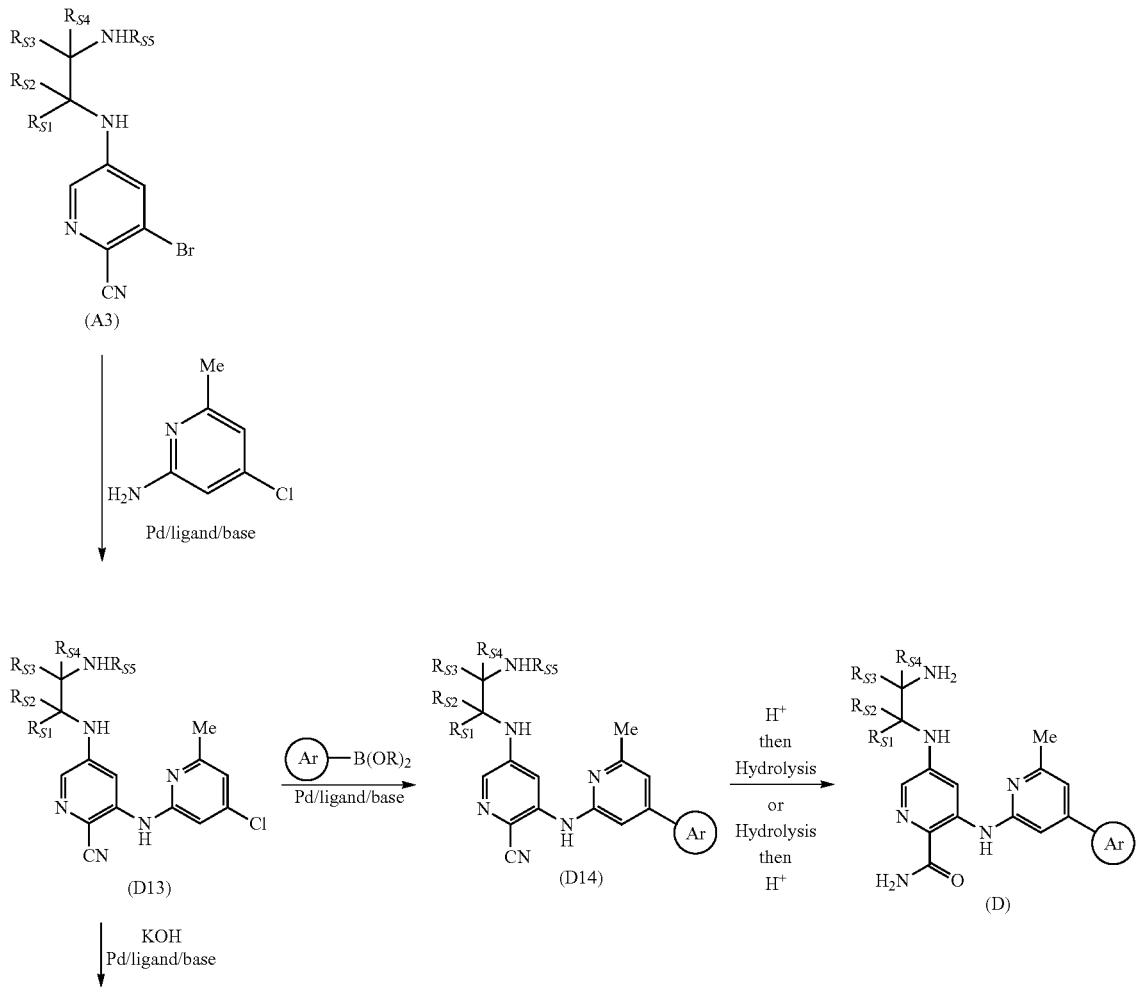

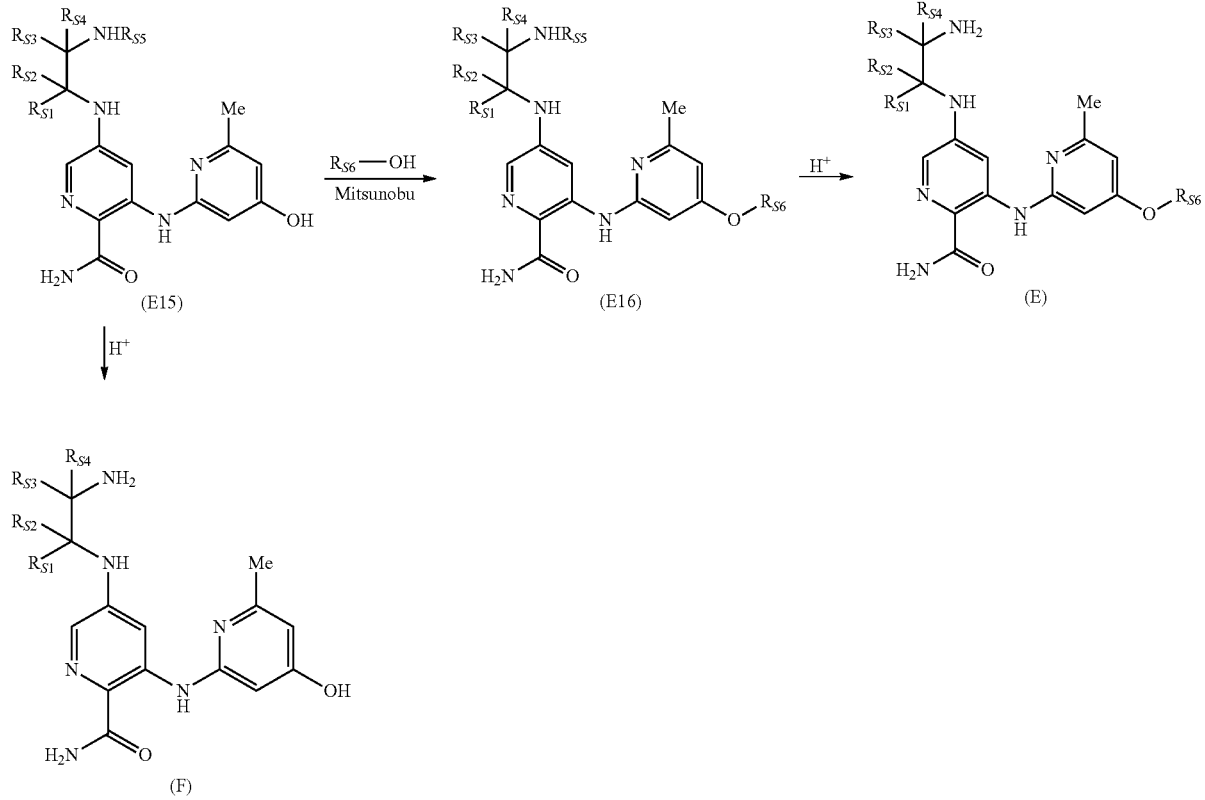

As shown in Scheme 3, compounds of structural subtype (D) are prepared from substituted pyridine-2-carbonitriles (D14) by either (a) acidic deprotection of the alkylamino protecting group followed by hydrolysis of the nitrile, or (b) hydrolysis of the nitrile followed by acidic deprotection of the alkylamino protecting group. Substituted pyridine-2-carbonitriles (D14) are prepared by the palladium-mediated reaction of aryl boronic acids with the 4-chloropyridine precursors (D13), which are formed by the reaction of substituted 3-bromopyridine-2-carbonitriles (A3) with 4-chloro-6-methylpyridin-2-amine under palladium-mediated conditions. Compounds of structural subtype (E) are formed from the acidic deprotection of substituted pyridine-2-carboxamides (E16). The substituted pyridine-2-carboxamides (E16) are prepared from the reaction of the phenols (E15) with various alcohols under Mitsunobu conditions. The phenols (E15) are formed from the reaction of the 4-chloropyridine precursors (D13) with a hydroxide source via palladium-mediated conditions. Compounds of formula (F) are formed by the acidic deprotection of phenols (E15).

SCHEME 4

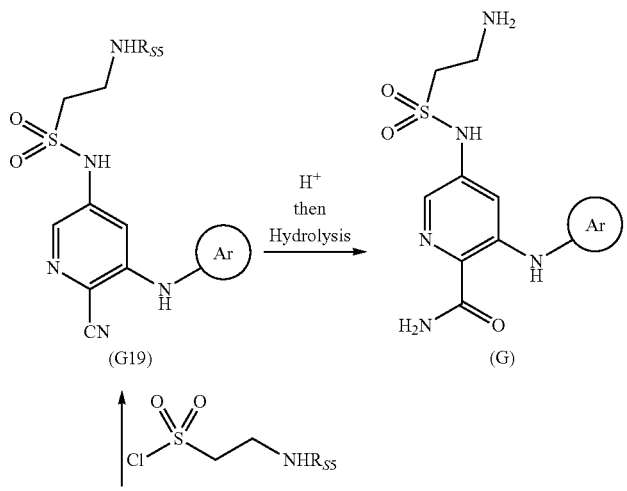

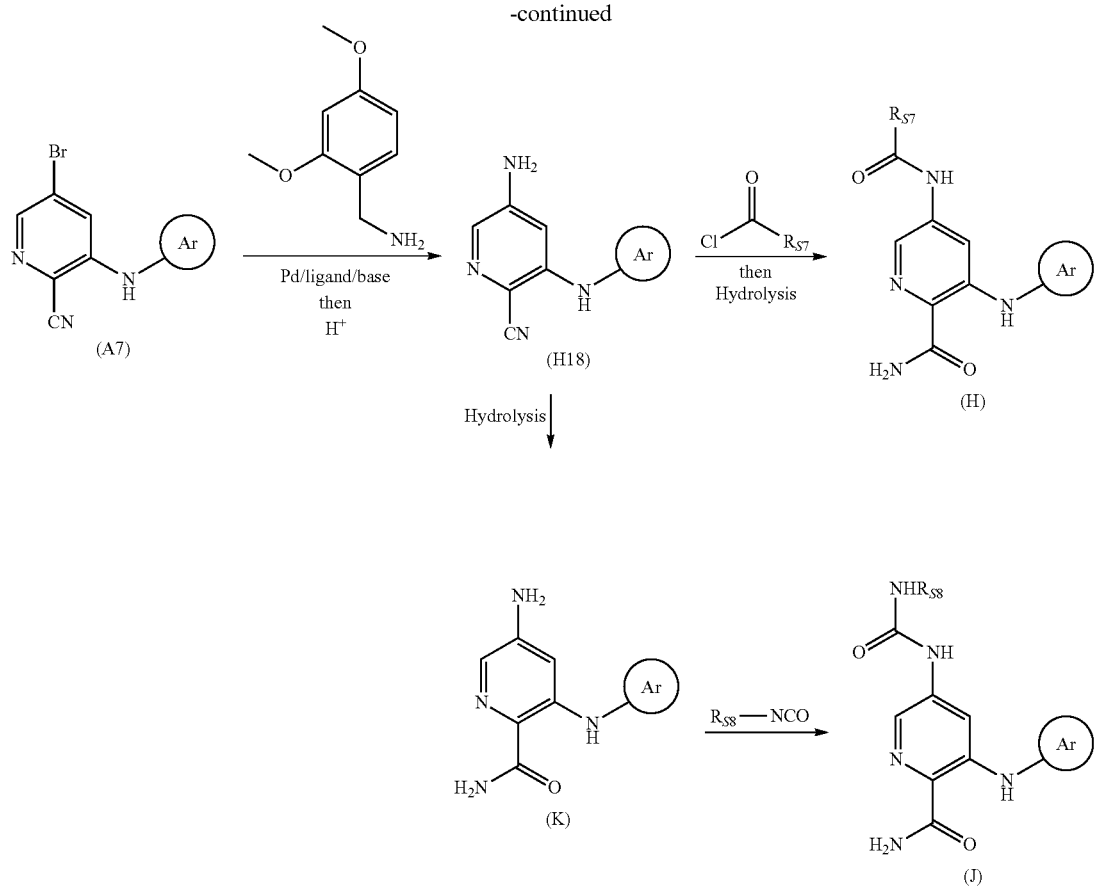

As shown in Scheme 4, compounds of structural subtype G are prepared from the sulfonamides (G19) by acidic deprotection of the alkylamino protecting group followed by hydrolysis of the nitrile. The sulfonamides (G19) are synthesized from the substituted 5-amino-pyridine-2-carbonitriles (H18) by reaction with a sulfonylchloride. The substituted 5-amino-pyridine-2-carbonitriles (H18), in turn, are prepared from the substituted 5-bromo-pyridine-2-carbonitriles (A7) via a palladium-mediated coupling with 2,4-dimethoxybenzylamine followed by an acidic deprotection. Alternatively, substituted 5-amino-pyridine-2-carbonitriles (H18) are reacted with acyl chlorides (wherein $R_{S7}$ is alkyl) and then subjected to hydrolysis conditions to provide compounds of structural subtype (H). Compounds of structural subtype (K) also are prepared from substituted 5-amino-pyridine-2-carbonitriles (H18) by hydrolysis of the nitrile. Compounds of structural subtype (J) (wherein $R_{S8}$ is alkyl) are prepared from compounds of formula (K) by reaction with alkylisocyanates.

SCHEME 5

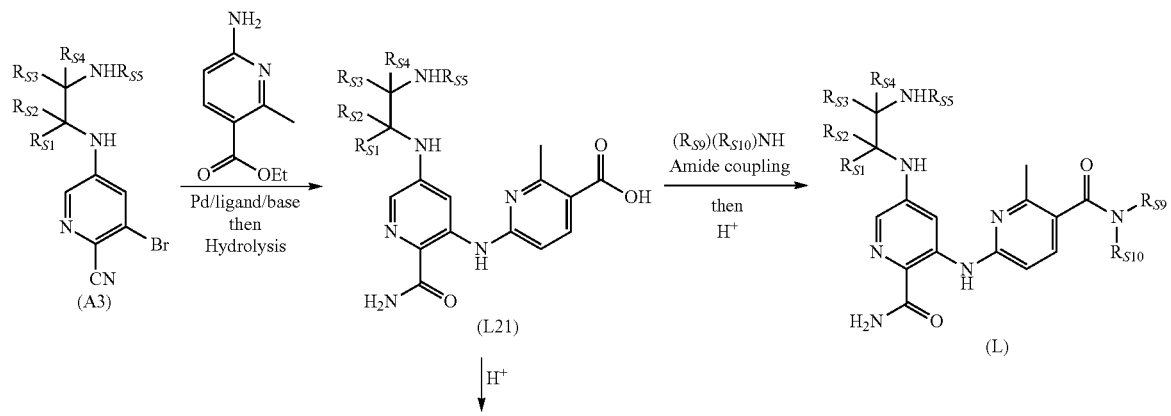

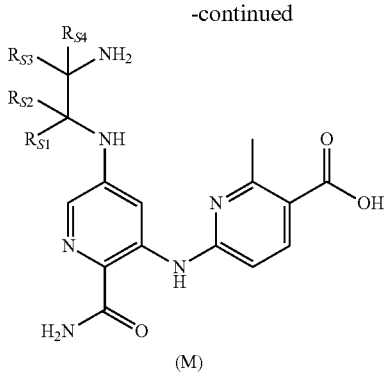

(M)

As shown in Scheme 5, compounds of structural subtype (L) are prepared from the pyridylcarboxylates (L21) by standard amide coupling with an alkylamine (wherein $R_{S9}$ and $R_{S10}$ are independent H or alkyl) followed by acid deprotection of the alkylamino protecting group. The pyridylcarboxylates (L21) are prepared from substituted 3-bromopyridine-2-carbonitriles (A3) by a palladium-mediated coupling with ethyl 6-amino-2-methylpyridine-3-carboxylate followed by a global hydrolysis of the nitrile and ethyl carboxylate. Alternatively, the pyridylcarboxylates (L21) are subjected to acidic deprotection conditions to afford compounds of structural subtype (M).

Compounds of structural subtypes A-M are prepared according to the procedures described in the Schemes and Examples herein, using appropriate materials, and are further exemplified by the following specific examples. The compounds exemplified are illustrative of the invention and are not, however, to be construed as limiting the scope of the invention in any manner. The examples further illustrate details for the preparation of the compounds of the present invention. Those skilled in the art will readily understand that known variations of protecting groups, of reagents, as well as of the conditions and processes of the following preparative procedures, can be used to prepare these compounds. It is also understood that whenever a chemical reagent is not commercially available, such a chemical reagent can be readily prepared by those skilled in the art by either following or adapting known methods described in the literature. All temperatures are degrees Celsius unless otherwise noted. Mass spectra (MS) were measured either by electrospray ion-mass spectroscopy (ESMS) or by atmospheric pressure chemical ionization mass spectroscopy (ESI).

For ease of reference, various moieties are referred in the Examples below as "A" moieties, "B" moieties, "E" moieties and the "pyridylcarboxamide" moiety. These moieties are illustrated in the structural formula below.

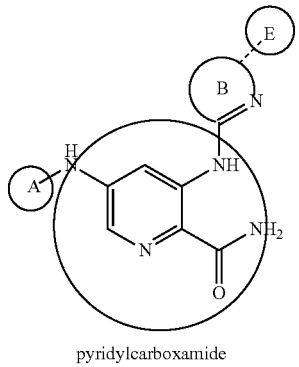

pyridylcarboxamide

The starting materials and reagents used in preparing compounds described are either available from commercial suppliers or were prepared by literature methods known to those skilled in the art.

These examples are being provided to further illustrate the present invention. They are for illustrative purposes only; the scope of the invention is not to be considered limited in any way thereby.

Where mass spectral (MS) data are presented in the examples below, analysis was performed using an Agilent Technologies 6120 quadrupole LC/MS. Resolution of enantiomers was typically performed using supercritical fluid chromatography utilizing a Chiral Technologies AD, AD-H, IB-H, or IC-H column (particle size of 5 or 10 micron stationary phase) with a mobile phase of $CO_2$ and a lower alcohol and/or THF.

EXAMPLES

Preparative Example 1

Preparation of Pyridylcarboxamide Precursors

Preparative Example 1.1 tert-butyl {(1S,2R)-2-[(5-bromo-6-cyanopyridin-3-yl)amino]cyclohexyl}carbamate

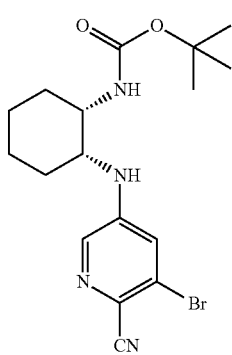

PrepEx 1.1

This example describes the procedure for conversion of (A1) to (A3) as shown in Scheme 1. Tert-butyl [(1S,2R)-2-aminocyclohexyl]carbamate was purchased from Small Molecules, Inc. (CAS: 365996-30-1, Hoboken, N.J.). DIPEA (18.5 mL, 106 mmol) and tert-butyl [(1S,2R)-2-aminocyclohexyl]carbamate (17.7 g, 82.7 mmol) were added to 3-bromo-5-fluoropyridine-2-carbonitrile (Frontier Scientific; CAS: 950670-18-5, Logan, Utah) (16.4 g, 81.6 mmol) dissolved in NMP (16.3 mL) in a 150 mL sealed tube. The reaction was heated to 120° C. for 24 hours before cooling to ambient temperature. Hydrochloric acid (1.0 M in water, 100 mL, 100 mmol) was added. Dichloromethane was then added dropwise until a freely stirring suspension was formed. The precipitate was collected by filtration, washed with cold diethyl ether (30 mL), and dried under reduced pressure to afford a portion of tert-butyl {(1S,2R)-2-[(5-bromo-6-cyanopyridin-3-yl)-amino]cyclohexyl}carbamate. The mother liquors were separated and the organic layer was dried over sodium sulfate, filtered, and concentrated under reduced pressure. The residue was triturated with diethyl ether and water to yield an additional portion of tert-butyl {(1S,2R)-2-[(5-bromo-6-cyanopyridin-3-yl)amino]cyclohexyl}carbamate. MS ESI calc'd. for $C_{17}H_{24}BrN_4O_2$ [M+H]$^+$ 395 and 397. found 395 and 397. $^1$H NMR (500 MHz, CD$_3$OD) δ 8.02 (d, J=2.3 Hz, 1H), 7.23 (br s, 1H), 6.59-6.46 (m, 1H), 3.83 (s, 1H), 1.65 (s, 6H), 1.56-1.17 (m, 11H).

Preparative Example 1.2 tert-butyl {(2S)-1-[(5-bromo-6-cyanopyridin-3-yl) amino]propan-2-yl}carbamate

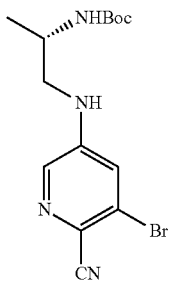

PrepEx 1.2

In another example of the conversion of (A1) to (A3), tert-butyl {(2S)-1-[(5-bromo-6-cyanopyridin-3-yl)amino]propan-2-yl}carbamate was prepared from 3-bromo-5-fluoropyridine-2-carbonitrile using chemistry analogous to that described for the synthesis of tert-butyl {(1S,2R)-2-[(5-bromo-6-cyanopyridin-3-yl)amino]cyclohexyl}carbamate (PrepEx 1.1). MS ESI calc'd. for $C_{14}H_{20}BrN_4O_2$ [M+H]$^+$ 355 and 357. found 355 and 357.

Preparative Example 1.3 tert-butyl {2-[(5-bromo-6-cyanopyridin-3-yl)amino] ethyl}carbamate

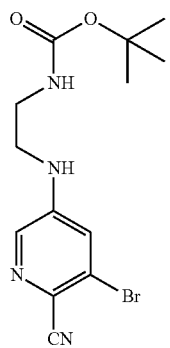

PrepEx 1.3

In another example of the conversion of (A1) to (A3), tert-butyl {2-[(5-bromo-6-cyanopyridin-3-yl)amino] ethyl}carbamate was prepared from 3-bromo-5-fluoropyridine-2-carbonitrile using chemistry analogous to that described for the synthesis of tert-butyl {(1S,2R)-2-[(5-bromo-6-cyanopyridin-3-yl)amino]cyclohexyl}carbamate (PrepEx 1.1). MS ESI calc'd. for $C_{13}H_{18}BrN_4O_2$ [M+H]$^+$ 341 and 343. found 341 and 343.

Preparative Example 1.4

5-bromo-3-[(4,6-dimethylpyridin-2-yl)amino]pyridine-2-carbonitrile

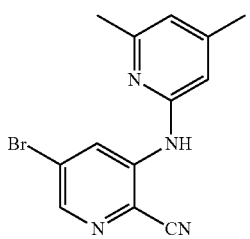

PrepEx 1.4

This example describes the conversion of (A6) to (A7) as illustrated in Scheme 1. To a solution of 2-amino-4,6-dimethylpyridine (30.4 g, 249 mmol) in THF (200 mL) at 0° C. was added potassium tert-butoxide (1.0 M in THF, 249 mL, 250 mmol) at such a rate to keep the internal temperature less then 10° C. After the addition was complete, the reaction mixture was stirred for 10 min, and then ~60% of the reaction mixture was transferred via cannula to a cooled solution of 5-bromo-2-cyano-3-fluoropyridine (Manchester Organics, Ltd.; CAS: 886373-28-0, Runcorn, UK) (25.0 g, 124 mmol) in THF (200 mL). The reaction mixture was analyzed by LC which indicated near-complete consumption of the 5-bromo-2-cyano-3-fluoropyridine. The reaction mixture was diluted with water (400 mL) followed by hydrochloric acid (1.0 M in water, 50 mL, 50 mmol), and the resulting mixture was filtered. The collected solids were washed with water (2×50 mL). After 2 hours, the filtrate was filtered. The two collections of solids were combined, diluted with 4:1 hexanes/ethyl acetate (400 mL), and stirred. After 30 minutes, the mixture was filtered to afford 5-bromo-3-[(4,6-dimethylpyridin-2-yl) amino]pyridine-2-carbonitrile. MS ESI calc'd. for $C_{13}H_{12}BrN_4$ [M+H]$^+$ 303 and 305. found 303 and 305. $^1$H NMR (600 MHz, CD$_3$OD) δ 8.89 (d, J=2.4 Hz, 1H), 8.24 (d, J=1.8 Hz, 1H), 6.71 (s, 1H), 6.68 (s, 1H), 2.37 (s, 3H), 2.27 (s, 3H).

Preparative Example 1.5

5-bromo-3-[(5-bromo-6-methylpyridin-2-yl)amino] pyridine-2-carbonitrile

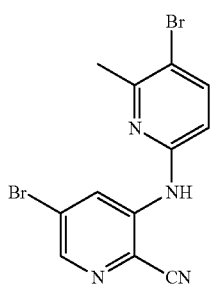

PrepEx 1.5

In another example of the conversion of (A6) to (A7), 5-bromo-3-[(5-bromo-6-methylpyridin-2-yl)amino]pyridine-2-carbonitrile was prepared from 5-bromo-2-cyano-3-fluoropyridine using chemistry analogous to that described for the synthesis of 5-bromo-3-[(4,6-dimethylpyridin-2-yl)amino]pyridine-2-carbonitrile (PrepEx 1.4). ¹H NMR (600 MHz, DMSO-d₆) δ 9.62 (s, 1H), 8.66 (s, 1H), 8.41 (s, 1H), 7.82 (d, J=2.4 Hz, 1H), 6.86 (d, J=3.0 Hz, 1H), 2.41 (s, 3H).

Preparative Example 1.6 tert-butyl (1S,2R)-2-(5-(5-bromo-6-methylpyridin-2-ylamino)-6-cyanopyridin-3-ylamino)cyclohexylcarbamate

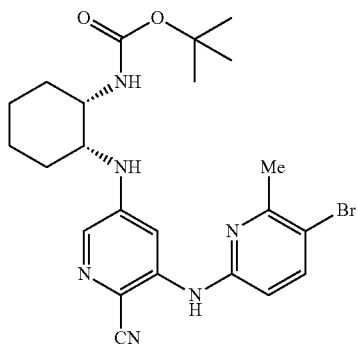

PrepEx 1.6

This example describes the conversion of (A3) to (B9) as illustrated in Scheme 2.

Dioxane (25 ml) was added to a nitrogen purged flask containing tert-butyl (1S,2R)-2-(5-bromo-6-cyanopyridin-3-ylamino)cyclohexylcarbamate (PrepEx 1.1) (2500 mg, 6.32 mmol), 5-bromo-6-methylpyridin-2-amine (1540 mg, 8.22 mmol), Xantphos (732 mg, 1.27 mmol), Pd₂(dba)₃ (579 mg, 0.632 mmol) and cesium carbonate (3090 mg, 9.49 mmol). Nitrogen was bubbled through the reaction mixture for 5 minutes, and the reaction mixture was heated at 85° C. for 4.5 hours. The reaction was then cooled to room temperature and poured into 10% aq. KHSO₄ (300 mL). The pH was adjusted to 4 with 10% aq. KHSO₄, and the mixture was sonicated. The solids were collected by filtration, dried under nitrogen, and diluted with DCM (50 mL). Sonication of the resulting suspension afforded a thick slurry. The solids were collected by filtration, and washed with DCM (10 mL) and hexanes (20 mL) to afford tert-butyl (1S,2R)-2-(5-(5-bromo-6-methylpyridin-2-ylamino)-6-cyanopyridin-3-ylamino)cyclohexylcarbamate. MS ESI calc'd. for C₂₃H₃₀BrN₆O₂ [M+H]⁺ 501 and 503 found 501 and 503. ¹H NMR (500 MHz, CD₃OD) δ 7.78 (s, 1H), 7.73-7.71 (m, 2H), 7.75 (d, J=8.8 Hz, 1H), 3.85 (br s, 1H), 3.75 (br s, 1H), 2.54 (s, 3H), 1.90-1.10 (m, 8H), 1.34 (s, 9H).

Preparative Example 1.7 tert-butyl [(1S,2R)-2-({5-[(4-chloro-6-methylpyridin-2-yl)amino]-6-cyanopyridin-3-yl}amino)cyclohexyl]carbamate

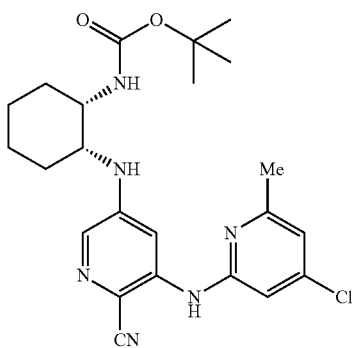

PrepEx 1.7

This example describes the conversion of (A3) to (D13) as illustrated in Scheme 3. tert-Butyl [(1S,2R)-2-({5-[(4-chloro-6-methylpyridin-2-yl)amino]-6-cyanopyridin-3-yl}amino)cyclohexyl]carbamate was prepared from tert-butyl (1S,2R)-2-(5-bromo-6-cyanopyridin-3-ylamino)cyclohexylcarbamate (PrepEx 1.1) using chemistry analogous to that described for the synthesis of tert-butyl (1S,2R)-2-(5-(5-bromo-6-methylpyridin-2-ylamino)-6-cyanopyridin-3-ylamino)cyclohexylcarbamate (Prep Ex 1.6). MS ESI calc'd. for C₂₃H₃₀ClN₆O₂ [M+H]⁺ 457. found 457.

Preparative Example 1.8

5-amino-3-[(4,6-dimethylpyridin-2-yl)amino]pyridine-2-carbonitrile

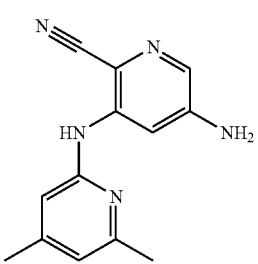

PrepEx 1.8

This example describes the conversion of (A7) to (H18) shown in Scheme 4.

Step 1: To a flask was added 5-bromo-3-[(4,6-dimethylpyridin-2-yl)amino]pyridine-2-carbonitrile (PrepEx 1.4) (500 mg, 1.65 mmol), Xantphos (95 mg, 0.17 mmol), Pd₂(dba)₃ (121 mg, 0.133 mmol) and cesium carbonate (1.08 g, 3.30 mmol). A solution of 2,4-Dimethoxybenzylamine (276 mg, 1.65 mmol) in degassed dioxane (16.5 mL) was added to the flask. The reaction was heated to 100° C. for one hour. The reaction mixture was cooled to room temperature, diluted with ethyl acetate and water, and the organic layer was separated, dried over magnesium sulfate, filtered, and concentrated under reduced pressure. The residue was purified by silica gel chromatography (0-40% ethyl acetate/hexanes, linear gradient) to afford 5-[(2,4-dimethoxybenzyl)amino]-3-[(4,6-dimethylpyridin-2-yl)amino]pyridine-2-carbonitrile. MS ESI calc'd for $C_{22}H_{24}N_5O_2$ [M+H]$^+$ 390. found 390. $^1$H NMR (500 MHz, DMSO-d$_6$) δ 8.62 (s, 1H), 7.71 (d, J=2.3 Hz, 1H), 7.43 (d, J=2.3 Hz, 1H), 7.21 (t, J=5.7 Hz, 1H), 7.08 (d, J=8.3 Hz, 1H), 6.57 (s, 1H), 6.54 (d, J=2.3 Hz, 1H), 6.53 (s, 1H), 6.45 (dd, J=2.3 Hz, 8.3 Hz, 1H), 4.16 (d, J=5.8 Hz, 2H), 3.73 (s, 3H), 3.70 (s, 3H), 2.18 (s, 3H), 2.15 (s, 3H).

Step 2: To a suspension of 5-[(2,4-dimethoxybenzyl)amino]-3-[(4,6-dimethylpyridin-2-yl)amino]pyridine-2-carbonitrile (240 mg, 0.62 mmol) in dichloromethane (5 mL) was added trifluoroacetic acid (0.96 mL, 12.5 mmol) dropwise, and the reaction mixture was stirred for 10 minutes. The reaction mixture was diluted with ethyl acetate and aqueous saturated sodium bicarbonate. The organic layer was separated, dried over magnesium sulfate, filtered, and concentrated under reduced pressure. The residue was purified by silica gel chromatography (0-65% ethyl acetate/hexanes, linear gradient) to afford 5-amino-3-[(4,6-dimethylpyridin-2-yl)amino]pyridine-2-carbonitrile. MS ESI calc'd for $C_{13}H_{14}N_5$ [M+H]$^+$ 240. found 240. $^1$H NMR (500 MHz, DMSO-d$_6$) δ 8.59 (s, 1H), 7.61 (d, J=2.3 Hz, 1H), 7.36 (d, J=2.2 Hz, 1H), 6.57 (s, 1H), 6.55 (s, 1H), 6.25 (s, 2H), 2.28 (s, 3H), 2.18 (s, 3H).

Preparative Example 1.9 tert-butyl [(1S,2R)-2-({6-carbamoyl-5-[(5-hydroxy-6-methylpyridin-2-yl)amino]pyridin-3-yl}amino)cyclohexyl]carbamate

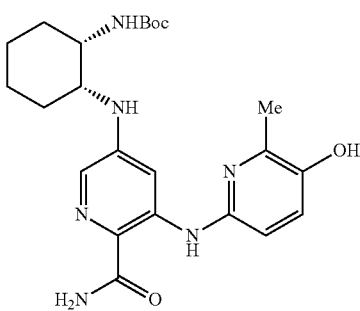

PrepEx 1.9

This example describes the conversion of (B9) to (C11) shown in Scheme 2. Dioxane (2.40 mL) and sodium hydroxide (4.0 N in water, 0.36 mL, 1.4 mmol) were added to tert-butyl [(1S,2R)-2-({5-[(5-bromo-6-methylpyridin-2-yl)amino]-6-cyanopyridin-3-yl}amino)cyclohexyl]carbamate (PrepEx 1.6) (0.241 g, 0.481 mmol) in a scintillation vial. The vial was purged and flushed with argon three times before Pd$_2$(dba)$_3$ (0.013 g, 0.014 mmol) and 2-di-tert-butylphosphino-3,4,5,6-tetramethyl-2',4',6'-tri-isopropylbiphenyl (0.028 g, 0.058 mmol) were added. The vial was purged and flushed three times with argon before the vial was sealed and heated to 80° C. After 4 hours, the reaction was cooled to room temperature, filtered through CELITE (washed with dichloromethane) and diluted with water. The organic layer was dried over sodium sulfate, filtered, and concentrated under reduced pressure. The residue was purified by silica gel chromatography (0-100% acetone/hexanes, linear gradient) to afford tert-butyl [(1S,2R)-2-({6-carbamoyl-5-[(5-hydroxy-6-methylpyridin-2-yl)amino]pyridin-3-yl}amino)cyclohexyl]carbamate. MS ESI calc'd. for $C_{23}H_{33}N_6O_4$ [M+H]$^+$ 457. found 457.

Preparative Example 1.10 tert-butyl [(1S,2R)-2-({6-carbamoyl-5-[(4-hydroxy-6-methylpyridin-2-yl)amino]pyridin-3-yl}amino)cyclohexyl]carbamate

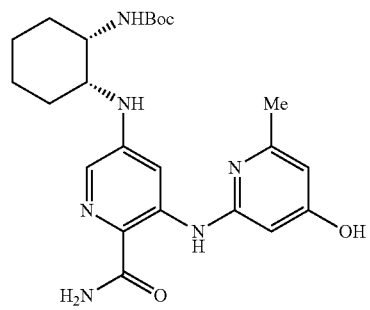

PrepEx 1.10

This example describes the conversion of (D13) to (E15) as shown in Scheme 3. tert-butyl [(1S,2R)-2-({6-carbamoyl-5-[(4-hydroxy-6-methylpyridin-2-yl)amino]pyridin-3-yl}amino)cyclohexyl]carbamate was prepared from tert-butyl [(1S,2R)-2-({5-[(4-chloro-6-methylpyridin-2-yl)amino]-6-cyanopyridin-3-yl}amino)cyclohexyl]carbamate (PrepEx 1.7) using chemistry analogous to that described for the synthesis of tert-butyl [(1S,2R)-2-({6-carbamoyl-5-[(5-hydroxy-6-methylpyridin-2-yl)amino]pyridin-3-yl}amino)cyclohexyl]carbamate (PrepEx 1.9). MS ESI calc'd. for $C_{23}H_{33}N_6O_4$ [M+H]$^+$ 457. found 457.

Preparative Example 1.11

N-[bis(4-methoxyphenyl)methyl]-5-bromo-3-[(4,6-dimethylpyridin-2-yl)amino]pyridine-2-carboxamide

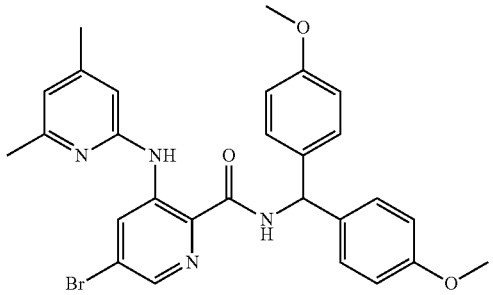

PrepEx 1.11

This example describes the conversion of (A7) to (A8) shown in Scheme 1.

Step 1: To a solution of 5-bromo-3-[(4,6-dimethylpyridin-2-yl)amino]pyridine-2-carbonitrile (PrepEx 1.4) (2.6 g, 8.6 mmol) in DMSO (60 mL) was added sodium hydroxide (6.0 M in water, 1.4 mL, 8.6 mmol). The reaction mixture was cooled in an ice bath, and hydrogen peroxide (30% w/w solution in water, 2.0 mL, 20 mmol) was added. After 2 hours, the reaction mixture was diluted with water (100 mL) and stirred. After 10 min, the reaction mixture was filtered, and the collected solids were washed with water (2×50 mL) and dried under reduced pressure to afford 5-bromo-3-[(4,6-dimethylpyridin-2-yl)amino]pyridine-2-carboxamide. $^1$H NMR (600 MHz, CD$_3$OD) δ 9.63 (d, J=2.4 Hz, 1H), 8.07 (d, J=2.4 Hz, 1H), 6.63 (s, 1H), 6.48 (s, 1H), 2.40 (s, 3H), 2.24 (s, 3H).

Step 2: To a solution of 5-bromo-3-[(4,6-dimethylpyridin-2-yl)amino]pyridine-2-carboxamide (1.65 g, 5.14 mmol) in toluene (20 ml) was added bis(4-methoxyphenyl)methanol (1.32 g, 5.39 mmol) and p-toluenesulfonic acid monohydrate (0.098 g, 0.51 mmol). The reaction mixture was heated to reflux with a Dean-Stark apparatus attached. After 2 hours, the reaction mixture was cooled to ambient temperature and diluted with ethyl acetate (600 mL). This mixture was washed with saturated aqueous sodium bicarbonate (2×100 mL) and brine (50 mL). The organic layer was dried over magnesium sulfate, filtered, and concentrated under reduced pressure. The residue was purified by chromatography on silica gel (0-60% ethyl acetate/hexanes). The isolated product was dissolved in 25 mL hot ethyl acetate (~50° C.). The mixture was allowed to cool to ambient temperature, and then it was diluted dropwise with hexanes (100 mL). After 4 hours, the mixture was filtered, and the collected solids were dried under reduced pressure to afford N-[bis(4-methoxyphenyl)methyl]-5-bromo-3-[(4,6-dimethylpyridin-2-yl)amino]pyridine-2-carboxamide. MS ESI calc'd. For $C_{28}H_{28}BrN_4O_3$ [M+H]$^+$ 547 and 549. found 547 and 549. $^1$H NMR (500 MHz, DMSO-d$_6$) δ 11.47 (s, 1H), 9.68 (d, J=2.0 Hz, 1H), 9.26 (d, J=8.5 Hz, 1H), 8.18 (d, J=2.0 Hz, 1H), 7.27 (d, J=8.5 Hz, 4H), 6.88 (d, J=8.5 Hz, 4H), 6.66 (s, 1H), 6.55 (s, 1H), 6.19 (d, J=9.0 Hz, 1H), 3.71 (s, 6H), 2.36 (s, 3H), 2.19 (s, 3H).

Preparative Example 2

Preparation of B Moiety Precursors

Preparative Example 2.1

1-methyl-6-phenyl-1H-pyrazolo[3,4-d]pyrimidin-4-amine

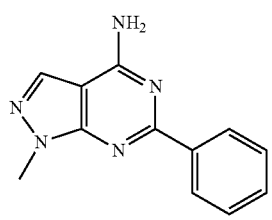

PrepEx 2.1

Step 1: 4,6-Dichloro-1-methyl-1H-pyrazolo[3,4-c]pyrimidine (150 mg, 0.74 mmol) was added to a 5 mL microwave vial containing ammonia (2.0 M in methanol, 3.0 mL, 6.0 mmol) and the resulting suspension was heated via microwave irradiation to 100° C. for 5 minutes. The reaction mixture was concentrated under reduced pressure to afford 6-chloro-1-methyl-1H-pyrazolo[3,4-d]pyrimidin-4-amine which was used without further purification. MS ESI calc'd. for $C_6H_7ClN_5$ [M+H]$^+$ 184. found 184. $^1$H NMR (500 MHz, DMSO-d$_6$) δ 8.27 (s, 1H), 8.11 (s, 1H), 8.05 (s, 1H), 3.82 (s, 3H).

Step 2: A suspension of 6-chloro-1-methyl-1H-pyrazolo[3,4-d]pyrimidin-4-amine (68 mg, 0.37 mmol), phenyl boronic acid (68 mg, 0.56 mmol), 1,1'-bis(diphenylphosphino)ferrocene-palladium(II)dichloride-dichloromethane complex (30 mg, 0.037 mmol), 1,4-dioxane (3 ml), water (0.2 ml), and aqueous sodium carbonate solution (2.0 M, 0.740 ml, 1.5 mmol) in a 5 mL microwave vial was deoxygenated using 10 alternate vacuum/argon flush cycles. The reaction mixture was then heated via microwave irradiation to 170° C. for 10 minutes. After cooling to room temperature, the reaction mixture was partitioned between ethyl acetate (40 mL) and saturated aqueous sodium bicarbonate solution (10 mL). The layers were separated and the organic layer was washed with brine (10 mL), dried over sodium sulfate, filtered, and concentrated under reduced pressure. The residue was purified by chromatography on silica gel (0.5-6.5% methanol/dichloromethane, linear gradient) to afford 1-methyl-6-phenyl-1H-pyrazolo[3,4-d]pyrimidin-4-amine. MS ESI calc'd. for $C_{12}H_{12}N_5$ [M+H]$^+$ 226. found 226.

Preparative Example 2.2

6-methyl-5-(1-methyl-1H-pyrazol-4-yl)pyridin-2-amine

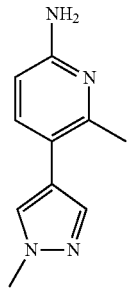

PrepEx 2.2

Dioxane (8.7 mL), 5-bromo-6-methylpyridin-2-amine (Maybridge, CAS: 42753-71-9, Cornwall, UK) (722 mg, 3.47 mmol), water (1.0 mL) and tribasic potassium phosphate (1.84 g, 8.68 mmol) were added to 1-methyl-4-(4,4,5,5-tetramethyl-1,3,2-dioxaborolan-2-yl)-1H-pyrazole (Sigma-Aldrich, CAS: 761446-44-0 St. Louis, Mo.) (541 mg, 2.89 mmol) in a scintillation vial. The vial was purged and flushed with argon 3 times before adding PdCl$_2$(dppf)-CH$_2$Cl$_2$ adduct (236 mg, 0.289 mmol). The vial was again purged and flushed 3 times with argon before sealing the vial and heating to 100° C. After 16 hours, the reaction mixture was cooled to room temperature and filtered through CELITE (washing with chloroform). The filtrate was diluted with water, and the organic layer was separated, dried over sodium sulfate, filtered, and concentrated under reduced pressure. The residue was purified by silica gel chromatography (10-100% (10% MeOH in chloroform)/hexanes, linear gradient) followed by reverse phase HPLC (5-50% acetonitrile/water with 0.1% TFA, linear gradient) to afford 6-methyl-5-(1-methyl-1H-pyrazol-4-yl)pyridin-2-amine TFA salt. MS ESI calc'd. for $C_{10}H_{13}N_4$ [M+H]$^+$ 189. found 189. $^1$H NMR (500 MHz, CD$_3$OD) δ 7.67 (s, 1H), 7.53 (s, 1H), 7.41 (d, J=8.4 Hz, 1H), 6.45 (d, J=8.4 Hz, 1H), 3.92 (s, 3H), 3.30 (s, 3H).

Preparative Example 2.3

6-(morpholin-4-yl)pyridin-2-amine

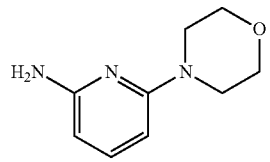

6-Chloropyridin-2-amine (244 mg, 1.90 mmol) and morpholine (0.827 mL, 9.49 mmol) were combined and heated for 2 hr at 200° C. via microwave irradiation. The reaction mixture was diluted with saturated aqueous ammonium chloride and DCM. The organics were separated, dried over sodium sulfate, and concentrated under reduced pressure. The residue was purified by silica gel chromatography (10-80% acetone/hexanes, linear gradient) to afford 6-(morpholin-4-yl)pyridin-2-amine. MS ESI calc'd. for $C_9H_{14}N_3O$ $[M+H]^+$ 180. found 180. $^1H$ NMR (500 MHz, $CDCl_3$) δ 7.29 (t, J=7.9 Hz, 1H), 5.99 (d, J=8.1 Hz, 1H), 5.91 (d, J=7.8 Hz, 1H), 3.82-3.75 (m, 4H), 3.46-3.38 (m, 4H).

Preparative Example 2.4

6-(2H-1,2,3-triazol-2-yl)pyridin-2-amine

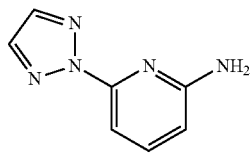

6-Chloropyridin-2-amine (2.00 g, 15.6 mmol) and 1H-1,2,3-triazole (3.22 g, 46.7 mmol) were combined in a 75 mL sealed flask and heated overnight at 180° C. The reaction mixture was cooled to room temperature, and diluted with DCM and a solution of saturated aqeuous ammonium chloride. The organics were dried over sodium sulfate, filtered, and concentrated under reduced pressure. The residue was purified by silica gel chromatography (0-50% acetone in hexanes, linear gradient) to afford a 1:1 mixture of 1H and 2H triazole regioisomers. Further purification by HPLC afforded the separated regioisomers (15-30% acetonitrile/water with 0.1% ammonium hydroxide, linear gradient). MS ESI calc'd. for $C_7H_8N_5$ $[M+H]^+$ 162. found 162. $^1H$ NMR (2H isomer, 500 MHz, DMSO-$d_6$) δ 8.03 (s, 2H), 7.56 (t, J=7.9 Hz, 1H), 7.03 (d, J=7.6 Hz, 1H), 6.46 (d, J=8.1 Hz, 1H), 6.39 (s, 2H).

Preparative Example 2.5

2-amino-N,N,6-trimethylpyridine-4-carboxamide

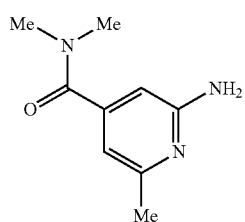

Step 1: DIPEA (1.02 mL, 5.83 mmol), 3-(ethyliminomethyleneamino)-N,N-dimethyl-propan-1-amine (838 mg, 4.37 mmol), and HOBt (669 mg, 4.37 mmol) were added to 2-chloro-6-methylpyridine-4-carboxylic acid (500 mg, 2.91 mmol) in DMF (6 mL) followed by dimethylamine (1.53 mL, 3.06 mmol). The reaction mixture was stirred at room temperature until complete consumption of limiting reagent as judged by LCMS analysis. The reaction mixture was then purified directly by reverse phase HPLC (5-60% acetonitrile/water with 0.1% TFA, linear gradient) to afford 2-chloro-N,N,6-trimethylpyridine-4-carboxamide TFA salt. MS ESI calc'd. for $C_9H_{12}ClN_2O$ $[M+H]^+$ 199. found 199.

Step 2: Dioxane (2.7 mL), 2-chloro-N,N,6-trimethylpyridine-4-carboxamide trifluoroacetate (250 mg, 0.80 mmol), and cesium carbonate (782 mg, 2.40 mmol) were added to benzophenone imine (0.134 mL, 0.80 mmol) in a scintillation vial. The vial was purged and flushed with argon 3 times before adding Xantphos (69 mg, 0.12 mmol) and $Pd_2(dba)_3$ (73 mg, 0.080 mmol). The vial was purged and flushed with argon 3 times before sealing the system and heating to 80° C. for 10 hours. The reaction mixture was cooled to room temperature, and purified directly by silica gel chromatography (10-80% acetone/hexanes, linear gradient) to afford 2-[(diphenylmethylidene)amino]-N,N,6-trimethylpyridine-4-carboxamide. The isolated material was diluted with DCM (1 mL) and TFA (1 mL). The reaction mixture was stirred at room temperature for 2 hours, and then directly purified by reverse phase HPLC (5-30% acetonitrile/water with 0.1% TFA, linear gradient) to afford 2-amino-N,N,6-trimethylpyridine-4-carboxamide TFA salt. MS ESI calc'd. for $C_9H_{14}N_3O$ $[M+H]^+$ 180. found 180. $^1H$ NMR (500 MHz, $CDCl_3$) δ 7.09 (s, 1H), 7.03 (s, 1H), 3.06 (s, 3H), 2.91 (s, 3H), 2.52 (s, 3H).

Preparative Example 2.6

6-methyl-5-(2H-1,2,3-triazol-2-yl)pyridin-2-amine and 6-methyl-5-(1H-1,2,3-triazol-1-yl)pyridin-2-amine

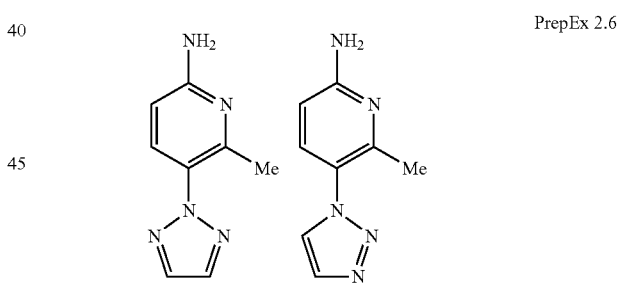

5-Iodo-6-methylpyridin-2-amine (361 mg, 1.54 mmol), DMF (6.17 mL), tribasic potassium phosphate (655 mg, 3.08 mmol), and N,N'-dimethylethylenediamine (27 mg, 0.31 mmol) were added to a microwave vial. The vial was then flushed and purged 3 times with argon before adding copper (I) iodide (15 mg, 0.077 mmol). The vial was again flushed and purged 3 times with argon and was then sonicated for 30 minutes. The vial was heated for 2 hours at 200° C. via microwave irradiation, cooled to room temperature, and then again heated for 16 hours at 200° C. via microwave irradiation. The reaction mixture was filtered and purified by reverse phase HPLC (5-30% acetonitrile/water with 0.1% TFA, linear gradient) to afford a mixture of 6-methylpyridin-2-amine TFA salt, 6-methyl-5-(2H-1,2,3-triazol-2-yl)pyridin-2-amine TFA salt and 6-methyl-5-(1H-1,2,3-triazol-1-yl)pyridin-2-amine TFA salt that was subsequently used without further purification. MS ESI calc'd. for $C_8H_{10}N_5$ $[M+H]^+$ 176. found 176.

Preparative Example 2.7

6-methyl-5-(1-methyl-1H-imidazol-4-yl)pyridin-2-amine

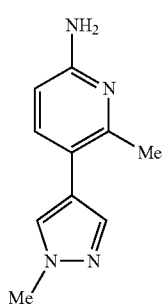

PrepEx 2.7

Dioxane (3.61 mL), 1-methyl-4-(4,4,5,5-tetramethyl-1,3,2-dioxaborolan-2-yl)-1H-imidazole (200 mg, 0.962 mmol), water (0.40 mL) and tribasic potassium phosphate, (511 mg, 2.41 mmol) were added to 5-bromo-6-methylpyridin-2-amine (150 mg, 0.802 mmol) in a scintillation vial. The vial was purged and flushed with argon 3 times before adding $PdCl_2(dppf)\cdot CH_2Cl_2$ adduct (66 mg, 0.080 mmol). The vial was then purged with argon, sealed, and heated to 100° C. After 16 hours, the reaction mixture was cooled to room temperature, filtered through CELITE (washed with chloroform), and diluted with water. The organic layer was dried over sodium sulfate, filtered, and concentrated under reduced pressure. The residue was purified by silica gel chromatography (10-100% (10% methanol in chloroform)/hexanes, linear gradient) to afford 6-methyl-5-(1-methyl-1H-imidazol-4-yl)pyridin-2-amine. MS ESI calc'd. for $C_{10}H_{13}N_4$ $[M+H]^+$ 189. found 189. $^1H$ NMR (500 MHz, $CDCl_3$) δ 7.52 (s, 1H), 7.37 (s, 1H), 7.35 (d, J=8.3 Hz, 1H), 6.38 (d, J=8.3 Hz, 1H), 3.94 (s, 3H), 2.44 (s, 3H).

Preparative Example 2.8

6-(morpholin-4-ylmethyl)pyridin-2-amine

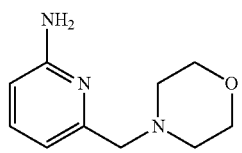

PrepEx. 2.8

Step 1: To a solution of methyl 6-aminopyridine-2-carboxylate (1.0 g, 6.6 mmol) in acetone (8.2 mL) and t-butanol (25 mL) was added di-tert-butyl dicarbonate (2.15 g, 9.86 mmol) and N,N-dimethylpyridin-4-amine (16 mg, 0.13 mmol). After 16 hours, additional di-tert-butyl dicarbonate (1.0 g, 4.6 mmol) was added, and the reaction was stirred for an additional 3 hours. The reaction mixture was concentrated under reduced pressure, and the residue was purified by silica gel chromatography to afford a mixture of methyl 6-[(tert-butoxycarbonyl)amino]pyridine-2-carboxylate and methyl 6-[bis(tert-butoxycarbonyl)amino]pyridine-2-carboxylate that was used in the next step without further purification.

Step 2: To a solution of the product of Step 1 (1.65 g) in THF (17 mL) at 0° C. was added dropwise lithium aluminum hydride (2.0 M in THF, 7.02 mL, 14 mmol). The reaction mixture was stirred at 0° C. for 3 hours. Sodium sulfate decahydrate was added slowly until bubbling ceased. The reaction mixture was filtered, dried over magnesium sulfate, filtered, and concentrated under reduced pressure. The residue was purified by silica gel chromatography to afford tert-butyl [6-(hydroxymethyl)pyridin-2-yl]carbamate. MS ESI calc'd for $C_{11}H_{17}N_2O_3$ $[M+H]^+$ 225. found 225. $^1H$ NMR (500 MHz, DMSO-$d_6$) δ 9.63 (s, 1H), 7.70 (t, J=7.9 Hz, 1H), 7.61 (d, J=8.3 Hz, 1H), 7.08 (d, J=7.4 Hz, 1H), 5.32 (t, J=5.8 Hz, 1H), 4.42 (d, J=5.7 Hz, 2H), 1.43 (s, 9H).

Step 3: To a solution of tert-butyl [6-(hydroxymethyl)pyridin-2-yl]carbamate (252 mg, 1.12 mmol) in acetonitrile (2.5 mL) and diisopropylethylamine (0.59 mL, 3.4 mmol) was added methanesulfonyl chloride (0.094 mL, 1.2 mmol) at 0° C. The reaction mixture was warmed to room temperature and stirred for 2 additional hours. The reaction mixture was quenched with saturated aqueous sodium bicarbonate and the mixture was extracted with ethyl acetate (2×). The combined organic layers were dried over magnesium sulfate, filtered, and concentrated under reduced pressure to afford {6-[(tert-butoxycarbonyl)amino]pyridin-2-yl}methyl methanesulfonate that was used without further purification. MS ESI calc'd for $C_{12}H_{19}N_2O_5S$ $[M+H]^+$ 303. found 303.

Step 4: To a solution of {6-[(tert-butoxycarbonyl)amino]pyridin-2-yl}methyl methanesulfonate (160 mg, 0.52 mmol) in acetonitrile (2.5 mL) was added morpholine (90 mg, 1.0 mmol) and potassium carbonate (214 mg, 1.55 mmol) at room temperature. After 16 hours, the reaction mixture was quenched with aqueous saturated sodium bicarbonate, partially concentrated under reduced pressure, and diluted with ethyl acetate. The organic layer was separated, dried over magnesium sulfate, filtered, and concentrated under reduced pressure to afford tert-butyl [6-(morpholin-4-ylmethyl)pyridin-2-yl]carbamate that was used without further purification. MS ESI calc'd for $C_{15}H_{24}N_3O_3$ $[M+H]^+$ 294. found 294.

Step 5: To a solution of tert-butyl [6-(morpholin-4-ylmethyl)pyridin-2-yl]carbamate (114 mg, 0.39 mmol) in dichloromethane (3 mL) was added trifluoroacetic acid (1.2 mL, 16 mmol) at room temperature. After 3 hours, the reaction mixture was concentrated under reduced pressure, and saturated aqueous sodium carbonate was added to adjust to pH~9. The mixture was extracted with ethyl acetate (3×), and the combined organic layers were dried over magnesium sulfate, filtered, and concentrated under reduced pressure to afford 6-(morpholin-4-ylmethyl)pyridin-2-amine that was used without further purification. MS ESI calc'd for $C_{10}H_{16}N_3O$ $[M+H]^+$ 194. found 194. $^1H$ NMR (500 MHz, DMSO-$d_6$) δ 7.32 (t, J=7.7 Hz, 1H), 6.52 (d, J=7.2 Hz, 1H), 6.30 (d, J=8.2 Hz, 1H), 5.90 (s, 2H), 3.63-3.49 (m, 4H), 3.40-3.25 (m, 2H), 2.41 (s, 4H).

Preparative Example 2.9

6-[(4-methylpiperazin-1-yl)methyl]pyridin-2-amine

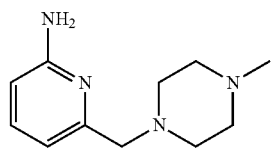

PrepEx. 2.9

Step 1: To a solution {6-[(tert-butoxycarbonyl)amino]pyridin-2-yl}methyl methanesulfonate (156 mg, 0.518 mmol) in acetonitrile (2.5 mL) was added N-methyl piperazine (103 mg, 1.03 mmol) and potassium carbonate (214 mg, 1.55 mmol) at room temperature. After 16 hours, the reaction mixture was quenched with saturated aqueous sodium bicarbonate, partially concentrated under reduced pressure, and then diluted with ethyl acetate. The organic layer was separated, dried over magnesium sulfate, filtered, and concentrated under reduced pressure to afford tert-butyl {6-[(4-methylpiperazin-1-yl)methyl]pyridin-2-yl}carbamate that was used without further purification. MS ESI calc'd for $C_{16}H_{27}N_4O_2$ [M+H]$^+$ 307. found 307.

Step 2: To a solution of tert-butyl {6-[(4-methylpiperazin-1-yl)methyl]pyridin-2-yl}carbamate (103 mg, 0.337 mmol) in dichloromethane (3 mL) was added trifluoroacetic acid (1.2 mL, 16 mmol) at room temperature. After 3 hours, the reaction mixture was concentrated under reduced pressure, and saturated aqueous sodium carbonate was added to adjust to pH~9. The mixture was then extracted with ethyl acetate (3×) and the combined organics were dried over magnesium sulfate, filtered, and concentrated to afford 6-[(4-methylpiperazin-1-yl)methyl]pyridin-2-amine that was used without further purification. MS ESI calc'd for $C_{11}H_{19}N_4$ [M+H]$^+$ 207. found 207. $^1$H NMR (500 MHz, CD$_3$OD) δ 7.46-7.40 (m, 1H), 6.66 (d, J=7.2 Hz, 1H), 6.47 (d, J=8.3 Hz, 1H), 3.47 (s, 2H), 2.85-2.46 (m, 8H), 2.39 (s, 3H).

Preparative Example 2.10

N-(6-aminopyridin-2-yl)methanesulfonamide

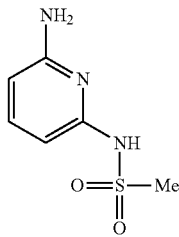

PrepEx 2.10

Pyridine (0.130 mL, 1.60 mmol) was added to pyridine-2,6-diamine (350 mg, 3.21 mmol) in DCM (6.4 mL). The reaction mixture was cooled to 0° C., and then methanesulfonyl chloride (0.124 mL, 1.60 mmol) was added dropwise. The reaction mixture was allowed to warm to room temperature, and then the reaction mixture was concentrated under reduced pressure. The residue was purified by silica gel chromatography (30-100% acetone/hexanes, linear gradient) to afford N-(6-aminopyridin-2-yl)methanesulfonamide (~50% purity) that was used without further purification. MS ESI calc'd. for $C_6H_{10}N_3O_2S$ [M+H]$^+$ 188. found 188.

Preparative Example 2.11

5-methoxy-6-methylpyridin-2-amine

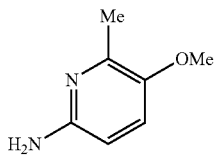

PrepEx 2.11

Toluene (10 mL), sodium tert-butoxide (0.344 g, 3.58 mmol) and benzophenone imine (0.649 g, 3.58 mmol) were added to 6-chloro-3-methoxy-2-methylpyridine (0.47 g, 3.0 mmol) in a scintillation vial. The vial was purged with argon 3 times before 2-dicyclohexylphosphino-2'-(N,N-dimethylamino)biphenyl (0.176 g, 0.447 mmol) and Pd$_2$(dba)$_3$ (0.137 g, 0.149 mmol) were added. The vial was purged 3 times with argon, sealed, and heated to 80° C. After 16 hours, the reaction mixture was cooled to room temperature, diluted with water, and extracted with DCM. The organic layer was dried over sodium sulfate, filtered, and concentrated under reduced pressure. The residue was treated with hydrochloric acid (4.0 M in 1,4-dioxane, 5.0 mL, 20 mmol) and was stirred at ambient temperature. After consumption of the intermediate imine, the reaction mixture was concentrated under reduced pressure and purified by HPLC (5-30% acetonitrile/water with 0.1% TFA, linear gradient) to afford 5-methoxy-6-methylpyridin-2-amine TFA salt. MS ESI calc'd. for $C_7H_{11}N_2O$ [M+H]$^+$ 139. found 139. $^1$H NMR (500 MHz, CDCl$_3$) δ 7.50 (d, J=9.4 Hz, 1H), 6.86 (d, J=9.3 Hz, 1H), 3.82 (s, 3H), 2.49 (s, 3H).

Preparative Example 2.12

6-chloro-4-methylpyridin-2-amine

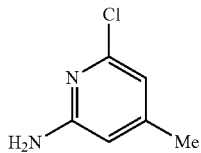

PrepEx 2.12

Step 1: Toluene (27 mL), sodium tert-butoxide (0.925 g, 9.63 mmol), and benzophenone imine (1.75 g, 9.63 mmol) were added to 2,6-dichloro-4-methylpyridine (1.3 g, 8.0 mmol). The flask was purged with argon 3 times before 2-dicyclophenylphosphino-2'-(N,N-dimethylamino)biphenyl (0.474 g, 1.20 mmol) and Pd$_2$(dba)$_3$ (0.367 g, 0.401 mmol) were added. The flask was purged 3 times with argon, sealed, and heated to 80° C. After 16 hours, the reaction mixture was cooled to room temperature, diluted with water, and extracted with DCM. The organic layer was dried over sodium sulfate, filtered, and concentrated under reduced pressure. The residue was purified by silica gel chromatography (0-40% acetone/hexanes, linear gradient) to afford 6-chloro-N-(diphenylmethylidene)-4-methylpyridin-2-amine. $^1$H NMR (500 MHz, CDCl$_3$) δ 7.83-7.73 (m, 2H), 7.49 (t, J=7.6 Hz, 2H), 7.44-7.34 (m, 2H), 7.34-7.27 (m, 2H), 7.21-7.12 (m, 2H), 6.72 (s, 1H), 6.27 (s, 1H), 2.15 (s, 3H).

Step 2: Hydrochloric acid (4.0 M in 1,4-dioxane, 2.0 mL, 8.0 mmol) was added to 6-chloro-N-(diphenylmethylidene)-4-methylpyridin-2-amine (815 mg, 2.66 mmol). The reaction mixture was stirred at room temperature until LCMS analysis indicated consumption of the limiting reagent. The reaction mixture was concentrated under reduced pressure. The residue was purified by HPLC (5-70% acetonitrile/water with 0.1% TFA, linear gradient) to afford 6-chloro-4-methylpyridin-2-amine trifluoroacetate. MS ESI calc'd. for $C_6H_8ClN_2$ [M+H]$^+$ 143. found 143. $^1$H NMR (500 MHz, DMSO-d$_6$) δ 6.34 (s, 1H), 6.15 (s, 1H), 2.10 (s, 3H).

Preparative Example 2.13

4-methyl-6-(1-methyl-1H-pyrazol-5-yl)pyridin-2-amine

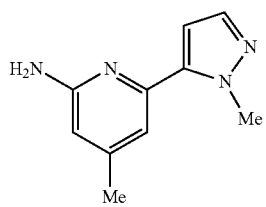

PrepEx 2.13

Dioxane (2.12 mL), water (0.24 mL), tribasic potassium phosphate (300 mg, 1.41 mmol), and 1-methyl-5-(4,4,5,5-tetramethyl-1,3,2-dioxaborolan-2-yl)-1H-pyrazole (120 mg, 0.58 mmol) were added to 6-bromo-4-methylpyridin-2-amine (88 mg, 0.47 mmol) in a scintillation vial. The vial was purged with argon 3 times before PdCl$_2$(dppf)-CH$_2$Cl$_2$ adduct (34 mg, 0.047 mmol) was added. The vial was purged 3 times with argon, sealed, and heated to 100° C. After 1.5 hours, the reaction was cooled to room temperature, filtered through CELITE (washed with dichloromethane), and diluted with water. The organic layer was dried over sodium sulfate, filtered, and concentrated under reduced pressure. The residue was purified by silica gel chromatography (0-70% acetone/hexanes, linear gradient) to afford 4-methyl-6-(1-methyl-1H-pyrazol-5-yl)pyridin-2-amine. MS ESI calc'd. for C$_{10}$H$_{13}$N$_4$ [M+H]$^+$ 189. found 189. $^1$H NMR (500 MHz, CDCl$_3$) δ 7.46 (s, 1H), 6.77 (s, 1H), 6.48 (d, J=1.8 Hz, 1H), 6.30 (s, 1H), 4.15 (s, 3H), 2.28 (s, 3H).

Analogous reaction conditions to those described for the synthesis of 4-methyl-6-(1-methyl-1H-pyrazol-5-yl)pyridin-2-amine (PrepEx 2.13) were used to prepare the following intermediates:

Preparative Example 2.18

2-(2-amino-6-methylpyridin-4-yl)propan-2-ol

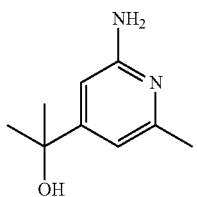

PrepEx 2.18

Step 1: To a solution of methyl 2-chloro-6-methylpyridine-4-carboxylate (325 mg, 1.75 mmol) in THF (10 mL) at −78° C. was added methyl magnesium bromide (3.0 M in THF, 1.3 mL, 3.9 mmol). After the addition, the reaction mixture was allowed to warm to ambient temperature. After 3 hours, the reaction mixture was quenched with aqueous saturated

| Prep Ex No. | Structure | Name | MS ESI [M + H]$^+$ |
|---|---|---|---|
| 2.14 | 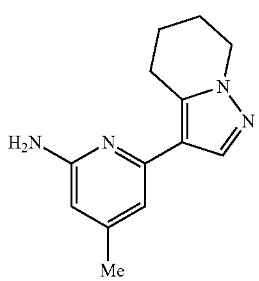 [SMILES: Cc1cc(N)nc(-c2cnn3c2CCCC3)c1] | 4-methyl-6-(4,5,6,7-tetrahydropyrazolo[1,5-a]pyridin-3-yl)pyridin-2-amine | 229 |
| 2.15 | 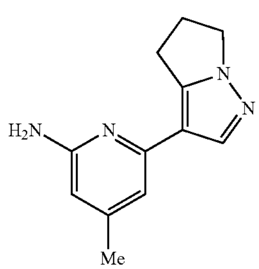 [SMILES: Cc1cc(N)nc(-c2cnn3c2CCC3)c1] | 6-(5,6-dihydro-4H-pyrrolo[1,2-b]pyrazol-3-yl)-4-methylpyridin-2-amine | 215 |
| 2.16 | 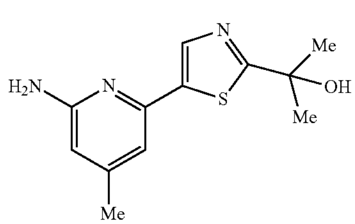 [SMILES: Cc1cc(N)nc(-c2cnc(C(C)(C)O)s2)c1] | 2-[5-(6-amino-4-methylpyridin-2-yl)-1,3-thiazol-2-yl]propan-2-ol | 250 |
| 2.17 | | 4-methyl-6-(1-methyl-1H-pyrazol-4-yl)pyridin-2-amine | 189 | sodium bicarbonate solution (10 mL) and diluted with ethyl acetate (200 mL). The organic layer was separated, dried over magnesium sulfate, filtered, and concentrated under reduced pressure. The residue was purified by chromatography on silica gel (0-100% ethyl acetate/hexanes, linear gradient) to afford 2-(2-chloro-6-methylpyridin-4-yl)propan-2-ol. MS ESI calcd. for $C_9H_{13}ClNO$ [M+H]$^+$ 186. found 186.

Step 2: A flask containing a mixture of 2-(2-chloro-6-methylpyridin-4-yl)propan-2-ol (303 mg, 1.63 mmol), tris(dibenzylideneacetone)dipalladium(0) (149 mg, 0.163 mmol), Xantphos (189 mg, 0.326 mmol), and cesium carbonate (798 mg, 2.45 mmol) was purged with argon for 5 minutes. To this mixture was added 2,4-dimethoxybenzylamine (0.983 mL, 6.53 mmol) and 1,4-dioxane (7 mL). The reaction mixture was purged with argon for 5 minutes, and then heated to 100° C. After 4 hours, the reaction mixture was cooled, diluted with ethyl acetate (50 mL), filtered through CELITE, and concentrated under reduced pressure. The residue was purified by chromatography on silica gel (0-60% ethyl acetate/hexanes, linear gradient) to afford 2-{2-[(2,4-dimethoxybenzyl)amino]-6-methylpyridin-4-yl}propan-2-ol. MS ESI calc'd. for $C_{18}H_{25}N_2O_3$ [M+H]$^+$ 317. found 317. $^1$H NMR (500 MHz, DMSO-d$_6$) δ 7.12 (d, J=8.5 Hz, 1H), 6.51 (d, J=2.5 Hz, 1H), 6.44-6.40 (m, 2H), 6.38 (d, J=7.0 Hz, 2H), 4.90 (s, 1H), 4.30 (d, J=5.5 Hz, 2H), 3.78 (s, 3H), 3.71 (s, 3H), 2.19 (s, 3H), 1.29 (s, 6H).

Step 3: To a solution of 2-{2-[(2,4-dimethoxybenzyl)amino]-6-methylpyridin-4-yl}propan-2-ol (234 mg, 0.740 mmol) in dichloromethane (5 mL) was added TFA (1 mL) at 20° C. After 2 hours, the reaction mixture was concentrated under reduced pressure. The residue was purified by reverse phase HPLC (5-50% acetonitrile/water with 0.1% TFA, linear gradient) to afford 2-(2-amino-6-methylpyridin-4-yl)propan-2-ol. MS ESI calc'd. for $C_9H_{15}N_2O$ [M+H]$^+$ 167. found 167.

Preparative Example 2.19

6-methyl-4-(2H-1,2,3-triazol-2-yl)pyridin-2-amine and 6-methyl-4-(1H-1,2,3-triazol-1-yl)pyridin-2-amine

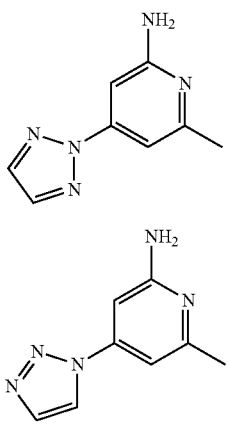

PrepEx 2.19A

PrepEx 2.19B

Step 1: To 4-chloro-6-methylpyridin-2-amine (100 mg, 0.701 mmol) and 1,2,3-triazole (0.133 mL, 2.30 mmol) in a pressure tube was added DIPEA (0.185 mL, 1.06 mmol). The reaction mixture was sealed and heated at 150° C. for 1.5 hours. The reaction mixture was cooled, diluted with DCM (20 mL), and washed with water (10 mL). The organics were separated, dried over sodium sulfate, filtered, and concentrated under reduced pressure. The residue was slurried in 5% methanol/ethyl acetate (5 mL) and sonicated. The mixture was filtered, and the collected solids were dried under reduced pressure to afford 6-methyl-4-(1H-1,2,3-triazol-1-yl)pyridin-2-amine. MS ESI calc'd. for $C_8H_{10}N_5$ [M+H]$^+$ 176. found 176. $^1$H NMR (500 MHz, DMSO-d$_6$) δ 8.79 (s, 1H), 7.95 (s, 1H), 6.90 (s, 1H), 6.75 (s, 1H), 6.28 (s, 2H), 2.23 (s, 3H).

The filtrate was concentrated under reduced pressure, and the residue was purified by silica gel chromatography (2-20% acetone/hexanes, linear gradient) to afford 6-methyl-4-(2H-1,2,3-triazol-2-yl)pyridin-2-amine. MS ESI calc'd. for $C_8H_{10}N_5$ [M+H]$^+$ 176. found 176. $^1$H NMR (500 MHz, DMSO-d$_6$) δ 8.12 (s, 2H), 6.95 (s, 1H), 6.85 (s, 1H), 6.22 (s, 2H), 2.28 (s, 3H).

Preparative Example 2.20

2-(2H-1,2,3-triazol-2-yl)pyrimidin-4-amine

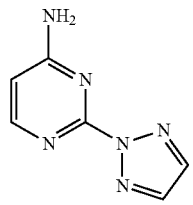

PrepEx 2.20

2-(2H-1,2,3-triazol-2-yl)pyrimidin-4-amine was prepared from 2-chloropyrimidin-4-amine using chemistry analogous to the synthesis of 6-methyl-4-(2H-1,2,3-triazol-2-yl)pyridin-2-amine (PrepEx 2.19 A). MS ESI calc'd. for $C_6H_7N_6$ [M+H]$^+$ 163. found 163. $^1$H NMR (500 MHz, DMSO-d$_6$) δ 8.14 (d, J=5.5 Hz, 1H), 8.06 (s, 2H), 7.42 (s, 2H), 6.46 (d, J=5.5 Hz, 1H).

Preparative Example 2.21

6-methyl-4-morpholinopyridin-2-amine

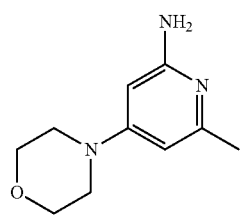

PrepEx 2.21

To 4-chloro-6-methylpyridin-2-amine (150 mg, 1.05 mmol) in a nitrogen purged vial was added morpholine (0.917 mL, 10.5 mmol). The reaction mixture was sealed and heated at 150° C. for 1.5 hours. The reaction mixture was concentrated under reduced pressure. The residue was dissolved in DCM (10 mL) and washed with aqueous saturated sodium bicarbonate solution. The organic layer was dried over sodium sulfate, filtered, and concentrated under reduced pressure. The residue was purified by silica gel chromatography (0-10% methanol/DCM with 1% ammonium hydroxide, linear gradient) to give 6-methyl-4-morpholinopyridin-2-amine. MS ESI calc'd. for $C_{10}H_{16}N_3O$ [M+H]$^+$ 194. found 194. $^1$H NMR (500 MHz, DMSO-$d_6$) δ 6.00 (s, 1H), 5.62 (s, 1H), 5.42 (s, 2H), 3.63 (m, 4H), 3.08 (m, 4H), 2.08 (s, 3H).

Preparative Example 2.22

$N^4,N^4$,6-trimethylpyridine-2,4-diamine

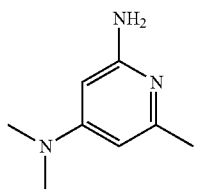

PrepEx 2.22

To 6-amino-4-chloro-2-picoline (500 mg, 3.51 mmol) in a vial under nitrogen was added dimethylamine (40% in water, 17.5 ml, 35.0 mmol). The reaction mixture was sealed and heated at 130° C. in a microwave for 2.5 hours. The reaction mixture was cooled, concentrated under reduced pressure, and purified by silica gel chromatography (2-10% methanol/DCM with 1% ammonium hydroxide, linear gradient) to give $N^4,N^4$,6-trimethylpyridine-2,4-diamine. MS ESI calc'd. for $C_8H_{14}N_3$ [M+H]$^+$ 152. found 152. $^1$H NMR (500 MHz, DMSO-$d_6$) δ 6.15 (s, 2H), 6.02 (s, 1H), 5.54 (s, 1H), 2.90 (s, 6H), 2.18 (s, 3H).

Preparative Example 2.23

1-m-tolyl-1H-pyrazol-3-amine

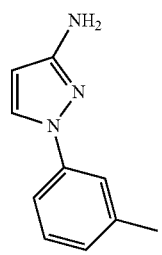

PrepEx 2.23 m-Tolylhydrazine (200 mg, 1.64 mmol), 3-methoxyacrylonitrile (0.137 mL, 1.64 mmol), and sodium ethoxide (111 mg, 1.64 mmol) were dissolved in ethanol (8 mL) and stirred at 80° C. for 2 hours. The reaction mixture was cooled to room temperature, concentrated under reduced pressure, and purified by silica gel chromatography (ethyl acetate/hexanes, linear gradient) to afford 1-m-tolyl-1H-pyrazol-3-amine. MS ESI calc'd. for $C_{10}H_{12}N_3$ [M+H]$^+$ 174. found 174. $^1$H NMR (500 MHz, DMSO-$d_6$) δ 8.08 (s, 1H), 7.46 (s, 1H), 7.40 (d, J=8.5 Hz, 1H), 7.23 (t, J=7.8 Hz, 1H), 6.91 (d, J=7.5 Hz, 1H), 5.69 (d, J=2.5 Hz, 1H), 5.01 (s, 2H), 2.31 (s, 3H).

Preparative Example 2.24

1-(pyridin-2-yl)-1H-pyrazol-3-amine

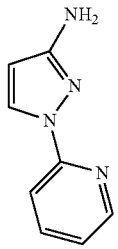

PrepEx 2.24

2-Hydrazinylpyridine (100 mg, 0.92 mmol), 3-methoxyacrylonitrile (0.077 mL, 0.92 mmol) and sodium ethoxide (62 mg, 0.92 mmol) were dissolved in ethanol (4.5 mL) and stirred at 80° C. for 2 hours. The reaction mixture was cooled to room temperature, concentrated under reduced pressure, and purified by silica gel chromatography (ethyl acetate/hexanes, linear gradient) to afford 1-(pyridin-2-yl)-1H-pyrazol-3-amine. The purified material contained impurities and was used without further purification. MS ESI calc'd. for $C_8H_9N_4$ [M+H]$^+$ 161. found 161.

Preparative Example 2.25

6-(1-benzyl-1H-1,2,3-triazol-4-yl)pyridin-2-amine

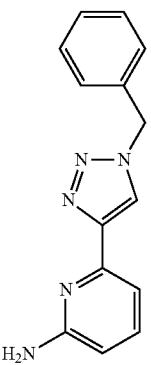

PrepEx 2.25

Sodium ascorbate (34 mg, 0.17 mmol) and copper (II) sulfate pentahydrate (11 mg, 0.042 mmol) were added to a solution of 6-ethynylpyridine-2-amine (100 mg, 0.85 mmol) and benzyl azide (113 mg, 0.846 mmol) in water (5 mL) and ethanol (5 mL). The reaction mixture was stirred vigorously in the absence of light for 14 hours. The reaction mixture was filtered and concentrated under reduced pressure. The residue was purified by silica gel column chromatography (10-100% ethyl acetate/hexanes, linear gradient) to afford 6-(1-benzyl-1H-1,2,3-triazol-4-yl)pyridin-2-amine. MS ESI calc'd. for $C_{14}H_{14}N_5$ [M+H]$^+$ 252. found 252. $^1$H NMR (500 MHz, CD$_3$OD) δ 8.21 (s, 1H), 7.49-7.44 (m, 1H), 7.37-7.26 (m, 5H), 7.22 (d, J=7.4 Hz, 1H), 6.49 (d, J=8.2 Hz, 1H), 5.58 (s, 2H).

Preparative Example 2.26

4-methyl-6-(2H-1,2,3-triazol-2-yl)pyridin-2-amine

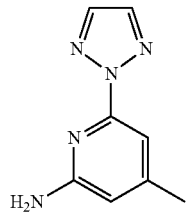

PrepEx 2.26

Step 1: 2,6-Dichloro-4-methylpyridine (2.00 g, 12.3 mmol) was suspended in NMP (10 mL). N,N-Diisopropylethylamine (4.31 mL, 24.7 mmol) and benzylamine (1.42 mL, 13.0 mmol) were added, and the reaction mixture was heated to 150° C. in a microwave for 90 minutes. The reaction mixture was allowed to cool to room temperature, diluted with water, and extracted with diethyl ether (2×). The combined organics were dried over sodium sulfate, filtered, and concentrated under reduced pressure. The residue was purified via silica gel column chromatography (0-10% ethyl acetate/hexanes, linear gradient) to give N-benzyl-6-chloro-4-methylpyridin-2-amine. MS ESI calc'd. for $C_{13}H_{14}ClN_2$ [M+H]$^+$ 233. found 233.

Step 2: N-Benzyl-6-chloro-4-methylpyridin-2-amine (760 mg, 3.27 mmol) and 1,2,3-triazole (1.49 g, 21.6 mmol) were added to N,N-diisopropylethylamine (1.71 mL, 9.80 mmol). The suspension was heated in a microwave at 220° C. for 1.5 hours. The reaction mixture was allowed to cool to room temperature. The residue was diluted with DCM and purified directly via silica gel column chromatography (0-25% ethyl acetate/hexanes, linear gradient) to give a 1:1 regioisomeric mixture of N-benzyl-4-methyl-6-(2H-1,2,3-triazol-2-yl)pyridin-2-amine and N-benzyl-4-methyl-6-(1H-1,2,3-triazol-1-yl)pyridin-2-amine, which was used without further purification. MS ESI calc'd. for $C_{15}H_{16}N_5$ [M+H]$^+$ 266. found 266.

Step 3: The 1:1 regioisomeric mixture of N-benzyl-4-methyl-6-(2H-1,2,3-triazol-2-yl)pyridin-2-amine (316 mg, 1.19 mmol) and N-benzyl-4-methyl-6-(1H-1,2,3-triazol-1-yl)pyridin-2-amine (316 mg, 1.19 mmol) from the previous step was dissolved in methanol (10 mL). Hydrochloric acid (37% in water, 1.96 mL, 23.8 mmol) and palladium on carbon (127 mg, 0.119 mmol, 10 wt %) were added. The flask was fitted with a hydrogen balloon and evacuated and backfilled with hydrogen (3×). The reaction mixture was stirred under an atmosphere of hydrogen for 14 hours. The reaction mixture was filtered, diluted with sodium hydroxide (1.0 M in water, 30 mL, 30 mmol), and extracted with ethyl acetate (3×). The combined organics were dried over sodium sulfate, filtered, and concentrated under reduced pressure. Purification by silica gel chromatography (25-50% ethyl acetate/hexanes, linear gradient) afforded 4-methyl-6-(2H-1,2,3-triazol-2-yl)pyridin-2-amine. MS ESI calc'd. for $C_8H_{10}N_5$ [M+H]$^+$ 176. found 176. $^1$H NMR (500 MHz, CD$_3$OD) δ 7.93 (s, 2H), 7.11 (s, 1H), 6.40 (s, 1H), 2.30 (s, 3H).

Preparative Example 2.27

5-methylthieno[2,3-c]pyridin-7-amine

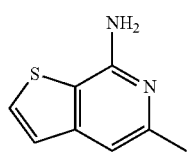

PrepEx 2.27

Step 1: A mixture of 7-chloro-5-methyl-thieno[2,3-c]-pyridine (100 mg, 0.544 mmol) and 2,4-dimethoxybenzylamine (0.245 mL, 1.63 mmol) in 1-methyl-2-pyrrolidinone (2 mL) was heated to 180° C. in an oil bath for 19 hours. After cooling to room temperature, the reaction mixture was diluted with ethyl acetate (30 mL) and aqueous phosphate buffer (1.0 M, pH 7, 20 mL). The separated organics were sequentially washed with water (10 mL), aqueous phosphate buffer (1.0 M, pH 7, 10 mL), water (10 mL), and brine (10 mL). The organics were dried over sodium sulfate, filtered, and concentrated under reduced pressure. The residue was purified by chromatography on silica gel (5-25% ethyl acetate/hexanes, linear gradient) to give N-(2,4-dimethoxybenzyl)-5-methylthieno[2,3-c]pyridin-7-amine. MS ESI calc'd. for $C_{17}H_{19}N_2O_2S$ [M+H]$^+$ 315. found 315.

Step 2: A solution of N-(2,4-dimethoxybenzyl)-5-methylthieno[2,3-c]pyridin-7-amine (235 mg, 0.747 mmol) in trifluoroacetic acid (6 mL) was heated to 40° C. for 1 hour. After cooling to room temperature, the reaction mixture was concentrated under reduced pressure. Toluene was added to the flask and the reaction mixture was concentrated under reduced pressure again. The residue was diluted with 10% 2-propanol/chloroform (30 mL), saturated aqueous sodium bicarbonate solution (20 mL), and saturated aqueous sodium carbonate solution (10 mL). The layers were separated, and the aqueous layer was extracted with additional 10% 2-propanol/chloroform (2×10 mL). The combined organics were washed with brine, dried over sodium sulfate, filtered, and concentrated under reduced pressure. The residue was purified by chromatography on silica gel (1-5% methanol/dichloromethane, linear gradient) to afford 5-methylthieno[2,3-c]pyridin-7-amine. MS ESI calc'd. for $C_8H_9N_2S$ [M+H]$^+$ 165. found 165. $^1$H NMR (500 MHz, CDCl$_3$) δ 7.54 (d, J=5.3 Hz, 1H), 7.23 (d, J=5.3 Hz, 1H), 7.03 (s, 1H), 4.66 (s, 2H), 2.49 (s, 3H).

Preparative Example 2.28

1-[(6-aminopyridin-2-yl)methoxy]-2-methylpropan-2-ol

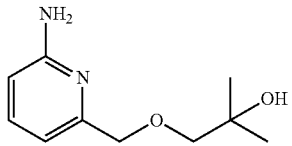

PrepEx 2.28

Step 1: To a suspension of sodium hydride (60% in mineral oil, 72 mg, 1.8 mmol) in DMF (3.30 mL) at 0° C. was added dropwise a mixture of 2-bromo-6-(bromomethyl)pyridine (493 mg, 1.97 mmol) and methyl glycolate (148 mg, 1.64 mmol) in DMF (1.5 mL), and the reaction mixture was stirred for 2 hours at 0° C. The reaction mixture was quenched with 1:1 isopropanol:methanol (5 mL) and then poured over ice. The reaction mixture was diluted with water and diethyl ether. The organics were separated, dried over magnesium sulfate, filtered, and concentrated under reduced pressure. The residue was purified by chromatography on silica gel to afford methyl [(6-bromopyridin-2-yl)methoxy]acetate. MS ESI calc'd. for $C_9H_{11}BrNO_3$ [M+H]$^+$ 260 and 262. found 260 and 262. $^1$H NMR (500 MHz, CDCl$_3$) δ 7.58 (t, J=7.7 Hz, 1H), 7.49 (d, J=7.5 Hz, 1H), 7.40 (d, J=7.8 Hz, 1H), 4.72 (s, 2H), 4.23 (s, 2H), 3.78 (s, 3H).

Step 2: To a solution of methyl [(6-bromopyridin-2-yl)methoxy]acetate (2.63 g, 10.1 mmol) in dichloromethane (60 mL) was added methylmagnesium bromide (3.0 M in diethyl ether, 7.40 mL, 22 mmol) and the reaction mixture was stirred for 1 hour. Saturated aqueous ammonium chloride was added, and the solution was diluted with diethyl ether and water. The organics were separated, dried over magnesium sulfate, filtered, and concentrated under reduced pressure. The residue was purified by chromatography on silica gel to afford 1-[(6-bromopyridin-2-yl)methoxy]-2-methylpropan-2-ol. MS ESI calc'd. for $C_{10}H_{15}BrNO_2$ $[M+H]^+$ 260 and 262. found 260 and 262. $^1$H NMR (500 MHz, CDCl$_3$) δ 7.57 (t, J=7.7 Hz, 1H), 7.41 (d, J=3.0 Hz, 1H), 7.39 (d, J=3.2 Hz, 1H), 4.68 (s, 2H), 3.42 (s, 2H), 2.45 (s, 1H), 1.26 (s, 6H).

Step 3: To a flask containing 1-[(6-bromopyridin-2-yl)methoxy]-2-methylpropan-2-ol (500 mg, 1.92 mmol), benzyl carbamate (349 mg, 2.31 mmol), Pd$_2$(dba)$_3$ (88 mg, 0.096 mmol), Xantphos (111 mg, 0.192 mmol) and cesium carbonate (939 mg, 2.88 mmol) was added degassed dioxane (15 mL). The flask was evacuated/purged with argon 5 times. The reaction mixture was heated to 80° C. for 18 hours. The reaction mixture was allowed to cool to room temperature, diluted with ethyl acetate, washed with water, dried over magnesium sulfate, filtered, and concentrated under reduced pressure. The residue was purified by chromatography on silica gel (0-50% ethyl acetate/hexanes, linear gradient) to afford benzyl {6-[(2-hydroxy-2-methylpropoxy)methyl]pyridin-2-yl}carbamate. MS ESI calc'd. for $C_{18}H_{23}N_2O_4$ $[M+H]^+$ 331. found 331. $^1$H NMR (500 MHz, CDCl$_3$) δ 7.88 (d, J=8.4 Hz, 1H), 7.69 (t, J=7.9 Hz, 1H), 7.46-7.30 (m, 5H), 7.07 (d, J=7.5 Hz, 1H), 5.22 (s, 2H), 4.57 (s, 2H), 3.39 (s, 2H), 1.24 (s, 6H).

Step 4: To a solution of benzyl {6-[(2-hydroxy-2-methylpropoxy)methyl]pyridin-2-yl}carbamate (368 mg, 1.11 mmol) in methanol (11 mL) was added palladium on carbon (10% w/w, 119 mg, 1.11 mmol). A hydrogen balloon was fitted on top of the flask and the flask was evacuated and then backfilled with hydrogen. The reaction mixture was stirred at room temperature for 1 hour. The reaction mixture was filtered through CELITE, and the CELITE was washed with methanol. The filtrate was concentrated under reduced pressure. The residue was purified by silica gel chromatography (0-12% methanol/DCM, linear gradient) to afford 1-[(6-aminopyridin-2-yl)methoxy]-2-methylpropan-2-ol. MS ESI calc'd. for $C_{10}H_{17}N_2O_2$ $[M+H]^+$ 197. found 197. $^1$H NMR (500 MHz, CDCl$_3$) δ 7.42 (t, J=7.8 Hz, 1H), 6.69 (d, J=7.3 Hz, 1H), 6.39 (d, J=8.2 Hz, 1H), 4.53 (s, 2H), 4.49 (s, 1H), 3.41 (s, 2H), 1.23 (s, 6H).

Preparative Example 2.29

4-methoxy-6-methylpyridin-2-amine

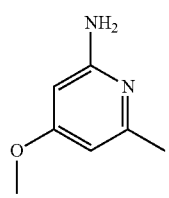

PrepEx 2.29

To 4-chloro-6-methylpyridin-2-amine (1.0 g, 7.0 mmol) was added sodium methoxide (25% solution in methanol, 9.2 ml, 35 mmol) under a nitrogen atmosphere. The reaction mixture was heated in a microwave at 130° C. for 12 hours. The reaction mixture was quenched with hydrochloric acid (1.0 M in water, 42 ml, 42 mmol), and the reaction mixture was partially concentrated under reduced pressure to remove methanol. The residue was diluted with ethyl acetate, and the pH was adjusted to ~7.5 with saturated aqueous sodium bicarbonate solution. The organics were separated, dried over sodium sulfate, filtered, and concentrated under reduced pressure. The residue was purified by silica gel chromatography (dichloromethane/methanol with ammonium hydroxide, linear gradient) to afford 4-methoxy-6-methylpyridin-2-amine. MS ESI calc'd. for $C_7H_{11}N_2O$ $[M+H]^+$ 139. found 139. $^1$H NMR (500 MHz, DMSO-d$_6$) δ 5.96 (d, J=1.5 Hz, 1H), 5.75 (d, J=2.0 Hz, 1H), 5.70 (br s, 2H), 3.66 (s, 3H), 2.13 (s, 3H).

Preparative Example 3

Preparation of E Moiety Precursors

Preparative Example 3.1

3-(4,4,5,5-tetramethyl-1,3,2-dioxaborolan-2-yl)-5,6-dihydro-4H-pyrrolo[1,2-b]pyrazole

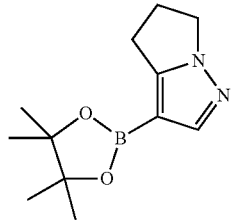

PrepEx 3.1

Step 1: To a solution of 4-chloro-butyric acid (50.0 g, 408 mmol) in ethanol (1.2 L) was added thionyl chloride (60.0 mL, 816 mmol) at 0° C. The reaction mixture was then heated to reflux. After 2 hours, the reaction mixture was cooled to ambient temperature, and then concentrated under reduced pressure. The residue was dissolved in diethyl ether (1000 mL) and then titanium isopropoxide (11.0 mL, 36.8 mmol) and ethylmagnesiumbromide (3.0 M in diethyl ether, 290 mL, 870 mmol) were added dropwise at ambient temperature. After 1.5 hours, the reaction mixture was quenched with 10% aqueous hydrochloride acid at 0° C. The mixture was extracted with diethyl ether (3×250 mL). The organics were combined, washed with saturated aqueous sodium bicarbonate solution and brine, dried over magnesium sulfate, and concentrated under reduced pressure. The residue was purified by chromatography on silica gel to afford 1-(3-chloropropyl)cyclopropanol.

Step 2: Bromine (2.0 mL, 39 mmol) was added slowly to a solution of 1-(3-chloropropyl)cyclopropanol (5.0 g, 34 mmol) in isopropanol (80% solution in water, 30 mL) at 0° C. The reaction mixture was stirred at ambient temperature for 1 hour and then was quenched with water (15 mL) and extracted with ethyl acetate (3×30 mL). The organic layers were combined, dried over magnesium sulfate, filtered, and concentrated under reduced pressure to afford 1-bromo-6-chlorohexan-3-one, which was used without further purification.

Step 3: Triethylamine (7.1 mL, 51 mmol) was slowly added to a solution of 1-bromo-6-chlorohexan-3-one in diethyl ether (30 mL) at ambient temperature. After 16 hours, the reaction mixture was concentrated under reduced pressure to afford 6-chlorohex-1-en-3-one, which was used without further purification.

Step 4: To a solution of 6-chlorohex-1-en-3-one (from step 3) in isopropanol (80% solution in water, 30 mL) at 0° C. were added potassium bromide (4.8 g, 40 mmol) and bromine (2.0 mL, 39 mmol). After 1 hour, the reaction mixture was quenched with water (15 mL) and extracted with ethyl acetate (3×30 mL). The organic layers were combined, dried over magnesium sulfate, filtered, and concentrated under reduced pressure to afford 1,2-dibromo-6-chlorohexan-3-one, which was used without further purification.

Step 5: To a solution of 1,2-dibromo-6-chlorohexan-3-one in isopropanol (80% solution in water, 30 mL) at ambient temperature was added hydrazine hydrate (8.4 g, 170 mmol). After 16 hours, the reaction mixture was quenched with water (15 mL) and extracted with ethyl acetate (3×30 mL). The organic layers were dried over magnesium sulfate, filtered, and concentrated under reduced pressure to afford 3-(3-chloropropyl)-1H-pyrazole, which was used without further purification.

Step 6: To a solution of 3-(3-chloropropyl)-1H-pyrazole in isopropanol (80% solution in water, 30 mL) was added potassium hydroxide (2.0 g, 36 mmol) and then the reaction mixture was heated to reflux. After 4 hours, the reaction mixture was cooled to ambient temperature, diluted with water (15 mL), and extracted with DCM (3×30 mL). The organic layers were combined, dried over magnesium sulfate, filtered, and concentrated under reduced pressure. The residue was purified by chromatography on silica gel to afford 5,6-dihydro-4H-pyrrolo[1,2-b]pyrazole.

Step 7: To a solution of 5,6-dihydro-4H-pyrrolo[1,2-b]pyrazole (47.2 g, 437 mmol) and sodium acetate (36.2 g, 440 mmol) in acetic acid (750 mL) at 0° C. was added bromine (22.4 mL, 435 mmol). After 10 minutes, the reaction mixture was neutralized with saturated aqueous sodium bicarbonate and extracted with ethyl acetate (5×200 mL). The organic layers were combined, dried over magnesium sulfate, and concentrated under reduced pressure to afford 3-bromo-5,6-dihydro-4H-pyrrolo[1,2-b]pyrazole.

Step 8: To a solution of 3-bromo-5,6-dihydro-4H-pyrrolo[1,2-b]pyrazole (73.5 g, 390 mmol) in THF (600 mL) was slowly added n-butyllithium (1.6 M in hexanes, 300 mL, 480 mmol) at −78° C. After 45 minutes, triisopropylborate (111 mL, 480 mmol) was added at −78° C., and the reaction mixture was allowed to warm to ambient temperature. After 1 hour, pinacol (1.8 M in THF, 300 mL, 540 mmol) was added. After 5 minutes, acetic acid (24 mL, 420 mmol) was added. After 30 minutes, the reaction mixture was filtered through CELITE, washed with saturated aqueous sodium bicarbonate solution, and extracted with ethyl acetate (2×500 mL). The organic layers were combined, dried over magnesium sulfate, and concentrated under reduced pressure. The residue was purified by chromatography on silica gel to afford 3-(4,4,5,5-tetramethyl-1,3,2-dioxaborolan-2-yl)-5,6-dihydro-4H-pyrrolo[1,2-b]pyrazole. MS ESI calc'd. for $C_{12}H_{20}BN_2O_2$ [M+H]$^+$ 235. found 235. $^1$H NMR (300 MHz, CDCl$_3$) δ 7.77 (s, 1H), 4.12 (t, J=6.9 Hz, 2H), 2.97 (t, J=6.9 Hz, 2H), 2.60 (t, J=6.9 Hz, 2H), 1.29 (s, 12H).

Preparative Example 3.2

2-[5-(4,4,5,5-tetramethyl-1,3,2-dioxaborolan-2-yl)-1,3-thiazol-2-yl]propan-2-ol

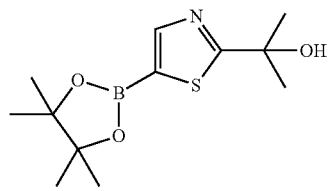

PrepEx 3.2

Step 1: To a −78° C. solution of n-butyllithium (2.5 M in diethyl ether, 160 ml, 0.40 mol) in diethyl ether (300 mL) was added slowly 2-bromo-1,3-thiazole (50 g, 0.30 mol). After 30 minutes, acetone (25 g, 0.43 mol) was added dropwise at −78° C. The reaction mixture was then warmed to ambient temperature, quenched with saturated aqueous ammonium chloride solution, and extracted with ethyl acetate. The organic layer was concentrated under reduced pressure, and the residue was purified by chromatography on silica gel (20% ethyl acetate/hexanes) to give 2-(1,3-thiazol-2-yl)propan-2-ol.

Step 2: To a solution of 2-(1,3-thiazol-2-yl)propan-2-ol (40 g, 0.28 mol) in THF (400 mL) was add n-butyllithium (2.5 M in hexanes, 260 mL, 0.64 mol) dropwise at −78° C. After 30 minutes, 4,4,5,5-tetramethyl-2-(propan-2-yloxy)-1,3,2-dioxaborolane (65 g, 0.35 mol) was added at −78° C. The reaction solution was then stirred at −78° C. After 1 hour, the reaction mixture was quenched with acetic acid, filtered, and concentrated under reduced pressure. The residue was diluted with hydrochloric acid (3.0 M solution in diethyl ether, 110 mL, 0.33 mol) and the mixture was filtered to afford 2-[5-(4,4,5,5-tetramethyl-1,3,2-dioxaborolan-2-yl)-1,3-thiazol-2-yl]propan-2-ol. MS ESI calc'd. for $C_{12}H_{21}BNO_3S$ [M+H]$^+$ 270. found 270. $^1$H NMR (300 MHz, DMSO-d$_6$): δ 8.01 (s, 1H), 1.49 (s, 6H), 1.28 (s, 12H).

Preparative Example 3.3

3-methyl-4-(4,4,5,5-tetramethyl-1,3,2-dioxaborolan-2-yl)isoxazole

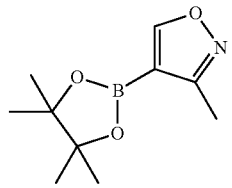

PrepEx 3.3

Step 1: To a solution of trimethylsilylacetylene (125 mL, 881 mmol) in THF (1240 mL) at −78° C. was slowly added n-butyllithium (1.6 M in hexanes, 580 mL, 930 mmol). After 15 minutes, 2-isopropoxy-4,4,5,5-tetramethyl-[1, 3, 2]-dioxaborane (164 g, 881 mmol) was slowly added and the reaction mixture was maintained at −78° C. After 2 hours, the reaction mixture was allowed to warm to ambient temperature and stirred for an additional 30 minutes. The reaction mixture was cooled to −30° C., and the pH was adjusted to 3 using anhydrous hydrochloric acid. The reaction mixture was filtered, and the filtrate was distilled (100-110° C.) to give trimethyl [(4,4,5,5-tetramethyl-1,3,2-dioxaborolan-2-yl)ethynyl]silane. $^1$H NMR (400 MHz, CDCl$_3$) δ 1.28 (s, 12H), 0.19 (s, 9H).

Step 2: To a solution of acetaldoxime (250 g, 4.23 mol) in dimethylformamide (8000 mL) was added N-chlorosuccinimide (565 g, 4.23 mol). The reaction mixture was heated at 50° C. for 3 hours, and then poured into ice, diluted with water (24 L) and extracted with ethyl acetate (3×6000 mL). The combined organic layers were washed with brine (9000 mL), dried over sodium sulfate, filtered, and concentrated under reduced pressure to give (1Z)—N-hydroxyethanimidoyl chloride. $^1$H NMR (400 MHz, CDCl$_3$) δ 8.53 (s, 1H), 2.24 (s, 3H).

Step 3: To a solution of trimethyl[(4,4,5,5-tetramethyl-1,3,2-dioxaborolan-2-yl)ethynyl]silane (240 g, 1.07 mol) in 1,2-dimethoxyethane (8000 mL) was added (1Z)—N-hydroxyethanimidoyl chloride (120 g, 1.28 mol) and potassium hydrogen carbonate (214.4 g, 2.141 mol). The reaction mixture was heated to 50° C. After 16 hours, the reaction mixture was filtered and concentrated under reduced pressure. The residue was purified via chromatography on silica gel (10% ethyl acetate/hexanes, linear gradient) to afford 3-methyl-4-(4,4,5,5-tetramethyl-1,3,2-dioxaborolan-2-yl)-5-(trimethylsilyl)isoxazole. MS ESI calc'd. for $C_{13}H_{24}BNO_3Si$ [M]$^+$ 281. found 281. $^1$H NMR (400 MHz, CDCl$_3$) δ 2.39 (s, 3H), 1.31 (s, 12H), 0.37 (s, 9H).

Step 4: To a sealed vessel were charged 3-methyl-4-(4,4,5,5-tetramethyl-1,3,2-dioxaborolan-2-yl)-5-(trimethylsilyl)isoxazole (169 g, 0.569 mol), 25% aqueous ammonia (1500 mL), and ethanol (1500 mL). The reaction mixture was heated to 60° C. After 6 hours, the reaction mixture was concentrated under reduced pressure. The residue was purified via chromatography on silica gel (0-5% methanol/dichloromethane, linear gradient) to give 3-methyl-4-(4,4,5,5-tetramethyl-1,3,2-dioxaborolan-2-yl)isoxazole. MS ESI calc'd. for $C_{10}H_{16}BNO_3$ [M]$^+$ 209. found 209. $^1$H NMR (400 MHz, CDCl$_3$) δ 8.54 (s, 1H), 2.40 (s, 3H), 1.31 (s, 12H).

Preparative Example 4

Preparation of A Moiety Precursors

Preparative Example 4.1 tert-butyl [1-(aminomethyl)cyclopropyl]carbamate

PrepEx 4.1

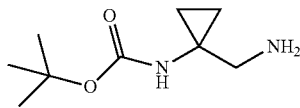

Step 1: To a solution of potassium cyanide (600 g, 9.22 mol) in methanol (10 L) was added formaldehyde (38% solution in water, 1457 g, 18 mol) dropwise at 0° C. After 1 hour, di-tert-butyl dicarbonate (3018 g, 13.83 mol) was added batchwise at 0° C. The reaction mixture was allowed to warm to ambient temperature. After 4 hours, the reaction mixture was quenched with water (2 L) and extracted with ethyl acetate (4×2 L). The organics were combined, dried over sodium sulfate, filtered, and concentrated under reduced pressure to afford tert-butyl cyanomethyl carbonate. The product was used without further purification.

Step 2: To a solution of tert-butyl cyanomethyl carbonate (1000 g, 6.36 mol) in diethyl ether (10 L) was added tetraisopropoxytitanium (1988 g, 6.995 mol) followed by ethylmagnesium bromide (1866 g, 14.00 mol) at 0° C. The reaction mixture was allowed to warm to ambient temperature. After 4 hours, the reaction mixture was quenched with water (1000 mL) and extracted with diethyl ether (3×2000 mL). The combined organics were dried over sodium sulfate, filtered, and concentrated under reduced pressure to afford the crude residue. The residue was washed with petroleum ether (3×200 mL) to afford tert-butyl 1-(hydroxymethyl)cyclopropylcarbamate. The material was used without further purification.

Step 3: To a solution of tert-butyl 1-(hydroxymethyl)cyclopropylcarbamate (290 g, 1.55 mol) in DCM (2900 mL) was added DMAP (227 g, 1.86 mol) followed by 4-methylbenzene-1-sulfonyl chloride (323 g, 1.69 mol) in several batches at 10° C. After 2 hours, the reaction mixture was washed with water (2×1000 mL), dried over sodium sulfate, and concentrated under reduced pressure to afford {1-[(tert-butoxycarbonyl)amino]cyclopropyl}methyl 4-methylbenzenesulfonate. The material was used without further purification.

Step 4: To a solution of {1-[(tert-butoxycarbonyl)amino]cyclopropyl}methyl 4-methylbenzenesulfonate (100 g, 293 mmol) in DMF (1000 mL) was added 18-crown-6 (76.8 g, 291 mmol) and phthalimide potassium salt (80.5 g, 435 mmol). The reaction mixture was heated to 50° C. After 3 hours, the reaction mixture was cooled to ambient temperature, quenched with cold water (2000 mL), and filtered to afford crude solids. The solids were washed with petroleum ether (3×200 mL) and dried under reduced pressure to afford tert-butyl {1-[(1,3-dioxo-1,3-dihydro-2H-isoindol-2-yl)methyl]cyclopropyl}carbamate. The material was used without further purification.

Step 5: To a solution of tert-butyl {1-[(1,3-dioxo-1,3-dihydro-2H-isoindol-2-yl)methyl]cyclopropyl}carbamate (80.0 g, 253 mmol) in methanol (1600 mL) was added hydrazine hydrate (80% solution in water, 15.9 g, 320 mmol). The reaction mixture was heated to reflux. After 4 hours, the reaction mixture was cooled to ambient temperature and concentrated under reduced pressure. The residue was washed with DCM (3×500 mL) and then the combined organic layers were concentrated under reduced pressure. This residue was dissolved in diethyl ether (1000 mL) and diluted with oxalic acid dihydrate (solution in ethanol, 35.2 g, 279 mmol), which was added dropwise. After 1 hour, the precipitated solids were collected by filtration, washed with diethyl ether (4×200 mL), and dried to give tert-butyl [1-(aminomethyl)cyclopropyl]carbamate oxalate salt. MS ESI calc'd. for $C_9H_{19}N_2O_2$ [M+H]$^+$ 187. found 187. $^1$H NMR (400 MHz, D$_2$O) δ 2.98 (s, 2H), 1.36-1.30 (m, 9H), 0.81 (s, 4H).

Preparative Example 4.2 tert-butyl [4-(aminomethyl)tetrahydro-2H-pyran-4-yl]carbamate

PrepEx 4.2

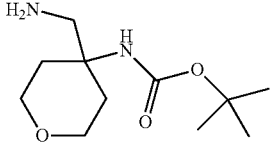

Step 1: To a solution of tetrahydropyran-4-one (150 g, 1.50 mol) in methanol (1500 mL) was added potassium cyanide (6.0 M in water, 400 mL, 2.4 mol), ammonium hydroxide (25% solution in water, 1000 mL, 7.4 mol), and ammonium chloride (161 g, 3.00 mol). The reaction mixture was heated to 70° C. After 16 hours, the reaction mixture was cooled, quenched with cold brine (2000 mL), and extracted with dichloromethane (4×1500 mL). The organic layers were combined, dried over anhydrous magnesium sulfate, filtered, and concentrated under reduced pressure to afford 4-amino-tetrahydro-2H-pyran-4-carbonitrile. The material was used without further purification.

Step 2: To a solution of 4-amino-tetrahydro-2H-pyran-4-carbonitrile (130 g, 1.03 mol) in dichloromethane (1000 mL) was added 4-dimethylaminopyridine (252 g, 2.06 mol) followed by di-tert-butyl dicarbonate (3.33 M in dichloromethane, 300 mL, 1.03 mol) at a temperature maintained between 0-10° C. The reaction mixture was then allowed to warm to ambient temperature. After 16 hours, the reaction mixture was adjusted to pH~7 by the addition of hydrochloric acid (10% aqueous solution). The reaction mixture was extracted with dichloromethane (3×800 mL). The organics were combined, washed with brine (600 mL), dried over magnesium sulfate, filtered, and concentrated under reduced pressure. The residue was purified via chromatography on silica gel (4-12% ethyl acetate/petroleum ether, linear gradient) to afford tert-butyl (4-cyanotetrahydro-2H-pyran-4-yl)carbamate.

Step 3: A mixture of tert-butyl (4-cyanotetrahydro-2H-pyran-4-yl)carbamate (59 g, 260 mmol) and Raney Nickel (25 g) in isopropanol and ammonia (700 mL) was stirred under a hydrogen atmosphere. After 36 hours, the solids were filtered and the filtrate was concentrated under reduced pressure. The residue was recrystallized from DCM (60 mL) to afford tert-butyl [4-(aminomethyl)tetrahydro-2H-pyran-4-yl]carbamate. MS ESI calc'd. for $C_{11}H_{23}N_2O_3$ [M+H]$^+$ 231. found 231. $^1$H NMR (400 MHz, CDCl$_3$) δ 4.42 (s, 1H), 3.77 (d, J=11.6 Hz, 2H), 3.66-3.60 (m, 2H), 2.94 (s, 2H), 1.97-1.94 (d, J=13.6 Hz, 2H), 1.57 (m, 2H), 1.44 (s, 9H), 1.28 (s, 2H).

Preparative Example 4.3 tert-butyl [3-(aminomethyl)tetrahydrofuran-3-yl]carbamate

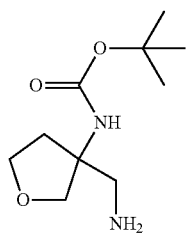

PrepEx 4.3

Step 1: To neat butane-1,2,4-triol (300 g, 2.83 mol) was added 4-methylbenzenesulfonic acid (10 g, 58 mmol). The reaction mixture was heated to 180° C. After 2 hours, the reaction mixture was cooled to ambient temperature and tetrahydrofuran-3-ol was afforded by distillation of the mixture under reduced pressure (10 mm Hg; the product fraction was collected at 46° C.).

Step 2: To a solution of tetrahydrofuran-3-ol (92.5 g, 1.05 mol) in dichloromethane (2000 mL) was added pyridinium chlorochromate (454 g, 2.10 mol) and silica gel (500 g). The reaction mixture was heated to 40° C. After 16 hours, the reaction mixture was filtered, and the filtrate was concentrated under reduced pressure to afford the crude residue. The residue was purified via chromatography on silica gel (methanol/DCM, linear gradient) to afford dihydrofuran-3(2H)-one.

Step 3: To a solution of dihydrofuran-3(2H)-one (10.0 g, 116 mmol) in ammonia (solution in methanol, 100 mL) at 0° C. was added acetic acid (7.67 g, 128 mmol) followed by potassium cyanide (7.56 g, 116 mmol). The reaction mixture was heated to 50° C. After 2 hours, the reaction mixture was cooled to ambient temperature and concentrated under reduced pressure to afford the crude residue. The residue was diluted with aqueous iron sulfate (100 mL) and extracted with ethyl acetate (3×20 mL). The organics were combined, dried over anhydrous sodium sulfate, and concentrated under reduced pressure to afford 3-aminotetrahydrofuran-3-carbonitrile. The material was used without purification.

Step 4: To neat 3-aminotetrahydrofuran-3-carbonitrile (56 g, 500 mmol) was added di-tert-butyl dicarbonate (200 g, 917 mmol). The reaction mixture was heated to reflux. After 2 hours, the reaction mixture was cooled to ambient temperature and concentrated under reduced pressure. The residue was purified via chromatography on silica gel (20% ethyl acetate/petroleum ether) to afford tert-butyl (3-cyanotetrahydrofuran-3-yl)carbamate.

Step 5: A mixture of tert-butyl (3-cyanotetrahydrofuran-3-yl)carbamate (80.0 g, 377 mmol) and Raney Nickel (20 g) in ammonia (solution in methanol, 500 mL) was stirred at ambient temperature under a hydrogen atmosphere. After 16 hours, the reaction mixture was decanted and the residual Raney Nickel was washed with methanol. The reaction mixture was filtered through silica gel and concentrated under reduced pressure. The residue was diluted with ethanol (1000 mL) followed by oxalic acid dropwise (1.3 M solution in ethanol, 200 mL, 260 mmol), and then concentrated under reduced pressure. The residue was diluted with diethyl ether (1000 mL) and filtered. The isolated solids were dried under reduced pressure to afford tert-butyl [3-(aminomethyl)tetrahydrofuran-3-yl]carbamate oxalic acid salt. MS ESI calc'd. for $C_{10}H_{21}N_2O_3$ [M+H]$^+$ 217. found 217. $^1$H NMR (300 MHz, CDCl$_3$) δ 3.96-3.81 (m, 4H), 3.40 (d, J=12.9 Hz, 1H), 3.22 (d, J=12.9 Hz, 1), 2.18-2.07 (m, 2H), 1.48 (s, 9H).

Preparative Example 4.4 tert-butyl (3-amino-1,1,1-trifluoropropan-2-yl)carbamate

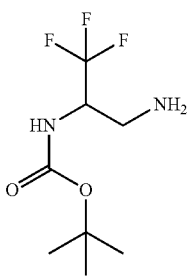

PrepEx 4.4

Step 1: To a solution of 3-bromo-1,1,1-trifluoropropan-2-one (150 g, 789 mmol) in methanol (600 mL) was added sodium borohydride (21 g, 550 mmol) in several batches at 0-5° C. over a period of 3 hours. After 2 hours post-addition, the reaction mixture was quenched with acetic acid (30 g). To this mixture was added dropwise sodium azide (5.22 M solution in water, 150 mL, 785 mmol). The reaction mixture was heated to 70° C. After 16 hours, the reaction mixture was cooled to ambient temperature, and triphenylphosphine (250 g, 954 mmol) was added. The reaction mixture was concentrated under reduced pressure, diluted with water (700 mL), and filtered. The filtrate was extracted with DCM (2×500 mL). To the combined organic layers were added potassium carbonate (2.0 g, 14 mmol) and N-(benzyloxycarbonyloxy) succinimide (1.76 M in acetone, 450 mL, 794 mmol). After 16 hours, the reaction mixture was diluted with dichloromethane (2400 mL), dried over anhydrous sodium sulfate, and concentrated under reduced pressure to afford the crude residue. The residue was purified via chromatography on silica gel (10-20% ethyl acetate/petroleum ether, linear gradient) to afford benzyl (3,3,3-trifluoro-2-hydroxypropyl)carbamate.

Step 2: To a solution of benzyl (3,3,3-trifluoro-2-hydroxypropyl)carbamate (100 g, 380 mmol) in dichloromethane (1700 mL) was added triethylamine (64 g, 630 mmol). The reaction mixture was cooled to −40° C. and triflic anhydride (118 g, 418 mmol) was added dropwise. After 1 hour, the reaction mixture was quenched with water (600 mL) at −40° C., then warmed to ambient temperature and washed with brine (3×600 mL). The organics were dried over anhydrous sodium sulfate, filtered, and concentrated under reduced pressure. The residue was purified via chromatography on silica gel (10% ethyl acetate/petroleum ether) to afford 3-{[(benzyloxy)carbonyl]amino}-1,1,1-trifluoropropan-2-yl trifluoromethanesulfonate.

Step 3: To a solution of 3-{[(benzyloxy)carbonyl]amino}-1,1,1-trifluoropropan-2-yl trifluoromethanesulfonate (150 g, 380 mmol) in DMSO (1200 mL) was added sodium azide (36.5 g, 562 mmol). The reaction mixture was heated to 40° C. After 5 hours, the reaction mixture was diluted with water (1000 mL) and extracted with diethyl ether (3×1200 mL). The organic layers were combined, dried over anhydrous sodium sulfate, filtered, and concentrated under reduced pressure to afford benzyl (2-azido-3,3,3-trifluoropropyl)carbamate. The material was used without further purification.

Step 4: To a solution of benzyl (2-azido-3,3,3-trifluoropropyl)carbamate (107 g, 371 mmol) in tetrahydrofuran (1000 mL) was added cobalt chloride (17.8 g, 137 mmol) followed by sodium borohydride (1.0 M in water, 1.5 L, 1.5 mol) dropwise over a period of 2 hours. After 2 hours post-addition, the reaction mixture was filtered, and the filtrate was extracted with ethyl acetate (3×200 mL). The organics were combined, dried over anhydrous sodium sulfate, filtered, and concentrated under reduced pressure. To the residue was added oxalic acid (0.37 M solution in ethyl acetate, 1.5 L, 560 mmol). After 16 hours, the reaction mixture was filtered to afford benzyl (2-amino-3,3,3-trifluoropropyl)carbamate oxalic acid salt. The material was used without further purification.

Step 5: To a solution of benzyl (2-amino-3,3,3-trifluoropropyl)carbamate oxalic acid salt (110 g, 313 mmol) in tetrahydrofuran (1500 mL) were added triethylamine (80 g, 790 mmol) and di-tert-butyl dicarbonate (140 g, 642 mmol) at ambient temperature. After 30 hours, the reaction mixture was concentrated under reduced pressure. The residue was purified via chromatography on silica gel (1-20% ethyl acetate/petroleum ether, linear gradient) to afford benzyl tert-butyl (3,3,3-trifluoropropane-1,2-diyl)biscarbamate.

Step 6: A mixture of benzyl tert-butyl (3,3,3-trifluoropropane-1,2-diyl)biscarbamate (160 g, 442 mmol) and palladium on carbon (10% w/w, 12 g) in methanol (1500 mL) was stirred at room temperature under a hydrogen atmosphere. After 16 hours, the reaction mixture was filtered. The filtrate was concentrated under reduced pressure, washed with hexane (500 mL), and dried in an oven under reduced pressure to afford tert-butyl (3-amino-1,1,1-trifluoropropan-2-yl)carbamate. MS ESI calc'd. for $C_8H_{16}F_3N_2O_2$ $[M+H]^+$ 229. found 229. $^1$H NMR (400 MHz, CDCl$_3$) δ 5.30 (d, J=6.8 Hz, 1H), 4.23 (s, 1H), 3.10-2.98 (m, 2H), 1.63 (s, 2H), 1.46 (s, 9H).

Preparative Example 4.5 tert-butyl (3-amino-1,1-difluoropropan-2-yl)carbamate

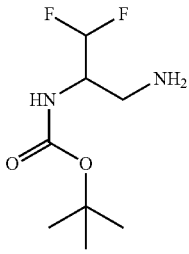

PrepEx 4.5

Step 1: To a solution of ethyl difluoroacetate (500 g, 4.03 mol) in THF (4000 mL) was added dibromomethane (840 g, 4.83 mol) followed by n-BuLi (2.5 M in hexanes, 1920 mL, 4.8 mol) dropwise at −78° C. over a period of 2 hours. After 3 hours post-addition, the reaction mixture was quenched with saturated aqueous ammonium chloride (2500 mL) at −78° C., and then warmed to ambient temperature and extracted with THF (2000 mL). The organics were dried over anhydrous sodium sulfate and filtered. To the filtrate was added sodium borohydride (102 g, 2.68 mol) in several batches at 0-5° C. over a period of 3 hours. After 2 hours, the reaction mixture was quenched with acetic acid (40 g) and water (100 mL). To this mixture was added dropwise sodium azide (6.67 M solution in water, 600 mL, 4.00 mol), and the reaction mixture was heated to 60° C. After 16 hours, triphenylphosphine (3.21 M solution in THF, 1500 mL, 4.81 mol) was added dropwise. After 16 hours, the reaction mixture was diluted with water (5500 mL) and filtered. The filtrate was extracted with DCM (3×2500 mL). To the organics were added potassium carbonate (12 g, 87 mmol) and N-(benzyloxycarbonyloxy)succinimide (2.0 M solution in acetone, 2000 mL, 4.0 mol). After 16 hours, the reaction mixture was partially concentrated under reduced pressure and then extracted with DCM (3×3000 mL). The organics were combined, dried over anhydrous sodium sulfate, and concentrated under reduced pressure. The residue was purified via chromatography on silica gel (10-20% ethyl acetate/petroleum ether, linear gradient) to afford benzyl (3,3-difluoro-2-hydroxypropyl)carbamate.

Step 2: To a solution of benzyl (3,3-difluoro-2-hydroxypropyl)carbamate (300 g, 1.22 mol) in dichloromethane (5000 mL) under a nitrogen atmosphere was added triethylamine (300 g, 2.97 mol). The reaction mixture was cooled to −40° C., and triflic anhydride (420 g, 1.49 mol) was added dropwise over a period of 2 hours. After 2 hours post-addition, the reaction mixture was quenched with water (2500 mL) at −40° C. The organic layer was separated and then washed sequentially with hydrochloric acid (1.0 M in water, 2500 mL), saturated aqueous sodium bicarbonate (2500 mL), and brine (2500 mL). The organic layer was dried over anhydrous sodium sulfate, filtered, and concentrated under reduced pressure to afford 3-{[(benzyloxy)carbonyl]amino}-1,1-difluoropropan-2-yl trifluoromethanesulfonate. The material was used without further purification.

Step 3: To a solution of 3-{[(benzyloxy)carbonyl]amino}-1,1-difluoropropan-2-yl trifluoromethanesulfonate (580 g, 1.54 mol) in DMF (3000 mL) was added sodium azide (240 g, 3.69 mol). After 3 hours, the reaction mixture was diluted with water (3000 mL) and extracted with diethyl ether (3×1500 mL). The organic layers were combined, dried over anhydrous sodium sulfate, filtered, and concentrated under reduced pressure to afford benzyl (2-azido-3,3-difluoropropyl)carbamate. The material was used without further purification.

Step 4: To a solution of benzyl (2-azido-3,3-difluoropropyl)carbamate (305 g, 1.13 mol) (1500 mL) and cobalt chloride (60 g, 460 mmol) in THF was added dropwise sodium borohydride (2.44 M solution in water, 2000 mL, 4.87 mol) over a period of 2 hours. After 2 hours, the reaction mixture was filtered, and the filtrate was extracted with ethyl acetate (2×2000 mL). The organic layers were combined, dried over anhydrous sodium sulfate, filtered, concentrated under reduced pressure, and diluted with oxalic acid (1.22 M solution in ethyl acetate, 1500 mL, 1.83 mol). After 2 hours, the mixture was filtered to afford benzyl (2-amino-3,3-difluoropropyl)carbamate oxalic acid salt. The material was used without further purification.

Step 5: To a solution of benzyl (2-amino-3,3-difluoropropyl)carbamate oxalic acid salt (202 g, 605 mmol) in THF (3000 mL) were added triethylamine (153 g, 1.51 mol) and di-tert-butyl dicarbonate (264 g, 1.21 mol). After 6 hours, the reaction mixture was filtered and concentrated under reduced pressure. The residue was purified by chromatography on silica gel (50% ethyl acetate/petroleum ether) to afford benzyl tert-butyl (3,3-difluoropropane-1,2-diyl)biscarbamate.

Step 6: A mixture of benzyl tert-butyl (3,3-difluoropropane-1,2-diyl)biscarbamate (195 g, 567 mmol) and palladium on carbon (10% w/w, 20 g) in methanol (2000 mL) was stirred at room temperature under a hydrogen atmosphere. After 16 hours, the reaction mixture was filtered and concentrated under reduced pressure. The residue was diluted with DCM (2500 mL) and oxalic acid (2.84 M solution in methanol, 200 mL, 567 mmol). After 2 hours, the mixture was filtered, and the collected solids were washed with DCM (500 mL) and dried in an oven under reduced pressure to afford tert-butyl (3-amino-1,1-difluoropropan-2-yl)carbamate oxalic acid salt. MS ESI calc'd. for $C_8H_{17}F_2N_2O_2$ $[M+H]^+$ 211. found 211. $^1$H NMR (400 MHz, $D_2O$) δ 6.14-5.86 (m, 1H), 4.25 (d, J=12.8 Hz, 1H), 3.36 (d, J=14 Hz, 1H), 3.11-3.05 (m, 1H), 1.41 (s, 9H).

Preparative Example 4.6 tert-butyl [4-(aminomethyl)-1,1-dioxidotetrahydro-2H-thiopyran-4-yl]carbamate

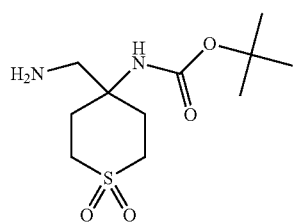

PrepEx 4.6

Step 1: To a solution of tetrahydro-4H-thiopyran-4-one (215 g, 1.85 mol) in ethanol (1500 mL) was bubbled ammonia gas at 0° C. After 4 hours, trimethylsilanecarbonitrile (184 g, 1.86 mol) was added dropwise and then the reaction mixture was allowed to warm to ambient temperature. After 5 hours, the reaction mixture was concentrated under reduced pressure and then diluted with hexane (800 mL). The mixture was filtered, and the solids were washed with hexanes (2×400 mL) and dried under reduced pressure to afford 4-aminotetrahydro-2H-thiopyran-4-carbonitrile. The material was used without further purification.

Step 2: A mixture of 4-aminotetrahydro-2H-thiopyran-4-carbonitrile (151 g, 1.07 mol) and di-tert-butyl dicarbonate (464 g, 2.13 mol) was heated to 80° C. After 3.5 hours, the reaction mixture was concentrated under reduced pressure, and then diluted with water (1000 mL) and extracted with ethyl acetate (2×2000 mL). The organic layers were combined, dried over anhydrous magnesium sulfate, filtered, and concentrated under reduced pressure. The residue was diluted with hexane (1000 mL) and stirred. The mixture was filtered, and the solids were washed with hexane (2×200 mL) and dried under reduced pressure to afford tert-butyl (4-cyanotetrahydro-2H-thiopyran-4-yl)carbamate. The material was used without further purification.

Step 3: To a solution of tert-butyl (4-cyanotetrahydro-2H-thiopyran-4-yl)carbamate (150 g, 620 mmol) in diethyl ether (1500 mL) was added dropwise m-chloroperoxybenzoic acid (3.72 M solution in diethyl ether, 500 mL, 1.86 mol) at 0° C., and then the reaction mixture was allowed to warm to ambient temperature. After 16 hours, the reaction mixture was filtered, and the collected solids were washed with saturated aqueous sodium carbonate (4×300 mL) and dried under reduced pressure to afford tert-butyl (4-cyano-1,1-dioxidotetrahydro-2H-thiopyran-4-yl)carbamate. The material was used without further purification.

Step 4: Methanol (800 mL) was bubbled with ammonia gas. After 1 hour, Raney Nickel (50 g) and tert-butyl (4-cyano-1,1-dioxidotetrahydro-2H-thiopyran-4-yl)carbamate (70 g, 255 mmol) were added. The reaction mixture was stirred under a hydrogen atmosphere. After 16 hours, the reaction mixture was filtered. The filtrate was concentrated under reduced pressure to afford tert-butyl [4-(aminomethyl)-1,1-dioxidotetrahydro-2H-thiopyran-4-yl]carbamate. MS ESI calc'd. for $C_{11}H_{23}N_2O_4S$ $[M+H]^+$ 279. found 279. $^1$H NMR (400 MHz, $CDCl_3$) δ 4.54 (s, 1H), 3.25-3.15 (m, 2H), 3.00-2.90 (m, 4H), 2.64-2.60 (m, 2H), 2.13-2.06 (m, 2H), 1.78 (bs, 2H), 1.45 (s, 9H).

Preparative Example 4.7 tert-butyl rel-[(1R,2R)-2-aminocyclopropyl]carbamate

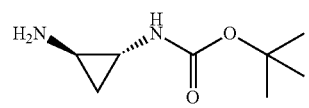

PrepEx 4.7

Step 1: Ethyl-2-chloroacetate (147 g, 1.20 mol) was added to a stirred solution of ethyl prop-2-enoate (150 g, 1.50 mol) in DMF (700 mL) at 0° C. Sodium hydride (60% w/w, 48.0 g, 1.20 mol) was added portion-wise to the reaction mixture at 0° C. over a period of 2 hours. The reaction mixture was allowed to warm to room temperature. After 16 hours, the reaction mixture was quenched with ice water (500 mL) and extracted with ethyl acetate (2×1.0 L). The organic layers were combined, washed with water (500 mL) and then brine (500 mL), dried over anhydrous sodium sulfate, filtered, and concentrated under reduced pressure. The residue was purified by chromatography on silica gel (10-20% ethyl acetate/petroleum ether, linear gradient) to afford diethyl rel-(1R,2R)-cyclopropane-1,2-dicarboxylate. $^1$H NMR (300 MHz, CDCl$_3$) δ 4.20-4.10 (m, 4H), 2.10-2.05 (m, 2H), 1.48-1.40 (m, 2H), 1.35-1.20 (m, 6H).

Step 2: Sodium hydroxide (86.0 g, 2.15 mol) in water (400 mL) was added drop-wise to a stirred solution of diethyl rel-(1R,2R)-cyclopropane-1,2-dicarboxylate (200.0 g, 1.075 mol) in ethanol (400 mL) at 0° C. The reaction mixture was allowed to warm to ambient temperature. After 16 hours, the reaction mixture was concentrated under reduced pressure. The residue was diluted with cold water (500 mL) and extracted with ethyl acetate (2×500 mL). The organic layers were separated, and the aqueous layer was adjusted to pH~2 using 1 N aqueous hydrochloric acid. The aqueous layer was extracted with ethyl acetate (2×1.0 L). The organic layers were combined, washed with water (1.0 L) and brine (500 mL), dried over anhydrous sodium sulfate, filtered, and concentrated under reduced pressure to afford rel-(1R,2R)-cyclopropane-1,2-dicarboxylic acid. $^1$H NMR (400 MHz, DMSO-d$_6$): δ 12.57 (s, 2H), 1.95-1.85 (m, 2H), 1.30-1.20 (m, 2H).

Step 3: Oxalyl chloride (112.0 mL, 1.153 mol) was added drop-wise to a stirred solution of rel-(1R,2R)-cyclopropane-1,2-dicarboxylic acid (60.0 g, 0.461 mol) in dichloromethane (600 mL) at 0° C. DMF (2 mL) was added to the reaction mixture at 0° C., and then the reaction mixture was allowed to warm to ambient temperature. After 2 hours, the reaction mixture was concentrated under reduced pressure to afford rel-(1R,2R)-cyclopropane-1,2-dicarbonyl dichloride. The material was used without further purification.

Step 4: Sodium azide (102 g, 1.57 mol) in water (300 mL) was added to a stirred solution of rel-(1R,2R)-cyclopropane-1,2-dicarbonyl dichloride (75.0 g, 0.449 mol) in acetone (150 mL) at 0° C. The reaction mixture was allowed to warm to ambient temperature. After 2 hours, the reaction mixture was extracted with diethyl ether (2×1.0 L). The organic layers were combined, washed with water (500 mL) and brine (500 mL), dried over anhydrous sodium sulfate, filtered, and partially concentrated to half-volume. The mixture was diluted with toluene (1.0 L), and then partially concentrated under reduced pressure to remove the remaining diethyl ether. The crude solution of rel-(1R,2R)-cyclopropane-1,2-dicarbonyl diazide in toluene was used in the next step without any further manipulation.

Step 5: Crude rel-(1R,2R)-cyclopropane-1,2-dicarbonyl diazide in toluene (from previous step) was heated to 70° C. The temperature was maintained until the evolution of nitrogen gas ceased completely (Caution: the reaction was highly exothermic). After completion of gas evolution, tert-butanol (80.0 mL) was added dropwise to the reaction mixture at 70° C.-80° C. After 2 hours, the reaction mixture was cooled to ambient temperature and then concentrated under reduced pressure. The residue was diluted with ice water (500 mL) and extracted with ethyl acetate (2×1.0 L). The organic layers were combined, washed with water (500 mL) and brine (500 mL), dried over anhydrous sodium sulfate, filtered, and concentrated under reduced pressure to afford di-tert-butyl rel-(1R,2R)-cyclopropane-1,2-diylbiscarbamate. The material was used without further purification.

Step 6: 37% hydrochloric acid (40.0 mL) in ethyl acetate (300 mL) was added dropwise to a solution of di-tert-butyl rel-(1R,2R)-cyclopropane-1,2-diylbiscarbamate (80.0 g) in ethyl acetate (500 mL) at 0° C. The reaction mixture was warmed to ambient temperature. After 16 hours, the reaction mixture was filtered. The collected solids were washed with diethyl ether and then dried under reduced pressure to afford tert-butyl rel-[(1R,2R)-2-aminocyclopropyl]carbamate HCl salt. MS ESI calc'd. for $C_8H_{17}N_2O_2$ [M+H]$^+$ 173. found 173. $^1$H NMR (300 MHz, DMSO-d$_6$) δ: 8.36 (bs, 3H), 7.14 (s, 1H), 2.87-2.86 (m, 1H), 2.50-2.49 (m, 1H), 1.39 (s, 9H), 1.09-1.02 (m, 1H), 0.92-0.86 (m, 1H).

Preparative Example 4.8

3-amino-N$^2$-(tert-butoxycarbonyl)-N-methylalaninamide

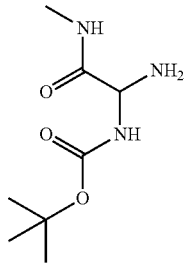

PrepEx 4.8

Step 1: To a mixture of 3-amino-N-(tert-butoxycarbonyl) alanine (5.0 g, 25 mmol), potassium hydroxide (1.6 g, 29 mmol) and potassium carbonate (6.9 g, 29 mmol) in THF (60 mL) and water (20 mL) was added dropwise benzyl chloroformate (5.0 g, 29 mmol) at 0° C. The reaction mixture was allowed to warm to ambient temperature. After 16 hours, the reaction mixture was concentrated under reduced pressure, and the residue was washed with water followed by petroleum ether to afford 3-{[(benzyloxy)carbonyl]amino}-N-(tert-butoxycarbonyl)alanine. MS ESI calc'd. for $C_{16}H_{23}N_2O_6$ [M+H]$^+$ 339. found 339. $^1$H NMR (300 MHz, CD$_3$OD) δ 7.33-7.26 (m, 5H), 5.03 (s, 2H), 4.03-4.01 (m, 1H), 3.49-3.35 (m, 2H), 1.44 (s, 9H).

Step 2: To a solution of 3-{[(benzyloxy)carbonyl]amino}-N-(tert-butoxycarbonyl)alanine (10.0 g, 30.0 mmol) in DMF (100 mL) was added HATU (14.0 g, 36.0 mmol). After 2 hours, methylamine (4.1 g, 60 mmol) and triethylamine (15.0 g, 149 mol) were added. After 16 hours, the reaction mixture was diluted with water and the aqueous layer was extracted with ethyl acetate (3×100 mL). The combined organic layers were dried over sodium sulfate, filtered, and concentrated under reduced pressure. The residue was purified via reverse phase HPLC (acetonitrile/water with 0.1% TFA, linear gradient) to give benzyl {2-[(tert-butoxycarbonyl)amino]-3-(methylamino)-3-oxopropyl}carbamate. MS ESI calc'd. for $C_{17}H_{26}N_3O_5$ [M+H]$^+$ 352. found 352. $^1$H NMR (300 MHz, CDCl$_3$) δ 7.33-7.31 (m, 5H), 6.59-6.57 (m, 1H), 5.69-5.66 (m, 1H), 5.42-5.39 (m, 1H), 5.14-5.05 (m, 2H), 4.19-4.16 (m, 1H), 3.63-3.41 (m, 2H), 2.78 (d, J=4.8 Hz, 3H), 1.43 (s, 9H).

Step 3: To a solution of benzyl {2-[(tert-butoxycarbonyl) amino]-3-(methylamino)-3-oxopropyl}carbamate (2.5 g, 7.4 mmol) in methanol (40 mL) was added palladium on carbon (0.25 g, 10% w/w). The mixture was stirred under a hydrogen atmosphere (50 psi) at 50° C. After 4 hours, the reaction mixture was filtered and concentrated under reduced pressure to afford 3-amino-N$^2$-(tert-butoxycarbonyl)-N-methylalaninamide. MS ESI calc'd. for $C_9H_{20}N_3O_3$ [M+H]$^+$ 218. found 218. $^1$H NMR (400 MHz, CD$_3$OD) δ 4.06-4.02 (m, 1H), 2.93-2.82 (m, 2H), 2.76 (s, 3H), 1.47 (s, 9H).

Preparative Example 4.9 tert-butyl (1-amino-3-ethoxypropan-2-yl)carbamate

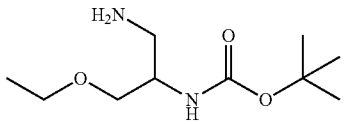

PrepEx 4.9

Step 1: To a solution of N-(tert-butoxycarbonyl)serine (10.26 g, 50.00 mmol) in DMSO (500 mL) was added sodium hydride (2.0 g, 50 mmol) at room temperature. After 1 hour, bromoethane (5.45 g, 50.0 mmol) was added and then additional sodium hydride (2.0 g, 50 mmol) was added immediately. After 16 hours, hydrochloric acid (1.0 M in water, 50 mL, 50 mmol) and water (2 L) were added. The mixture was extracted with ethyl acetate, and the organics were dried over sodium sulfate, filtered, and concentrated under reduced pressure to afford N-(tert-butoxycarbonyl)-O-ethylserine which was used without further purification. MS ESI calc'd. for C$_{10}$H$_{20}$NO$_5$ [M+H]$^+$ 234. found 234.

Step 2: To a mixture of N-(tert-butoxycarbonyl)-O-ethylserine (5.3 g, 22 mmol) and potassium carbonate (6.3 g, 45 mmol) in DMSO (80 mL) was added iodomethane (6.5 g, 45 mmol) at room temperature. After 12 hours, the mixture was diluted with water and extracted with ethyl acetate. The combined organic layers were dried over sodium sulfate, filtered, and concentrated under reduced pressure. The residue was purified via chromatography on silica gel to afford methyl N-(tert-butoxycarbonyl)-O-ethylserinate. MS ESI calc'd. for C$_{11}$H$_{22}$NO$_5$ [M+H]$^+$ 248. found 248. $^1$H NMR (400 MHz, CDCl$_3$) δ 5.36 (d, J=8.0 Hz, 1H), 4.42-4.39 (m, 1H), 3.84-3.81 (m, 1H), 2.75 (s, 3H), 3.64-3.60 (m, 1H), 3.49-3.45 (m, 2H), 1.45 (s, 9H), 1.15 (t, J=7.2 Hz, 3H).

Step 3: To a solution of methyl N-(tert-butoxycarbonyl)-O-ethylserinate (2.7 g, 10.9 mmol) in THF (40 mL) was added lithium aluminum hydride (0.84 g, 22 mmol) at 0° C. The reaction mixture was allowed to warm to ambient temperature. After 1 hour, the reaction mixture was diluted with water, filtered, and concentrated under reduced pressure to give tert-butyl (1-ethoxy-3-hydroxypropan-2-yl)carbamate which was used without further purification. MS ESI calc'd. for C$_{10}$H$_{22}$NO$_4$ [M+H]$^+$ 220. found 220. $^1$H NMR (400 MHz, CDCl$_3$) δ 5.21 (s, 1H), 3.78-3.59 (m, 3H), 3.58-3.56 (m, 2H), 3.52-3.45 (m, 2H), 1.44 (s, 9H), 1.18 (t, J=6.8 Hz, 3H).

Step 4: To a solution of tert-butyl (1-ethoxy-3-hydroxypropan-2-yl)carbamate (2.2 g, 9.4 mmol) in DCM (40 mL) was added methanesulfonylchloride (2.10 g, 18.8 mmol) at 0° C. The reaction mixture was allowed to warm to ambient temperature. After 12 hours, the reaction mixture was concentrated under reduced pressure. The residue was purified via chromatography on silica gel to afford 2-[(tert-butoxycarbonyl)amino]-3-ethoxypropyl methanesulfonate. MS ESI calc'd. for C$_{11}$H$_{24}$NO$_6$S [M+H]$^+$ 298. found 298. $^1$H NMR (400 MHz, CDCl$_3$) δ 4.95 (s, 1H), 4.28 (d, J=8.0 Hz, 1H), 4.13-4.11 (m, 1H), 3.58-3.48 (m, 5H), 3.03 (s, 3H), 1.45 (s, 9H), 1.18 (t, J=6.8 Hz, 3H).

Step 5: To a solution of 2-[(tert-butoxycarbonyl)amino]-3-ethoxypropyl methanesulfonate (1.6 g, 5.4 mmol) in DMF (20 mL) was added sodium azide (1.10 g, 16.2 mmol) and then the reaction mixture was heated to 50° C. After 24 hours, the reaction mixture was diluted with water and the aqueous layer was extracted with ethyl acetate. The combined organic layers were concentrated under reduced pressure and the resulting residue was purified via silica chromatography to give tert-butyl (1-azido-3-ethoxypropan-2-yl)carbamate. MS ESI calc'd. for C$_{10}$H$_{21}$N$_4$O$_3$ [M+H]$^+$ 245. found 245.

Step 6: To a solution of tert-butyl (1-azido-3-ethoxypropan-2-yl)carbamate (1.3 g, 5.4 mmol) in methanol (40 mL) was added palladium on carbon (0.13 g, 10% w/w). The mixture was stirred under a hydrogen (15 psi) atmosphere at room temperature. After 14 hours, the reaction mixture was filtered and concentrated under reduced pressure to give tert-butyl (1-amino-3-ethoxypropan-2-yl)carbamate. MS ESI calc'd. for C$_{10}$H$_{23}$N$_2$O$_3$ [M+H]$^+$ 219. found 219. $^1$H NMR (400 MHz, CD$_3$OD) δ 3.93 (d, J=6.0 Hz, 1H), 3.59-3.51 (m, 3H), 3.45 (dd, J=9.7 Hz, 6.0 Hz, 1H), 3.18 (dd, J=12.8 Hz, 4.4 Hz, 1H), 2.97 (dd, J=12.8 Hz, 8.8 Hz, 1H), 1.48 (s, 9H), 1.22 (t, J=7.0 Hz, 3H).

Preparative Example 4.10 benzyl (2-amino-3-ethoxypropyl)carbamate

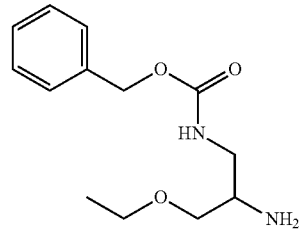

PrepEx 4.10

Step 1: To a mixture of tert-butyl (1-amino-3-ethoxypropan-2-yl)carbamate (0.45 g, 2.6 mol) and sodium carbonate (0.29 g, 3.2 mol) in THF (5 mL) and water (3 mL) was added dropwise benzyl chloroformate (0.58 g, 3.4 mol) at 0° C. and then the reaction mixture was allowed to warm to ambient temperature. After 3 hours, the reaction mixture was concentrated under reduced pressure and the resulting residue was purified via reverse phase HPLC (acetonitrile/water with 0.1% TFA, linear gradient) to give benzyl tert-butyl (3-ethoxypropane-1,2-diyl)biscarbamate. MS ESI calc'd. for C$_{18}$H$_{29}$N$_2$O$_5$ [M+H]$^+$ 353. found 353. $^1$H NMR (400 MHz, CD$_3$OD) δ 7.36-7.35 (m, 5H), 5.09 (s, 2H), 3.52-3.49 (m, 1H), 3.42-3.32 (m, 6H), 1.45 (s, 9H), 1.19 (t, J=7.0 Hz, 3H).

Step 2: A mixture of benzyl tert-butyl (3-ethoxypropane-1,2-diyl)biscarbamate (3.0 g, 8.5 mmol) in hydrochloric acid (4.0 M in methanol, 20 mL, 80 mmol) was stirred at ambient temperature. After 2 hours, the reaction mixture was concentrated under reduced pressure to give benzyl (2-amino-3-ethoxypropyl)carbamate. MS ESI calc'd. for C$_{13}$H$_{21}$N$_2$O$_3$ [M+H]$^+$ 253. found 253. $^1$H NMR (400 MHz, CD$_3$OD) δ 7.45-7.26 (m, 5H), 5.13 (s, 2H), 3.67-3.51 (m, 4H), 3.45-3.39 (m, 3H), 1.24 (t, J=7.0 Hz, 3H).

Preparative Example 4.11 tert-butyl
[1-amino-3-(methylsulfonyl)propan-2-yl]carbamate

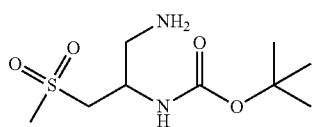

PrepEx 4.11

Step 1: To a solution of N-(tert-butoxycarbonyl)-S-methylcysteine (23.5 g, 0.100 mol) in THF (400 mL) was added dropwise ethylchloroformate (9.6 mL, 0.10 mol) and triethylamine (10.1 g, 0.100 mol) slowly at −10° C. The reaction mixture was stirred at −10° C. for 30 minutes, and then the reaction mixture was diluted with water and extracted with ethyl acetate. The combined organic layers were washed with brine, dried over sodium sulfate, filtered and concentrated under reduced pressure to give ethoxycarbonyl N-(tert-butoxycarbonyl)-S-methylcysteinate which was used without further purification.

Step 2: To a solution of ethoxycarbonyl N-(tert-butoxycarbonyl)-S-methylcysteinate (18.5 g, 60.3 mmol) in methanol (300 mL) was added sodium borohydride (9.12 g, 0.240 mol) at 0° C., and then the reaction mixture was allowed to warm to ambient temperature. After 2 hours, the reaction mixture was diluted with saturated aqueous ammonium chloride solution and extracted with ethyl acetate. The combined organic layers were washed with brine, dried over sodium sulfate, filtered, and concentrated under reduced pressure to give tert-butyl [1-hydroxy-3-(methylsulfanyl)propan-2-yl]carbamate which was used without further purification.

Step 3: To a solution of tert-butyl [1-hydroxy-3-(methylsulfanyl)propan-2-yl]carbamate (14.0 g, 63.3 mmol) in THF (200 mL) was added phthalimide (11.2 g, 76.0 mmol) and triphenylphosphine (25.3 g, 94.9 mmol) under a nitrogen atmosphere. Diethylazodicarboxylate was added dropwise and the reaction mixture was stirred at room temperature. After 2 hours, the reaction mixture was concentrated under reduced pressure. The residue was purified via chromatography on silica gel to afford tert-butyl [1-(1,3-dioxo-1,3-dihydro-2H-isoindol-2-yl)-3-(methylsulfanyl)propan-2-yl]carbamate. MS ESI calc'd. for $C_{17}H_{22}N_2O_4SNa$ [M+Na]$^+$ 373. found 373. $^1$H NMR (400 MHz, $CD_3OD$) δ 7.85-7.77 (m, 4H), 4.16-4.05 (m, 1H), 3.92-3.68 (m, 2H), 2.69-2.15 (m, 2H), 2.15 (s, 3H), 1.25 (s, 9H).

Step 4: To a solution of tert-butyl [1-(1,3-dioxo-1,3-dihydro-2H-isoindol-2-yl)-3-(methylsulfanyl)propan-2-yl]carbamate (10.0 g, 28.6 mmol) in methanol (100 mL) was added Oxone (53.1 g, 85.7 mmol) and water (100 mL). The reaction mixture was stirred at ambient temperature for 3 hours and then quenched with 20% aqueous sodium bisulfite solution, diluted with water, and extracted with DCM. The combined organic layers were washed with brine, dried over sodium sulfate, filtered, and concentrated under reduced pressure to give tert-butyl [1-(1,3-dioxo-1,3-dihydro-2H-isoindol-2-yl)-3-(methylsulfonyl)propan-2-yl]carbamate which was used without further purification. MS ESI calc'd. for $C_{17}H22N_2O_6SNa$ [M+H]$^+$ 405. found 405. $^1$H NMR (400 MHz, $CD_3OD$) δ 7.89-7.81 (m, 4H), 4.51-4.48 (m, 1H), 3.88-3.82 (m, 2H), 3.44-3.40 (m, 2H), 3.01 (s, 3H), 1.26 (s, 9H).

Step 5: To a solution of tert-butyl [1-(1,3-dioxo-1,3-dihydro-2H-isoindol-2-yl)-3-(methylsulfonyl)propan-2-yl]carbamate (10.0 g, 26.2 mmol) in ethanol (150 mL) was added dropwise hydrazine hydrate (15.7 g, 262 mmol) at 0° C., and the reaction mixture was allowed to warm to ambient temperature. After 30 minutes, the reaction mixture was heated to reflux. After two hours, the reaction mixture was cooled, filtered, and concentrated under reduced pressure. The residue was purified via chromatography on silica gel to afford tert-butyl [1-amino-3-(methylsulfonyl)propan-2-yl]carbamate. MS ESI calc'd. for $C_9H_{21}N_2O_4S$ [M+H]$^+$ 253. found 253. $^1$H NMR (400 MHz, $CD_3OD$) δ 4.06-4.00 (m, 1H), 3.30-3.27 (m, 2H), 3.00 (s, 3H), 2.82-2.69 (m, 2H), 1.44 (s, 9H).

Preparative Example 4.12 tert-butyl
[1-amino-3-(methylsulfanyl)propan-2-yl]carbamate

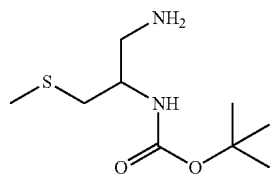

PrepEx 4.12

Step 1: To a solution of tert-butyl [1-(1,3-dioxo-1,3-dihydro-2H-isoindol-2-yl)-3-(methylsulfanyl)propan-2-yl]carbamate (from Step 3 of PrepEx 4.11) (10.0 g, 28.6 mmol) in ethanol (150 mL) was added dropwise hydrazine hydrate (15.7 g, 286 mmol) at 0° C. and then the reaction mixture was allowed to warm to ambient temperature. After 30 minutes, the reaction mixture was heated to reflux. After two hours, the reaction mixture was cooled, filtered, and concentrated under reduced pressure. The residue was purified by chromatography on silica gel to give tert-butyl [1-amino-3-(methylsulfanyl)propan-2-yl]carbamate. MS ESI calc'd. for $C_9H_{21}N_2O_2S$ [M+H]$^+$ 221. found 221. $^1$H NMR (400 MHz, $CD_3OD$) δ 3.66-3.63 (m, 1H), 2.83-2.79 (m, 1H), 2.64-2.50 (m, 3H), 2.12 (s, 3H), 1.45 (s, 9H).

Preparative Example 4.13

3-amino-$N^2$-(tert-butoxycarbonyl)-N,N-dimethylalaninamide

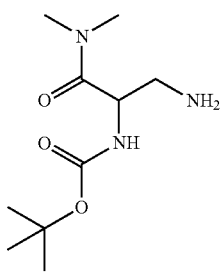

PrepEx 4.13

Step 1: To a solution of 3-{[(benzyloxy)carbonyl]amino}-N-(tert-butoxycarbonyl)alanine (10.0 g, 30.0 mmol) in DMF (100 mL) was added HATU (14.0 g, 36.0 mmol). After 2 hours, dimethylamine (4.9 g, 60 mmol) and triethylamine (15.0 g, 149 mmol) were added. After 16 hours, the reaction mixture was diluted with water and the aqueous layer was extracted with ethyl acetate (3×100 mL). The combined organic layers were dried over sodium sulfate, filtered, and concentrated under reduced pressure. The residue was purified by reverse phase HPLC (acetonitrile/water gradient) to give benzyl {2-[(tert-butoxycarbonyl)amino]-3-(dimethylamino)-3-oxopropyl}carbamate. MS ESI calc'd. for $C_{18}H_{28}N_3O_5$ [M+H]$^+$ 366. found 366. $^1$H NMR (400 MHz, CD$_3$OD) δ 7.33-7.31 (m, 5H), 5.31-5.20 (m, 2H), 4.61-4.48 (m, 1H), 2.93 (s, 3H), 2.87 (s, 3H), 2.74-2.71 (m, 1H), 2.71-2.68 (m, 1H), 1.43 (s, 9H).

Step 2: To a solution of benzyl {2-[(tert-butoxycarbonyl)amino]-3-(dimethylamino)-3-oxopropyl}carbamate (5.5 g, 15 mmol) in methanol (100 mL) was added palladium on carbon (0.55 g, 10% w/w). The reaction mixture was stirred under a hydrogen (50 psi) atmosphere at 50° C. After 4 hours, the reaction mixture was filtered and concentrated under reduced pressure to afford 3-amino-N$^2$-(tert-butoxycarbonyl)-N,N-dimethylalaninamide. MS ESI calc'd. for $C_{10}H_{22}N_3O_3$ [M+H]$^+$ 232. found 232. $^1$H NMR (400 MHz, CD$_3$OD) δ 4.59-4.46 (m, 1H), 2.91 (s, 3H), 2.86 (s, 3H), 2.75-2.72 (m, 1H), 2.71-2.69 (m, 1H) 1.43 (s, 9H).

Preparative Example 4.14 tert-butyl [1-amino-4-(methylsulfonyl)butan-2-yl]carbamate

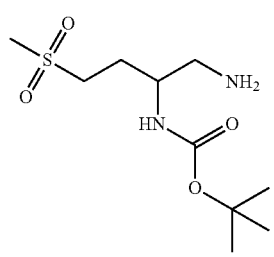

PrepEx 4.14

Step 1: To a solution of methionine (30.0 g, 201 mmol) in methanol (500 mL) was added dropwise thionyl chloride (36 g, 0.30 mol) at 0° C. The reaction mixture was heated to 80° C. After 2 hours, the reaction mixture was concentrated under reduced pressure to give methyl methioninate. The material was used without purification. MS ESI calc'd. for $C_6H_{14}NO_2S$ [M+H]$^+$ 164. found 164. $^1$H NMR (300 MHz, CD$_3$OD) δ 4.19 (t, J=6.6 Hz, 1H), 3.84 (s, 3H), 2.64 (t, J=6.6 Hz, 2H), 2.24-2.12 (m, 2H), 2.10 (s, 3H).

Step 2: To a solution of methyl methioninate (40.0 g, 245 mmol) in DCM (500 mL) was added dropwise triethylamine (60.6 g, 0.600 mol) and di-tert-butyl dicarbonate (52 g, 0.24 mol) at 0° C. The reaction mixture was allowed to warm to ambient temperature. After 8 hours, the reaction mixture was concentrated under reduced pressure and the residue was purified by chromatography on silica gel to give methyl N-(tert-butoxycarbonyl)methioninate. MS ESI calc'd. for $C_{11}H_{22}NO_4S$ [M+H]$^+$ 264. found 264. $^1$H NMR (400 MHz, CDCl$_3$) δ 5.08 (s, 1H), 4.35-4.34 (m, 1H), 3.68 (s, 3H), 2.46 (t, J=6.6 Hz, 2H), 2.03-1.85 (m, 2H), 1.97 (s, 3H), 1.37 (s, 9H).

Step 3: To a solution of methyl N-(tert-butoxycarbonyl)methioninate (47.7 g, 0.181 mol) in THF (500 mL) was added lithium borohydride (16.0 g, 0.734 mol) at 0° C. The reaction mixture was allowed to warm to room temperature. After 2 hours, the reaction mixture was diluted with saturated aqueous ammonium chloride solution and extracted with ethyl acetate. The combined organic layers were washed with brine, dried over sodium sulfate, filtered, and concentrated under reduced pressure to give tert-butyl [1-hydroxy-4-(methylsulfanyl)butan-2-yl]carbamate. MS ESI calc'd. for $C_{10}H_{22}NO_3S$ [M+H]$^+$ 236. found 236. $^1$H NMR (400 MHz, CD$_3$OD) δ 3.68-3.64 (m, 1H), 3.54-3.47 (m, 2H), 2.59-2.48 (m, 2H), 2.10 (s, 3H), 1.88-1.64 (m, 2H), 1.49 (s, 9H).

Step 4: To a solution of tert-butyl [1-hydroxy-4-(methylsulfanyl)butan-2-yl]carbamate (18.5 g, 84.5 mmol) in THF (400 mL) was added phthalimide (14.9 g, 0.101 mol) and triphenylphosphine (26.9 g, 0.101 mol) under a nitrogen atmosphere. Diethylazodicarboxylate (27.3 g, 0.135 mol) was added dropwise at room temperature. After 2 hours, the reaction mixture was concentrated under reduced pressure, and the residue was purified by chromatography on silica gel to give tert-butyl {1-(1,3-dioxo-1,3-dihydro-2H-isoindol-2-yl)-4-(methylsulfanyl)butan-2-yl}carbamate. MS ESI calc'd. for $C_{18}H_{25}N_2O_4S$ [M+H]$^+$ 365. found 365. $^1$H NMR (400 MHz, CDCl$_3$) δ 7.87-7.71 (m, 4H), 4.72 (s, 1H), 4.16-4.07 (m, 1H), 3.76 (d, J=6.6 Hz, 2H), 2.68-2.54 (m, 2H), 2.13 (s, 3H), 1.75-1.55 (m, 2H), 1.35 (s, 9H).

Step 5: To a solution of tert-butyl [1-(1,3-dioxo-1,3-dihydro-2H-isoindol-2-yl)-4-(methylsulfanyl)butan-2-yl]carbamate (29 g, 80 mmol) in methanol (700 mL) was added Oxone (148 g, 0.241 mol) and water (700 mL) at room temperature. After 3 hours, the reaction mixture was quenched with 20% aqueous sodium bisulfate solution, diluted with water, and extracted with DCM. The combined organics were washed with brine, dried over sodium sulfate, filtered, and concentrated under reduced pressure to give tert-butyl [1-(1,3-dioxo-1,3-dihydro-2H-isoindol-2-yl)-4-(methylsulfonyl)butan-2-yl]carbamate which was used in the next step without purification. MS ESI calc'd. for $C_{18}H_{25}N_2O_6S$ [M+H]$^+$ 397. found 397. $^1$H NMR (400 MHz, CD$_3$OD) δ 7.87-7.82 (m, 4H), 4.05-3.95 (m, 1H), 3.77-3.75 (m, 2H), 3.25-3.10 (m, 2H), 3.00 (s, 3H), 2.11-1.89 (m, 2H), 1.24 (s, 9H).

Step 6: To a solution of tert-butyl [1-(1,3-dioxo-1,3-dihydro-2H-isoindol-2-yl)-4-(methylsulfonyl)butan-2-yl]carbamate (25 g, 63 mmol) in ethanol (500 mL) was added dropwise hydrazine hydrate (32 g, 0.63 mol) at 0° C. The reaction mixture was stirred at room temperature for 30 minutes and then heated to reflux. After 2 hours, the reaction mixture was cooled to ambient temperature and filtered. The filtrate was concentrated under reduced pressure, and the residue was purified by chromatography on silica gel to give tert-butyl [1-amino-4-(methylsulfonyl)butan-2-yl]carbamate. MS ESI calc'd. for $C_{10}H_{23}N_2O_4S$ [M+H]$^+$ 267. found 267. $^1$H NMR (300 MHz, CD$_3$OD) δ 3.59-3.54 (m, 1H), 3.29-3.09 (m, 2H), 2.96 (s, 3H), 2.71-2.56 (m, 2H), 2.08-1.76 (m, 2H), 1.45 (s, 9H).

Preparative Example 4.15 tert-butyl [1-(acetylamino)-3-aminopropan-2-yl]carbamate

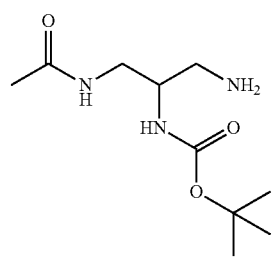

PrepEx 4.15

Step 1: A mixture of 3-{[(benzyloxy)carbonyl]amino}-N-(tert-butoxycarbonyl)alanine (100 g, 0.29 mol), potassium carbonate (82 g, 0.59 mol) and methyl iodide (42 g, 0.29 mol) in DMSO (1200 mL) was stirred at room temperature. After 12 hours, the reaction mixture was extracted with ethyl acetate, and the organics were separated and concentrated under reduced pressure. The residue was purified by chromatography on silica gel to give methyl 3-{[(benzyloxy)carbonyl]amino}-N-(tert-butoxycarbonyl)alaninate. MS ESI calc'd. for $C_{17}H_{25}N_2O_6$ $[M+H]^+$ 353. found 353. $^1$H NMR (400 MHz, $CDCl_3$) δ 7.36-7.33 (m, 5H), 5.09 (s, 2H), 4.34-4.30 (m, 1H), 3.74 (s, 2H), 3.59 (t, J=6.0 Hz, 2H), 2.62 (s, 3H), 1.44 (s, 9H).

Step 2: To a solution of methyl 3-{[(benzyloxy)carbonyl]amino}-N-(tert-butoxycarbonyl)alaninate (80 g, 230 mmol) in THF (800 mL) was added lithium borohydride (20 g, 920 mmol) at 0° C. The reaction mixture was allowed to warm to room temperature. After 1 hour, the reaction mixture was diluted with water and filtered. The filtrate was concentrated under reduced pressure to give benzyl tert-butyl (3-hydroxypropane-1,2-diyl)biscarbamate. MS ESI calc'd. for $C_{16}H_{25}N_2O_5$ $[M+H]^+$ 325. found 325. $^1$H NMR (400 MHz, $CDCl_3$) δ 7.38-7.35 (m, 5H), 5.11 (s, 2H), 4.70 (s, 1H), 4.13-4.11 (m, 1H), 3.66-3.28 (m, 4H), 2.04 (s, 2H), 1.43 (s, 9H).

Step 3: To a mixture of benzyl tert-butyl (3-hydroxypropane-1,2-diyl)biscarbamate (60.0 g, 185 mmol) in DCM (1000 mL) was added methanesulfonylchloride (23 g, 200 mmol) at 0° C. The reaction mixture was allowed to warm to room temperature. After 12 hours, the reaction mixture was concentrated under reduced pressure and purified directly by chromatography on silica gel to give 3-{[(benzyloxy)carbonyl]amino}-2-[(tert-butoxycarbonyl)amino]propyl methanesulfonate. MS ESI calc'd. for $C_{17}H_{27}N_2O_7S$ $[M+H]^+$ 403. found 403. $^1$H NMR (400 MHz, $CD_3OD$) δ 7.34-7.32 (m, 5), 5.17-5.07 (m, 2H), 4.18-4.16 (m, 2H), 4.09-3.91 (m, 1H), 3.29-3.28 (m, 2H), 3.05 (s, 3H), 1.42 (s, 9H).

Step 4: To a solution of 3-{[(benzyloxy)carbonyl]amino}-2-[(tert-butoxycarbonyl)amino]propyl methanesulfonate (20.0 g, 49.7 mmol) in DMF (400 mL) was added sodium azide (8.0 g, 120 mmol). The reaction mixture was heated to 50° C. After 24 hours, the reaction mixture was cooled to ambient temperature and extracted with ethyl acetate. The organic layers were concentrated under reduced pressure to afford benzyl tert-butyl (3-azidopropane-1,2-diyl)biscarbamate. The material was used without purification. MS ESI calc'd. for $C_{16}H_{24}N_5O_4$ $[M+H]^+$ 350. found 350.

Step 5: To a solution of benzyl tert-butyl (3-azidopropane-1,2-diyl)biscarbamate (1.3 g, 5.4 mmol) in methanol (40 mL) was added palladium on carbon (0.13 g, 10% w/w). The mixture was stirred under a hydrogen atmosphere at room temperature. After 14 hours, the reaction mixture was filtered through CELITE, and the filtrate was concentrated under reduced pressure to give benzyl tert-butyl (3-aminopropane-1,2-diyl)biscarbamate. MS ESI calc'd. for $C_{16}H_{26}N_3O_4$ $[M+H]^+$ 324. found 324. $^1$H NMR (400 MHz, $CD_3OD$) 7.28-7.24 (m, 5H), 5.02 (s, 2H), 3.81-3.75 (m, 1H), 3.50-3.42 (m, 2H), 2.68-2.55 (m, 2H), 1.39 (s, 9H).

Step 6: To a solution of benzyl tert-butyl (3-aminopropane-1,2-diyl)biscarbamate (8.0 g, 25 mmol) and triethylamine (7.9 g, 78 mmol) in DCM (100 mL) was added acetic anhydride (2.8 g, 27 mmol) at 0° C. After 1 hour, the reaction mixture was diluted with ethyl acetate. The organic layer was concentrated under reduced pressure and the residue was purified by chromatography on silica gel to give benzyl tert-butyl [3-(acetylamino)propane-1,2-diyl]biscarbamate. MS ESI calc'd. for $C_{18}H_{28}N_3O_5$ $[M+H]^+$ 366. found 366. $^1$H NMR (400 MHz, $CD_3OD$) δ 7.34-7.30 (m, 5H), 5.01 (s, 2H), 3.59-3.51 (m, 3H), 2.87-2.77 (m, 2H), 2.0 (s, 3H), 1.42 (s, 9H).

Step 7: To a solution of benzyl tert-butyl [3-(acetylamino)propane-1,2-diyl]biscarbamate (1.3 g, 3.6 mmol) in methanol (40 mL) was added 10% palladium on carbon (0.13 g, 10% w/w). The reaction mixture was stirred under a hydrogen atmosphere at room temperature. After 14 hours, the reaction mixture was filtered, and the filtrate was concentrated under reduced pressure to give tert-butyl [1-(acetylamino)-3-aminopropan-2-yl]carbamate. MS ESI calc'd. for $C_{10}H_{22}N_3O_3$ $[M+H]^+$ 232. found 232. $^1$H NMR (400 MHz, $CD_3OD$) δ 3.78-3.73 (m, 1H), 3.29-3.24 (m, 2H), 2.89-2.70 (m, 2H), 1.96 (s, 3H), 1.45 (s, 9H).

Preparative Example 4.16 tert-butyl 1-amino-3-hydroxypropan-2-ylcarbamate

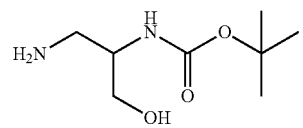

PrepEx 4.16

Benzyl tert-butyl (3-hydroxypropane-1,2-diyl)biscarbamate (400 mg, 1.23 mmol) was dissolved in methanol (12.3 mL) and put under a hydrogen atmosphere with 3 cycles of evacuation and hydrogen balloon flushing. The reaction mixture was stirred at room temperature under a hydrogen atmosphere for 2 hours, and then filtered through CELITE. The filtrate was concentrated under reduced pressure to afford tert-butyl 1-amino-3-hydroxypropan-2-ylcarbamate. MS ESI calcd. for $C_8H_{19}N_2O_3$ $[M+H]^+$ 191. found 191. $^1$H NMR (500 MHz, $CDCl_3$) δ 5.25 (s, 1H), 3.87 (d, J=10.0 Hz, 1H), 3.71 (d, J=10.5 Hz, 1H), 3.59-3.63 (m, 1H), 3.08 (d, J=10.6 Hz, 1H), 2.90 (d, J=10.1 Hz, 1H), 1.84 (s, 2H), 1.45 (s, 9H).

Additional A moiety precursors were prepared using the published procedures which are specified below.

Tert-butyl (1R,2R)-2-amino-3,3-difluorocyclohexylcarbamate was prepared according to the procedures described at pages 51-54 in International Patent Application Publication No. WO 2010/017046. Similarly, the enantiomer, tert-butyl (1S,2S)-2-amino-3,3-difluorocyclohexylcarbamate was prepared analogously.

Tert-butyl rel-(3S,4S)-3-amino-1,1-dioxohexahydro-1-thiopyran-4-ylcarbamate (mixture of cis isomers) and tert-butyl rel-(3R,4S)-3-amino-1,1-dioxohexahydro-1-thiopyran-4-ylcarbamate (mixture of trans isomers) were prepared according to the procedures described in Referential Example No. 179 at page 92 of U.S. Patent Application Publication No. 2005/0020645.

(R)-tert-butyl 1-amino-3-methoxypropan-2-ylcarbamate was prepared according to the procedure described in Preparation 32 at page 87 of U.S. Patent Application Publication No. 2011/0152273. (S)-tert-butyl 1-amino-3-methoxypropan-2-ylcarbamate was prepared according to the procedures described at page 37 in International Patent Application Publication No. WO 2009/136995.

Benzyl tert-butyl (3-hydroxypropane-1,2-diyl)biscarbamate was prepared according to the procedure described at pages 37-38 in International Patent Application Publication No. WO 2006/123020.

Tert-butyl [(3R,4R)-4-aminotetrahydro-2H-pyran-3-yl] carbamate was prepared according to the procedures described at pages 32-39 of International Patent Application Publication No. WO 2010/097248.

Tert-Butyl [(1S,2R)-2-aminocyclohexyl]carbamate is commerically available from Small Molecules, Inc.; CAS: 365996-30-1.

Example 1

Conversions from Scheme 1—Conversion of A1 to Structural Subtype A

The preparations in this example describe the procedure for conversion of A1 to compounds of structural subtype A.

Example 1.1

Preparation of 5-{[(1R,2S)-2-aminocyclohexyl]amino}-3-[(4,6-dimethylpyridin-2-yl)amino]pyridine-2-carboxamide

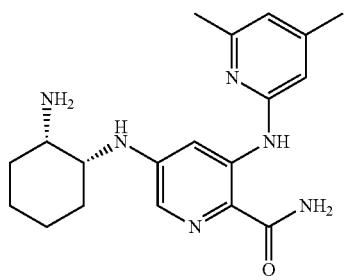

1.1

Step 1: To a flask were added 3-bromo-5-fluoropyridine-2-carbonitrile (14.8 g, 73.5 mmol), tert-butyl [(1S,2R)-2-aminocyclohexyl]carbamate (15 g, 70 mmol) and DIPEA (49 mL, 280 mmol). The resulting mixture was heated at 110° C. After 14 hours, the reaction mixture was cooled to room temperature, diluted with dichloromethane, absorbed on silica gel, and purified via silica gel chromatography to afford tert-butyl {(1S,2R)-2-[(5-bromo-6-cyanopyridin-3-yl)amino]cyclohexyl}carbamate. $^1$H NMR (600 MHz, DMSO-$d_6$) δ 8.06 (s, 1H), 7.22 (s, 1H), 6.86 (d, J=7.8 Hz, 1H), 6.68 (d, J=7.8 Hz, 1H), 3.78 (s, 1H), 3.62 (s, 1H), 1.64-1.44 (m, 6H), 1.30 (s, 9), 1.14-1.08 (m, 2H).

Step 2: To a flask were added tert-butyl {(1S,2R)-2-[(5-bromo-6-cyanopyridin-3-yl)amino]cyclohexyl}carbamate (21.5 g, 54.4 mmol), 2-amino-4,6-dimethylpyridine (9.97 g, 81.7 mmol), $Pd_2(dba)_3$ (2.49 g, 2.72 mmol), Xantphos (3.15 g, 5.44 mmol), cesium carbonate (35.4 g, 109 mmol) and dioxane (215 mL). The mixture was degassed by bubbling nitrogen through the reaction mixture. After 15 minutes, the nitrogen purge was ceased and the reaction mixture was heated to 80° C. After 5 hours, the reaction mixture was cooled to ambient temperature, and filtered through CELITE (washing with ethyl acetate). To the filtrate was added silica gel, and the solvent was removed under reduced pressure. The residue was purified via silica gel chromatography to afford tert-butyl [(1S,2R)-2-({6-cyano-5-[(4,6-dimethylpyridin-2-yl)amino]pyridin-3-yl}amino)cyclohexyl]carbamate. MS ESI calc'd. for $C_{24}H_{33}N_6O_2$ [M+H]$^+$ 437. found 437. $^1$H NMR (600 MHz, DMSO-$d_6$) δ 8.61 (s, 1H), 7.72 (d, J=2.4 Hz, 1H), 7.52 (s, 1H), 6.60 (s, 1H), 6.54 (d, J=8.4 Hz, 1H), 6.53 (s, 1H), 6.33 (d, J=7.2 Hz, 1H), 3.71 (s, 1H), 3.55 (s, 1H), 2.56 (s, 3H), 2.16 (s, 3H), 1.74-1.66 (m, 1H), 1.64-1.54 (m, 2H), 1.51-1.42 (m, 3), 1.32-1.23 (m, 10), 1.12-1.08 (m, 1H).

Step 3: To a flask were added tert-butyl [(1S,2R)-2-({6-cyano-5-[(4,6-dimethylpyridin-2-yl)amino]pyridin-3-yl}amino)cyclohexyl]carbamate (18.9 g, 43.3 mmol) and DMSO (380 mL). The resulting mixture was cooled in an ice bath. To the reaction mixture was added sodium hydroxide (6.0 M in water, 21.7 mL, 130 mmol) followed by the slow addition of hydrogen peroxide (35% solution in water, 7.96 mL, 91 mmol). The addition was performed at such a rate to maintain the internal reaction temperature between 25° C. and 30° C. After 20 minutes, the reaction mixture was slowly diluted with water (500 mL). After 30 minutes, the mixture was filtered, and the collected solids were washed with water and then dried overnight under a nitrogen bag. The collected solids were suspended in ethyl acetate (500 mL) and the resulting slurry was seeded with a previously processed batch of tert-butyl [(1S,2R)-2-({6-carbamoyl-5-[(4,6-dimethylpyridin-2-yl)amino]pyridin-3-yl}amino)cyclohexyl]carbamate. After 1 hour, the mixture was diluted with hexanes (150 mL), filtered, washed with hexanes, and dried in a nitrogen bag to afford tert-butyl [(1S,2R)-2-({6-carbamoyl-5-[(4,6-dimethylpyridin-2-yl)amino]pyridin-3-yl}amino)cyclohexyl]carbamate. MS ESI calc'd. for $C_{24}H_{35}N_6O_3$ [M+H]$^+$ 455. found 455. $^1$H NMR (600 MHz, DMSO-$d_6$) δ 11.68 (s, 1H), 8.51 (d, J=1.8 Hz, 1H), 7.81 (d, J=3.0 Hz, 1H), 7.55 (d, J=1.8 Hz, 1H), 7.21 (s, 1H), 6.54-6.50 (m, 2H), 6.40 (s, 1H), 6.05 (d, J=6.0 Hz, 1H), 3.81 (s, 1H), 3.54 (s, 1H), 2.34 (s, 3H), 2.17 (s, 3H), 1.82-1.76 (m, 1H), 1.72-1.64 (m, 1H), 1.60-1.42 (m, 4H), 1.36-1.28 (m, 1H), 1.27 (s, 9), 1.10-1.06 (m, 1H).

Step 4: tert-Butyl [(1S,2R)-2-({6-carbamoyl-5-[(4,6-dimethylpyridin-2-yl)amino]pyridin-3-yl]amino)cyclohexyl]carbamate (22.5 g, 49.5 mmol) was diluted with dioxane (140 mL). To this solution was added hydrochloric acid (4.0 M in dioxane, 62 mL, 250 mmol). After 30 minutes, the reaction mixture was diluted with hexanes (400 mL) and filtered. The collected solids were dried in a nitrogen bag. The solids were diluted with dioxane (140 mL) followed by hydrochloric acid (4.0 M in dioxane, 62 mL, 250 mmol). After 1 hour, the reaction mixture was diluted with hexanes (400 mL), filtered, and washed with hexanes (2×150 mL). The isolated solids were dried under reduced pressure, and then suspended in dichloromethane (300 mL). After stirring for 3 hours, the mixture was filtered and dried in a nitrogen bag to afford 5-{[(1R,2S)-2-aminocyclohexyl]amino}-3-[(4,6-dimethylpyridin-2-yl)amino]pyridine-2-carboxamide hydrochloric acid salt.

The 5-{[(1R,2S)-2-aminocyclohexyl]amino}-3-[(4,6-dimethylpyridin-2-yl)amino]pyridine-2-carboxamide hydrochloric acid salt (21.5 g, 50.3 mmol) was diluted with methanol (200 mL) and ammonia (7.0 M solution in methanol, 21.6 mL, 151 mmol). After 30 minutes, the reaction mixture was diluted with water (190 mL) and stirred. After 30 minutes, the reaction mixture was filtered, and the solids were washed with water (2×75 mL) and dried to afford 5-{[(1R,2S)-2-aminocyclohexyl]amino}-3-[(4,6-dimethylpyridin-2-yl)amino]pyridine-2-carboxamide. MS ESI calc'd. for $C_{19}H_{27}N_6O$ [M+H]$^+$ 355. found 355. $^1$H NMR (600 MHz, CD$_3$OD) δ 8.47 (d, J=2.4 Hz, 1H), 7.58 (d, J=2.4 Hz, 1H), 6.58 (s, 1H), 6.47 (s, 1H), 3.61-3.49 (m, 1H), 3.26-3.22 (m, 1H), 2.39 (s, 3H), 2.23 (s, 3H), 1.87-1.55 (m, 6H), 1.49-1.39 (m, 2H).

Example 1.2

5-{[(1R,2S)-2-aminocyclohexyl]amino}-3-{[6-(2H-1,2,3-triazol-2-yl)pyridin-2-yl]amino}pyridine-2-carboxamide

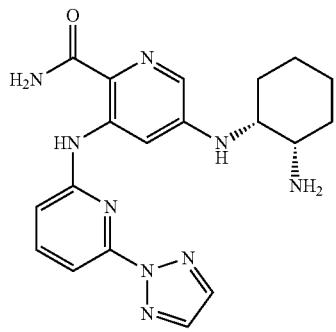

1.2

Dioxane (1.06 mL), 6-(2H-1,2,3-triazol-2-yl)pyridin-2-amine (51 mg, 0.32 mmol) and cesium carbonate (311 mg, 0.955 mmol) were added to tert-butyl {(1S,2R)-2-[(5-bromo-6-cyanopyridin-3-yl)amino]cyclohexyl}carbamate (PrepEx 1.1) (94 mg, 0.32 mmol) in a scintillation vial. The vial was purged and flushed with argon three times before $Pd_2 dba_3$ (29 mg, 0.032 mmol) and Xantphos (28 mg, 0.048 mmol) were added. The vial was purged and flushed 3 times with argon before the vial was sealed and heated to 80° C. After 16 hours, the reaction mixture was cooled to room temperature, filtered through CELITE (washed with dichloromethane), and diluted with water. The organic layer was dried over sodium sulfate, filtered, and concentrated under reduced pressure. The residue was purified by silica gel chromatography (10-70% acetone in hexanes, linear gradient) to afford tert-butyl {(1S,2R)-2-[(6-cyano-5-{[6-(2H-1,2,3-triazol-2-yl)pyridin-2-yl]amino}pyridin-3-yl)amino]cyclohexyl}carbamate. The isolated solids were dissolved in DCM (1 mL) and TFA (1 mL), and stirred at room temperature. After 30 minutes, the reaction mixture was concentrated under reduced pressure. The residue was dissolved in DMSO (1 mL). To this solution was added sodium hydroxide (4.0 M in water, 0.1 mL, 0.4 mmol) and hydrogen peroxide (30 wt % in water, 0.050 mL, 0.49 mmol). The reaction mixture was stirred at room temperature until complete conversion of the nitrile intermediate was observed by LCMS. The reaction mixture was diluted with DMSO and filtered. The filtrate was purified directly by reverse phase HPLC (acetonitrile/water with 0.1% TFA, linear gradient) to afford 5-{[(1R,2S)-2-aminocyclohexyl]amino}-3-{[6-(2H-1,2,3-triazol-2-yl)pyridin-2-yl]amino}pyridine-2-carboxamide TFA salt. MS ESI calc'd. for $C_{19}H_{24}N_9O$ [M+H]$^+$ 394. found 394. $^1$H NMR (500 MHz, $CD_3OD$) δ 9.20 (s, 1H), 8.07 (s, 2H), 7.83 (t, J=8.0 Hz, 1H), 7.80 (d, J=2.5 Hz, 1H), 7.55 (d, J=7.5 Hz, 1H), 6.87 (d, J=7.8 Hz, 1H), 4.38 (s, 1H), 3.75-3.67 (m, 1H), 2.01-1.66 (m, 6), 1.66-1.51 (m, 2H).

Example 1.3

5-{[(2S)-2-aminopropyl]amino}-3-[(4,6-dimethylpyridin-2-yl)amino]pyridine-2-carboxamide

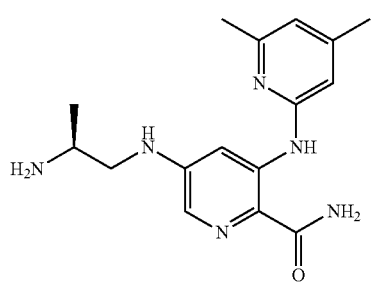

1.3

Step 1: To a microwave vial were added 3-bromo-5-fluoropyridine-2-carbonitrile (150 mg, 0.746 mmol), tert-butyl [(2S)-1-aminopropan-2-yl]carbamate hydrochloride (157 mg, 0.755 mmol), DIPEA (0.260 mL, 1.49 mmol), and N-methyl-2-pyrrolidone (1.5 mL). The mixture was then heated by microwave irradiation to a temperature of 150° C. for 30 minutes. The reaction mixture was cooled to room temperature and then diluted with ethyl acetate and washed with water. The organics were dried over magnesium sulfate, filtered, and concentrated under reduced pressure. The residue was purified by chromatography on silica gel to afford tert-butyl {(2S)-1-[(5-bromo-6-cyanopyridin-3-yl)amino]propan-2-yl}carbamate. MS ESI calc'd. for $C_{14}H_{20}BrN_4O_2$ [M+H]$^+$ 355 and 357. found 355 and 357.

Step 2: To a flask were added tert-butyl {(2S)-1-[(5-bromo-6-cyanopyridin-3-yl)amino]propan-2-yl}carbamate (200 mg, 0.56 mmol), 2-amino-4,6-dimethylpyridine (103 mg, 0.844 mmol), tris(dibenzylideneacetone)dipalladium(0)-dichloromethane complex (52 mg, 0.051 mmol), Xantphos (65 mg, 0.11 mmol), and cesium carbonate (367 mg, 1.13 mmol). 1,4-Dioxane (3 mL) was then added and nitrogen was bubbled into the reaction for 5 minutes. The reaction mixture was then stirred at 80° C. for 16 hours. The reaction mixture was cooled to room temperature and diluted with ethyl acetate. The mixture was washed with saturated aqueous ammonium chloride, and the organics were separated, dried over magnesium sulfate, filtered, and concentrated under reduced pressure. The residue was purified by chromatography on silica gel to afford tert-butyl [(2S)-1-({6-cyano-5-[(4,6-dimethylpyridin-2-yl)-amino]pyridin-3-yl}amino)propan-2-yl]carbamate. MS ESI calc'd. for $C_{21}H_{29}N_6O_2$ [M+H]$^+$ 397. found 397.

Step 3: To a flask containing tert-butyl [(2S)-1-({6-cyano-5-[(4,6-dimethylpyridin-2-yl)amino]pyridin-3-yl}amino)propan-2-yl]carbamate (160 mg, 0.404 mmol) were added DCM (3 mL) and trifluoroacetic acid (0.3 mL). After 1 hour, the reaction mixture was concentrated under reduced pressure to afford 5-{[(2S)-2-aminopropyl]amino}-3-[(4,6-dimethylpyridin-2-yl)amino]pyridine-2-carbonitrile TFA salt. The material was used without further purification. MS ESI calc'd. for $C_{16}H_{21}N_6$ [M+H]$^+$ 297. found 297.

Step 4: To a solution of 5-{[(2S)-2-aminopropyl]amino}-3-[(4,6-dimethylpyridin-2-yl)amino]pyridine-2-carbonitrile TFA salt (166 mg, 0.404 mmol) in DMSO (3 ml) were added hydrogen peroxide (35% aqueous solution, 0.053 ml, 0.61 mmol) and sodium hydroxide (4.0 M aqueous solution, 0.32 mL, 1.3 mmol) at 20° C. After 16 hour, the reaction mixture was purified directly by reverse phase HPLC (acetonitrile/water with 0.1% TFA) to give 5-{[(2S)-2-aminopropyl]amino}-3-[(4,6-dimethylpyridin-2-yl)amino]pyridine-2-carboxamide TFA salt. MS ESI calc'd. for $C_{16}H_{23}N_6O$ [M+H]$^+$ 315. found 315. $^1$H NMR (500 MHz, CD$_3$OD) δ 7.81 (s, 1H), 7.59 (s, 1H), 7.10 (s, 1H), 6.90 (s, 1H), 3.72-3.49 (m, 1H), 3.52-3.33 (m, 2H), 2.53 (s, 3H), 2.40 (s, 3H), 1.39 (d, J=6.6 Hz, 3H).

The following compounds were prepared according to procedures which were analogous to those described in Example 1.

TABLE A

| Ex. No. | A | B | Name | [M + H]$^+$ Calc'd | [M + H]$^+$ Obsv'd | Form(s) |
|---|---|---|---|---|---|---|
| 1.4 | H$_2$N-CH$_2$CH$_2$CH$_2$- | 6-methylpyridin-2-yl | 5-[(2-aminoethyl)amino]-3-[(6-methylpyridin-2-yl)amino]pyridine-2-carboxamide | 287 | 287 | TFA Salt |
| 1.5 | H$_2$N-CH$_2$CH$_2$CH$_2$- | 4,6-dimethylpyridin-2-yl | 5-[(2-aminoethyl)amino]-3-[(4,6-dimethylpyridin-2-yl)amino]pyridine-2-carboxamide | 301 | 301 | TFA Salt |
| 1.6 | (1R,2S)-2-aminocyclohexyl | 5,6-dimethylpyridin-2-yl | 5-{[(1R,2S)-2-aminocyclohexyl]amino}-3-[(5,6-dimethylpyridin-2-yl)amino]pyridine-2-carboxamide | 355 | 355 | TFA Salt |
| 1.7 | (1R,2S)-2-aminocyclohexyl | 6-methylpyridin-2-yl | 5-{[(1R,2S)-2-aminocyclohexyl]amino}-3-[(6-methylpyridin-2-yl)amino]pyridine-2-carboxamide | 341 | 341 | TFA Salt |
| 1.8 | (1R,2S)-2-aminocyclohexyl | 3,5-dimethylphenyl | 5-{[(1R,2S)-2-aminocyclohexyl]amino}-3-[(3,5-dimethylphenyl)amino]pyridine-2-carboxamide | 354 | 354 | TFA Salt |
| 1.9 | (1R,2S)-2-aminocyclohexyl | quinolin-2-yl | 5-{[(1R,2S)-2-aminocyclohexyl]amino}-3-(quinolin-2-ylamino)pyridine-2-carboxamide | 377 | 377 | TFA Salt |

TABLE A-continued

| Ex. No. | A | B | Name | [M + H]+ Calc'd | [M + H]+ Obsv'd | Form(s) |
|---|---|---|---|---|---|---|
| 1.10 | "S" (H₂N-CH(CH₃)-CH₂-) | 1-methyl-1H-imidazol-4-yl / 2-methylpyridin-6-yl | 5-{[(2S)-2-aminopropyl]amino}-3-{[6-methyl-5-(1-methyl-1H-imidazol-4-yl)pyridin-2-yl]amino}pyridine-2-carboxamide | 381 | 381 | TFA Salt |
| 1.11 | "1R, 2S" aminocyclohexyl | 1-methyl-1H-pyrazol-4-yl / 2-methylpyridin-6-yl | 5-{[(1R,2S)-2-aminocyclohexyl]amino}-3-{[6-methyl-5-(1-methyl-1H-pyrazol-4-yl)pyridin-2-yl]amino}pyridine-2-carboxamide | 421 | 421 | TFA Salt |
| 1.12 | "1R, 2S" aminocyclohexyl | 4-chloro-6-methylpyridin-2-yl | 5-{[(1R,2S)-2-aminocyclohexyl]amino}-3-[(4-chloro-6-methylpyridin-2-yl)amino]pyridine-2-carboxamide | 375 | 375 | TFA Salt |
| 1.13 | "1R, 2S" aminocyclohexyl | 6-methoxypyridin-2-yl | 5-{[(1R,2S)-2-aminocyclohexyl]amino}-3-[(6-methoxypyridin-2-yl)amino]pyridine-2-carboxamide | 357 | 357 | TFA Salt |
| 1.14 | "1R, 2S" aminocyclohexyl | 1-phenyl-1H-pyrazol-3-yl | 5-{[(1R,2S)-2-aminocyclohexyl]amino}-3-[(1-phenyl-1H-pyrazol-3-yl)amino]pyridine-2-carboxamide | 392 | 392 | TFA Salt |

TABLE A-continued

| Ex. No. | A | B | Name | [M + H]+ Calc'd | [M + H]+ Obsv'd | Form(s) |
|---|---|---|---|---|---|---|
| 1.15 | cyclohexyl-NH2 "1R, 2S" | 2,3-dihydrobenzofuran-pyridinyl | 5-{[(1R,2S)-2-aminocyclohexyl]amino}-3-{[6-(2,3-dihydro-1-benzofuran-5-yl)pyridin-2-yl]amino}pyridine-2-carboxamide | 445 | 445 | TFA Salt |
| 1.16 | cyclohexyl-NH2 "1R, 2S" | 2,3-dihydro-1,4-benzodioxin-pyridinyl | 5-{[(1R,2S)-2-aminocyclohexyl]amino}-3-{[6-(2,3-dihydro-1,4-benzodioxin-6-yl)pyridin-2-yl]amino}pyridine-2-carboxamide | 461 | 461 | TFA Salt |
| 1.17 | cyclohexyl-NH2 "1R, 2S" | imidazo[1,2-b]pyridazinyl | 5-{[(1R,2S)-2-aminocyclohexyl]amino}-3-(imidazo[1,2-b]pyridazin-6-ylamino)pyridine-2-carboxamide | 367 | 367 | TFA Salt |
| 1.18 | cyclopentyl-NH2 "RACEMIC, CIS" | 4,6-dimethylpyridin-2-yl | rel-5-{[(1R,2S)-2-aminocyclopentyl]amino}-3-[(4,6-dimethylpyridin-2-yl)amino]pyridine-2-carboxamide | 341 | 341 | TFA Salt |
| 1.19 | H2N-CH2-C(CH3)2- | 4,6-dimethylpyridin-2-yl | 5-[(2-amino-1,1-dimethylethyl)amino]-3-[(4,6-dimethylpyridin-2-yl)amino]pyridine-2-carboxamide | 329 | 329 | TFA Salt |
| 1.20 | 1,1-dioxidotetrahydro-2H-thiopyran-NH2 "RACEMIC, CIS" | 4,6-dimethylpyridin-2-yl | rel-5-{[(3S,4S)-4-amino-1,1-dioxidotetrahydro-2H-thiopyran-3-yl]amino}-3-[(4,6-dimethylpyridin-2-yl)amino]pyridine-2-carboxamide | 405 | 405 | TFA Salt |

TABLE A-continued

| Ex. No. | A | B | Name | [M + H]+ Calc'd | [M + H]+ Obsv'd | Form(s) |
|---|---|---|---|---|---|---|
| 1.21 | (H2N-CH2-CH(Ph)-) RACEMIC | 4,6-dimethylpyridin-2-yl | 5-[(2-amino-1-phenylethyl)amino]-3-[(4,6-dimethylpyridin-2-yl)amino]pyridine-2-carboxamide | 377 | 377 | TFA Salt |
| 1.22 | (H2N-CH2-CH(Ph)-) SINGLE ENANTIOMER | 4,6-dimethylpyridin-2-yl | 5-[(2-amino-1-phenylethyl)amino]-3-[(4,6-dimethylpyridin-2-yl)amino]pyridine-2-carboxamide | 377 | 377 | Free Base |
| 1.23 | (H2N-CH2-CH(Ph)-) SINGLE ENANTIOMER | 4,6-dimethylpyridin-2-yl | 5-[(2-amino-1-phenylethyl)amino]-3-[(4,6-dimethylpyridin-2-yl)amino]pyridine-2-carboxamide | 377 | 377 | Free Base |
| 1.24 | (1R,2S)-2-aminocyclohexyl "1R, 2S" | 5-fluoro-6-methylpyridin-2-yl | 5-{[(1R,2S)-2-aminocyclohexyl]amino}-3-[(5-fluoro-6-methylpyridin-2-yl)amino]pyridine-2-carboxamide | 359 | 359 | TFA Salt |
| 1.25 | (1S,2R)-2-aminocyclopentyl SINGLE ENANTIOMER, CIS | 4,6-dimethylpyridin-2-yl | rel-5-{[(1S,2R)-2-aminocyclopentyl]amino}-3-[(4,6-dimethylpyridin-2-yl)amino]pyridine-2-carboxamide | 341 | 341 | Free Base |

TABLE A-continued

| Ex. No. | A | B | Name | [M + H]+ Calc'd | [M + H]+ Obsv'd | Form(s) |
|---|---|---|---|---|---|---|
| 1.26 | cyclopentyl-NH2 SINGLE ENANTIOMER, CIS | 4,6-dimethylpyridin-2-yl | rel-5-{[(1S,2R)-2-aminocyclopentyl]amino}-3-[(4,6-dimethylpyridin-2-yl)amino]pyridine-2-carboxamide | 341 | 341 | Free Base |
| 1.27 | cyclohexyl-NH2 "1R, 2S" | 2,4'-bipyridin-6-yl | 5-{[(1R,2S)-2-aminocyclohexyl]amino}-3-(2,4'-bipyridin-6-ylamino)pyridine-2-carboxamide | 404 | 404 | TFA Salt |
| 1.28 | cyclohexyl-NH2 "1R, 2S" | 6-phenylpyridin-2-yl | 5-{[(1R,2S)-2-aminocyclohexyl]amino}-3-[(6-phenylpyridin-2-yl)amino]pyridine-2-carboxamide | 403 | 403 | TFA Salt |
| 1.29 | 4-amino-1,1-dioxidotetrahydro-2H-thiopyran-4-yl)methyl RACEMIC | 4,6-dimethylpyridin-2-yl | 5-{[(4-amino-1,1-dioxidotetrahydro-2H-thiopyran-4-yl)methyl]amino}-3-[(4,6-dimethylpyridin-2-yl)amino]pyridine-2-carboxamide | 419 | 419 | TFA Salt |
| 1.30 | H2N-CH2-CH(Me)- RACEMIC | 4,6-dimethylpyridin-2-yl | 5-[(2-amino-1-methylethyl)amino]-3-[(4,6-dimethylpyridin-2-yl)amino]pyridine-2-carboxamide | 315 | 315 | TFA Salt |
| 1.31 | cyclohexyl-NH2 "1R, 2S" | 5-bromo-6-methylpyridin-2-yl | 5-{[(1R,2S)-2-aminocyclohexyl]amino}-3-[(5-bromo-6-methylpyridin-2-yl)amino]pyridine-2-carboxamide | 419, 421 | 419, 421 | TFA Salt |

TABLE A-continued

| Ex. No. | A | B | Name | [M + H]+ Calc'd | [M + H]+ Obsv'd | Form(s) |
|---|---|---|---|---|---|---|
| 1.32 | SINGLE ENANTIOMER, TRANS | | rel-5-{[(3R,4S)-4-amino-1,1-dioxidotetrahydro-2H-thiopyran-3-yl]amino}-3-[(4,6-dimethylpyridin-2-yl)amino]pyridine-2-carboxamide | 405 | 405 | TFA Salt |
| 1.33 | "1R, 2S" | | 5-{[(1R,2S)-2-aminocyclohexyl]amino}-3-[(1-methyl-1H-pyrazol-3-yl)amino]pyridine-2-carboxamide | 330 | 330 | TFA Salt |
| 1.34 | RACEMIC | | 5-{[(4-aminotetrahydro-2H-pyran-4-yl)methyl]amino}-3-[(4,6-dimethylpyridin-2-yl)amino]pyridine-2-carboxamide | 371 | 371 | Free Base |
| 1.35 | RACEMIC | | 5-{[(3-aminotetrahydrofuran-3-yl)methyl]amino}-3-[(4,6-dimethylpyridin-2-yl)amino]pyridine-2-carboxamide | 357 | 357 | Free Base |
| 1.36 | SINGLE ENANTIOMER, CIS | | rel-5-{[(3R,4R)-4-amino-1,1-dioxidotetrahydro-2H-thiopyran-3-yl]amino}-3-[(4,6-dimethylpyridin-2-yl)amino]pyridine-2-carboxamide | 405 | 405 | Free Base |
| 1.37 | SINGLE ENANTIOMER, TRANS | | rel-5-{[(3R,4S)-4-amino-1,1-dioxidotetrahydro-2H-thiopyran-3-yl]amino}-3-[(4,6-dimethylpyridin-2-yl)amino]pyridine-2-carboxamide | 405 | 405 | Free Base |

TABLE A-continued

| Ex. No. | A | B | Name | [M + H]+ Calc'd | [M + H]+ Obsv'd | Form(s) |
|---|---|---|---|---|---|---|
| 1.38 | "1R, 2S" | | 5-{[(1R,2S)-2-aminocyclohexyl]amino}-3-[(6-chloro-4-methylpyridin-2-yl)amino]pyridine-2-carboxamide | 375 | 375 | TFA Salt |
| 1.39 | RACEMIC | | 5-[(2-amino-1-methyl-2-oxoethyl)amino]-3-[(4,6-dimethylpyridin-2-yl)amino]pyridine-2-carboxamide | 329 | 329 | TFA Salt |
| 1.40 | RACEMIC | | N²-{6-carbamoyl-5-[(4,6-dimethylpyridin-2-yl)amino]pyridin-3-yl}leucinamide | 371 | 371 | TFA Salt |
| 1.41 | RACEMIC | | 5-[(1-carbamoyl-2-methylpropyl)amino]-3-[(4,6-dimethylpyridin-2-yl)amino]pyridine-2-carboxamide | 357 | 357 | TFA Salt |
| 1.42 | "1R, 2S" | | 5-{[(1R,2S)-2-aminocyclohexyl]amino}-3-(2,2'-bipyridin-6-ylamino)pyridine-2-carboxamide | 404 | 404 | TFA Salt |
| 1.43 | "1R, 2S" | | 5-{[(1R,2S)-2-aminocyclohexyl]amino}-3-{[6-(trifluoromethyl)pyridin-2-yl]amino}pyridine-2-carboxamide | 395 | 395 | TFA Salt |

TABLE A-continued

| Ex. No. | A | B | Name | [M + H]+ Calc'd | [M + H]+ Obsv'd | Form(s) |
|---|---|---|---|---|---|---|
| 1.44 | (1R,2S)-2-aminocyclohexyl | 1-phenyl-1H-1,2,4-triazol-3-yl | 5-{[(1R,2S)-2-aminocyclohexyl]amino}-3-[(1-phenyl-1H-1,2,4-triazol-3-yl)amino]pyridine-2-carboxamide | 393 | 393 | TFA Salt |
| 1.45 | leucinamide (single enantiomer) | 4,6-dimethylpyridin-2-yl | N²-{6-carbamoyl-5-[(4,6-dimethylpyridin-2-yl)amino]pyridin-3-yl}-leucinamide | 371 | 371 | TFA Salt |
| 1.46 | leucinamide (single enantiomer) | 4,6-dimethylpyridin-2-yl | N²-{6-carbamoyl-5-[(4,6-dimethylpyridin-2-yl)amino]pyridin-3-yl}-leucinamide | 371 | 371 | TFA Salt |
| 1.47 | (1S,6S)-6-amino-2,2-difluorocyclohexyl | 4,6-dimethylpyridin-2-yl | 5-{[(1S,6S)-6-amino-2,2-difluorocyclohexyl]amino}-3-[(4,6-dimethylpyridin-2-yl)amino]pyridine-2-carboxamide | 391 | 391 | TFA Salt |
| 1.48 | (1R,2S)-2-aminocyclohexyl | 6-fluoropyridin-2-yl | 5-{[(1R,2S)-2-aminocyclohexyl]amino}-3-[(6-fluoropyridin-2-yl)amino]pyridine-2-carboxamide | 345 | 345 | TFA Salt |
| 1.49 | (1R,2S)-2-aminocyclohexyl | 1-ethyl-1H-pyrazol-3-yl | 5-{[(1R,2S)-2-aminocyclohexyl]amino}-3-[(1-ethyl-1H-pyrazol-3-yl)amino]pyridine-2-carboxamide | 344 | 344 | TFA Salt |

TABLE A-continued

| Ex. No. | A | B | Name | [M + H]+ Calc'd | [M + H]+ Obsv'd | Form(s) |
|---|---|---|---|---|---|---|
| 1.50 | (1R,2S)-2-aminocyclohexyl | 1-benzyl-1H-pyrazol-3-yl | 5-{[(1R,2S)-2-aminocyclohexyl]amino}-3-[(1-benzyl-1H-pyrazol-3-yl)amino]pyridine-2-carboxamide | 406 | 406 | TFA Salt |
| 1.51 | (1R,2S)-2-aminocyclohexyl | 2-phenyl-2H-1,2,3-triazol-4-yl | 5-{[(1R,2S)-2-aminocyclohexyl]amino}-3-[(2-phenyl-2H-1,2,3-triazol-4-yl)amino]pyridine-2-carboxamide | 393 | 393 | TFA Salt |
| 1.52 | 2-amino-3-(methylsulfonyl)propyl, RACEMIC | 4,6-dimethylpyridin-2-yl | 5-{[2-amino-3-(methylsulfonyl)propyl]amino}-3-[(4,6-dimethylpyridin-2-yl)amino]pyridine-2-carboxamide | 393 | 393 | Formate Salt |
| 1.53 | (1R,2S)-2-aminocyclohexyl | 6-cyclopropylpyridin-2-yl | 5-{[(1R,2S)-2-aminocyclohexyl]amino}-3-[(6-cyclopropylpyridin-2-yl)amino]pyridine-2-carboxamide | 367 | 367 | Formate Salt |
| 1.54 | (1R,2S)-2-aminocyclohexyl | 6-(1-methylethyl)pyridin-2-yl | 5-{[(1R,2S)-2-aminocyclohexyl]amino}-3-{[6-(1-methylethyl)pyridin-2-yl]amino}pyridine-2-carboxamide | 369 | 369 | Formate Salt |
| 1.55 | (1R,2S)-2-aminocyclohexyl | 5,7-dimethylpyrazolo[1,5-a]pyrimidin-2-yl | 5-{[(1R,2S)-2-aminocyclohexyl]amino}-3-[(5,7-dimethylpyrazolo[1,5-a]pyrimidin-2-yl)amino]pyridine-2-carboxamide | 395 | 395 | TFA Salt |

TABLE A-continued

| Ex. No. | A | B | Name | [M + H]+ Calc'd | [M + H]+ Obsv'd | Form(s) |
|---|---|---|---|---|---|---|
| 1.56 | (1R,2S)-2-aminocyclohexyl | 1-ethyl-1H-1,2,4-triazol-3-yl | 5-{[(1R,2S)-2-aminocyclohexyl]amino}-3-[(1-ethyl-1H-1,2,4-triazol-3-yl)amino]pyridine-2-carboxamide | 345 | 345 | TFA Salt |
| 1.57 | (1R,2S)-2-aminocyclohexyl | 6-morpholin-4-ylpyridin-2-yl | 5-{[(1R,2S)-2-aminocyclohexyl]amino}-3-[(6-morpholin-4-ylpyridin-2-yl)amino]pyridine-2-carboxamide | 412 | 412 | TFA Salt |
| 1.58 | 2-aminoethyl | 6-(2H-1,2,3-triazol-2-yl)pyridin-2-yl | 5-[(2-aminoethyl)amino]-3-{[6-(2H-1,2,3-triazol-2-yl)pyridin-2-yl]amino}pyridine-2-carboxamide | 340 | 340 | TFA Salt |
| 1.59 | (1R,2S)-2-aminocyclohexyl | 4-(dimethylcarbamoyl)-6-methylpyridin-2-yl | 5-{[(1R,2S)-2-aminocyclohexyl]amino}-3-{[4-(dimethylcarbamoyl)-6-methylpyridin-2-yl]amino}pyridine-2-carboxamide | 412 | 412 | TFA Salt |
| 1.60 | (1R,2S)-2-aminocyclohexyl | 6-(morpholin-4-ylmethyl)pyridin-2-yl | 5-{[(1R,2S)-2-aminocyclohexyl]amino}-3-{[6-(morpholin-4-ylmethyl)pyridin-2-yl]amino}pyridine-2-carboxamide | 426 | 426 | TFA Salt |
| 1.61 | (1R,2S)-2-aminocyclohexyl | 6-[(4-methylpiperazin-1-yl)methyl]pyridin-2-yl | 5-{[(1R,2S)-2-aminocyclohexyl]amino}-3-({6-[(4-methylpiperazin-1-yl)methyl]pyridin-2-yl}amino)pyridine-2-carboxamide | 439 | 439 | TFA Salt |

TABLE A-continued

| Ex. No. | A | B | Name | [M + H]+ Calc'd | [M + H]+ Obsv'd | Form(s) |
|---|---|---|---|---|---|---|
| 1.62 | (1R,2S)-2-aminocyclohexyl | 1-methyl-2H-1,2,3-triazol-4-yl | 5-{[(1R,2S)-2-aminocyclohexyl]amino}-3-[(2-methyl-2H-1,2,3-triazol-4-yl)amino]pyridine-2-carboxamide | 331 | 331 | TFA Salt |
| 1.63 | (1R,2S)-2-aminocyclohexyl | 1-(4-chlorophenyl)-1H-pyrazol-3-yl | 5-{[(1R,2S)-2-aminocyclohexyl]amino}-3-{[1-(4-chlorophenyl)-1H-pyrazol-3-yl]amino}pyridine-2-carboxamide | 426 | 426 | TFA Salt |
| 1.64 | (1R,2S)-2-aminocyclohexyl | 1-(4-methylphenyl)-1H-pyrazol-3-yl | 5-{[(1R,2S)-2-aminocyclohexyl]amino}-3-{[1-(4-methylphenyl)-1H-pyrazol-3-yl]amino}pyridine-2-carboxamide | 406 | 406 | TFA Salt |
| 1.65 | (1R,2S)-2-aminocyclohexyl | 1-(4-fluorophenyl)-1H-pyrazol-3-yl | 5-{[(1R,2S)-2-aminocyclohexyl]amino}-3-{[1-(4-fluorophenyl)-1H-pyrazol-3-yl]amino}pyridine-2-carboxamide | 410 | 410 | TFA Salt |
| 1.66 | (1R,2S)-2-aminocyclohexyl | 1-(3,4-dimethylphenyl)-1H-pyrazol-3-yl | 5-{[(1R,2S)-2-aminocyclohexyl]amino}-3-{[1-(3,4-dimethylphenyl)-1H-pyrazol-3-yl]amino}pyridine-2-carboxamide | 420 | 420 | TFA Salt |

TABLE A-continued

| Ex. No. | A | B | Name | [M + H]⁺ Calc'd | [M + H]⁺ Obsv'd | Form(s) |
|---|---|---|---|---|---|---|
| 1.67 | "1R, 2S" | | 5-{[(1R,2S)-2-aminocyclohexyl]amino}-3-{[6-methyl-5-(2H-1,2,3-triazol-2-yl)pyridin-2-yl]amino}pyridine-2-carboxamide | 408 | 408 | Formate Salt |
| 1.68 | R | | 5-{[(2R)-2-amino-3-methoxypropyl]amino}-3-[(4,6-dimethylpyridin-2-yl)amino]pyridine-2-carboxamide | 345 | 345 | TFA Salt |
| 1.69 | "1R, 2S" | | 5-{[(1R,2S)-2-aminocyclohexyl]amino}-3-[(1-methyl-6-phenyl-1H-pyrazolo[3,4-d]pyrimidin-4-yl)amino]pyridine-2-carboxamide | 458 | 458 | Free Base |
| 1.70 | RACEMIC | | 5-[(2-amino-3-ethoxypropyl)amino]-3-[(4,6-dimethylpyridin-2-yl)amino]pyridine-2-carboxamide | 359 | 359 | TFA Salt |
| 1.71 | SINGLE ENANTIOMER, CIS | | rel-5-{[(3S,4S)-4-amino-1,1-dioxidotetrahydro-2H-thiopyran-3-yl]amino}-3-[(4,6-dimethylpyridin-2-yl)amino]pyridine-2-carboxamide | 405 | 405 | TFA Salt |
| 1.72 | "1R, 2S" | | 5-{[(1R,2S)-2-aminocyclohexyl]amino}-3-{[1-(4-methoxyphenyl)-1H-pyrazol-3-yl]amino}pyridine-2-carboxamide | 422 | 422 | Formate Salt |

TABLE A-continued

| Ex. No. | A | B | Name | [M + H]+ Calc'd | [M + H]+ Obsv'd | Form(s) |
|---|---|---|---|---|---|---|
| 1.73 | (1R,2S)-2-aminocyclohexyl | 4,6-dichloropyridin-2-yl | 5-{[(1R,2S)-2-aminocyclohexyl]amino}-3-[(4,6-dichloropyridin-2-yl)amino]pyridine-2-carboxamide | 395 | 395 | TFA Salt |
| 1.74 | (1R,2S)-2-aminocyclohexyl | 6-methyl-5-(1H-1,2,3-triazol-1-yl)pyridin-2-yl | 5-{[(1R,2S)-2-aminocyclohexyl]amino}-3-{[6-methyl-5-(1H-1,2,3-triazol-1-yl)pyridin-2-yl]amino}pyridine-2-carboxamide | 408 | 408 | Formate Salt |
| 1.75 | (1R,2S)-2-aminocyclohexyl | 6-methyl-4-(1H-1,2,3-triazol-1-yl)pyridin-2-yl | 5-{[(1R,2S)-2-aminocyclohexyl]amino}-3-{[6-methyl-4-(1H-1,2,3-triazol-1-yl)pyridin-2-yl]amino}pyridine-2-carboxamide | 408 | 408 | Formate Salt |
| 1.76 | (1R,2S)-2-aminocyclohexyl | 6-methyl-4-(2H-1,2,3-triazol-2-yl)pyridin-2-yl | 5-{[(1R,2S)-2-aminocyclohexyl]amino}-3-{[6-methyl-4-(2H-1,2,3-triazol-2-yl)pyridin-2-yl]amino}pyridine-2-carboxamide | 408 | 408 | Formate Salt |
| 1.77 | (1R,2S)-2-aminocyclohexyl | 6-methyl-4-morpholin-4-ylpyridin-2-yl | 5-{[(1R,2S)-2-aminocyclohexyl]amino}-3-[(6-methyl-4-morpholin-4-ylpyridin-2-yl)amino]pyridine-2-carboxamide | 426 | 426 | TFA Salt |
| 1.78 | (1R,2S)-2-aminocyclohexyl | 4-(dimethylamino)-6-methylpyridin-2-yl | 5-{[(1R,2S)-2-aminocyclohexyl]amino}-3-{[4-(dimethylamino)-6-methylpyridin-2-yl]amino(pyridine-2-carboxamide | 384 | 384 | TFA Salt |

TABLE A-continued

| Ex. No. | A | B | Name | [M + H]+ Calc'd | [M + H]+ Obsv'd | Form(s) |
|---|---|---|---|---|---|---|
| 1.79 | "1R, 2S" cyclohexyl-NH2 | 5-methyl-1-(4-methylphenyl)-1H-pyrazol-3-yl | 5-{[(1R,2S)-2-aminocyclohexyl]amino}-3-{[5-methyl-1-(4-methylphenyl)-1H-pyrazol-3-yl]amino}pyridine-2-carboxamide | 420 | 420 | TFA Salt |
| 1.80 | "1R, 2S" cyclohexyl-NH2 | 1-(3-methylphenyl)-1H-pyrazol-3-yl | 5-{[(1R,2S)-2-aminocyclohexyl]amino}-3-{[1-(3-methylphenyl)-1H-pyrazol-3-yl]amino}pyridine-2-carboxamide | 406 | 406 | TFA Salt |
| 1.81 | "1R, 2S" cyclohexyl-NH2 | 1-(pyridin-2-yl)-1H-pyrazol-3-yl | 5-{[(1R,2S)-2-aminocyclohexyl]amino}-3-[(1-pyridin-2-yl-1H-pyrazol-3-yl)amino]pyridine-2-carboxamide | 393 | 393 | TFA Salt |
| 1.82 | R, MeO-CH2-CH(NH2)-CH2- | 6-(2H-1,2,3-triazol-2-yl)pyridin-2-yl | 5-{[(2R)-2-amino-3-methoxypropyl]amino}-3-{[6-(2H-1,2,3-triazol-2-yl)pyridin-2-yl]amino}pyridine-2-carboxamide | 384 | 384 | Free Base |
| 1.83 | "1S, 6S" 2,2-difluorocyclohexyl-NH2 | 6-(2H-1,2,3-triazol-2-yl)pyridin-2-yl | 5-{[(1S,6S)-6-amino-2,2-difluorocyclohexyl]amino}-3-{[6-(2H-1,2,3-triazol-2-yl)pyridin-2-yl]amino}pyridine-2-carboxamide | 430 | 430 | Free Base |
| 1.84 | RACEMIC, CIS 1,1-dioxidotetrahydro-2H-thiopyran-3-yl-NH2 | 6-(2H-1,2,3-triazol-2-yl)pyridin-2-yl | rel-5-{[(3S,4S)-4-amino-1,1-dioxidotetrahydro-2H-thiopyran-3-yl]amino(-3-{[6-(2H-1,2,3-triazol-2-yl)pyridin-2-yl]amino}pyridine-2-carboxamide | 444 | 444 | TFA Salt |

TABLE A-continued

| Ex. No. | A | B | Name | [M + H]+ Calc'd | [M + H]+ Obsv'd | Form(s) |
|---|---|---|---|---|---|---|
| 1.85 | RACEMIC | | 5-{[1-(aminomethyl)propyl]amino}-3-{[6-(2H-1,2,3-triazol-2-yl)pyridin-2-yl]amino}pyridine-2-carboxamide | 368 | 368 | TFA Salt |
| 1.86 | "1S, 6S" | | 5-{[(1S,6S)-6-amino-2,2-difluorocyclohexyl]amino}-3-[(1-methyl-1H-pyrazol-3-yl)amino]pyridine-2-carboxamide | 366 | 366 | TFA Salt |
| 1.87 | "1S, 6S" | | 5-{[(1S,6S)-6-amino-2,2-difluorocyclohexyl]amino}-3-{[1-(4-fluorophenyl)-1H-pyrazol-3-yl]amino}pyridine-2-carboxamide | 446 | 446 | TFA Salt |
| 1.88 | "1S, 6S" | | 5-{[(1S,6S)-6-amino-2,2-difluorocyclohexyl]amino}-3-[(6-ethylpyridin-2-yl)amino]pyridine-2-carboxamide | 391 | 391 | TFA Salt |
| 1.89 | RACEMIC, CIS | | rel-5-{[(3S,4S)-4-amino-1,1-dioxidotetrahydro-2H-thiopyran-3-yl]amino}-3-[(1-methyl-1H-pyrazol-3-yl)amino]pyridine-2-carboxamide | 380 | 380 | TFA Salt |
| 1.90 | RACEMIC, CIS | | rel-5-{[(3S,4S)-4-amino-1,1-dioxidotetrahydro-2H-thiopyran-3-yl]amino}-3-{[1-(4-fluorophenyl)-1H-pyrazol-3-yl]amino}pyridine-2-carboxamide | 460 | 460 | TFA Salt |

TABLE A-continued

| Ex. No. | A | B | Name | [M + H]+ Calc'd | [M + H]+ Obsv'd | Form(s) |
|---|---|---|---|---|---|---|
| 1.91 | RACEMIC, CIS | | rel-5-{[(3S,4S)-4-amino-1,1-dioxidotetrahydro-2H-thiopyran-3-yl]amino}-3-[(6-ethylpyridin-2-yl)amino]pyridine-2 carboxamide | 405 | 405 | TFA Salt |
| 1.92 | S | | 5-{[(2S)-2-aminopropyl]amino}-3-[(1-methyl-1H-pyrazol-3-yl)amino]pyridine-2-carboxamide | 290 | 290 | Free Base |
| 1.93 | S | | 5-{[(2S)-2-aminopropyl]amino}-3-{[1-(4-fluorophenyl)-1H-pyrazol-3-yl]amino}pyridine-2-carboxamide | 370 | 370 | Free Base |
| 1.94 | S | | 5-{[(2S)-2-aminopropyl]amino}-3-[(6-ethylpyridin-2-yl)amino]pyridine-2-carboxamide | 315 | 315 | Free Base |
| 1.95 | RACEMIC | | 5-{[1-(aminomethyl)propyl]amino}-3-[(1-methyl-1H-pyrazol-3-yl)amino]pyridine-2-carboxamide | 304 | 304 | Free Base |
| 1.96 | RACEMIC | | 5-{[1-(aminomethyl)propyl]amino}-3-{[1-(4-fluorophenyl)-1H-pyrazol-3-yl]amino}pyridine-2-carboxamide | 384 | 384 | Free Base |

TABLE A-continued

| Ex. No. | A | B | Name | [M + H]+ Calc'd | [M + H]+ Obsv'd | Form(s) |
|---|---|---|---|---|---|---|
| 1.97 | H2N-, RACEMIC | 6-ethylpyridin-2-yl | 5-{[1-(aminomethyl)propyl]amino}-3-[(6-ethylpyridin-2-yl)amino]pyridine-2-carboxamide | 329 | 329 | Free Base |
| 1.98 | (2R)-1-methoxy-2-aminopropyl, R | 1-methyl-1H-pyrazol-3-yl | 5-{[(2R)-2-amino-3-methoxypropyl]amino}-3-[(1-methyl-1H-pyrazol-3-yl)amino]pyridine-2-carboxamide | 320 | 320 | Free Base |
| 1.99 | (2R)-1-methoxy-2-aminopropyl, R | 1-(4-fluorophenyl)-1H-pyrazol-3-yl | 5-{[(2R)-2-amino-3-methoxypropyl]amino}-3-{[1-(4-fluorophenyl)-1H-pyrazol-3-yl]amino}pyridine-2-carboxamide | 400 | 400 | Free Base |
| 1.100 | (2R)-1-methoxy-2-aminopropyl, R | 6-ethylpyridin-2-yl | 5-{[(2R)-2-amino-3-methoxypropyl]amino}-3-[(6-ethylpyridin-2-yl)amino]pyridine-2-carboxamide | 345 | 345 | Free Base |
| 1.101 | (1R,2S)-2-aminocyclohexyl, "1R, 2S" | 6-(1-benzyl-1H-1,2,3-triazol-4-yl)pyridin-2-yl | 5-{[(1R,2S)-2-aminocyclohexyl]amino}-3-{[6-(1-benzyl-1H-1,2,3-triazol-4-yl)pyridin-2-yl]amino}pyridine-2-carboxamide | 484 | 484 | TFA Salt |
| 1.102 | (1R,2S)-2-aminocyclohexyl, "1R, 2S" | 4-methyl-6-(2H-1,2,3-triazol-2-yl)pyridin-2-yl | 5-{[(1R,2S)-2-aminocyclohexyl]amino}-3-{[4-methyl-6-(2H-1,2,3-triazol-2-yl)pyridin-2-yl]amino}pyridine-2-carboxamide | 408 | 408 | TFA Salt |

TABLE A-continued

| Ex. No. | A | B | Name | [M + H]+ Calc'd | [M + H]+ Obsv'd | Form(s) |
|---|---|---|---|---|---|---|
| 1.103 | (1-aminocyclopropyl)methyl | 6-(trifluoromethyl)pyridin-2-yl | 5-{[(1-aminocyclopropyl)methyl]amino}-3-{[6-(trifluoromethyl)pyridin-2-yl]amino}pyridine-2-carboxamide | 367 | 367 | TFA Salt |
| 1.104 | (2S)-2-aminopropyl, S | 6-(trifluoromethyl)pyridin-2-yl | 5-{[(2S)-2-aminopropyl]amino}-3-{[6-(trifluoromethyl)pyridin-2-yl]amino}pyridine-2-carboxamide | 355 | 355 | TFA Salt |
| 1.105 | (2R)-2-amino-3-methoxypropyl, R | 6-(trifluoromethyl)pyridin-2-yl | 5-{[(2R)-2-amino-3-methoxypropyl]amino}-3-{[6-(trifluoromethyl)pyridin-2-yl]amino}pyridine-2-carboxamide | 385 | 385 | TFA Salt |
| 1.106 | (1S,6S)-6-amino-2,2-difluorocyclohexyl, "1S, 6S" | 6-(trifluoromethyl)pyridin-2-yl | 5-{[(1S,6S)-6-amino-2,2-difluorocyclohexyl]amino}-3-{[6-(trifluoromethyl)pyridin-2-yl]amino}pyridine-2-carboxamide | 431 | 431 | TFA Salt |
| 1.107 | (1R,2S)-2-aminocyclohexyl, "1R, 2S" | 5-methylthieno[2,3-c]pyridin-7-yl | 5-{[(1R,2S)-2-aminocyclohexyl]amino}-3-[(5-methylthieno[2,3-c]pyridin-7-yl)amino]pyridine-2-carboxamide | 397 | 397 | Free Base |
| 1.108 | (1R,2S)-2-aminocyclohexyl, "1R, 2S" | 4-(1-hydroxy-1-methylethyl)-6-methylpyridin-2-yl | 5-{[(1R,2S)-2-aminocyclohexyl]amino}-3-{[4-(1-hydroxy-1-methylethyl)-6-methylpyridin-2-yl]amino}pyridine-2-carboxamide | 399 | 399 | TFA Salt |

TABLE A-continued

| Ex. No. | A | B | Name | [M + H]+ Calc'd | [M + H]+ Obsv'd | Form(s) |
|---|---|---|---|---|---|---|
| 1.109 | cyclohexyl "1R, 2S" with NH2 | N-(pyridin-2-yl)methanesulfonamide | 6-{[(1R,2S)-2-aminocyclohexyl]amino}-4-({6-[(methylsulfonyl)amino]pyridin-2-yl}amino)pyridine-3-carboxamide | 420 | 420 | TFA Salt |
| 1.110 | cyclohexyl "1R, 2S" with NH2 | 4-methyl-6-(1-methyl-1H-pyrazol-4-yl)pyridine | 5-{[(1R,2S)-2-aminocyclohexyl]amino}-3-{[4-methyl-6-(1-methyl-1H-pyrazol-4-yl)pyridin-2-yl]amino}pyridine-2-carboxamide | 421 | 421 | TFA Salt |
| 1.111 | cyclohexyl "1R, 2S" with NH2 | 5-methoxy-6-methylpyridine | 5-{[(1R,2S)-2-aminocyclohexyl]amino}-3-[(5-methoxy-6-methylpyridin-2-yl)amino]pyridine-2-carboxamide | 371 | 371 | TFA Salt |
| 1.112 | cyclohexyl "1R, 2S" with NH2 | 4-methyl-6-(1-methyl-1H-pyrazol-5-yl)pyridine | 5-{[(1R,2S)-2-aminocyclohexyl]amino}-3-{[4-methyl-6-(1-methyl-1H-pyrazol-5-yl)pyridin-2-yl]amino}pyridine-2-carboxamide | 421 | 421 | TFA Salt |
| 1.113 | cyclohexyl "1R, 2S" with NH2 | 4-methyl-6-(4,5,6,7-tetrahydropyrazolo[1,5-a]pyridin-3-yl)pyridine | 5-{[(1R,2S)-2-aminocyclohexyl]amino}-3-{[4-methyl-6-(4,5,6,7-tetrahydropyrazolo[1,5-a]pyridin-3-yl)pyridin-2-yl]amino}pyridine-2-carboxamide | 461 | 461 | TFA Salt |
| 1.114 | cyclohexyl "1R, 2S" with NH2 | 6-[2-(1-hydroxy-1-methylethyl)-1,3-thiazol-5-yl]-4-methylpyridine | 5-{[(1R,2S)-2-aminocyclohexyl]amino}-3-({6-[2-(1-hydroxy-1-methylethyl)-1,3-thiazol-5-yl]-4-methylpyridin-2-yl}amino)pyridine-2-carboxamide | 482 | 482 | TFA Salt |

TABLE A-continued

| Ex. No. | A | B | Name | [M + H]+ Calc'd | [M + H]+ Obsv'd | Form(s) |
|---|---|---|---|---|---|---|
| 1.115 | "1R, 2S" | | 5-{[(1R,2S)-2-aminocyclohexyl]amino}-3-{[6-(5,6-dihydro-4H-pyrrolo[1,2-b]pyrazol-3-yl)-4-methylpyridin-2-yl]amino}pyridine-2-carboxamide | 447 | 447 | TFA Salt |
| 1.116 | RACEMIC, TRANS | | rel-5-{[(1S,2S)-2-aminocyclobutyl]amino}-3-[(4,6-dimethylpyridin-2-yl)amino]pyridine-2-carboxamide | 327 | 327 | TFA Salt |
| 1.117 | RACEMIC | | 5-[(2-amino-2-methylbutyl)amino]-3-[(4,6-dimethylpyridin-2-yl)amino]pyridine-2-carboxamide | 343 | 343 | Free Base |
| 1.118 | | | 5-[(2-amino-2-cyclopropylethyl)amino]-3-[(4,6-dimethylpyridin-2-yl)amino]pyridine-2-carboxamide | 341 | 341 | Free Base |
| 1.119 | "1R, 2S" | | 5-{[(1R,2S)-2-aminocyclohexyl]amino}-3-{[6-(4-methylpiperazin-1-yl)pyridin-2-yl]amino}pyridine-2-carboxamide | 425 | 425 | TFA Salt |
| 1.120 | "1R, 2S" | | 5-{[(1R,2S)-2-aminocyclohexyl]amino}-3-({6-[(2-hydroxy-2-methylpropoxy)methyl]pyridin-2-yl}amino)pyridine-2-carboxamide | 429 | 429 | TFA Salt |
| 1.121 | "1R, 2S" | | 5-{[(1R,2S)-2-aminocyclohexyl]amino}-3-[(6-methylpyrazin-2-yl)amino]pyridine-2-carboxamide | 342 | 342 | TFA Salt |

TABLE A-continued

| Ex. No. | A | B | Name | [M + H]+ Calc'd | [M + H]+ Obsv'd | Form(s) |
|---|---|---|---|---|---|---|
| 1.122 | (1R,2S)-2-aminocyclohexyl | 2-(2H-1,2,3-triazol-2-yl)pyrimidin-4-yl | 5-{[(1R,2S)-2-aminocyclohexyl]amino}-3-{[2-(2H-1,2,3-triazol-2-yl)pyrimidin-4-yl]amino}pyridine-2-carboxamide | 395 | 395 | TFA Salt |
| 1.123 | (1R,2S)-2-aminocyclohexyl | pyrimidin-4-yl | 5-{[(1R,2S)-2-aminocyclohexyl]amino}-3-(pyrimidin-4-ylamino)pyridine-2-carboxamide | 328 | 328 | Formate Salt |
| 1.124 | (1R,2S)-2-aminocyclohexyl | 2,6-dimethoxypyrimidin-4-yl | 5-{[(1R,2S)-2-aminocyclohexyl]amino}-3-[(2,6-dimethoxypyrimidin-4-yl)amino]pyridine-2-carboxamide | 388 | 388 | Formate Salt |
| 1.125 | (1R,2S)-2-aminocyclohexyl | 2,6-dimethylpyrimidin-4-yl | 5-{[(1R,2S)-2-aminocyclohexyl]amino}-3-[(2,6-dimethylpyrimidin-4-yl)amino]pyridine-2-carboxamide | 356 | 356 | Formate Salt |
| 1.126 | (1R,2S)-2-aminocyclohexyl | 5-chloro-2,6-dimethylpyrimidin-4-yl | 5-{[(1R,2S)-2-aminocyclohexyl]amino}-3-[(5-chloro-2,6-dimethylpyrimidin-4-yl)amino]pyridine-2-carboxamide | 390 | 390 | Formate Salt |
| 1.127 | (1R,2S)-2-aminocyclohexyl | 6-chloro-2-methylpyrimidin-4-yl | 5-{[(1R,2S)-2-aminocyclohexyl]amino}-3-[(6-chloro-2-methylpyrimidin-4-yl)amino]pyridine-2-carboxamide | 376 | 376 | Formate Salt |
| 1.128 | (1R,2S)-2-aminocyclohexyl | 2-chloro-5-fluoropyrimidin-4-yl | 5-{[(1R,2S)-2-aminocyclohexyl]amino}-3-[(2-chloro-5-fluoropyrimidin-4-yl)amino]pyridine-2-carboxamide | 380 | 380 | Formate Salt |

TABLE A-continued

| Ex. No. | A | B | Name | [M + H]+ Calc'd | [M + H]+ Obsv'd | Form(s) |
|---|---|---|---|---|---|---|
| 1.129 | (1R,2S)-2-aminocyclohexyl | 2-cyclopropylpyrimidin-4-yl | 5-{[(1R,2S)-2-aminocyclohexyl]amino}-3-[(2-cyclopropylpyrimidin-4-yl)amino]pyridine-2-carboxamide | 368 | 368 | TFA Salt |
| 1.130 | (3R,4R)-3-aminotetrahydro-2H-pyran-4-yl | 4,6-dimethylpyridin-2-yl | 5-{[(3R,4R)-3-aminotetrahydro-2H-pyran-4-yl]amino}-3-[(4,6-dimethylpyridin-2-yl)amino]pyridine-2-carboxamide | 357 | 357 | TFA Salt |
| 1.131 | (3R,4R)-3-aminotetrahydro-2H-pyran-4-yl | 4-methoxy-6-methylpyridin-2-yl | 5-{[(3R,4R)-3-aminotetrahydro-2H-pyran-4-yl]amino}-3-[(4-methoxy-6-methylpyridin-2-yl)amino]pyridine-2-carboxamide | 373 | 373 | TFA Salt |

Example 2

Conversions from Scheme 1—Conversion of A7 to Structural Subtype A

The preparation in this example describes the procedure for conversion of A7 to compounds of structural subtype A.

Example 2.1

5-{[2-amino-3-(methylamino)-3-oxopropyl]amino}-3-[(4,6-dimethylpyridin-2-yl)amino]pyridine-2-carboxamide

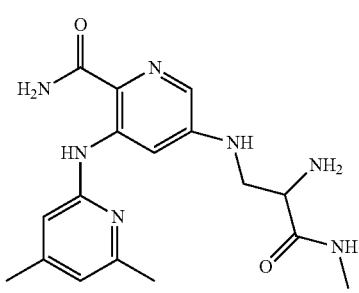

Step 1: Dioxane (1.65 ml) was added to a nitrogen purged flask containing 5-bromo-3-[(4,6-dimethylpyridin-2-yl)amino]pyridine-2-carbonitrile (PrepEx 1.4) (100 mg, 0.330 mmol), tert-butyl 3-amino-1-(methylamino)-1-oxopropan-2-ylcarbamate (72 mg, 0.33 mmol), Xantphos (19 mg, 0.033 mmol), Pd$_2$(dba)$_3$ (24 mg, 0.026 mmol) and cesium carbonate (215 mg, 0.660 mmol). Nitrogen was bubbled through the reaction mixture for 5 minutes. The reaction vessel was then sealed and heated at 100° C. for 2 hours. The reaction mixture was cooled to room temperature, filtered through CELITE, and the filter cake was washed with ethyl acetate (10 mL). The filtrate was concentrated under reduced pressure. The residue was purified by silica gel chromatography (0-5% methanol/ethyl acetate, linear gradient) to afford tert-butyl [3-({6-cyano-5-[(4,6-dimethylpyridin-2-yl)amino]pyridin-3-yl}amino)-1-(methylamino)-1-oxopropan-2-yl]carbamate. MS ESI calc'd. for C$_{22}$H$_{30}$N$_7$O$_3$ [M+H]$^+$ 440. found 440.

Step 2: TFA (1.0 ml, 13 mmol) was added to a solution of tert-butyl [3-({6-cyano-5-[(4,6-dimethylpyridin-2-yl)amino]pyridin-3-yl}amino)-1-(methylamino)-1-oxopropan-2-yl]carbamate (72 mg, 0.16 mmol) in DCM (2 ml) at room temperature. After 30 minutes, the reaction mixture was concentrated under reduced pressure to afford 3-({6-cyano-5-[(4,6-dimethylpyridin-2-yl)amino]pyridin-3-yl}amino)-N-methylalaninamide. The material was used in the next step without purification. MS ESI calc'd. for C$_{17}$H$_{22}$N$_7$O [M+H]$^+$ 340. found 340.

Step 3: To a solution of 3-({6-cyano-5-[(4,6-dimethylpyridin-2-yl)amino]pyridin-3-yl}amino)-N-methylalaninamide (56 mg, 0.16 mmol) in DMSO (0.8 mL) were added sodium hydroxide (6.0 M in water, 0.14 mL, 0.84 mmol) and hydrogen peroxide (30% w/w in water, 0.167 mL, 1.6 mmol).

The reaction mixture was stirred at room temperature for 2.5 hours, then additional sodium hydroxide (6.0 M in water, 0.10 mL, 0.60 mmol) and hydrogen peroxide (30% w/w in water, 0.125 mL, 1.2 mmol) were added. After 12 hours, the reaction mixture was acidified with hydrochloric acid (2.0 M in water, 0.66 mL, 1.3 mmol) and purified by reverse phase HPLC (acetonitrile/water with 0.1% TFA, linear gradient) to afford 5-{[2-amino-3-(methylamino)-3-oxopropyl]amino}-3-[(4,6-dimethylpyridin-2-yl)amino]pyridine-2-carboxamide TFA salt. MS ESI calc'd. for $C_{17}H_{24}N_7O_2$ [M+H]$^+$ 358. found 358. $^1$H NMR (500 MHz, CD$_3$OD) δ 7.83 (s, 1H), 7.41 (s, 1H), 7.26 (s, 1H), 6.95 (s, 1H), 3.99 (t, J=6.6 Hz, 1H), 3.75-3.70 (m, 1H), 3.66-3.60 (m, 1H), 2.73 (s, 3H), 2.55 (s, 3H), 2.46 (s, 3H).

The following compounds in Table B were prepared according to procedures which were analogous to those described in Example 2.

TABLE B

| Ex. No. | A | B | Name | [M + H]$^+$ Calc'd | [M + H]$^+$ Obsv'd | Form(s) |
|---|---|---|---|---|---|---|
| 2.1 | RACEMIC | | 5-{[2-amino-3-(methylamino)-3-oxopropyl]amino}-3-[(4,6-dimethylpyridin-2-yl)amino]pyridine-2-carboxamide | 358 | 358 | TFA Salt |
| 2.2 | | Br | 5-{[(2S)-2-aminopropyl]amino}-3-[(5-bromo-6-methylpyridin-2-yl)amino]pyridine-2-carboxamide | 378, 380 | 378, 380 | TFA Salt |
| 2.3 | RACEMIC | | 5-[(2-amino-3,3,3-trifluoropropyl)amino]-3-[(4,6-dimethylpyridin-2-yl)amino]pyridine-2-carboxamide | 369 | 369 | TFA Salt |
| 2.4 | RACEMIC | | 5-[(2-amino-3,3-difluoropropyl)amino]-3-[(4,6-dimethylpyridin-2-yl)amino]pyridine-2-carboxamide | 351 | 351 | Free Base |
| 2.5 | "1R,6R" | | 5-{[(1R,6R)-6-amino-2,2-difluorocyclohexyl]amino}-3-[(4,6-dimethylpyridin-2-yl)amino]pyridine-2-carboxamide | 391 | 391 | TFA Salt |

TABLE B-continued

| Ex. No. | A | B | Name | [M + H]+ Calc'd | [M + H]+ Obsv'd | Form(s) |
|---|---|---|---|---|---|---|
| 2.6 | H₂N, tetrahydrothiophene-1,1-dioxide (RACEMIC, TRANS) | 4,6-dimethylpyridin-2-yl | rel-5-{[(3R,4R)-4-amino-1,1-dioxidotetrahydrothiophen-3-yl]amino}-3-[(4,6-dimethylpyridin-2-yl)amino]pyridine-2-carboxamide | 391 | 391 | TFA Salt |
| 2.7 | (2S)-1-methoxy-3-aminopropyl | 4,6-dimethylpyridin-2-yl | 5-{[(2S)-2-amino-3-methoxypropyl]amino}-3-[(4,6-dimethylpyridin-2-yl)amino]pyridine-2-carboxamide | 345 | 345 | TFA Salt |
| 2.8 | 2-amino-3-(methylsulfanyl)propyl (RACEMIC) | 4,6-dimethylpyridin-2-yl | 5-{[2-amino-3-(methylsulfanyl)propyl]amino}-3-[(4,6-dimethylpyridin-2-yl)amino]pyridine-2-carboxamide | 361 | 361 | Formate Salt |
| 2.9 | 2-amino-3-(dimethylamino)-3-oxopropyl (RACEMIC) | 4,6-dimethylpyridin-2-yl | 5-{[2-amino-3-(dimethylamino)-3-oxopropyl]amino}-3-[(4,6-dimethylpyridin-2-yl)amino]pyridine-2-carboxamide | 372 | 372 | TFA Salt |
| 2.10 | piperidin-4-yl | 4,6-dimethylpyridin-2-yl | 3-[(4,6-dimethylpyridin-2-yl)amino]-5-(piperidin-4-ylamino)pyridine-2-carboxamide | 341 | 341 | TFA Salt |
| 2.11 | (1-aminocyclopropyl)methyl | 4,6-dimethylpyridin-2-yl | 5-{[(1-aminocyclopropyl)methyl]amino}-3-[(4,6-dimethylpyridin-2-yl)amino]pyridine-2-carboxamide | 327 | 327 | Free Base |
| 2.12 | 2-amino-3-phenylpropyl (RACEMIC) | 4,6-dimethylpyridin-2-yl | 5-[(2-amino-3-phenylpropyl)amino]-3-[(4,6-dimethylpyridin-2-yl)amino]pyridine-2-carboxamide | 391 | 391 | TFA Salt |

TABLE B-continued

| Ex. No. | A | B | Name | [M + H]+ Calc'd | [M + H]+ Obsv'd | Form(s) |
|---|---|---|---|---|---|---|
| 2.13 | RACEMIC, TRANS | | rel-5-{[(1R,2R)-2-aminocyclopropyl]amino}-3-[(4,6-dimethylpyridin-2-yl)amino]pyridine-2-carboxamide | 313 | 313 | TFA Salt |
| 2.14 | RACEMIC | | 5-[(2-amino-3-hydroxypropyl)amino]-3-[(4,6-dimethylpyridin-2-yl)amino]pyridine-2-carboxamide | 331 | 331 | TFA Salt |
| 2.15 | CIS | | 5-[(3-aminocyclobutyl)amino]-3-[(4,6-dimethylpyridin-2-yl)amino]pyridine-2-carboxamide | 327 | 327 | TFA Salt |

Example 3

Conversions from Scheme 2—Conversion of B9 to Structural Subtype B

The preparation in this example describes the procedure for conversion of B9 to compounds of structural subtype B as shown in Scheme 2.

Example 3.1

5-{[(1R,2S)-2-aminocyclohexyl]amino}-3-({5-[3-(2,2-difluoro-1-hydroxyethyl)phenyl]-6-methylpyridin-2-yl}amino)pyridine-2-carboxamide

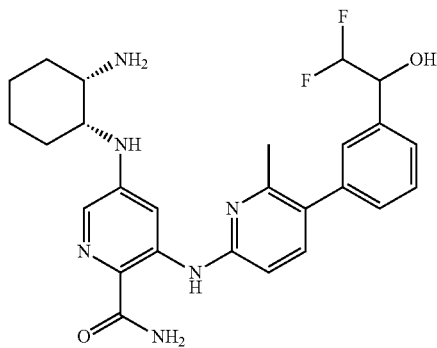

To a solution of tert-butyl (1S,2R)-2-(5-(5-bromo-6-methylpyridin-2-ylamino)-6-cyanopyridin-3-ylamino)cyclohexylcarbamate (PrepEx 1.6) (40 mg, 0.080 mmol) in degassed 1,4-dioxane (0.75 mL) was added 3-(2,2-difluoro-1-hydroxyethyl)phenylboronic acid (32 mg, 0.16 mmol), potassium phosphate tribasic (50 mg, 0.24 mmol), and 1,1'-bis(diphenylphosphino) ferrocene-palladium(II) dichloride dichloromethane complex (6 mg, 0.008 mmol), and the reaction vessel was flushed with argon. The reaction mixture was heated to 80° C. and stirred for 16 hours. The reaction mixture was cooled to room temperature, and diluted with trifluoroacetic acid (0.5 mL). The reaction mixture was immediately concentrated under reduced pressure. The residue was dissolved in a 1:1 DCM/methanol solution (1 ml) and SiliaBond DMT resin (83 mg, 0.050 mmol) was then added at room temperature. After 16 hours, the reaction mixture was filtered and concentrated under reduced pressure. The residue was dissolved in NMP (0.5 mL). Sodium hydroxide (6.0 M aqueous solution, 0.10 mL, 0.60 mmol) and hydrogen peroxide (35% solution in water, 0.30 mL, 3.4 mmol) were added and the reaction mixture was stirred at room temperature for 3 hours. The reaction was diluted with DMSO (1.0 mL) and purified by reverse phase HPLC (acetonitrile/water with 0.1% ammonium hydroxide, linear gradient) to afford 5-{[(1R,2S)-2-aminocyclohexyl]amino}-3-({5-[3-(2,2-difluoro-1-hydroxyethyl)phenyl]-6-methylpyridin-2-yl}amino)pyridine-2-carboxamide. MS ESI calc'd. for $C_{26}H_{31}F_2N_6O_2$ [M+H]+ 497 found 497. $^1$H NMR (600 MHz, DMSO) δ 10.10 (s, 1H), 8.72 (s, 1H), 8.64 (s, 1H), 8.48 (d, J=5.1 Hz, 1H), 8.05 (d, J=8.8 Hz, 1H), 7.25 (s, 1H), 7.18 (d, J=5.1 Hz, 1H), 7.12 (s, 1H), 6.58 (t, J=8.4 Hz, 1H), 3.65-3.43

(m, 1H), 3.35-3.24 (m, 2H), 3.22-3.12 (m, 2H), 2.50 (dd, J=7.2 Hz, 5.4 Hz, 3H), 2.31 (s, 3H), 2.24-2.17 (m, 4H), 1.95-1.81 (m, 4H), 1.69 (dt, J=14.5 Hz, 7.1 Hz, 2H).

The following compounds in Table C were prepared according to procedures which were analogous to those described in Example 3.

TABLE C

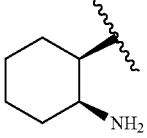

| Ex. No. | A | B | Name | [M + H]+ Calc'd | [M + H]+ Obsv'd | Form(s) |
|---|---|---|---|---|---|---|
| 3.2 | 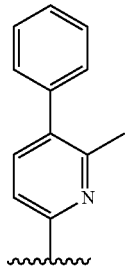 [SMILES: *c1ccc(-c2ccccc2)c(C)n1] "1R, 2S" | 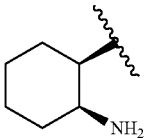 | 5-{[(1R,2S)-2-aminocyclohexyl]amino}-3-[(6-methyl-5-phenylpyridin-2-yl)amino]pyridine-2-carboxamide | 417 | 417 | TFA Salt |
| 3.3 | 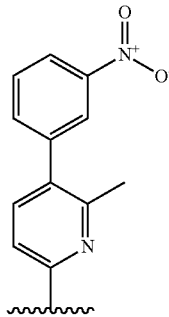 "1R, 2S" | 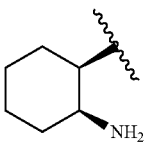 | 5-{[(1R,2S)-2-aminocyclohexyl]amino}-3-{[6-methyl-5-(3-nitrophenyl)pyridin-2-yl]amino}pyridine-2-carboxamide | 462 | 462 | TFA Salt |
| 3.4 | 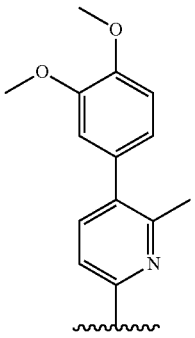 "1R, 2S" | 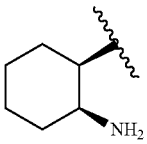 | 5-{[(1R,2S)-2-aminocyclohexyl]amino}-3-{[5-(3,4-dimethoxyphenyl)-6-methylpyridin-2-yl]amino}pyridine-2-carboxamide | 477 | 477 | Free Base |
| 3.5 | 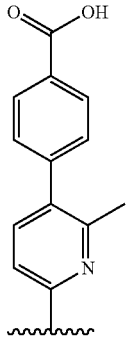 "1R, 2S" | | 4-{6-[(5-{[(1R,2S)-2-aminocyclohexyl]amino}-2-carbamoylpyridin-3-yl)amino]-2-methylpyridin-3-yl}benzoic acid | 461 | 461 | Free Base |

TABLE C-continued

| Ex. No. | A | B | Name | [M + H]⁺ Calc'd | [M + H]⁺ Obsv'd | Form(s) |
|---|---|---|---|---|---|---|
| 3.6 | "1R, 2S" | | 3-{6-[(5-{[(1R,2S)-2-aminocyclohexyl]amino}-2-carbamoylpyridin-3-yl)amino]-2-methylpyridin-3-yl}benzoic acid | 461 | 461 | Free Base |
| 3.7 | "1R, 2S" | | 5-{[(1R,2S)-2-aminocyclohexyl]amino}-3-({5-[4-(hydroxymethyl)phenyl]-6-methylpyridin-2-yl}amino)pyridine-2-carboxamide | 447 | 447 | Free Base |
| 3.8 | "1R, 2S" | RACEMIC | 5-{[(1R,2S)-2-aminocyclohexyl]amino}-3-({5-[4-(2,2-difluoro-1-hydroxyethyl)phenyl]-6-methylpyridin-2-yl}amino)pyridine-2-carboxamide | 497 | 497 | Free Base |
| 3.9 | "1R, 2S" | | 5-{[(1R,2S)-2-aminocyclohexyl]amino}-3-{[6-methyl-5-(1-methyl-1H-benzotriazol-6-yl)pyridin-2-yl]amino}pyridine-2-carboxamide | 472 | 472 | Free Base |

TABLE C-continued

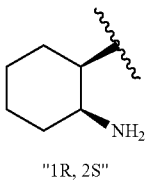 [SMILES: *[C@@H]1CCCC[C@@H]1N]

| Ex. No. | A | B | Name | [M + H]+ Calc'd | [M + H]+ Obsv'd | Form(s) |
|---|---|---|---|---|---|---|
| 3.10 | 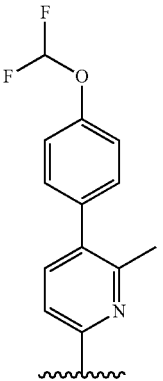 "1R, 2S" | 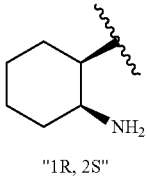 [SMILES: *[C@@H]1CCCC[C@@H]1N] | 5-{[(1R,2S)-2-aminocyclohexyl]amino}-3-({5-[4-(difluoromethoxy)phenyl]-6-methylpyridin-2-yl}amino)pyridine-2-carboxamide | 483 | 483 | Free Base |
| 3.11 | 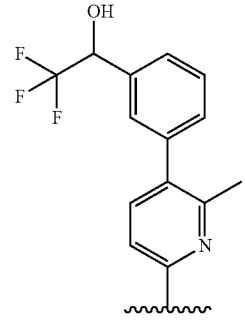 "1R, 2S" | 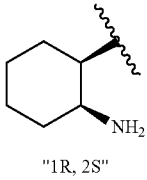 [SMILES: *[C@@H]1CCCC[C@@H]1N] RACEMIC | 5-{[(1R,2S)-2-aminocyclohexyl]amino}-3-({6-methyl-5-[3-(2,2,2-trifluoro-1-hydroxyethyl)phenyl]pyridin-2-yl}amino)pyridine-2-carboxamide | 515 | 515 | Free Base |
| 3.12 | 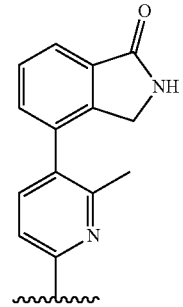 [SMILES: *c1ccc(-c2cccc3c2CNC3=O)c(C)n1] "1R, 2S" | | 5-{[(1R,2S)-2-aminocyclohexyl]amino}-3-{[6-methyl-5-(1-oxo-2,3-dihydro-1H-isoindol-4-yl)pyridin-2-yl]amino}pyridine-2-carboxamide | 472 | 472 | Free Base |

149

150

TABLE C-continued

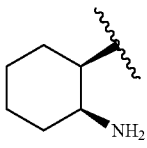

| Ex. No. | A | B | Name | [M + H]+ Calc'd | [M + H]+ Obsv'd | Form(s) |
|---|---|---|---|---|---|---|
| 3.13 | 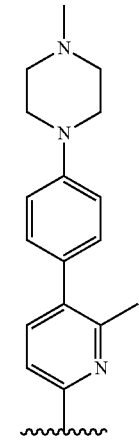 [SMILES: *c1ccc(-c2ccc(N3CCN(C)CC3)cc2)c(C)n1]  "1R, 2S" | 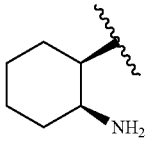 | 5-{[(1R,2S)-2-aminocyclohexyl]amino}-3-({6-methyl-5-[4-(4-methylpiperazin-1-yl)phenyl]pyridin-2-yl}amino)pyridine-2-carboxamide | 515 | 258 (M/2 + 1) | Free Base |
| 3.14 | 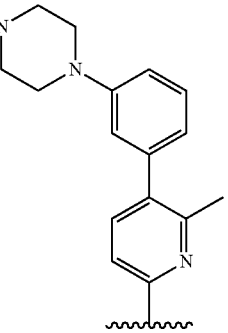  "1R, 2S" | 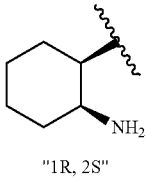 [SMILES: *[C@@H]1CCCC[C@@H]1N] | 5-{[(1R,2S)-2-aminocyclohexyl]amino}-3-({6-methyl-5-[3-(4-methylpiperazin-1-yl)phenyl]pyridin-2-yl}amino)pyridine-2-carboxamide | 515 | 515 | Free Base |
| 3.15 | 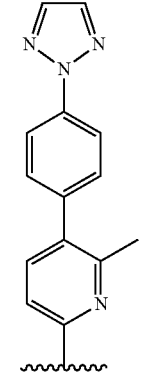 [SMILES: *c1ccc(-c2ccc(-n3nccn3)cc2)c(C)n1]  "1R, 2S" | | 5-{[(1R,2S)-2-aminocyclohexyl]amino}-3-({6-methyl-5-[4-(2H-1,2,3-triazol-2-yl)phenyl]pyridin-2-yl}amino)pyridine-2-carboxamide | 484 | 484 | Free Base |

TABLE C-continued

| Ex. No. | A | B | Name | [M + H]+ Calc'd | [M + H]+ Obsv'd | Form(s) |
|---|---|---|---|---|---|---|
| 3.16 | "1R, 2S" | | 5-{[(1R,2S)-2-aminocyclohexyl]amino}-3-{[6-methyl-5-(3-oxo-2,3-dihydro-1H-isoindol-5-yl)pyridin-2-yl]amino}pyridine-2-carboxamide | 472 | 472 | Free Base |
| 3.17 | "1R, 2S" | | 5-{[(1R,2S)-2-aminocyclohexyl]amino}-3-{[6-methyl-5-(1-oxo-2,3-dihydro-1H-isoindol-5-yl)pyridin-2-yl]amino}pyridine-2-carboxamide | 472 | 472 | Free Base |
| 3.18 | "1R, 2S" | | 5-{[(1R,2S)-2-aminocyclohexyl]amino}-3-{[6-methyl-5-(1-methyl-1H-indazol-5-yl)pyridin-2-yl]amino}pyridine-2-carboxamide | 471 | 471 | Free Base |
| 3.19 | "1R, 2S" | | 5-{[(1R,2S)-2-aminocyclohexyl]amino}-3-[(6-methyl-5-{3-[methyl(methylsulfonyl)amino]phenyl}pyridin-2-yl)amino]pyridine-2-carboxamide | 524 | 524 | Free Base |

TABLE C-continued

| Ex. No. | A | B | Name | [M + H]+ Calc'd | [M + H]+ Obsv'd | Form(s) |
|---|---|---|---|---|---|---|
| 3.20 | "1R, 2S" | | 5-{[(1R,2S)-2-aminocyclohexyl]amino}-3-({6-methyl-5-[3-(2H-1,2,3-triazol-2-yl)phenyl]pyridin-2-yl}amino)pyridine-2-carboxamide | 484 | 484 | Free Base |
| 3.21 | "1R, 2S" | | 5-{[(1R,2S)-2-aminocyclohexyl]amino}-3-{[6-methyl-5-(4-oxo-1,4-dihydroquinazolin-7-yl)pyridin-2-yl]amino}pyridine-2-carboxamide | 485 | 485 | Free Base |
| 3.22 | "1R, 2S" | | 5-{[(1R,2S)-2-aminocyclohexyl]amino}-3-[(6'-methoxy-2-methyl-3,3'-bipyridin-6-yl)amino]pyridine-2-carboxamide | 448 | 448 | Free Base |
| 3.23 | "1R, 2S" | | 5-{[(1R,2S)-2-aminocyclohexyl]amino}-3-[(2-methyl-3,4'-bipyridin-6-yl)amino]pyridine-2-carboxamide | 418 | 418 | Free Base |

TABLE C-continued

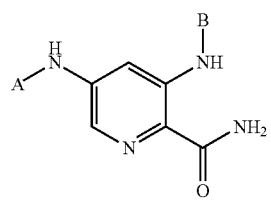

| Ex. No. | A | B | Name | [M + H]+ Calc'd | [M + H]+ Obsv'd | Form(s) |
| --- | --- | --- | --- | --- | --- | --- |
| 3.24 | "1R, 2S" | | 5-{[(1R,2S)-2-aminocyclohexyl]amino}-3-{[5-(2-methoxypyrimidin-5-yl)-6-methylpyridin-2-yl]amino}pyridine-2-carboxamide | 449 | 449 | Free Base |
| 3.25 | "1R, 2S" | | 5-{[(1R,2S)-2-aminocyclohexyl]amino}-3-[(6-methyl-5-pyrimidin-5-ylpyridin-2-yl)amino]pyridine-2-carboxamide | 419 | 419 | Free Base |
| 3.26 | "1R, 2S" | | 5-{[(1R,2S)-2-aminocyclohexyl]amino}-3-[(2'-methoxy-2-methyl-3,3'-bipyridin-6-yl)amino]pyridine-2-carboxamide | 448 | 448 | Free Base |
| 3.27 | "1R, 2S" | | 5-{[(1R,2S)-2-aminocyclohexyl]amino}-3-[(6-methyl-5-quinolin-7-ylpyridin-2-yl)amino]pyridine-2-carboxamide | 468 | 234 (M/2 + 1) | Free Base |

TABLE C-continued

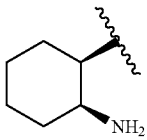

| Ex. No. | A | B | Name | [M + H]+ Calc'd | [M + H]+ Obsv'd | Form(s) |
|---|---|---|---|---|---|---|
| 3.28 | 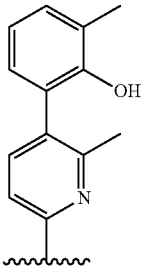 [SMILES: *c1ccc(-c2cccc(C)c2O)c(C)n1] "1R, 2S" | 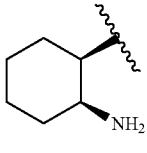 | 5-{[(1R,2S)-2-aminocyclohexyl]amino}-3-{[5-(2-hydroxy-3-methylphenyl)-6-methylpyridin-2-yl]amino}pyridine-2-carboxamide | 447 | 447 | Free Base |
| 3.29 | 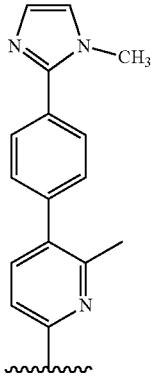 [SMILES: *c1ccc(-c2ccc(-c3nccn3C)cc2)c(C)n1] "1R, 2S" | 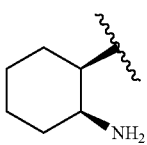 | 5-{[(1R,2S)-2-aminocyclohexyl]amino}-3-({6-methyl-5-[4-(1-methyl-1H-imidazol-2-yl)phenyl]pyridin-2-yl}amino)pyridine-2-carboxamide | 497 | 249 (M/2 + 1) | Free Base |
| 3.30 | 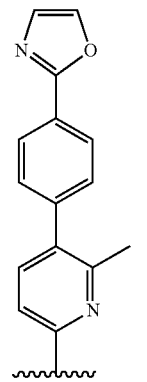 "1R, 2S" |  | 5-{[(1R,2S)-2-aminocyclohexyl]amino}-3-({6-methyl-5-[4-(1,3-oxazol-2-yl)phenyl]pyridin-2-yl}amino)pyridine-2-carboxamide | 484 | 484 | Free Base |

TABLE C-continued

| Ex. No. | A | B | Name | [M + H]+ Calc'd | [M + H]+ Obsv'd | Form(s) |
|---|---|---|---|---|---|---|
| 3.31 | "1R, 2S" | | 5-{[(1R,2S)-2-aminocyclohexyl]amino}-3-{[5-(1,3-dimethyl-2-oxo-2,3-dihydro-1H-benzimidazol-5-yl)-6-methylpyridin-2-yl]amino}pyridine-2-carboxamide | 501 | 501 | Free Base |
| 3.32 | "1R, 2S" | | 5-{[(1R,2S)-2-aminocyclohexyl]amino}-3-{[6-methyl-5-(8-methylquinolin-5-yl)pyridin-2-yl]amino}pyridine-2-carboxamide | 482 | 242 (M/2 + 1) | Free Base |

Example 4

Conversions from Scheme 3—Conversion of D13 to Structural Subtype D

The preparation in this example describes the procedure for conversion of D13 to compounds of structural subtype D as shown in Scheme 3.

Example 4.1

5-{[(1R,2S)-2-aminocyclohexyl]amino}-3-[(6-methyl-4-phenylpyridin-2-yl)amino]pyridine-2-carboxamide

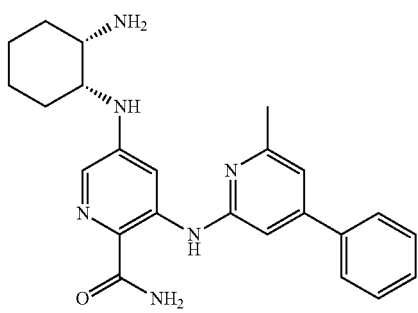

Step 1: Dioxane (1.1 mL), phenylboronic acid (27 mg, 0.22 mmol), and potassium phosphate tribasic (70 mg, 0.33 mmol) were added to a nitrogen purged flask containing tert-butyl [(1S,2R)-2-({5-[(4-chloro-6-methylpyridin-2-yl)amino]-6-cyanopyridin-3-yl}amino)cyclohexyl]carbamate (PrepEx 1.7) (50 mg, 0.11 mmol). The flask was purged and flushed with nitrogen, and then $PdCl_2(dPPf)$-$CH_2Cl_2$ (9 mg, 0.01 mmol) was added. The flask was purged with nitrogen, sealed, and heated to 90° C. for 2 hours. The reaction mixture was cooled to room temperature, diluted with 10% aqueous sodium bicarbonate (10 mL) and extracted with ethyl acetate (10 mL). The organics were dried over sodium sulfate, filtered, and concentrated under reduced pressure. The residue was purified by chromatography on silica gel (10-50% ethyl acetate/hexanes, linear gradient) to afford tert-butyl (1S,2R)-2-(6-cyano-5-(6-methyl-4-phenylpyridin-2-ylamino)pyridin-3-ylamino)cyclohexylcarbamate. MS ESI calc'd. for $C_{29}H_{35}N_6O_2$ [M+H]+ 499. found 499.

Step 2: TFA (1.0 ml, 13 mmol) was added to a solution of tert-butyl (1S,2R)-2-(6-cyano-5-(6-methyl-4-phenylpyridin-2-ylamino)pyridin-3-ylamino)cyclohexylcarbamate (24 mg, 0.048 mmol) in DCM (2 ml). The reaction mixture was stirred for 30 minutes at room temperature. The reaction mixture was concentrated under reduced pressure to afford 5-((1R,2S)-2-aminocyclohexylamino)-3-(6-methyl-4-phenylpyridin-2-ylamino)picolinonitrile. The material was used in the next step without further purification. MS ESI calc'd. for $C_{24}H_{27}N_6$ [M+H]+ 399. found 399.

Step 3: 5-((1R,2S)-2-aminocyclohexylamino)-3-(6-methyl-4-phenylpyridin-2-ylamino)picolinonitrile (19 mg, 0.048 mmol) was dissolved in DMSO (0.25 mL), and then sodium hydroxide (6.0 M in water, 0.040 mL, 0.24 mmol) and hydrogen peroxide (30% w/w solution in water, 0.050 mL, 0.49 mmol) were added. The reaction mixture was stirred at room temperature for 2.5 hours. Additional sodium hydroxide (6.0 M in water, 0.010 mL, 0.060 mmol) and hydrogen peroxide (30% w/w solution in water, 0.012 mL, 0.12 mmol) were added and the reaction mixture was stirred an additional 5 hours. The reaction mixture was acidified with hydrochloric acid (2.0 M in water, 0.14 mL, 0.28 mmol), and directly purified by reverse phase HPLC (acetonitrile/water with 0.1% TFA, linear gradient) to afford 5-{[(1R,2S)-2-aminocyclohexyl]amino}-3-[(6-methyl-4-phenylpyridin-2-yl)amino]pyridine-2-carboxamide TFA salt. MS ESI calc'd. for $C_{24}H_{29}N_6O$ [M+H]$^+$ 417. found 417. $^1$H NMR (500 MHz, CD$_3$OD) δ 8.05 (s, 1H), 7.86 (s, 1H), 7.78-7.72 (m, 2H), 7.56-7.48 (m, 3H), 7.31-7.24 (m, 2H), 3.95 (br s, 1H), 3.62 (br s, 1H), 2.61 (s, 3H), 1.96-1.83 (m, 3H), 1.79-1.66 (m, 3H), 1.62-1.51 (m, 2H).

The following compounds in Table D were prepared according to procedures which were analogous to those described in Example 4.

TABLE D

| Ex. No. | A | B | Name | [M + H]$^+$ Calc'd | [M + H]$^+$ Obsv'd | Form(s) |
|---|---|---|---|---|---|---|
| 4.2 | (1R,2S)-2-aminocyclohexyl | 6'-methyl-3,4'-bipyridin-2'-yl | 5-{[(1R,2S)-2-aminocyclohexyl]amino}-3-[(6'-methyl-3,4'-bipyridin-2'-yl)amino]pyridine-2-carboxamide | 418 | 418 | Free Base |
| 4.3 | (1R,2S)-2-aminocyclohexyl | 6-methyl-4-(1-methyl-1H-pyrazol-4-yl)pyridin-2-yl | 5-{[(1R,2S)-2-aminocyclohexyl]amino}-3-{[6-methyl-4-(1-methyl-1H-pyrazol-4-yl)pyridin-2-yl]amino}pyridine-2-carboxamide | 421 | 421 | Formate Salt |
| 4.4 | (1R,2S)-2-aminocyclohexyl | 6-methyl-4-(1-methyl-1H-pyrazol-5-yl)pyridin-2-yl | 5-{[(1R,2S)-2-aminocyclohexyl]amino}-3-{[6-methyl-4-(1-methyl-1H-pyrazol-5-yl)pyridin-2-yl]amino}pyridine-2-carboxamide | 421 | 421 | TFA Salt |

Example 5

Conversions from Scheme 3—Conversion of E15 to Structural Subtype E

The preparation in this example describes the procedure for conversion of E15 to compounds of structural subtype E as shown in Scheme 3.

Example 5.1

5-{[(1R,1S)-2-aminocyclohexyl]amino}-3-{[6-methyl-5-(propan-2-yloxy)pyridin-2-yl]amino}pyridine-2-carboxamide

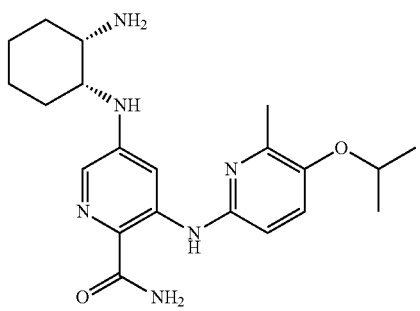

5.1

A mixture of polystyrene-bond triphenylphosphine resin (102 mg, 0.193 mmol) and tert-butyl [(1S,2R)-2-({6-carbamoyl-5-[(5-hydroxy-6-methylpyridin-2-yl)amino]pyridin-3-yl}amino)cyclohexyl]carbamate (PrepEx 1.9) (40 mg, 0.088 mmol) in THF (1.5 mL) was stirred for 5 min at room temperature. A solution of di-tert-butyl azodicarboxylate (32 mg, 0.14 mmol) in THF (0.50 mL) was added, and the reaction mixture was stirred at room temperature. After 30 minutes, 2-propanol (6 mg, 0.1 mmol) was added, and the reaction mixture was stirred at room temperature. Additional PS-triphenylphosphine (102 mg, 0.193 mmol), di-tert-butyl azodicarboxylate (32 mg, 0.14 mmol), and 2-propanol (6 mg, 0.1 mmol) were then added, and the reaction mixture was stirred for an additional 10 hours at room temperature. The reaction mixture was filtered (washing with methanol) and the filtrate was concentrated under reduced pressure. The residue was diluted with DCM (1 mL) and TFA (1 mL) and stirred. After 10 minutes, the reaction mixture was concentrated under reduced pressure. The residue was diluted with DMSO and purified directly by reverse phase HPLC (acetonitrile/water with 0.1% TFA, linear gradient) to afford 5-{[(1R,2S)-2-aminocyclohexyl]amino}-3-{[6-methyl-5-(propan-2-yloxy)pyridin-2-yl]amino}pyridine-2-carboxamide TFA salt. MS ESI calc'd. for $C_{21}H_{31}N_6O_2$ [M+H]$^+$ 399. found 399. $^1$H NMR (500 MHz, CD$_3$OD). δ 7.83 (d, J=2.3 Hz, 1H), 7.78 (d, J=9.2 Hz, 1H), 7.53 (s, 1H), 7.32 (d, J=9.2 Hz, 1), 4.69-4.56 (m, 1H), 3.98 (s, 1H), 3.57 (s, 1H), 2.49 (s, 3H), 1.95-1.83 (m, 3H), 1.80-1.63 (m, 3H), 1.62-1.41 (m, 2H), 1.36 (d, J=6.0 Hz, 6H).

The following compounds in Table E were prepared according to procedures which were analogous to those described in Example 5.

TABLE E

| Ex. No. | A | B | Name | [M + H]$^+$ Calc'd | [M + H]$^+$ Obsv'd | Form(s) |
|---|---|---|---|---|---|---|
| 5.2 | "1R,2S" | (isopropoxy pyridinyl) | 5-{[(1R,2S)-2-aminocyclohexyl]amino}-3-{[6-methyl-4-(1-methylethoxy)pyridin-2-yl]amino}pyridine-2-carboxamide | 399 | 399 | Free Base |
| 5.3 | "1R,2S" | (benzyloxy methylpyridinyl) | 5-{[(1R,2S)-2-aminocyclohexyl]amino}-3-{[4-(benzyloxy)-6-methylpyridin-2-yl]amino}pyridine-2-carboxamide | 447 | 447 | TFA Salt |

TABLE E-continued

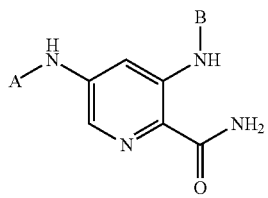

| Ex. No. | A | B | Name | [M + H]+ Calc'd | [M + H]+ Obsv'd | Form(s) |
|---|---|---|---|---|---|---|
| 5.4 | ![cyclohexyl with NH2] "1R,2S" | ![methoxy methylpyridine] | 5-{[(1R,2S)-2-aminocyclohexyl]amino}-3-[(4-methoxy-6-methylpyridin-2-yl)amino]pyridine-2-carboxamide | 371 | 371 | Free Base, TFA Salt |

Example 6

Conversions from Scheme 1—Conversion of A8 to Structural Subtype A

The preparation in this example describes the procedure for conversion of A8 to compounds of structural subtype A as shown in Scheme 1.

Example 6.1

5-{[3-(acetylamino)-2-aminopropyl]amino}-3-[(4,6-dimethylpyridin-2-yl)amino]pyridine-2-carboxamide

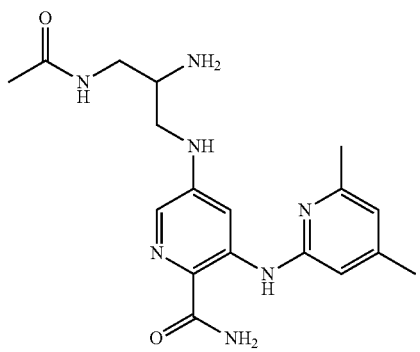

6.1

Step 1: To a flask were added N-[bis(4-methoxyphenyl)methyl]-5-bromo-3-[(4,6-dimethylpyridin-2-yl)amino]pyridine-2-carboxamide (100 mg, 0.183 mmol) (PrepEx 1.11), tert-butyl [1-(acetylamino)-3-aminopropan-2-yl]carbamate (51 mg, 0.22 mmol), tris(dibenzylideneacetone)dipalladium (0) (17 mg, 0.018 mmol), Xantphos (21 mg, 0.037 mmol) and cesium carbonate (131 mg, 0.402 mmol). 1,4-Dioxane (1 mL) was added, and the reaction mixture was purged with nitrogen for 5 minutes. The reaction mixture was then stirred at 80° C. for 16 hours. The reaction mixture was cooled to room temperature, and then diluted with ethyl acetate and saturated aqueous ammonium chloride. The organics were separated, dried over magnesium sulfate, filtered, and concentrated under reduced pressure. The residue was purified by chromatography on silica gel to afford tert-butyl {1-(acetylamino)-3-[(6-{[bis(4-methoxyphenyl)methyl]carbamoyl}-5-[(4,6-dimethylpyridin-2-yl)amino]pyridin-3-yl)amino]propan-2-yl}carbamate. MS ESI calc'd for $C_{38}H_{48}N_7O_6$ [M+H]+ 698. found 698.

Step 2: To a solution of tert-butyl {1-(acetylamino)-3-[(6-{[bis(4-methoxyphenyl)methyl]carbamoyl}-5-[(4,6-dimethylpyridin-2-yl)amino]pyridin-3-yl)amino]propan-2-yl}carbamate in DCM (1 mL) were added TFA (0.2 mL) and triethylsilane (0.146 mL, 0.917 mmol). The reaction mixture was stirred at room temperature for 4 hours, and then concentrated under reduced pressure. The residue was purified via reverse phase HPLC (acetonitrile/water with 0.1% TFA, linear gradient) to give 5-{[3-(acetylamino)-2-aminopropyl]amino}-3-[(4,6-dimethylpyridin-2-yl)amino]pyridine-2-carboxamide TFA salt. MS ESI calc'd for $C_{18}H_{26}N_7O_2$ [M+H]+ 372. found 372. $^1$H NMR (500 MHz, CD$_3$OD) δ 7.84 (d, J=2 Hz, 1H), 7.41 (s, 1H), 7.21 (s, 1H), 6.95 (s, 1H), 3.60-3.42 (m, 5H), 2.54 (s, 3H), 2.43 (s, 3H), 1.99 (s, 3H).

The following compound in Table F was prepared according to procedures which were analogous to those described in Example 6.

TABLE F

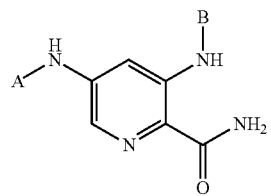

| Ex. No. | A | B | Name | [M + H]+ Calc'd | [M + H]+ Obsv'd | Form(s) |
|---|---|---|---|---|---|---|
| 6.2 | 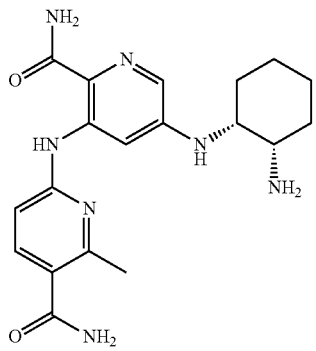 RACEMIC | (4,6-dimethylpyridin-2-yl fragment shown) | 5-{[2-amino-4-(methylsulfonyl)butyl]amino}-3-[(4,6-dimethylpyridin-2-yl)amino]pyridine-2-carboxamide | 407 | 407 | TFA Salt |

Example 7

5-{[(1R,2S)-2-aminocyclohexyl]amino}-3-[(5-carbamoyl-6-methylpyridin-2-yl)amino]pyridine-2-carboxamide

7

Step 1: To a flask containing tert-butyl {(1S,2R)-2-[(5-bromo-6-cyanopyridin-3-yl)amino]cyclohexyl}carbamate (PrepEx 1.1) (120 mg, 0.30 mmol), 6-amino-2-methylpyridine-3-carbonitrile (40 mg, 0.30 mmol), 2-dicyclohexylphosphino-2',4',6'-triisopropylbiphenyl (29 mg, 0.061 mmol), Pd$_2$(dba)$_3$ (28 mg, 0.031 mmol) and cesium carbonate (198 mg, 0.609 mmol) was added degassed dioxane (3 mL). The reaction mixture was heated to 100° C. overnight. The reaction mixture was cooled to room temperature, diluted with ethyl acetate and water, and the organic layer was separated, dried over magnesium sulfate, filtered, and concentrated under reduced pressure. Purification by chromatography on silica gel (0-40% ethyl acetate/hexanes, linear gradient) afforded tert-butyl [(1S,2R)-2-({6-cyano-5-[(5-cyano-6-methylpyridin-2-yl)amino]pyridin-3-yl}amino)cyclohexyl]carbamate. MS ESI calc'd for C$_{24}$H$_{30}$N$_7$O$_2$ [M+H]+ 448. found 448. $^1$H NMR (500 MHz, DMSO-d$_6$) δ 9.62 (s, 1H), 7.92-7.86 (m, 2H), 7.26 (s, 1H), 6.81 (d, J=8.8 Hz, 1H), 6.64 (d, J=8.5 Hz, 1H), 6.56 (d, J=7.7 Hz, 1), 3.75-3.64 (m, 2H), 2.47 (s, 3H), 1.75-1.42 (m, 8H), 1.26 (s, 9H).

Step 2: To a solution of tert-butyl [(1S,2R)-2-({6-cyano-5-[(5-cyano-6-methylpyridin-2-yl)amino]pyridin-3-yl}amino)cyclohexyl]carbamate (58 mg, 0.13 mmol) in dichloromethane (1.3 mL) was added trifluoroacetic acid (1.0 mL, 13 mmol) at room temperature. After 16 hours, the reaction mixture was concentrated under reduced pressure to afford 5-{[(1R,2S)-2-aminocyclohexyl]amino}-3-[(5-cyano-6-methylpyridin-2-yl)amino]pyridine-2-carbonitrile. The material was used in the next step without further purification. MS ESI calc'd for C$_{19}$H$_{22}$N$_7$ [M+H]+ 348. found 348.

Step 3: To a solution of 5-{[(1R,2S)-2-aminocyclohexyl]amino}-3-[(5-cyano-6-methylpyridin-2-yl)amino]pyridine-2-carbonitrile (45 mg, 0.13 mmol) in DMSO (1.3 mL) was added potassium hydroxide (73 mg, 1.3 mmol) and hydrogen peroxide (35% solution in water, 0.23 mL, 2.6 mmol) and the reaction was stirred for one hour at room temperature. The reaction mixture was filtered and purified by reverse phase HPLC to afford 5-{[(1R,2S)-2-aminocyclohexyl]amino}-3-[(5-carbamoyl-6-methylpyridin-2-yl)amino]pyridine-2-carboxamide TFA salt. MS ESI calc'd for C$_{19}$H$_{26}$N$_7$O$_2$ [M+H]+ 384. found 384. $^1$H NMR (500 MHz, DMSO-d$_6$) δ 12.01 (s, 1H), 8.63 (s, 1H), 7.96 (s, 1H), 7.84 (s, 3H), 7.72 (d, J=2.4 Hz, 1H), 7.71-7.68 (m, 2H), 7.41 (s, 1H), 7.29 (s, 1H), 6.68 (d, J=8.4 Hz, 1H), 6.39 (d, J=7.9 Hz, 1H), 3.88-3.73 (m, 1H), 3.62-3.47 (m, 1H), 2.56 (s, 3H), 1.92-1.77 (m, 2H), 1.79-1.68 (m, 1H), 1.69-1.54 (m, 3H), 1.50-1.32 (m, 2H).

Example 8

5-{[(1R,2S)-2-aminocyclohexyl]amino}-3-{[6-(piperazin-1-ylmethyl)pyridin-2-yl]amino}pyridine-2-carboxamide

8

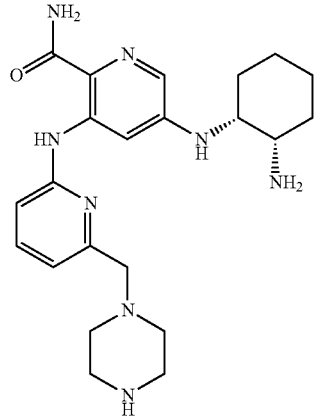

Step 1: To a flask containing tert-butyl {(1S,2R)-2-[(5-bromo-6-cyanopyridin-3-yl)amino]cyclohexyl}carbamate (PrepEx 1.1) (120 mg, 0.30 mmol), tert-butyl 4-[(6-aminopyridin-2-yl)methyl]piperazine-1-carboxylate (89 mg, 0.30 mmol), 2-dicyclohexylphosphino-2',4',6'-triisopropylbiphenyl (29 mg, 0.061 mmol), $Pd_2(dba)_3$ (28 mg, 0.031 mmol) and cesium carbonate (198 mg, 0.609 mmol) was added degassed dioxane (3 mL), and the reaction mixture was heated to 100° C. After 16 hours, the reaction mixture was cooled to room temperature, diluted with ethyl acetate and water, and the organic layer was separated, dried over magnesium sulfate, filtered, and concentrated under reduced pressure. Purification by chromatography on silica gel (0-60% ethyl acetate/hexanes, linear gradient) afforded tert-butyl 4-[(6-{[5-({(1R,2S)-2-[(tert-butoxycarbonyl)amino]cyclohexyl}amino)-2-cyanopyridin-3-yl]amino}pyridin-2-yl)methyl]piperazine-1-carboxylate. MS ESI calc'd for $C_{32}H_{47}N_8O_4$ $[M+H]^+$ 607. found 607. $^1$H NMR (500 MHz, DMSO-$d_6$) δ 8.85 (s, 1H), 7.77 (s, 1H), 7.58 (t, J=7.7 Hz, 1H), 7.52 (s, 1H), 6.94-6.82 (m, 2H), 6.60 (d, J=7.8 Hz, 1H), 6.40 (d, J=7.6 Hz, 1H), 3.74-3.60 (m, 2H), 3.52-3.36 (m, 2H), 3.36-3.24 (m, 4H), 2.34 (s, 4H), 1.75-1.40 (m, 8H), 1.36 (s, 9H), 1.25 (s, 9H).

Step 2: To a solution of tert-butyl 4-[(6-{[5-({(1R,2S)-2-[(tert-butoxycarbonyl)amino]cyclohexyl}amino)-2-cyanopyridin-3-yl]amino}pyridin-2-yl)methyl]piperazine-1-carboxylate (90 mg, 0.15 mmol) in dichloromethane (1.5 mL) was added trifluoroacetic acid (0.17 mL, 2.2 mmol) and the reaction mixture was stirred for 1 hour at room temperature. The reaction was then concentrated under reduced pressure to afford 5-{[(1R,2S)-2-aminocyclohexyl]amino}-3-{[6-(piperazin-1-ylmethyl)pyridin-2-yl]amino}pyridine-2-carbonitrile. The material was used in the next step without further purification. MS ESI calc'd for $C_{22}H_{31}N_8$ $[M+H]^+$ 407. found 407.

Step 3: To a solution of the product from Step 2 (60 mg, 0.15 mmol) in DMSO (1.5 mL) was added potassium hydroxide (41 mg, 0.74 mmol) and hydrogen peroxide (35% solution in water, 0.13 mL, 1.5 mmol) and the reaction mixture was stirred for 1 hour at room temperature. The reaction mixture was then filtered and purified by reverse phase HPLC to afford 5-{[(1R,2S)-2-aminocyclohexyl]amino}-3-{[6-(piperazin-1-ylmethyl)pyridin-2-yl]amino}pyridine-2-carboxamide TFA salt. MS ESI calc'd for $C_{22}H_{33}N_8O$ $[M+H]^+$ 425. found 425. $^1$H NMR (500 MHz, DMSO-$d_6$) δ 11.87 (s, 1H), 8.75 (s, 2H), 8.38 (s, 1H), 8.03-7.84 (m, 3H), 7.71 (d, J=2.4 Hz, 1H), 7.67 (t, J=7.8 Hz, 1H), 7.37 (s, 1H), 6.98 (d, J=7.4 Hz, 1H), 6.81 (d, J=8.1 Hz, 1H), 6.41 (d, J=8.2 Hz, 1), 3.86-3.68 (m, 3H), 3.56-3.43 (m, 1H), 3.27-3.05 (m, 4H), 2.92-2.68 (m, 4H), 1.92-1.79 (m, 2H), 1.79-1.71 (m, 1H), 1.71-1.54 (m, 3), 1.49-1.37 (m, 2H).

Example 9

5-amino-3-[(4,6-dimethylpyridin-2-yl)amino]pyridine-2-carboxamide

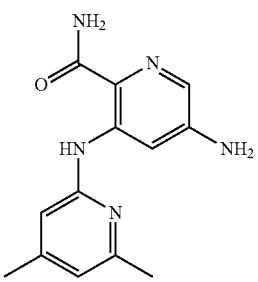

9

To a solution of 5-amino-3-[(4,6-dimethylpyridin-2-yl)amino]pyridine-2-carbonitrile (PrepEx 1.8) (125 mg, 0.523 mmol) in DMSO (4.0 mL) was added potassium hydroxide (147 mg, 2.61 mmol) and hydrogen peroxide (35% solution in water, 0.46 mL, 5.3 mmol) and the reaction mixture was stirred for 1 hour at room temperature. The reaction mixture was then filtered and purified by reverse phase HPLC (0-100% acetonitrile/water with 0.1% TFA, linear gradient) to afford 5-amino-3-[(4,6-dimethylpyridin-2-yl)amino]pyridine-2-carboxamide TFA salt. MS ESI calc'd for $C_{13}H_{16}N_5O$ $[M+H]^+$ 258. found 258. $^1$H NMR (500 MHz, DMSO-$d_6$) δ 11.72 (s, 1H), 7.93 (s, 1H), 7.56 (s, 1H), 7.38 (s, 1H), 7.07-6.52 (m, 2H), 2.42 (s, 3H), 2.28 (s, 3H).

Example 10

3-[(4,6-dimethylpyridin-2-yl)amino]-5-(glycylamino)pyridine-2-carboxamide

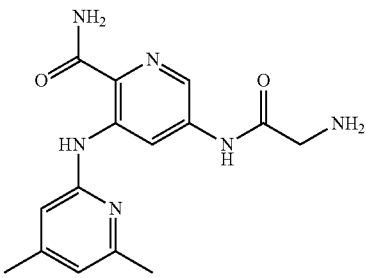

10

Step 1: To a solution of 5-amino-3-[(4,6-dimethylpyridin-2-yl)amino]pyridine-2-carbonitrile (PrepEx 1.8) (100 mg, 0.418 mmol), 9H-fluoren-9-ylmethyl (2-chloro-2-oxoethyl)carbamate (264 mg, 0.835 mmol), and diisopropylethylamine (0.15 mL, 0.84 mmol) in DMF (3.2 mL) at 0° C. was added 1-propanephosphonic acid cyclic anhydride (50% solution in ethyl acetate, 0.29 mL, 0.50 mmol). The reaction mixture was stirred for 2 hours while warming to room temperature. The reaction mixture was diluted with ethyl acetate and washed with sodium hydroxide (1.0 M in water). The organics were dried over magnesium sulfate, filtered, and concentrated under reduced pressure. Dichloromethane (3 mL) was slowly added, and the precipitated solids were filtered and collected to afford 9H-fluoren-9-ylmethyl [2-({6-cyano-5-[(4,6-dimethylpyridin-2-yl)amino]pyridin-3-yl}amino)-2-oxoethyl]carbamate. MS ESI calc'd for $C_{30}H_{27}N_6O_3$ $[M+H]^+$ 519. found 519. $^1$H NMR (500 MHz, DMSO-$d_6$) δ 10.54 (s, 1H), 9.09 (s, 1H), 8.78 (d, J=2.0 Hz, 1H), 8.39 (d, J=2.1 Hz, 1H), 7.88 (d, J=7.5 Hz, 2), 7.75-7.65 (m, 3H), 7.40 (t, J=7.4 Hz, 2H), 7.31 (t, J=7.4 Hz, 2H), 6.65 (s, 1H), 6.61 (s, 1H), 4.29 (d, J=7.0 Hz, 2), 4.24-4.20 (m, 1H), 3.84 (d, J=6.1 Hz, 2H), 2.28 (s, 3H), 2.20 (s, 3H).

Step 2: To a suspension of 9H-fluoren-9-ylmethyl [2-({6-cyano-5-[(4,6-dimethylpyridin-2-yl)amino]pyridin-3-yl}amino)-2-oxoethyl]carbamate (120 mg, 0.23 mmol) in DMF (1.8 mL) was added piperidine (394 mg, 4.63 mmol). After 1 hour, the reaction mixture was concentrated under reduced pressure, and the residue was purified by chromatography on silica gel (0-70% ethyl acetate/hexanes, linear gradient, followed by 0-12% methanol/dichloromethane, linear gradient) to afford N-{6-cyano-5-[(4,6-dimethylpyridin-2-yl)amino]pyridin-3-yl}glycinamide. MS ESI calc'd for $C_{15}H_{17}N_6O$ $[M+H]^+$ 297. found 297. $^1$H NMR (500 MHz, DMSO-$d_6$) δ 9.09 (s, 1H), 8.85 (d, J=2.1 Hz, 1H), 8.43 (d, J=2.1 Hz, 1H), 6.64 (s, 1H), 6.61 (s, 1H), 3.31 (s, 2H), 2.29 (s, 3H), 2.21 (s, 3H).

Step 3: To a solution of N-{6-cyano-5-[(4,6-dimethylpyridin-2-yl)amino]pyridin-3-yl}glycinamide (40 mg, 0.14 mmol) in DMSO (1 mL) was added potassium hydroxide (38 mg, 0.68 mmol) and hydrogen peroxide (35% w/w solution in water, 0.12 mL, 1.4 mmol) and the reaction was stirred for 1 hour at room temperature. The reaction mixture was filtered and purified by reverse phase HPLC (0-100% acetonitrile/water with 0.1% TFA, linear gradient) to afford 3-[(4,6-dimethylpyridin-2-yl)amino]-5-(glycylamino)pyridine-2-carboxamide TFA salt. MS ESI calc'd for $C_{15}H_{19}N_6O_2$ [M+H]$^+$ 315. found 315. $^1$H NMR (500 MHz, DMSO-$d_6$) δ 11.72 (s, 1H), 10.79 (s, 1H), 9.63 (s, 1H), 8.30 (d, J=2.2 Hz, 1H), 8.24 (s, 1H), 8.14 (s, 3H), 7.74 (s, 1H), 6.65 (s, 1H), 6.55 (s, 1H), 3.85 (d, J=5.6 Hz, 2H), 2.43 (s, 3H), 2.22 (s, 3H).

Example 11

5-{[(1R,2S)-2-aminocyclohexyl]amino}-3-[(4-hydroxy-6-methylpyridin-2-yl)amino]pyridine-2-carboxamide

11

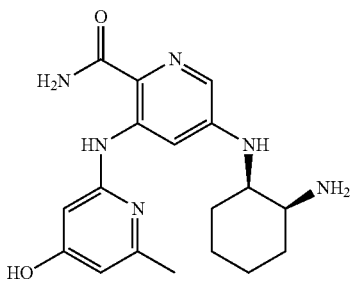

Step 1: To a nitrogen purged flask containing a mixture of tert-butyl (1S,2R)-2-(5-(4-chloro-6-methylpyridin-2-ylamino)-6-cyanopyridin-3-ylamino)cyelohexylcarbamate (PrepEx 1.7) (100 mg, 0.219 mmol), 2-di-t-butylphosphino-3,4,5,6-tetramethyl-2',4',6'-tri-i-propylbiphenyl (13 mg, 0.026 mmol) and Pd$_2$(dba)$_3$ (6 mg, 0.007 mmol) in dioxane (1.2 ml) was added potassium hydroxide (1.0 M in water, 0.66 ml, 0.66 mmol). The reaction mixture was sealed and heated in an oil bath at 90° C. for 3 hours. The reaction mixture was cooled to ambient temperature, quenched with 10% aqueous potassium hydrogen sulfate (5 mL), diluted with ethyl acetate (10 mL), and the pH adjusted to ~8.5 with 10% aqueous sodium bicarbonate solution. The organics were separated, dried over sodium sulfate, filtered, and concentrated under reduced pressure. The residue was purified by silica gel chromatography (0-5% methanol/ethyl acetate, linear gradient) to afford tert-butyl [(1S,2R)-2-({6-carbamoyl-5-[(4-hydroxy-6-methylpyridin-2-yl)amino]pyridin-3-yl}amino)cyclohexyl]carbamate. MS ESI calc'd. for $C_{23}H_{33}N_6O_4$ [M+H]$^+$ 457. found 457.

Step 2: To a solution of tert-butyl [(1S,2R)-2-({6-carbamoyl-5-[(4-hydroxy-6-methylpyridin-2-yl)amino]pyridin-3-yl]amino)cyclohexyl}carbamate (32 mg, 0.070 mmol) in DCM (2 ml) was added TFA (1.0 mL, 13 mmol), and the reaction mixture was stirred for 30 minutes at ambient temperature. The reaction mixture was concentrated under reduced pressure, dissolved in DMSO (1 mL), and purified by reverse phase HPLC (acetonitrile/water with 0.1% formic acid, linear gradient) to afford 5-{[(1R,2S)-2-aminocyclohexyl]amino}-3-[(4-hydroxy-6-methylpyridin-2-yl)amino]pyridine-2-carboxamide formic acid salt. MS ESI calc'd. for $C_{18}H_{25}N_6O_2$ [M+H]$^+$ 357. found 357. $^1$H NMR (500 MHz, CD$_3$OD) δ 8.10 (s, 1H), 7.85 (s, 1H), 7.40 (s, 1H), 6.39 (s, 1H), 6.25 (s, 1H), 3.95 (br s, 1H), 3.56 (br s, 1H), 2.38 (s, 3H), 1.90-1.82 (m, 3H), 1.80-1.62 (m, 3H), 1.60-1.50 (m, 2H).

Example 12

2-[(5-{[(1R,2S)-2-aminocyclohexyl]amino}-2-carbamoylpyridin-3-yl)amino]-6-methylpyridine-4-carboxylic acid

12

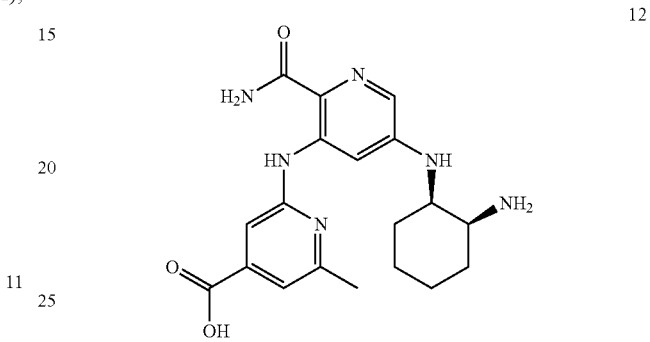

Step 1: To tert-butyl (1S,2R)-2-(5-(4-chloro-6-methylpyridin-2-ylamino)-6-cyanopyridin-3-ylamino)cyclohexylcarbamate (PrepEx 1.7) (50 mg, 0.11 mmol), 3-methyl-4-(4,4,5,5-tetramethyl-1,3,2-dioxaborolan-2-yl)isoxazole (27 mg, 0.13 mmol), and tricyclohexylphosphine (4 mg, 0.01 mmol) in a nitrogen purged vial was added dioxane (0.6 ml) and potassium phosphate tribasic (1.25 M in water, 0.26 ml, 0.33 mmol). The reaction mixture was purged with nitrogen, and then Pd$_2$ dba$_3$ (5 mg, 0.005 mmol) was added. The reaction vessel was sealed and heated at 100° C. for 1 hour. The reaction mixture was diluted with ethyl acetate (10 mL) and washed with aqueous saturated sodium bicarbonate solution (10 mL). The organics were separated, dried over sodium sulfate, filtered, and concentrated under reduced pressure. The residue was purified by silica gel chromatography (5-50% ethyl acetate/hexanes, linear gradient) to give tert-butyl (1S,2R)-2-(6-cyano-5-(6-methyl-4-(3-methylisoxazol-4-yl)pyridin-2-ylamino)pyridin-3-ylamino)cyclohexylcarbamate. MS ESI calc'd. for $C_{27}H_{34}N_7O_3$ [M+H]$^+$ 504. found 504.

Step 2: To tert-butyl (1S,2R)-2-(6-cyano-5-(6-methyl-4-(3-methylisoxazol-4-yl)pyridin-2-ylamino)pyridin-3-ylamino)cyclohexylcarbamate (50 mg, 0.099 mmol) in DCM (1 ml) was added TFA (1.0 ml, 13 mmol). The reaction mixture was stirred at ambient temperature for 1 hour. The reaction mixture was concentrated under reduced pressure to give 54(1R,2S)-2-aminocyclohexylamino)-3-(6-methyl-4-(3-methylisoxazol-4-yl)pyridin-2-ylamino)picolinonitrile. MS ESI calc'd. for $C_{22}H_{26}N_7O$ [M+H]$^+$ 404. found 404.

Step 3: 5-((1R,2S)-2-aminocyclohexylamino)-3-(6-methyl-4-(3-methylisoxazol-4-yl)pyridin-2-ylamino)picolinonitrile (40 mg, 0.099 mmol) was dissolved in DMSO (0.50 mL), and sodium hydroxide (6.0 M in water, 0.165 mL, 0.99 mmol) and hydrogen peroxide (30% solution in water, 0.10 mL, 0.98 mmol) were added. The reaction mixture was stirred at room temperature for 24 hours. The reaction mixture was quenched with hydrochloric acid (2.0 M in water, 0.50 mL, 1.0 mmol) and purified directly by reverse phase HPLC to give 2-[(5-{[(1R,2S)-2-aminocyclohexyl]amino}-2-carbamoylpyridin-3-yl)amino]-6-methylpyridine-4-carboxylic acid TFA salt. MS ESI calc'd. for $C_{19}H_{25}N_6O_3$ [M+H]+ 385. found 385. 1H NMR (500 MHz, CD3OD) δ 8.62 (s, 1H), 7.75 (s, 1H), 7.22 (s, 1H), 7.20 (s, 1H), 3.94-3.90 (m, 1H), 3.74-3.70 (m, 1H), 2.54 (s, 3H), 2.00-1.88 (m, 3H), 1.80-1.68 (m, 3H), 1.62-1.54 (m, 2H).

Example 13

5-{[(1R,2S)-2-aminocyclohexyl]amino}-3-[(6-ethylpyridin-2-yl)amino]pyridine-2-carboxamide

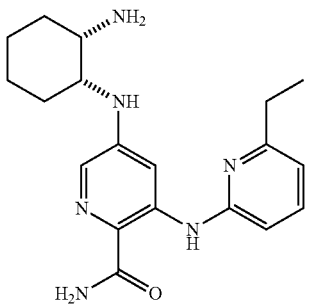

Step 1: tert-Butyl {(1S,2R)-2-[(5-bromo-6-cyanopyridin-3-yl)amino]cyclohexyl}carbamate (PrepEx 1.1) (100 mg, 0.253 mmol) was suspended in dichloromethane (1 mL). TFA (0.390 mL, 5.06 mmol) was added, and the reaction mixture was maintained at room temperature for 1.5 hours. The reaction mixture was concentrated under reduced pressure to afford 5-{[(1R,2S)-2-aminocyclohexyl]amino}-3-bromopyridine-2-carbonitrile TFA salt. The material was used without further purification in the subsequent transformation. MS ESI calc'd. for $C_{12}H_{16}BrN_4$ [M+H]+ 295 and 297. found 295 and 297.

Step 2: A mixture of 5-{[(1R,2S)-2-aminocyclohexyl]amino}-3-bromopyridine-2-carbonitrile TFA salt (62 mg, 0.15 mmol), 2-amino-6-ethylpyridine (19 mg, 0.15 mmol), Xantphos (13 mg, 0.023 mmol), Pd2(dba)3 (14 mg, 0.015 mmol), and cesium carbonate (197 mg, 0.606 mmol) was evacuated and backfilled with nitrogen (3×). Dioxane (1 mL) was added, and the reaction mixture was heated to 80° C. for 3 hours. The reaction mixture was allowed to cool to room temperature, filtered, and concentrated under reduced pressure to afford 5-{[(1R,2S)-2-aminocyclohexyl]amino}-3-[(6-ethylpyridin-2-yl)amino]pyridine-2-carbonitrile. The material was used without further purification in the subsequent transformation. MS ESI calc'd. for $C_{19}H_{25}N_6$ [M+H]+ 337. found 337.

Step 3: A suspension of 5-{[(1R,2S)-2-aminocyclohexyl]amino}-3-[(6-ethylpyridin-2-yl)amino]pyridine-2-carbonitrile (51 mg, 0.152 mmol) and potassium trimethylsilanolate (486 mg, 3.79 mmol) in dioxane (3 mL) was heated to 100° C. for 3 hours. The reaction mixture was allowed to cool to room temperature, filtered, and concentrated under reduced pressure. The residue was dissolved in DMSO, filtered, and purified via reverse phase HPLC (acetonitrile/water with 0.1% TFA, linear gradient) to afford 5-{[(1R,2S)-2-aminocyclohexyl]amino}-3-[(6-ethylpyridin-2-yl)amino]pyridine-2-carboxamide. MS ESI calc'd. for $C_{19}H_{27}N_6O$[M+H]+ 355. found 355. 1H NMR (500 MHz, DMSO-d6) δ 11.84 (s, 1H), 8.56 (s, 1H), 7.92 (s, 1H), 7.88-7.80 (m, 2H), 7.70 (d, J=2.5 Hz, 1H), 7.58-7.54 (m, 1H), 7.34 (s, 1H), 6.76 (d, J=7.3 Hz, 1H), 6.65 (d, J=8.2 Hz, 1H), 6.34 (d, J=8.4 Hz, 1H), 3.81 (br s, 1H), 2.68 (q, J=7.5 Hz, 2H), 1.86-1.79 (m, 2H), 1.73-1.67 (m, 1H), 1.67-1.54 (m, 3H), 1.45-1.35 (m, 2H), 1.24 (t, J=7.6 Hz, 3H).

Example 14

5-[(3-aminopropyl)amino]-3-[(4,6-dimethylpyridin-2-yl)amino]pyridine-2-carboxamide

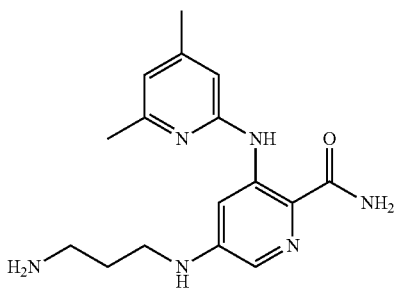

Step 1: N-[bis(4-methoxyphenyl)methyl]-5-bromo-3-[(4,6-dimethylpyridin-2-yl)amino]pyridine-2-carboxamide (PrepEx 1.11) (50 mg, 0.091 mmol), tert-butyl (3-aminopropyl)carbamate (32 mg, 0.18 mmol), tris(dibenzylideneacetone)dipalladium(0) (8 mg, 0.01 mmol), Xantphos (11 mg, 0.018 mmol), and cesium carbonate (66 mg, 0.20 mmol) were combined in a dry flask and purged with argon for 5 minutes. To this mixture was added 1,4-dioxane (0.75 mL), and the reaction mixture was deoxygenated by flushing it with argon for 5 minutes. The reaction mixture was heated to 95° C. After 6 hours, the reaction mixture was cooled, diluted with ethyl acetate (50 mL), filtered through CELITE, and concentrated under reduced pressure. The residue was purified by chromatography on silica gel (0-60% ethyl acetate/hexanes, linear gradient) to afford tert-butyl {3-[(6-{[bis(4-methoxyphenyl)methyl]carbamoyl}-5-[(4,6-dimethylpyridin-2-yl)amino]pyridin-3-yl)amino}propyl]carbamate. MS ESI calc'd. for $C_{36}H_{45}N_6O_5$ [M+H]+ 641. found 641. 1H NMR (500 MHz, DMSO-d6) δ 11.48 (s, 1H), 8.70 (d, J=8.5 Hz, 1H), 8.51 (d, J=2.5 Hz, 1H), 7.53 (d, J=2.0 Hz, 1H), 7.22 (d, J=8.5 Hz, 4H), 6.92-6.84 (m, 5H), 6.64-6.60 (m, 1H), 6.57 (s, 1H), 6.45 (s, 1H), 6.11 (d, J=8.5 Hz, 1H), 3.71 (s, 6H), 3.12-3.05 (m, 2H), 3.04-2.97 (m, 2H), 2.35 (s, 3H), 2.18 (s, 3H), 1.74-1.66 (m, 2H), 1.32 (s, 9H).

Step 2: To a solution of tert-butyl {3-[(6-{[bis(4-methoxyphenyl)methyl]carbamoyl}-5-[(4,6-dimethylpyridin-2-yl)amino]pyridin-3-yl)amino}propyl]carbamate (51 mg, 0.080 mmol) in dichloromethane (4 mL) was added triethylsilane (0.064 mL, 0.40 mmol) followed by TFA (0.8 mL) at ambient temperature. After 2 hours, the reaction mixture was concentrated under reduced pressure, and the residue was purified by reverse phase HPLC (acetonitrile/water with 0.1% TFA, linear gradient) to afford 5-[(3-aminopropyl)amino]-3-[(4,6-dimethylpyridin-2-yl)amino]pyridine-2-carboxamide TFA salt. MS ESI calc'd. for $C_{16}H_{23}N_6O$ [M+H]+ 315. found 315. 1H NMR (500 MHz, DMSO-d6) δ 11.74 (s, 1H), 8.22-8.04 (br s, 1H), 7.92-7.76 (m, 4H), 7.58 (s, 1H), 7.37 (s, 1H), 6.74-6.66 (br s, 2H), 3.22-3.16 (m, 2H), 2.94-2.84 (m, 2H), 2.40 (s, 3H), 2.25 (s, 3H), 1.90-1.82 (m, 2H).

Example 15

3-[(4,6-dimethylpyridin-2-yl)amino]-5-[(ethylcarbamoyl)amino]pyridine-2-carboxamide

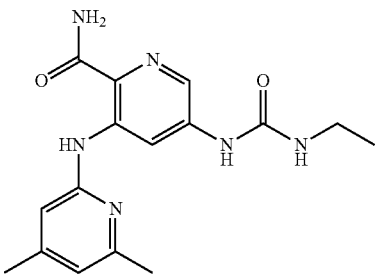

Step 1: To a solution of 5-amino-3-[(4,6-dimethylpyridin-2-yl)amino]pyridine-2-carbonitrile (PrepEx 1.8) (125 mg, 0.523 mmol) in DMSO (4 mL) was added potassium hydroxide (147 mg, 2.61 mmol) and hydrogen peroxide (35% solution in water, 0.46 mL, 5.3 mmol), and the reaction mixture was stirred for 1 hour. The reaction mixture was filtered and purified by reverse phase HPLC (0-100% acetonitrile/water with 0.1% TFA, linear gradient) to afford 5-amino-3-[(4,6-dimethylpyridin-2-yl)amino]pyridine-2-carboxamide TFA salt. MS ESI calc'd. for $C_{13}H_{16}N_5O$ [M+H]$^+$ 258. found 258. $^1$H NMR (500 MHz, DMSO-$d_6$) δ 11.72 (s, 1H), 7.93 (s, 1H), 7.56 (s, 1H), 7.38 (s, 1H), 6.74 (s, 2H), 6.17 (s, 1H), 2.42 (s, 3H), 2.28 (s, 3H).

Step 2: To a solution of 5-amino-3-[(4,6-dimethylpyridin-2-yl)amino]pyridine-2-carboxamide TFA salt (50 mg, 0.13 mmol) in THF (1 mL) was added ethyl isocyanate (12 mg, 0.18 mmol) and triethylamine (0.075 mL, 0.54 mmol), and the reaction mixture was stirred for 2 hours at room temperature. Additional ethyl isocyanate (12 mg, 0.18 mmol) and triethylamine (0.075 mL, 0.54 mmol) were added, and the reaction mixture was heated to 55° C. for 18 hours. The reaction mixture was allowed to cool to room temperature and concentrated under reduced pressure. The residue was purified by reverse phase HPLC (acetonitrile/water with 0.1% TFA, linear gradient) to afford 3-[(4,6-dimethylpyridin-2-yl)amino]-5-[(ethylcarbamoyl)amino]pyridine-2-carboxamide. MS ESI calc'd. for $C_{16}H_{21}N_6O_2$ [M+H]$^+$ 329. found 329. $^1$H NMR (500 MHz, DMSO-$d_6$) δ 11.61 (s, 1H), 9.24 (s, 1H), 8.86 (s, 1H), 8.23 (d, J=2.2 Hz, 1H), 8.13 (s, 1H), 7.57 (s, 1H), 6.63 (s, 1H), 6.53 (s, 1H), 6.33 (t, J=5.3 Hz, 1H), 3.20-3.07 (m, 2H), 2.40 (s, 3H), 2.23 (s, 3H), 1.06 (t, J=7.2 Hz, 3H).

Example 16

6-[(5-{[(1R,2S)-2-aminocyclohexyl]amino}-2-carbamoylpyridin-3-yl)amino]-2-methylpyridine-3-carboxylic acid

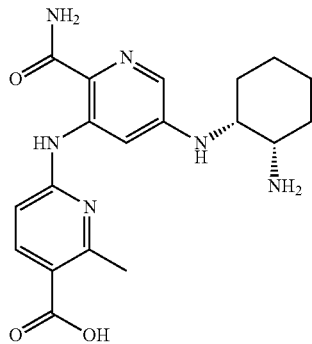

Step 1: To a suspension of 6-amino-2-methylpyridine-3-carboxylic acid (1.0 g, 6.6 mmol) in ethanol (17 mL) at 0° C. was added thionyl chloride (1.55 mL, 21.2 mmol). The mixture was warmed to room temperature and then heated to 70° C. for 18 hours. The reaction mixture was then cooled to room temperature and methanol (6 mL) was added. The reaction mixture was heated to 70° C. for 16 hours. The reaction mixture was cooled to room temperature and concentrated under reduced pressure. The residue was diluted with ethyl acetate and aqueous saturated sodium bicarbonate. The organics were separated, dried over magnesium sulfate, filtered, and concentrated under reduced pressure. The residue was purified by chromatography on silica gel (0-12% methanol/DCM, linear gradient) to afford a 1:1 mixture of ethyl 6-amino-2-methylpyridine-3-carboxylate and methyl 6-amino-2-methylpyridine-3-carboxylate. Characterization data for ethyl 6-amino-2-methylpyridine-3-carboxylate: MS ESI calc'd. for $C_9H_{13}N_2O_2$ [M+H]$^+$ 181. found 181. Characterization data for methyl 6-amino-2-methylpyridine-3-carboxylate: MS ESI calc'd. for $C_8H_{11}N_2O_2$ [M+H]$^+$ 167. found 167. The mixture was used in the subsequent step without further purification.

Step 2: To a flask containing the mixture of ethyl 6-amino-2-methylpyridine-3-carboxylate and methyl 6-amino-2-methylpyridine-3-carboxylate from Step 1 (207 mg), tert-butyl {(1S,2R)-2-[(5-bromo-6-cyanopyridin-3-yl)amino]cyclohexyl}carbamate (PrepEx 1.1) (350 mg, 0.89 mmol), 2-dicyclohexylphosphino-2',4',6'-triisopropylbiphenyl (84 mg, 0.18 mmol), Pd$_2$(dba)$_3$ (81 mg, 0.089 mmol), and cesium carbonate (577 mg, 1.77 mmol) was added degassed dioxane (9 mL) and the flask was evacuated and backfilled with argon 5 times. The reaction mixture was heated to 100° C. for 18 hours. The reaction mixture was allowed to cool to room temperature and diluted with ethyl acetate and water. The organics were separated, dried over magnesium sulfate, filtered, and concentrated under reduced pressure. The residue was purified by column chromatography on silica gel (0-100% ethyl acetate/hexanes, linear gradient) to afford a mixture of methyl 6-{[5-({(1R,2S)-2-[(tert-butoxycarbonyl)amino]cyclohexyl}amino)-2-cyanopyridin-3-yl]amino}-2-methylpyridine-3-carboxylate and ethyl 6-{[5-({(1R,2S)-2-[(tert-butoxycarbonyl)amino]cyclohexyl}amino)-2-cyanopyridin-3-yl]amino}-2-methylpyridine-3-carboxylate that was taken on to the next step without further purification. Characterization for methyl 6-{[5-({(1R,2S)-2-[(tert-butoxycarbonyl)amino]cyclohexyl}amino)-2-cyanopyridin-3-yl]amino}-2-methylpyridine-3-carboxylate: MS ESI calc'd. for $C_{25}H_{33}N_6O_4$ [M+H]$^+$ 481. found 481. Characterization for ethyl 6-{[54{(1R,2S)-2-[(tert-butoxycarbonyl)amino]cyclohexyl}amino)-2-cyanopyridin-3-yl]amino}-2-methylpyridine-3-carboxylate: MS ESI calc'd. for $C_{26}H_{35}N_6O_4$ [M+H]$^+$ 495. found 495.

Step 3: To a solution of the mixture from Step 2 (210 mg) in ethanol (2 mL) was added potassium hydroxide (6.0 M in water, 0.57 mL, 3.4 mmol) and the reaction was stirred for 2 hours. The reaction mixture was concentrated under reduced pressure. The residue was purified by reverse phase HPLC (acetonitrile/water with 0.1% TFA, linear gradient) to afford 6-{[5-({(1R,2S)-2-[(tert-butoxycarbonyl)amino}cyclohexyl]amino)-2-carbamoylpyridin-3-yl]amino}-2-methylpyridine-3-carboxylic acid TFA salt. MS ESI calc'd. for $C_{24}H_{33}N_6O_5$ [M+H]$^+$ 485. found 485. $^1$H NMR (500 MHz, DMSO-$d_6$) δ 12.64 (s, 1H), 12.20 (s, 1H), 8.58 (s, 1H), 8.02 (d, J=8.7 Hz, 1H), 7.93 (s, 1H), 7.66 (d, J=2.1 Hz, 1H), 7.37 (s, 1H), 6.68 (d, J=8.6 Hz, 1H), 6.58 (s, 1H), 6.20 (s, 1H), 3.89-3.73 (m, 1H), 3.70-3.55 (m, 1H), 2.71 (s, 3H), 1.86-1.75 (m, 1H), 1.76-1.65 (m, 1H), 1.65-1.43 (m, 4H), 1.43-1.31 (m, 2H), 1.28 (s, 9H).

Step 4: To a solution of 6-{[5-({(1R,2S)-2-[(tert-butoxycarbonyl)amino]cyclohexyl}amino)-2-carbamoylpyridin-3-yl]amino}-2-methylpyridine-3-carboxylic acid (49 mg, 0.10 mmol) in dichloromethane (1 mL) was added TFA (0.12 mL, 1.5 mmol), and the reaction mixture was stirred for 1 hour at room temperature. The reaction mixture was concentrated under reduced pressure. The residue was purified by reverse phase HPLC (acetonitrile/water with 0.1% TFA, linear gradient) to afford 6-[(5-{[(1R,2S)-2-aminocyclohexyl]amino}-2-carbamoylpyridin-3-yl)amino]-2-methylpyridine-3-carboxylic acid TFA salt. MS ESI calc'd. for $C_{19}H_{25}N_6O_3$ [M+H]$^+$ 385. found 385. $^1$H NMR (500 MHz, DMSO-$d_6$) δ 12.73 (s, 1H), 12.22 (s, 1H), 8.67 (s, 1H), 8.05 (d, J=8.6 Hz, 1H), 8.01 (s, 1H), 7.85 (s, 3H), 7.76 (s, 1H), 7.48 (s, 1H), 6.73 (d, J=8.6 Hz, 1H), 6.45 (d, J=7.8 Hz, 1H), 3.93-3.77 (m, 1H), 3.64-3.49 (m, 1H), 2.72 (s, 3H), 1.94-1.79 (m, 2H), 1.79-1.70 (m, 1H), 1.71-1.50 (m, 3H), 1.51-1.36 (m, 2H).

Example 17

5-{[(1R,2S)-2-aminocyclohexyl]amino}-3-{[5-(dimethylcarbamoyl)-6-methylpyridin-2-yl]amino}pyridine-2-carboxamide

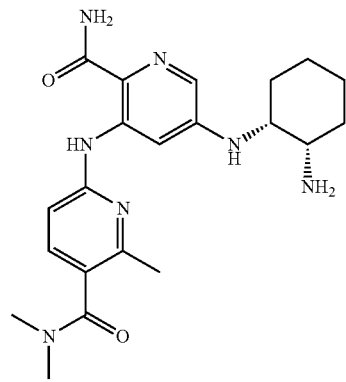

To a solution of 6-{[5-({(1R,2S)-2-[(tert-butoxycarbonyl)amino]cyclohexyl}amino)-2-carbamoylpyridin-3-yl]amino}-2-methylpyridine-3-carboxylic acid (from Step 4 of Example 16) (45 mg, 0.093 mmol), dimethylamine (2.0 M in methanol, 0.093 mL, 0.19 mmol) and N,N'-diisopropylethylamine (0.032 mL, 0.19 mmol) in DMF (1 mL) was added dropwise 1-propanephosphonic acid cyclic anhydride (50% in ethyl acetate, 0.065 mL, 0.11 mmol) at 0° C. The reaction mixture was stirred for 2 hours while warming to room temperature. The reaction mixture was concentrated under reduced pressure. The residue was purified by reverse phase HPLC (0-100% acetonitrile/water with 0.1% TFA, linear gradient) to afford tert-butyl {(1S,2R)-2-[(6-carbamoyl-5-{[5-(dimethylcarbamoyl)-6-methylpyridin-2-yl]amino}pyridin-3-yl)amino]cyclohexyl}carbamate. MS ESI calc'd. for $C_{26}H_{38}N_7O_4$ [M+H]$^+$ 512. found 512. $^1$H NMR (500 MHz, DMSO-$d_6$) δ 11.95 (s, 1H), 8.51 (s, 1H), 7.88 (s, 1H), 7.62 (s, 1H), 7.42 (d, J=8.1 Hz, 1H), 7.29 (s, 1H), 6.65 (d, J=8.2 Hz, 1H), 6.61-6.51 (m, 1H), 6.21-6.03 (m, 1H), 3.87-3.74 (m, 1H), 3.69-3.56 (m, 1H), 2.97 (s, 3H), 2.81 (s, 3H), 2.33 (s, 3H), 1.87-1.74 (m, 1H), 1.74-1.63 (m, 1H), 1.64-1.42 (m, 4H), 1.33 (s, 2H), 1.27 (s, 9H).

Step 2: To a solution of tert-butyl {(1S,2R)-2-[(6-carbamoyl-5-{[5-(dimethylcarbamoyl)-6-methylpyridin-2-yl]amino}pyridin-3-yl)amino]cyclohexyl}carbamate (48 mg, 0.094 mmol) in dichloromethane (1 mL) was added trifluoroacetic acid (0.10 mL, 1.3 mmol). The reaction mixture was stirred at room temperature for 1 hour. The reaction mixture was concentrated under reduced pressure and purified by reverse phase HPLC to afford 5-{[(1R,2S)-2-aminocyclohexyl]amino}-3-{[5-(dimethylcarbamoyl)-6-methylpyridin-2-yl]amino}pyridine-2-carboxamide. MS ESI calc'd. for $C_{21}H_{30}N_7O_2$ [M+H]$^+$ 412. found 412. $^1$H NMR (500 MHz, DMSO-$d_6$) δ 11.98 (s, 1H), 8.55 (d, J=2.3 Hz, 1H), 7.91 (s, 1H), 7.69 (d, J=2.3 Hz, 1H), 7.45 (d, J=. 8.4 Hz, 1H), 7.33 (s, 1H), 6.67 (d, J=8.4 Hz, 1H), 6.62 (d, J=7.0 Hz, 1), 3.63-3.50 (m, 1H), 3.37-3.27 (m, 1H), 2.99 (s, 3H), 2.82 (s, 3H), 2.34 (s, 3H), 1.88-1.72 (m, 2H), 1.69-1.50 (m, 4H), 1.48-1.31 (m, 2H).

Example 18

5-[{(1R,2S)-2-aminoeyelohexyl]amino}-3-[(5-methyl-7,8-dihydroquinolin-2-yl)amino]pyridine-2-carboxamide

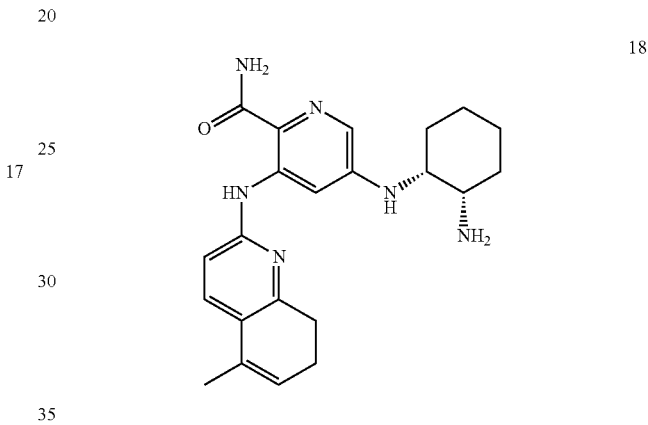

Step 1: To a solution of 2-chloro-7,8-dihydroquinolin-5(6H)-one (500 mg, 2.75 mmol) in tetrahydrofuran (20 mL) at 0° C. was added methylmagnesium chloride (3.0 M in tetrahydrofuran, 0.92 ml, 2.8 mmol) over 2 minutes dropwise. Additional methylmagnesium chloride (3.0 M in tetrahydrofuran) were added at the following time intervals after the initial addition: 40 minutes (0.46 ml, 1.4 mmol); 60 minutes (0.46 ml, 1.4 mmol); and 120 minutes (0.92 ml, 2.8 mmol). At 1 hour after the final addition, the reaction mixture was quenched with saturated aqueous ammonium chloride solution (10 mL), and diluted with ethyl acetate (30 mL). The organic layer was separated and washed sequentially with saturated aqueous sodium bicarbonate solution and brine, dried over sodium sulfate, filtered, and concentrated under reduced pressure. The residue was purified by chromatography on silica gel (10-50% ethyl acetate/hexanes, linear gradient) to give 2-chloro-5-methyl-5,6,7,8-tetrahydroquinolin-5-ol. MS ESI calc'd. for $C_{10}H_{13}ClNO$ [M+H]$^+$ 198. found 198.

Step 2: A mixture of 2-chloro-5-methyl-5,6,7,8-tetrahydroquinolin-5-ol (306 mg, 1.55 mmol), Xantphos (107 mg, 0.185 mmol), tris(dibenzylideneacetone)dipalladium(0) (71 mg, 0.077 mmol), cesium carbonate (1.01 g, 3.09 mmol), and benzophenone imine (0.272 mL, 1.63 mmol) in 1,4-dioxane (10 ml) under an argon atmosphere was heated at 100° C. in an oil bath for 6 hours. After cooling to room temperature, the reaction mixture was diluted with ethyl acetate (40 mL), saturated aqueous sodium bicarbonate solution (10 mL), and brine (20 mL). The layers were separated and the organic layer was washed with brine, dried over sodium sulfate, filtered, and concentrated under reduced pressure. The residue was purified by chromatography on silica gel (10-80% ethyl acetate/hexanes linear gradient) to afford 2-[(diphenylmethylidene)amino]-5-methyl-5,6,7,8-tetrahydroquinolin-5-ol. MS ESI calc'd. for $C_{23}H_{23}N_2O$ [M+H]$^+$ 343. found 343.

Step 3: To a solution of 2-(diphenylmethyleneamino)-5-methyl-5,6,7,8-tetrahydroquinolin-5-ol (180 mg, 0.526 mmol) in THF (20 ml) was added aqueous hydrochloric acid (2.0 M, 1.00 ml, 2.0 mmol). After 20 minutes, the reaction mixture was partially concentrated under reduced pressure to a volume of approximately 2 mL. The mixture was diluted with ethyl acetate (30 mL), saturated aqueous sodium bicarbonate solution (15 mL), saturated aqueous sodium carbonate (10 mL), and brine (15 mL). The layers were separated and the aqueous layer was extracted with ethyl acetate (2×15 mL). The combined organics were dried over sodium sulfate, filtered, and concentrated under reduced pressure. The residue was purified by chromatography on silica gel (0.5-10% methanol/dichloromethane linear gradient) to yield 2-amino-5-methyl-5,6,7,8-tetrahydroquinolin-5-ol. MS ESI calc'd. for $C_{10}H_{15}N_2O$ [M+H]$^+$ 179. found 179. $^1$H NMR (500 MHz, CDCl$_3$) δ 7.64 (d, J=8.5 Hz, 1H), 6.38 (d, J=8.5 Hz, 1H), 4.42 (s, 2H), 2.80-2.63 (m, 2H), 2.02-1.75 (m, 5H), 1.50 (s, 3H).

Step 4: A mixture of 2-amino-5-methyl-5,6,7,8-tetrahydroquinolin-5-ol (45.4 mg, 0.255 mmol), tert-butyl (1S,2R)-2-(5-bromo-6-cyanopyridin-3-ylamino)cyclohexylcarbamate (PrepEx 1.1) (111 mg, 0.280 mmol), Xantphos (15 mg, 0.025 mmol), tris(dibenzylideneacetone)dipalladium(0) (12 mg, 0.013 mmol), and cesium carbonate (207 mg, 0.637 mmol) in 1,4-dioxane (10 ml) under an argon atmosphere was heated at 80° C. in an oil bath for 2.25 hours. After cooling to room temperature, the reaction mixture was diluted with ethyl acetate (30 mL) and saturated aqueous sodium bicarbonate solution (10 mL). The layers were separated, and the organic layer was washed with brine (10 mL), dried over sodium sulfate, filtered, and concentrated under reduced pressure. The residue was purified by chromatography on silica gel (1-5% methanol/dichloromethane, linear gradient) to give tert-butyl (1S,2R)-2-(6-cyano-5-(5-hydroxy-5-methyl-5,6,7,8-tetrahydroquinolin-2-ylamino)pyridin-3-ylamino)cyclohexylcarbamate. MS ESI calc'd. for $C_{27}H_{37}N_6O_3$ [M+H]$^+$ 493. found 493.

Step 5: To a suspension of tert-butyl (1S,2R)-2-(6-cyano-5-(5-hydroxy-5-methyl-5,6,7,8-tetrahydroquinolin-2-ylamino)pyridin-3-ylamino)cyclohexylcarbamate (25 mg, 0.051 mmol) in dichlormethane (1.5 mL) was added trifluoroacetic acid (0.5 mL). After 20 minutes, the reaction mixture was diluted with toluene (1 mL) and dichloromethane (10 mL), and then concentrated under reduced pressure. The residue was dissolved in methanol (1 mL) and toluene (1 mL) and then concentrated under reduced pressure. This entire procedure was repeated again to afford 5-((1R,2S)-2-aminocyclohexylamino)-3-(5-methyl-7,8-dihydroquinolin-2-ylamino)picolinonitrile which was used without further purification. MS ESI calc'd. for $C_{22}H_{27}N_6$ [M+H]$^+$ 375. found 375.

Step 6: A suspension of 5-((1R,2S)-2-aminocyclohexylamino)-3-(5-methyl-7,8-dihydroquinolin-2-ylamino)picolinonitrile (19 mg, 0.051 mmol) and potassium trimethylsilanolate (98 mg, 0.76 mmol) in 1,4-dioxane (1 mL) was heated to 100° C. in an oil bath for 3 hours. After cooling to room temperature, the reaction mixture was concentrated under reduced pressure. The residue was diluted with DMSO, filtered, and purified by reverse phase HPLC (acetonitrile/water with 0.1% TFA, linear gradient) to yield 5-{[(1R,2S)-2-aminocyclohexyl]amino}-3-[(5-methyl-7,8-dihydroquinolin-2-yl)amino]pyridine-2-carboxamide. MS ESI calc'd. for $C_{22}H_{29}N_6O$ [M+H]$^+$ 393. found 393.

Example 19

5-{[(2-aminoethyl)sulfonyl]amino}-3-[(4,6-dimethylpyridin-2-yl)amino]pyridine-2-carboxamide

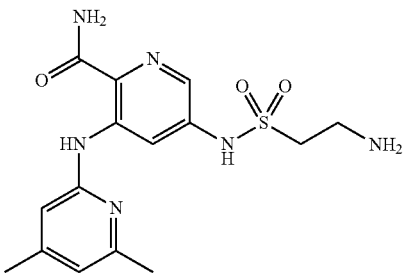

19

Step 1: To a solution of 5-amino-3-[(4,6-dimethylpyridin-2-yl)amino]pyridine-2-carbonitrile (PrepEx 1.8) (150 mg, 0.63 mmol) in DCM (5 mL) was added triethylamine (0.26 mL, 1.88 mmol) followed by the dropwise addition of tert-butyl [2-(chlorosulfonyl)ethyl]carbamate (25% w/w in DCM, 920 mg, 0.94 mmol). The reaction mixture was stirred for 3 hours at room temperature. Additional tert-butyl [2-(chlorosulfonyl)ethyl]carbamate (25% w/w in DCM, 920 mg, 0.94 mmol) was added and the reaction mixture was stirred for 16 hours. The reaction mixture was diluted with ethyl acetate and saturated aqueous sodium bicarbonate. The organics were separated, dried over magnesium sulfate, filtered, and concentrated under reduced pressure. The residue was purified by chromatography on silica gel to afford tert-butyl [2-({6-cyano-5-[(4,6-dimethylpyridin-2-yl)amino]pyridin-3-yl}sulfamoyl)ethyl]carbamate. MS ESI calc'd. for $C_{20}H_{27}N_6O_4S$ [M+H]$^+$ 447. found 447. $^1$H NMR (500 MHz, DMSO-d$_6$) δ 10.70 (s, 1H), 9.19 (s, 1H), 8.50 (s, 1H), 8.01 (s, 1H), 6.86 (t, J=5.5 Hz, 1H), 6.73 (s, 1H), 6.65 (s, 1H), 3.41 (t, J=6.7 Hz, 2H), 3.32-3.29 (m, 2H), 2.31 (s, 3H), 2.22 (s, 3H), 1.30 (s, 9H).

Step 2: To a solution of tert-butyl [2-({6-cyano-5-[(4,6-dimethylpyridin-2-yl)amino]pyridin-3-yl}sulfamoyl)ethyl]carbamate (100 mg, 0.22 mmol) in dichloromethane (1.8 mL) was added trifluoroacetic acid (0.26 mL, 3.4 mmol). The reaction mixture was stirred for 1 hour at room temperature. The reaction mixture was concentrated under reduced pressure to afford 2-amino-N-{6-cyano-5-[(4,6-dimethylpyridin-2-yl)amino]pyridin-3-yl}ethanesulfonamide, which was used without further purification. MS ESI calc'd. for $C_{15}H_{19}N_6O_2S$ [M+H]$^+$ 347. found 347.

Step 3: To a solution of 2-amino-N-{6-cyano-5-[(4,6-dimethylpyridin-2-yl)-amino]pyridin-3-yl}ethanesulfonamide (78 mg, 0.23 mmol) in DMSO (1.8 mL) was added potassium hydroxide (63 mg, 1.1 mmol) and hydrogen peroxide (35% w/w in water, 0.20 mL, 2.3 mmol). The reaction mixture was stirred for 1 hour. The reaction mixture was filtered and the filtrate directly purified by reverse phase HPLC to afford 5-{[(2-aminoethyl)sulfonyl]amino}-3-[(4,6-dimethylpyridin-2-yl)amino]pyridine-2-carboxamide. MS ESI calc'd. for $C_{15}H_{21}N_6O_3S$ [M+H]$^+$ 365. found 365. $^1$H NMR (500 MHz, DMSO-d$_6$) δ 11.33 (s, 1H), 8.45 (d, J=2.3 Hz, 1H), 7.80 (s, 1H), 7.46 (d, J=2.3 Hz, 1H), 7.12 (s, 1H), 6.51 (s, 1H), 6.47 (s, 1H), 2.92 (t, J=6.1 Hz, 2H), 2.89-2.81 (m, 2H), 2.32 (s, 3H), 2.18 (s, 3H).

Example 20 rel-5-{[(3S,4S)-4-amino-1,1-dioxidotetrahydro-2H-thiopyran-3-yl]amino}-3-[(4-methoxy-6-methylpyridin-2-yl)amino]pyridine-2-carboxamide (Enantiomer 1)

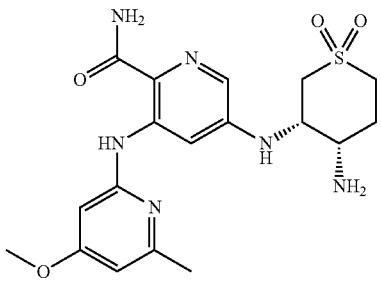

Step 1: A mixture of Hunig's base (2.69 ml, 15.4 mmol), 3-bromo-5-fluoropyridine-2-carbonitrile (1.55 g, 7.69 mmol), tert-butyl rel-[(3S,4S)-3-amino-1,1-dioxidotetrahydro-2H-thiopyran-4-yl]carbamate (2.51 g, 9.50 mmol) in NMP (8 ml) was heated to 150° C. for 30 minutes. The reaction mixture was diluted with water (50 mL) and stirred. The reaction mixture was filtered, and the collected solids were washed with cold water. The solids were dried under reduced pressure to afford tert-butyl rel-{(3S,4S)-3-[(5-bromo-6-cyanopyridin-3-yl)amino]-1,1-dioxidotetrahydro-2H-thiopyran-4-yl}carbamate. MS ESI calc'd. for $C_{16}H_{22}BrN_4O_4S$ [M+H]$^+$ 445 and 447. found 445 and 447.

Step 2: tert-butyl rel-{(3S,4S)-3-[(5-bromo-6-cyanopyridin-3-yl)amino]-1,1-dioxidotetrahydro-2H-thiopyran-4-yl}carbamate (890 mg, 2.00 mmol) was separated into its respective enantiomers by SFC column chromatography (20% ethanol in $CO_2$ on chiral IC-H 2.1×25 cm column, 5 uM particle size) to afford tert-butyl rel-{(3S,4S)-3-[(5-bromo-6-cyanopyridin-3-yl)amino]-1,1-dioxidotetrahydro-2H-thiopyran-4-yl}carbamate (Enantiomer 1, elution time 8.31 minutes) and tert-butyl rel-{(3R,4R)-3-[(5-bromo-6-cyanopyridin-3-yl)amino]-1,1-dioxidotetrahydro-2H-thiopyran-4-yl}carbamate (Enantiomer 2, elution time 9.93 minutes).

Step 3: A mixture of tert-butyl rel-{(3S,4S)-3-[(5-bromo-6-cyanopyridin-3-yl)amino]-1,1-dioxidotetrahydro-2H-thiopyran-4-yl}carbamate (Enantiomer 1 from previous step) (50 mg, 0.11 mmol), 4-methoxy-6-methylpyridin-2-amine (16 mg, 0.11 mmol), Pd$_2$(dba)$_3$ (10 mg, 0.011 mmol), cesium carbonate (91 mg, 0.28 mmol), and Xanthpos (13 mg, 0.022 mmol) was purged with argon for 5 minutes. 1,4-Dioxane (1.0 ml) was added, and the reaction mixture was purged with argon for 5 minutes, and then heated to 90° C. for 2 hours. The reaction mixture was cooled to room temperature, filtered through CELITE, and concentrated under reduced pressure to afford tert-butyl rel-[(3S,4S)-3-({6-cyano-5-[(4-methoxy-6-methylpyridin-2-yl)amino]pyridin-3-yl}amino)-1,1-dioxidotetrahydro-2H-thiopyran-4-yl]carbamate, which was used directly in the next step without purification. MS ESI calc'd. for $C_{23}H_{31}N_6O_5S$ [M+H]$^+$ 503. found 503.

Step 4: To a solution of tert-butyl rel-[(3S,4S)-3-({6-cyano-5-[(4-methoxy-6-methylpyridin-2-yl)amino]pyridin-3-yl}amino)-1,1-dioxidotetrahydro-2H-thiopyran-4-yl]carbamate (56 mg, 0.11 mmol) in DCM (2 mL) was added TFA (1 mL). After 30 minutes, the reaction mixture was concentrated under reduced pressure to afford rel-5-{[(3S,4S)-4-amino-1,1-dioxidotetrahydro-2H-thiopyran-3-yl]amino}-3-[(4-methoxy-6-methylpyridin-2-yl)amino]pyridine-2-carbonitrile, which was used directly in the next step without purification. MS ESI calc'd. for $C_{18}H_{23}N_6O_3S$ [M+H]$^+$ 403. found 403.

Step 5: To a solution of rel-5-{[(3S,4S)-4-amino-1,1-dioxidotetrahydro-2H-thiopyran-3-yl]amino}-3-[(4-methoxy-6-methylpyridin-2-yl)amino]pyridine-2-carbonitrile (45 mg, 0.11 mmol) in DMSO (2 mL) was added potassium hydroxide (1.0 M in water, 1.1 mL, 1.1 mmol) and hydrogen peroxide (35% w/w solution in water, 0.098 ml, 1.1 mmol) at room temperature. After 16 hours, the reaction mixture was filtered, and the filtrate was purified directly by reverse phase HPLC (acetonitrile/water with 0.1% TFA, linear gradient) to afford rel-5-{[(3S,4S)-4-amino-1,1-dioxidotetrahydro-2H-thiopyran-3-yl]amino}-3-[(4-methoxy-6-methylpyridin-2-yl)amino]pyridine-2-carboxamide TFA salt. MS ESI calc'd. for $C_{18}H_{25}N_6O_4S$ [M+H]$^+$ 421. found 421. $^1$H NMR (500 MHz, DMSO-d$_6$) δ 11.71 (s, 1H), 8.26-8.12 (m, 3H), 8.01 (s, 1H), 7.71 (s, 1H), 7.55-7.45 (br s, 1H), 6.74-6.20 (br s, 2H), 6.65 (s, 1H), 4.26 (s, 1H), 3.88-3.76 (m, 4H), 3.54-3.42 (m, 2H), 3.36-3.24 (m, 2H), 2.46-2.32 (m, 4H), 2.30-2.21 (m, 1H).

Example 21 rel-5-{[(3R,4R)-4-amino-1,1-dioxidotetrahydro-2H-thiopyran-3-yl]amino}-3-[(4-methoxy-6-methylpyridin-2-yl)amino]pyridine-2-carboxamide (Enantiomer 2)

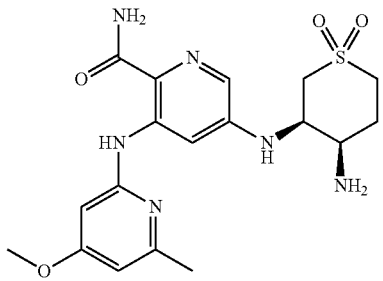

rel-5-{[(3R,4R)-4-amino-1,1-dioxidotetrahydro-2H-thiopyran-3-yl]amino}-[(4-methoxy-6-methylpyridin-2-yl)amino]pyridine-2-carboxamide TFA salt (Enantiomer 2) was prepared from tert-butyl rel-{(3R,4R)-3-[(5-bromo-6-cyanopyridin-3-yl)amino]-1,1-dioxidotetrahydro-2H-thiopyran-4-yl}carbamate (Enantiomer 2, from Step 2 of Example 20) using chemistry analogous to that described for the synthesis of rel-5-{[(3S,4S)-4-amino-1,1-dioxidotetrahydro-2H-thiopyran-3-yl]amino}-3-[(4-methoxy-6-methylpyridin-2-yl)amino]pyridine-2-carboxamide (Example 20, Enantiomer 1). MS ESI calc'd. for $C_{18}H_{25}N_6O_4S$ [M+H]$^+$ 421. found 421. $^1$H NMR (500 MHz, DMSO-d$_6$) δ 11.71 (s, 1H), 8.26-8.14 (m, 3H), 8.01 (s, 1H), 7.72 (s, 1H), 7.55-7.45 (br s, 1H), 6.74-6.20 (br s, 2H), 6.65 (s, 1H), 4.26 (s, 1H), 3.86-3.76 (m, 4H), 3.55-3.42 (m, 2H), 3.38-3.26 (m, 2H), 2.46-2.34 (m, 4), 2.30-2.21 (m, 1H).

Biological Assay

Homogeneous Time-Resolved Fluorescence (HTRF) Assay for the Recombinant Human Syk Enzyme A recombinant GST-hSYK fusion protein was used to measure potency of compounds to inhibit human Syk activity. The recombinant human GST-SYK (Carna Biosciences #08-

176) (5 pM final concentration) was incubated with various concentrations of the inhibitor diluted in DMSO (0.1% final concentration) for 10 minutes at room temperature in 15 mM Tris-HCl (pH 7.5), 0.01% tween 20, 2 mM DTT in 384 well plate format. To initiate the reaction the biotinylated substrate peptide (250 nM final concentration) that contains the phosphorylation site for Syk was added with magnesium (5 mM final concentration) and ATP (25 µM final concentration). Final volume of the reaction was 10 µL. Phosphorylation of the peptide was allowed to proceed for 45 minutes at room temperature. To quench the reaction and detect the phosphorylated product, 2 nM of a Europium-anti-phosphotyrosine antibody (Perkin Elmer #AD0161) and 70 nM SA-APC (Perkin-Elmer #CR130-100) were added together in 15 mM Tris pH 7.5, 40 mM EDTA, 0.01% tween 20. Final volume of the quenching solution was 10 µL. The resulting HTRF signal was measured after 30 minutes on an EnVision (Perkin-Elmer) reader using a time-resolved fluorescence protocol. $IC_{50}$ was determined following 10-dose titration (10 µM to 0.508 nM) and four parameter logistic curve fitting using an assay data analyzer. Table 1 below lists activity for representative compounds of the invention whereby the $IC_{50}$ values are rated "A" for $IC_{50}$ values <10 nM, "B" for $IC_{50}$ values between 10 nM and 100 nM, "C" for $IC_{50}$ values between 100 nM and 1,000 nM, and "D" for $IC_{50}$ values between 1,000 nM and 10,000 nM.

TABLE 1

| Example | rhSYK Activity |
| --- | --- |
| 1.1 | A |
| 1.2 | A |
| 1.3 | A |
| 1.4 | B |
| 1.5 | A |
| 1.6 | A |
| 1.7 | A |
| 1.8 | A |
| 1.9 | A |
| 1.10 | A |
| 1.11 | A |
| 1.12 | A |
| 1.13 | A |
| 1.14 | A |
| 1.15 | A |
| 1.16 | A |
| 1.17 | A |
| 1.18 | A |
| 1.19 | B |
| 1.20 | A |
| 1.21 | A |
| 1.22 | A |
| 1.23 | B |
| 1.24 | A |
| 1.25 | B |
| 1.26 | A |
| 1.27 | A |
| 1.28 | A |
| 1.29 | B |
| 1.30 | A |
| 1.31 | A |
| 1.32 | B |
| 1.33 | B |
| 1.34 | B |
| 1.35 | B |
| 1.36 | B |
| 1.37 | C |
| 1.38 | A |
| 1.39 | B |
| 1.40 | A |
| 1.41 | B |
| 1.42 | A |
| 1.43 | A |
| 1.44 | B |
| 1.45 | A |
| 1.46 | A |
| 1.47 | A |
| 1.48 | A |
| 1.49 | B |
| 1.50 | B |
| 1.51 | A |
| 1.52 | C |
| 1.53 | A |
| 1.54 | A |
| 1.55 | A |
| 1.56 | C |
| 1.57 | A |
| 1.58 | A |
| 1.59 | B |
| 1.60 | C |
| 1.61 | C |
| 1.62 | B |
| 1.63 | A |
| 1.64 | A |
| 1.65 | A |
| 1.66 | A |
| 1.67 | A |
| 1.68 | A |
| 1.69 | A |
| 1.70 | A |
| 1.71 | A |
| 1.72 | A |
| 1.73 | A |
| 1.74 | A |
| 1.75 | A |
| 1.76 | A |
| 1.77 | A |
| 1.78 | A |
| 1.79 | A |
| 1.80 | A |
| 1.81 | A |
| 1.82 | A |
| 1.83 | A |
| 1.84 | A |
| 1.85 | A |
| 1.86 | B |
| 1.87 | A |
| 1.88 | A |
| 1.89 | C |
| 1.90 | A |
| 1.91 | A |
| 1.92 | B |
| 1.93 | A |
| 1.94 | A |
| 1.95 | C |
| 1.96 | A |
| 1.97 | A |
| 1.98 | C |
| 1.99 | A |
| 1.100 | A |
| 1.101 | A |
| 1.102 | A |
| 1.103 | A |
| 1.104 | A |
| 1.105 | A |
| 1.106 | A |
| 1.107 | A |
| 1.108 | A |
| 1.109 | A |
| 1.110 | A |
| 1.111 | A |
| 1.112 | A |
| 1.113 | A |
| 1.114 | A |
| 1.115 | A |
| 1.116 | B |
| 1.117 | A |
| 1.118 | A |
| 1.119 | A |
| 1.120 | A |

TABLE 1-continued

| Example | rhSYK Activity |
|---|---|
| 1.121 | A |
| 1.122 | A |
| 1.123 | C |
| 1.124 | A |
| 1.125 | A |
| 1.126 | D |
| 1.127 | A |
| 1.128 | B |
| 1.129 | A |
| 1.130 | A |
| 1.131 | A |
| 2.1 | C |
| 2.2 | A |
| 2.3 | C |
| 2.4 | B |
| 2.5 | A |
| 2.6 | C |
| 2.7 | B |
| 2.8 | A |
| 2.9 | C |
| 2.10 | C |
| 2.11 | A |
| 2.12 | B |
| 2.13 | C |
| 2.14 | B |
| 2.15 | B |
| 3.1 | A |
| 3.2 | A |
| 3.3 | A |
| 3.4 | A |
| 3.5 | A |
| 3.6 | A |
| 3.7 | A |
| 3.8 | A |
| 3.9 | A |
| 3.10 | A |
| 3.11 | A |
| 3.12 | A |
| 3.13 | A |
| 3.14 | A |
| 3.15 | A |
| 3.16 | A |
| 3.17 | A |
| 3.18 | A |
| 3.19 | A |
| 3.20 | A |
| 3.21 | A |
| 3.22 | A |
| 3.23 | A |
| 3.24 | A |
| 3.25 | A |
| 3.26 | A |
| 3.27 | A |
| 3.28 | B |
| 3.29 | A |
| 3.30 | A |
| 3.31 | A |
| 3.32 | A |
| 4.1 | A |
| 4.2 | A |
| 4.3 | A |
| 4.4 | A |
| 5.1 | A |
| 5.2 | A |
| 5.3 | A |
| 5.4 | A |
| 6.1 | B |
| 6.2 | A |
| 7 | A |
| 8 | C |
| 9 | D |
| 10 | C |
| 11 | B |
| 12 | B |
| 13 | A |
| 14 | B |
| 15 | C |
| 16 | A |
| 17 | B |
| 18 | A |
| 19 | C |
| 20 | A |
| 21 | B |

Representative compounds of the invention have the $IC_{50}$ values specified in parentheses immediately following the compound number in the above-described assay: 1.1 (<0.51 nM), 1.2 (<0.51 nM), 1.6 (0.53 nM), 1.41 (12 nM), 1.46 (7.8 nM), 1.84 (1.8 nM), 1.86 (63 nM), 1.89 (340 nM), 1.95 (120 nM), 1.109 (4.8 nM), 1.116 (55 nM), 1.126 (1300 nM), 2.7 (28 nM), 2.13 (770 nM), 3.2 (3.9 nM), 9 (2900 nM), and 20 (0.7 nM).

While the present invention has been described in conjunction with the specific embodiments set forth above, many alternatives, modifications and other variations thereof will be apparent to those of ordinary skill in the art. All such alternatives, modifications and variations are intended to fall within the spirit and scope of the present invention.

What is claimed is:

1. A compound of the Formula (I)

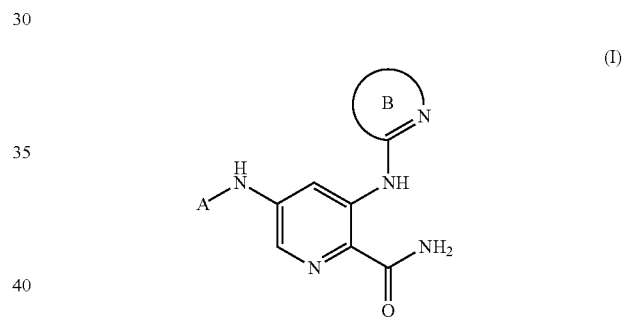

or a pharmaceutically acceptable salt thereof, wherein
B is pyridyl;
  wherein B is unsubstituted or substituted by 1 to 3 $R^3$ moieties, wherein each $R^3$ moiety is independently selected from the group consisting of $C_1$-$C_3$ alkyl, $C_1$-$C_3$ alkoxy, $C_1$-$C_3$ fluoroalkyl, $C_1$-$C_3$ hydroxyalkyl, halo, hydroxy, amino, ($C_1$-$C_3$ alkyl)amino, di($C_1$-$C_3$ alkyl)amino, —N(H)SO$_2$—($C_1$-$C_3$ alkyl), —CO$_2$H, —C(O)NH$_2$, —C(O)N(H)($C_1$-$C_3$ alkyl), —C(O)N(H)($C_1$-$C_3$ alkyl)$_2$, —CH$_2$O—($C_1$-$C_4$ alkylene)-OH, and E;
E is
  (a) -E',
  (b) —CH$_2$-E$^1$ or
  (c) —O—CH$_2$-E$^1$;
  wherein E$^1$ is:
    (i) phenyl; or
    (ii) $C_3$-$C_6$ cycloalkyl;
    wherein E$^1$ is unsubstituted or substituted by 1 to 2 moieties independently selected from the group consisting of $C_1$-$C_3$ alkyl, $C_1$-$C_3$ alkoxy, halo, hydroxy, nitro, carboxy, $C_1$-$C_3$ hydroxyalkyl, —O—($C_1$-$C_3$ fluoroalkyl), —C(H)(OH)—($C_1$-$C_3$ fluoroalkyl), —N(CH$_3$)SO$_2$—($C_1$-$C_3$ alkyl), and $R^{E1}$;

wherein $R^{E1}$ is
(a) $—(CH_2)_x—R^{E1a}$, wherein x is 1, 2, or 3; or
(b) $—R^{E1a}$;
wherein $R^{E1a}$ is
phenyl;
wherein $R^{E1a}$ is unsubstituted or substituted by 1 to 2 moieties independently selected from the group consisting of $C_1$-$C_3$ alkyl, $C_1$-$C_3$ alkoxy and halo;

A is selected from the group consisting of
(a)

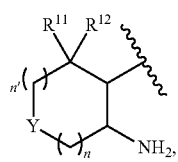

wherein
Y is —CH—;
$R^{11}$ and $R^{12}$ are independently H or F; and
n is 1 or 2;
n' is 0 or 1; or
(b)

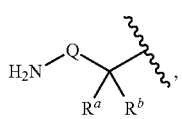

wherein
$R^a$ and $R^b$ are independently H, $C_1$-$C_6$ alkyl, or phenyl; or $R^a$ and $R^b$ together with the carbon atom to which they are attached form —C(O)—;
Q is

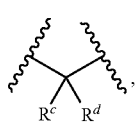

—C(O)—, or —CH$_2$CH$_2$—;
wherein $R^c$ is H, $C_1$-$C_6$ alkyl, $C_1$-$C_3$ fluoroalkyl, $C_3$-$C_6$ cycloalkyl, —(CH$_2$)$_r$OR$^{13}$, —C(O)NH$_2$, —C(O)N(H)(C$_1$-C$_3$ alkyl), —C(O)N(C$_1$-C$_3$ alkyl)$_2$, —(CH$_2$)$_r$S(O)$_t$R$^{14}$, —(CH$_2$)$_r$-phenyl, or —(CH$_2$)$_r$N(H)C(O)—(C$_1$-C$_3$ alkyl);
$R^{13}$ is H or $C_1$-$C_3$ alkyl; and
$R^{14}$ is $C_1$-$C_3$ alkyl;
r is 1 or 2;
t is 0, 1, or 2;
$R^d$ is H or $C_1$-$C_6$ alkyl, or
$R^c$ and $R^d$ together with the carbon atom to which they are attached form a group of the formula

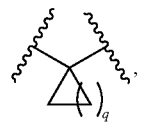

wherein q is 1, 2, 3, or 4; or
(c)

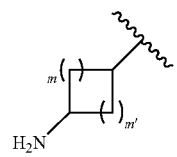

wherein m is 1 or 2 and m' is 0 or 1;
(e) H;
(f) —C(O)N(H)—(C$_1$-C$_3$ alkyl); and
(g) —S(O)$_2$CH$_2$CH$_2$NH$_2$.

2. The compound of claim 1 or a pharmaceutically acceptable salt thereof, wherein B is selected from the group consisting of:

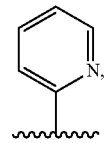

wherein said B is unsubstituted or substituted by 1 to 2 $R^3$ moieties.

3. The compound of claim 1 or a pharmaceutically acceptable salt thereof, wherein B is substituted by no more than 2 $R^3$ moieties, and no more than 1 of said $R^3$ moieties is E.

4. The compound of claim 1 or a pharmaceutically acceptable salt thereof,
A is

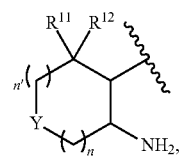

Y is —CH$_2$—;
$R^{11}$ and $R^{12}$ are independently H or F; and
n is 1 or 2;
n' is 0 or 1.

5. The compound of claim 4 or a pharmaceutically acceptable salt thereof, wherein A is selected from the group consisting of:

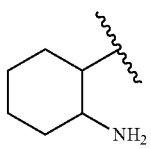 and 

6. The compound of claim 1 or a pharmaceutically acceptable salt thereof, wherein A is

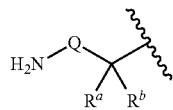

wherein $R^a$ and $R^b$ are independently H, $C_1$-$C_6$ alkyl, or phenyl;
or $R^a$ and $R^b$ together with the carbon atom to which they are attached form —C(O)—;
Q

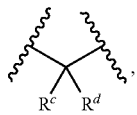

is —C(O)—, or —CH$_2$CH$_2$—;
wherein $R^c$ is H, $C_1$-$C_6$ alkyl, $C_1$-$C_3$ fluoroalkyl, $C_3$-$C_6$ cycloalkyl, —(CH$_2$)$_r$OR$^{13}$, —C(O)NH$_2$, —C(O)N(H)(C$_1$-C$_3$ alkyl), —C(O)N(C$_1$-C$_3$ alkyl)$_2$, —(CH$_2$)$_r$S(O)$_t$R$^{14}$, —(CH$_2$)$_r$-phenyl, or —(CH$_2$)$_r$N(H)C(O)—(C$_1$-C$_3$ alkyl);
$R^{13}$ is H or $C_1$-$C_3$ alkyl; and
$R^{14}$ is $C_1$-$C_3$ alkyl;
r is 1 or 2;
t is 0, 1, or 2;
$R^d$ is H or $C_1$-$C_6$ alkyl; or
$R^c$ and $R^d$ together with the carbon atom to which they are attached form a group of the formula

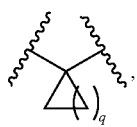

wherein q is 1, 2, 3, or 4.

7. The compound of claim 6 or a pharmaceutically acceptable salt thereof, wherein
$R^a$ and $R^b$ are independently H or $C_1$-$C_4$ alkyl;
Q is —C(O)— or

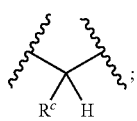

$R^c$ is H, $C_1$-$C_4$ alkyl, cyclopropyl, —CH$_2$OR$^{13}$, or —CH$_2$SR$^{14}$;
$R^{13}$ is H or $C_1$-$C_3$ alkyl; and
$R^{14}$ is $C_1$-$C_3$ alkyl.

8. The compound of claim 1 having the Formula (IA)

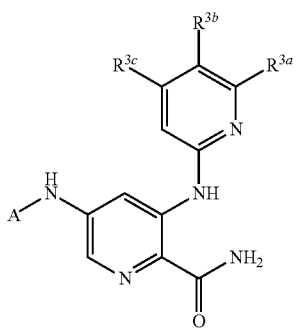

(IA)

or a pharmaceutically acceptable salt thereof, wherein
$R^{3a}$ is halo, $C_1$-$C_3$ alkyl, $C_3$-$C_6$ cycloalkyl, or $C_1$-$C_3$ fluoroalkyl;
$R^{3b}$ is H, $C_1$-$C_3$ alkyl, $C_1$-$C_3$ alkoxy, halo, $C_3$-$C_6$ cycloalkyl, or $C_1$-$C_3$ fluoroalkyl;
$R^{3c}$ is H, $C_1$-$C_3$ alkyl, $C_1$-$C_3$ alkoxy, halo, $C_3$-$C_6$ cycloalkyl, or $C_1$-$C_3$ fluoroalkyl;
A is selected from the group consisting of
(a)

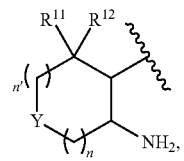

wherein
Y is —CH$_2$—;
$R^{11}$ and $R^{12}$ are independently H or F; and
n is 1 or 2;
n' is 0 or 1; or
(b)

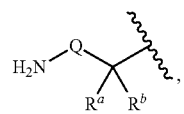

wherein
$R^a$ and $R^b$ are independently H or $C_1$-$C_4$ alkyl; and
Q is —C(O)— or

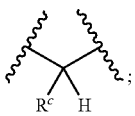

$R^c$ is H, $C_1$-$C_3$ alkyl, cyclopropyl, —CH$_2$OR$^{13}$, or —CH$_2$SR$^{14}$;
$R^{13}$ is H or $C_1$-$C_3$ alkyl; and
$R^{14}$ is $C_1$-$C_3$ alkyl.

9. The compound of claim 8 or a pharmaceutically acceptable salt thereof, wherein no more than one of $R^{3a}$, $R^{3b}$, and $R^{3c}$ is $C_3$-$C_6$ cycloalkyl.

10. The compound of claim 9 or a pharmaceutically acceptable salt thereof, wherein $R^{3a}$ and $R^{3c}$ are both methyl, and $R^{3b}$ is H.

11. The compound of claim 8 or a pharmaceutically acceptable salt thereof, wherein A is selected from the group consisting of:

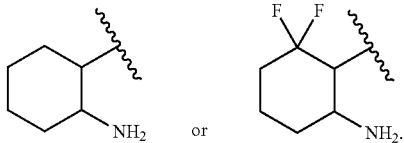 [SMILES: *C1CCCCC1N ; "or" ; *C1C(N)CCCC1(F)F]

12. The compound of claim 8 or a pharmaceutically acceptable salt thereof, wherein A is

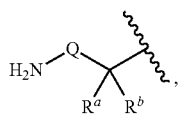

wherein
$R^a$ and $R^b$ are independently H or $C_1$-$C_4$ alkyl; and
Q is —C(O)— or

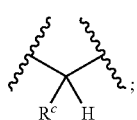

$R^c$ is H, $C_1$-$C_3$ alkyl, cyclopropyl, —CH$_2$OR$^{13}$, or —CH$_2$SR$^{14}$,
$R^{13}$ is H or $C_1$-$C_3$ alkyl; and
$R^{14}$ is $C_1$-$C_3$ alkyl.

13. The compound of claim 12 or a pharmaceutically acceptable salt thereof, wherein
$R^a$ and $R^b$ are both H;
Q is

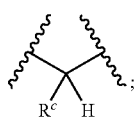

$R^c$ is H or —CH$_2$OR$^{13}$, and $R^{13}$ is $C_1$-$C_3$ alkyl.

14. The compound of claim 1 selected from the group consisting of:
rel-5-{[(1R,2S)-2-aminocyclohexyl]amino}-3-[(5,6-dimethylpyridin-2-yl)amino]pyridine-2-carboxamide;
rel-5-{[(1R,2S)-2-aminocyclohexyl]amino}-3-[(6-methylpyridin-2-yl)amino]pyridine-2-carboxamide;
rel-5-{[(1R,2S)-2-aminocyclohexyl]amino}-3-[(6-cyclopropylpyridin-2-yl)amino]pyridine-2-carboxamide;
rel-5-{[(1R,2S)-2-aminocyclohexyl]amino}-3-{[6-(1-methylethyl)pyridin-2-yl]amino}pyridine-2-carboxamide;
rel-5-{[(1R,2S)-2-aminocyclohexyl]amino}-3-[(4-chloro-6-methylpyridin-2-yl)amino]pyridine-2-carboxamide;
rel-5-{[(1R,2S)-2-aminocyclohexyl]amino}-3-[(6-chloro-4-methylpyridin-2-yl)amino]pyridine-2-carboxamide;
rel-5-{[(1R,2S)-2-aminocyclohexyl]amino}-3-[(4,6-dimethylpyridin-2-yl)amino]pyridine-2-carboxamide;
rel-5-{[(1R,2S)-2-aminocyclohexyl]amino}-3-[(4,6-dichloropyridin-2-yl)amino]pyridine-2-carboxamide;
rel-5-{[(1R,2S)-2-aminocyclohexyl]amino}-3-[(6-ethylpyridin-2-yl)amino]pyridine-2-carboxamide;
5-{[2-aminopropyl]amino}-3-{[6-(trifluoromethyl)pyridin-2-yl]amino}pyridine-2-carboxamide;
rel-5-{[(1S,6S)-6-amino-2,2-difluorocyclohexyl]amino}-3-{[6-(trifluoromethyl)pyridin-2-yl]amino}pyridine-2-carboxamide;
rel-5-{[(1R,2S)-2-aminocyclohexyl]amino}-3-[(5-methoxy-6-methylpyridin-2-yl)amino]pyridine-2-carboxamide;
5-{[2-aminopropyl]amino}-3-[(6-ethylpyridin-2-yl)amino]pyridine-2-carboxamide;
rel-5-{[(1R,2S)-2-aminocyclohexyl]amino}-3-{[6-methyl-4-(1-methylethoxy)pyridin-2-yl]amino}pyridine-2-carboxamide;
rel-5-{[(1R,2S)-2-aminocyclohexyl]amino}-3-[(4-methoxy-6-methylpyridin-2-yl)amino]pyridine-2-carboxamide;
rel-5-{[(1R,2S)-2-aminocyclohexyl]amino}-3-{[6-methyl-5-(propan-2-yloxy)pyridin-2-yl]amino}pyridine-2-carboxamide;
rel-5-{[(1R,2S)-2-aminocyclohexyl]amino}-3-{[6-(trifluoromethyl)pyridin-2-yl]amino}pyridine-2-carboxamide;
5-{[2-amino-3-methoxypropyl]amino}-3-[(4,6-dimethylpyridin-2-yl)amino]pyridine-2-carboxamide;
5-[(2-amino-3-ethoxypropyl)amino]-3-[(4,6-dimethylpyridin-2-yl)amino]pyridine-2-carboxamide;
5-{[2-amino-3-methoxypropyl]amino}-3-{[6-(trifluoromethyl)pyridin-2-yl]amino}pyridine-2-carboxamide;
rel-5-{[(1R,2S)-2-aminocyclohexyl]amino}-3-[(6-fluoropyridin-2-yl)amino]pyridine-2-carboxamide;
rel-5-{[(1R,2S)-2-aminocyclohexyl]amino}-3-[(6-methoxypyridin-2-yl)amino]pyridine-2-carboxamide;
$N^2$-{6-carbamoyl-5-[(4,6-dimethylpyridin-2-yl)amino]pyridin-3-yl}-leucinamide;
5-{[2-aminopropyl]amino}-3-[(5-bromo-6-methylpyridin-2-yl)amino]pyridine-2-carboxamide;
5-{[2-amino-3-(methylsulfanyl)propyl]amino}-3-[(4,6-dimethylpyridin-2-yl)amino]pyridine-2-carboxamide;
5-{[1-(aminomethyl)propyl]amino}-3-[(6-ethylpyridin-2-yl)amino]pyridine-2-carboxamide;
$N^2$-{6-carbamoyl-5-[(4,6-dimethylpyridin-2-yl)amino]pyridin-3-yl}leucinamide;
5-{[2-amino-3-methoxypropyl]amino}-3-[(6-ethylpyridin-2-yl)amino]pyridine-2-carboxamide;
rel-5-{[(1R,2S)-2-aminocyclohexyl]amino}-3-[(5-fluoro-6-methylpyridin-2-yl)amino]pyridine-2-carboxamide;
rel-5-{[(1S,6S)-6-amino-2,2-difluorocyclohexyl]amino}-3-[(4,6-dimethylpyridin-2-yl)amino]pyridine-2-carboxamide;
rel-5-{[(1S,6S)-6-amino-2,2-difluorocyclohexyl]amino}-3-[(6-ethylpyridin-2-yl)amino]pyridine-2-carboxamide;
5-[(2-amino-1-methylethyl)amino]-3-[(4,6-dimethylpyridin-2-yl)amino]pyridine-2-carboxamide;
5-[(2-amino-2-cyclopropylethyl)amino]-3-[(4,6-dimethylpyridin-2-yl)amino]pyridine-2-carboxamide;

5-[(2-aminoethyl)amino]-3-[(4,6-dimethylpyridin-2-yl)
amino]pyridine-2-carboxamide;

N²-{6-carbamoyl-5-[(4,6-dimethylpyridin-2-yl)amino]
pyridin-3-yl}-leucinamide;

rel-5-{[(1R,2S)-2-aminocyclohexyl]amino}-3-{[4-(1-hydroxy-1-methylethyl)-6-methylpyridin-2-yl]
amino}pyridine-2-carboxamide;

5-[(2-amino-1,1-dimethylethyl)amino]-3-[(4,6-dimethylpyridin-2-yl)amino]pyridine-2-carboxamide;

5-[(1-carbamoyl-2-methylpropyl)amino]-3-[(4,6-dimethylpyridin-2-yl)amino]pyridine-2-carboxamide;

5-[(2-amino-1-methyl-2-oxoethyl)amino]-3-[(4,6-dimethylpyridin-2-yl)amino]pyridine-2-carboxamide;

5-[(2-aminoethyl)amino]-3-[(6-methylpyridin-2-yl)
amino]pyridine-2-carboxamide;

5-{[2-amino-3-methoxypropyl]amino}-3-[(4,6-dimethylpyridin-2-yl)amino]pyridine-2-carboxamide;

5-[(2-amino-3,3-difluoropropyl)amino]-3-[(4,6-dimethylpyridin-2-yl)amino]pyridine-2-carboxamide; and 5-[(2-amino-3-hydroxypropyl)amino]-3-[(4,6-dimethylpyridin-2-yl)amino]pyridine-2-carboxamide;

or a pharmaceutically acceptable salt thereof.

15. A pharmaceutical composition comprising a therapeutically effective amount of the compound of claim 1 or a pharmaceutically acceptable salt thereof and a pharmaceutically acceptable carrier.

16. The compound of claim 1 wherein the compound is 5-{[(1R,2S)-2-aminocyclohexyl]amino}-3-[(4,6-dimethylpyridin-2-yl)amino]pyridine-2-carboxamide or a pharmaceutically acceptable salt thereof.

* * * * *